US009198595B2

(12) United States Patent
Neitz et al.

(10) Patent No.: US 9,198,595 B2
(45) Date of Patent: Dec. 1, 2015

(54) REAGENTS AND METHODS FOR MODULATING CONE PHOTORECEPTOR ACTIVITY

(71) Applicants: Jay Neitz, Seattle, WA (US); Maureen Neitz, Seattle, WA (US); James A. Kuchenbecker, Seattle, WA (US); William W. Hauswirth, Gainesville, FL (US)

(72) Inventors: Jay Neitz, Seattle, WA (US); Maureen Neitz, Seattle, WA (US); James A. Kuchenbecker, Seattle, WA (US); William W. Hauswirth, Gainesville, FL (US)

(73) Assignees: University of Washington Through its Center for Commercialization, Seattle, WA (US); University of Florida Research Foundation, Incorporated, Gainesville, FL (US); Medical College of Wisconsin, Milwaukee, WI (US)

( * ) Notice: Subject to any disclaimer, the term of this patent is extended or adjusted under 35 U.S.C. 154(b) by 0 days.

(21) Appl. No.: 14/075,415

(22) Filed: Nov. 8, 2013

(65) Prior Publication Data
US 2014/0080900 A1 Mar. 20, 2014

Related U.S. Application Data

(63) Continuation of application No. 13/395,609, filed as application No. PCT/US2010/048964 on Sep. 15, 2010, now abandoned.

(60) Provisional application No. 61/242,587, filed on Sep. 15, 2009.

(51) Int. Cl.
C12N 15/85 (2006.01)
A61K 48/00 (2006.01)
A61B 5/0496 (2006.01)
A61B 5/00 (2006.01)
A61N 5/06 (2006.01)

(52) U.S. Cl.
CPC ............ *A61B 5/0496* (2013.01); *A61B 5/4836* (2013.01); *A61B 5/4848* (2013.01); *A61B 5/6821* (2013.01); *A61B 5/7225* (2013.01); *A61K 48/0058* (2013.01); *A61K 48/0075* (2013.01); *A61N 5/0622* (2013.01); *C12N 15/85* (2013.01); *A61N 2005/0652* (2013.01); *A61N 2005/0661* (2013.01); *A61N 2005/0663* (2013.01); *C12N 2799/025* (2013.01); *C12N 2830/008* (2013.01); *C12N 2830/42* (2013.01); *C12N 2840/44* (2013.01)

(58) Field of Classification Search
None
See application file for complete search history.

(56) References Cited

U.S. PATENT DOCUMENTS

| | | | |
|---|---|---|---|
| 4,874,237 A | 10/1989 | Cringle | |
| 5,436,146 A | 7/1995 | Shenk et al. | |
| 5,753,500 A | 5/1998 | Shenk et al. | |
| 6,040,183 A | 3/2000 | Ferrari et al. | |
| 6,093,570 A | 7/2000 | Ferrari et al. | |
| 6,548,286 B1 | 4/2003 | Samulski et al. | |
| 7,972,278 B2 | 7/2011 | Graham et al. | |
| 8,075,137 B2 | 12/2011 | Klistorner et al. | |
| 8,118,752 B2 | 2/2012 | Hetling et al. | |
| 8,343,067 B2 | 1/2013 | Jones et al. | |
| 2002/0168342 A1 | 11/2002 | Wang et al. | |
| 2007/0188710 A1 | 8/2007 | Hetling et al. | |
| 2009/0128776 A1 | 5/2009 | Keating et al. | |
| 2010/0091242 A1 | 4/2010 | Baglini et al. | |
| 2011/0116046 A1 | 5/2011 | Haeri et al. | |

FOREIGN PATENT DOCUMENTS

WO 02/082904 10/2002

OTHER PUBLICATIONS

Mauck, et al. "Longitudinal in vivo Characterization of Expression of Viral Delivered Genes for L-opsin and Green Fluorescent Protein in Cone Photoreceptors of Gerbils," Invest Opthalmol Vis Sci 2006, 47:E-abstract 4071.
Mancuso, et al., "Colorblindness Cure: Gene Therapy Confers a New Sensation," Invest Opthalmol Vis Sci 2008, 49: E-abstract 3252.
Mancuso, et al., (2005) Annual Meeting of the Association for Research in Vision and Ophthalmology, Ft. Lauderdale, FL, 46(Supp S): 4565.
Mancuso, et al., (2007), Journal of Optical Society of America A: Optics and Image Science and Vision, vol. 24(5), pp. 1411-1416.
Mauck, et al., (2008), Visual Neurosceince, 25(3):273-282.
Li, et al. (2008) Cone-specific expression using a human red opsin promoter in recombinant AAV, Vision Research, 48(3):332-338.
Kuchenbecker, et al. (2008) Visual Neurosceince, 25 (3): 301-306.
Cai, et al., (2010) FASEB Journal, 24(4): 1178-1191.
Komaromy, et al. (2010) Human Molecular Genetics, 19(13): 2581-2593.
Mancuso, et al., (2009) Nature, 461(7265): 784.
Pang, et al. (2006) Molecular Therapy, 13(3): 565-572.
Lai, et al. (2007) Survey of ophthalmology, 52(1): 61-96.
Sutter, E. E. (1991). The Fast m-Transform: A Fast Computation of Cross-Correlations with Binary m-Sequences. SIAM Journal on Computing, 20(4),686-694.
Swanson, W. H., Ueno, T., Smith, V. C., & Pokorny, J. (1987). Temporal modulation sensitivity and pulse-detection thresholds for chromatic and luminance perturbations. Journal of the Optical Society of America A-Optics, Image Science and Vision, 4(10), 13.
Lindenberg, T., Horn, F. K., & Korth, M. (2003). Cyclic summation versus m-sequence technique in the multifocal ERG. Graefes Archive of Clinical Experimental Ophthalmology., 241(6),505-510.
Wiesel, T.N. & Hubel, D.H. Single-cell responses in striate cortex of kittens deprived of vision in one eye. J Neurophysiol. 26, 1003-1017 (1963).
Jacobs, G.H. A perspective on color vision in platyrrhine monkeys. Vision Res. 38, 3307-3313 (1998).
Reffin, J.P., Astell, S. & Mollon, J.D. Trials of a computer-controlled colour vision test that preserves the advantages of pseudo-isochromatic plates. in Colour Vision Deficiencies X69-76 (Kluwer Academic Publishers, Dordrecht, 1991).

(Continued)

*Primary Examiner* — Doug Schultz
(74) *Attorney, Agent, or Firm* — McDonnell Boehnen Hulbert & Berghoff LLP

(57) ABSTRACT

The present invention provides reagents and methods for modulating cone photoreceptor activity, and devices for assessment of cone photoreceptor activity.

12 Claims, 8 Drawing Sheets

(56) References Cited

OTHER PUBLICATIONS

Regan, B.C., Reffin, J.P. & Mollon, J.D. Luminance noise and the rapid determination of discrimination ellipses in colour deficiency. Vision Res. 34, 1279-1299 (1994).

Mancuso, K., Neitz, M. & Neitz, J. An adaptation of the Cambridge Colour Test for use with animals. Vis. Neurosci. (2006).

Nathans, J., Piantanida, T.P., Eddy, R.L., Shows, T.B. & Hogness, D.S. Molecular genetics of inherited variation in human color vision. Science 232, 203-210 (1986).

Shapley, R. Specificity of cone connections in the retina and color vision. Focus on "Specificity of cone inputs to macaque retinal ganglion cells". J Neurophysiol. 95, 587-588 (2006).

DeValois, R.L. & DeValois, K.K. A multi-stage color model. Vision Res. 33, 1053-1065 (1993).

Jacobs, G.H., Williams, G.A., Cahill, H. & Nathans, J. Emergence of Novel Color Vision in Mice Engineered to Express a Human Cone Photopigment. Science 315, 1723-1725 (2007).

Makous, W. Comment on "Emergence of Novel Color Vision in Mice Engineered to Express a Human Cone Photopigment". Science 318, 196 (2007).

Maguire, A.M. et al. Safety and efficacy of gene transfer for Leber's congenital amaurosis. N. Engl. J Med. 358, 2240-2248 (2008).

Bainbridge, J.W. & Ali, R.R. Success in sight: The eyes have it! Ocular gene therapy trials for LCA look promising. Gene Ther. 15, 1191-1192 (2008).

Cideciyan, A.V. et al. Human gene therapy for RPE65 isomerase deficiency activates the retinoid cycle of vision but with slow rod kinetics. Proc. Natl. Acad. Sci. USA 105, 15112-15117 (2008).

Wang, Y. et al. A locus control region adjacent to the human red and green visual pigment genes. Neuron 9, 429-440 (1992).

Nathans, J., Thomas, D. & Hogness, D.S. Molecular genetics of human color vision: the genes encoding blue, green, and red pigments. Science 232, 193-202 (1986).

Neitz, M., Neitz, J. & Jacobs, G.H. Spectral tuning of pigments underlying red green color vision. Science 252, 971-974 (1991).

Buning, H., Perabo, L., Coutelle, 0., Quadt-Humme, S. & Hallek, M. Recent developments in adeno-associated virus vector technology. J Gene Med. 10, 717-733 (2008).

ISR PCT/US2010/048964, mailed Jun. 17, 2011.

Figure 6

|  |  | Typical SNR | Highest SNR |
|---|---|---|---|
| GRN | Ring 2 | 82.98129 | 139.6429 |
|  | Ring 3 | 34.42575 | 47.00658 |
|  | Ring 4 | 33.5582 | 49.9321 |
| RED | Ring 2 | 47.16825 | 87.55556 |
|  | Ring 3 | 20.84694 | 34.38312 |
|  | Ring 4 | 16.75357 | 20.45714 |

REAGENTS AND METHODS FOR MODULATING CONE PHOTORECEPTOR ACTIVITY

RELATED APPLICATIONS

This application claims priority to U.S. Provisional Patent Application Ser. No. 61/242,587 filed Sep. 15, 2009, incorporated by reference herein in its entirety.

STATEMENT OF U.S. GOVERNMENT SUPPORT

This invention was made with government support under grants P30 EY001730, R01 EY016861, and R01 EY011123, awarded by the National Institutes of Health. The government has certain rights in the invention.

BACKGROUND

Classic visual deprivation experiments have led to the expectation that neural connections established during development would not appropriately process an input that was not present from birth. Therefore, it was believed that treatment of congenital vision disorders would be ineffective unless administered to the very young.

SUMMARY OF THE INVENTION

In a first aspect, the present invention provides methods for cone cell gene therapy in a primate, comprising administering to the eye of a primate in need of cone cell gene therapy a recombinant gene delivery vector comprising:

(a) a promoter region, wherein the promoter region is specific for retinal cone cells; and (b) a gene encoding a therapeutic, wherein the gene is operatively linked to the promoter region;

wherein in vivo expression of the therapeutic in cone cells of the primate serves to treat the primate in need of cone cell gene therapy.

The method of this aspect of the invention can be used, for example, to treat a cone cell disorder, including but not limited to color blindness, blue cone monochomacy, achromatopsia, incomplete achromatopsia, rod-cone degeneration, retinitis pigmentosa (RP), macular degeneration, cone dystrophy, blindness, Stargardes Disease, and Leber's congenital amaurosis. In one embodiment, the methods restore visual capacity in the primate; in another embodiment, the primate is able to visualize new colors as a result of the therapy. In another embodiment, the primate has a vision disorder in which its photoreceptors are healthy. In a further embodiment, the primate is an adult primate.

In another aspect, the present invention provides isolated nucleic acid expression vector comprising:

(a) a promoter region, wherein the promoter region is specific for primate retinal cone cells; and (b) a gene encoding a therapeutic, wherein the gene is operatively linked to the promoter region. In various embodiments, the vectors further comprise an enhancer element upstream of the promoter, wherein the gene is operatively linked to the enhancer element, and/or intron comprising a splice donor/acceptor region, wherein the intron is located downstream of the promoter region and is located upstream of the gene. The vectors can be used, for example, in the methods of the invention.

In another aspect, the present invention provides color multi-focal electroretinogram (mf-ERG) comprising:

(a) electroretinogram (ERG) comprising
  (i) a recording electrode that is (A) designed for placement on at least one of a cornea and a sclera of at least one eye of a subject and (B) arranged to output at least one signal generated by the at least one eye; and
  (ii) a computing system communicatively coupled to the recording electrode, the computing system comprising (A) at least one processor and (B) data storage containing instructions executable by the at least one processor to carry out a set of functions, the set of functions including processing and saving the at least one signal generated by the at least one eye;

(b) a retinal stimulator comprising matched light sources selected from the group consisting of red, green, blue, and ultraviolet light sources, wherein the matched light sources are connected to the ERG and in operation can be independently frequency modulated at rates between about 1 Hz and about 60 Hz, inclusive, wherein the stimulator in operation is capable of stimulating a retinal field of a subject throughout an operating radius of at least about 70 degrees;

(c) one or more constant current integrated circuit chips arranged to drive the stimulator; and (d) a pulse-frequency modulator connected to the retinal stimulator, wherein in operation the pulse-frequency modulator is capable of controlling individual stimulator segments while keeping relative spectral content of the light constant. In various preferred embodiments, the matched light sources are paired red and green light sources; triplets of red, green, and blue light sources; or quartets of red, green, blue, and ultraviolet light sources. In another preferred embodiment the retinal stimulator comprises a concave surface comprising a series of trapezoidal-shaped circuit boards placed edge-to-edge, wherein the concave surface positions the matched light sources so in operation they are held equidistantly from and pointing toward a single focal point where a subject's pupil can be positioned.

BRIEF DESCRIPTION OF THE FIGURES

FIG. 6. The signal to noise ratio (SNR) for as a function of degrees of eccentricity for a typical (averaged) subject and for the highest subject recorded.

DETAILED DESCRIPTION OF THE INVENTION

Figure 1:
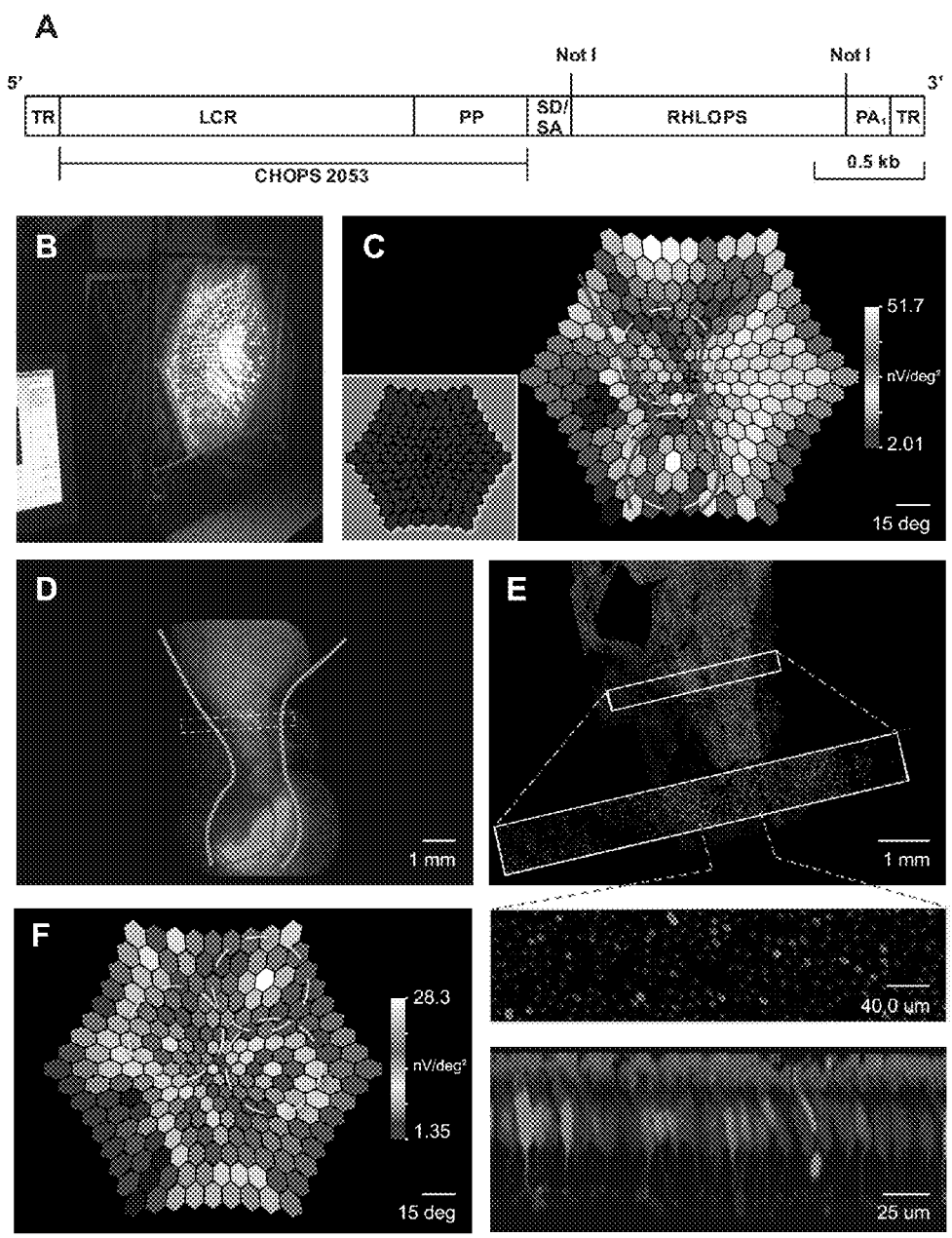
FIG. 1. rAAV2/5 vector produced functional L-opsin in primate retina, a) Molecular map; TR=terminal repeats; LCR=locus control region; PP=proximal promoter; SD/SA=splice donor/acceptor; RHLOPS=recombinant human L opsin cDNA; $PA_1$=polyadenylation signal. b) Red light Multi-focal electroretinogram (Mf-ERG) stimulus. c) mf-ERG 40 weeks after two injections (yellow circles) of a mixture of L-opsin- and green fluorescent protein (GFP)-coding viruses. Grey lines show borders of highest response; for comparison, inset=mfERG 16 weeks post-injection; there was no reliable signal from L-opsin, unchanged from baseline. High responses in far peripheral retina were measured reliably and may have originated, from offshoot of one of the injections. d) Fluorescence photographs from a similar retinal area as c; grey lines from c were copied in d. e) Confocal microscopy revealed a mosaic pattern of GFP expression in 5-12% of cones. Because GFP-coding virus was diluted to ⅓ compared to L-opsin virus, an estimated 15-36% of cones in behaviourally tested animals express L-opsin. f) Mf-ERG from a behaviourally tested animal 70 weeks after 3 injections of L-opsin virus.

In a first aspect, the present invention provides methods for cone cell gene therapy in a primate, comprising administering to the eye of a primate in need of cone cell gene therapy a recombinant gene delivery vector comprising:
(a) a promoter region, wherein the promoter region is specific for retinal cone cells; and
(b) a gene encoding a therapeutic, wherein the gene is operatively linked to the promoter region;
wherein in vivo expression of the therapeutic in cone cells of the primate serves to treat the primate in need of cone cell gene therapy.

Cone cells are photoreceptor cells in the retina of the eye that function best in relatively bright light. The cone cells gradually become sparser towards the periphery of the retina. The methods of the present invention can be used for treatment of any condition that can be addressed, at least in part, by gene therapy of retinal cone photoreceptor cells. The inventors have demonstrated effective treatment of congenital vision disorders in adult primates, a result that is completely unexpected in the art.

In one preferred embodiment, the gene therapy serves to treat a cone cell disorder. As used herein, a "cone cell disorder" is any disorder impacting retinal cone cells, including but not limited to color blindness, blue cone monochomacy, achromatopsia, incomplete achromatopsia, rod-cone degeneration, retinitis pigmentosa (RP), macular degeneration, cone dystrophy, blindness, Stargardt's Disease, and Leber's congenital amaurosis.

The gene encoding a therapeutic to be expressed in the cone cells can comprise or consist of any gene or cDNA that encodes a polypeptide or RNA-based therapeutic (siRNA, antisense, ribozyme, shRNA, etc.) that can be used as a therapeutic for treating a cone cell disorder. In a preferred embodiment, the primate is of the Parvorder Catarrhini. As is known in the art, Catarrhini is one of the two subdivisions of the higher primates (the other being the New World monkeys), and includes Old World monkeys and the apes, which in turn are farther divided into the lesser apes or gibbons and the great apes, consisting of the orangutans, gorillas, chimpanzees, bonobos, and humans. In a further preferred embodiment, the primate is a human.

A "promoter" is a DNA sequence that directs the binding of RNA polymerase and thereby promotes RNA synthesis, i.e., a minimal sequence sufficient to direct transcription. Any suitable promoter region can be used in the gene therapy vectors, so long as it specifically promotes expression of the gene in retinal cone cells. In a preferred embodiment, the promoter specifically promotes expression of the gene in primate retinal cone cells; more preferably in Catarrhini retinal cone cells; even more preferably in human retinal cone cells. As used herein, "specifically" means that the promoter predominately promotes expression of the gene in retinal cone cells compared to other cell types, such that at least 80%, and preferably 85%, 90%, 91%, 92%, 93%, 94%, 95%, 96%, 97%, 97%, 98%, 99%, 99.5%, or more of expression of the gene after delivery of the vector to the eye will be in cone cells. Exemplary suitable promoter regions include the promoter region for any cone-specific gene, such as the L opsin promoter (SEQ ID NO:1), the M opsin promoter (SEQ ID NO:2), and the S opsin promoter (SEQ ID NO:3), or portions thereof suitable to promote expression in a cone-specific manner. Any suitable method for identifying promoter sequences capable of driving expression in primate cone cells can be used to identify such promoters, as will be understood by those of skill in the art based on the teachings herein.

In a preferred embodiment, the gene delivery vector further comprises an enhancer element upstream of the promoter, wherein the gene is operatively linked to the enhancer element. Enhancers are cis-acting elements that stimulate transcription of adjacent genes. Any suitable enhancer element can be used in the gene therapy vectors, so long as it enhances expression of the gene when used in combination with the promoter, in a preferred embodiment, the enhancer element is specific for retinal cone cells; more preferably, it is specific for primate retinal cone cells; more preferably in Catarrhini retinal cone cells; even more preferably in human retinal cone cells. As used herein, "specifically" means that the enhancer predominately enhances expression of the gene in retinal cone cells compared to other cell types, such that at least 80%, and preferably 85%, 90%, 91%, 92%, 93%, 94%, 95%, 96%, 97%, 97%, 98%, 99%, 99.5%, or more of expression of the gene after delivery of the vector to the eye will be in cone cells. Exemplary suitable enhancer regions comprise or consist of the enhancer region for any cone-specific gene, such as the L/M minimal opsin enhancer (SEQ ID NO: 51), L/M enhancer elements of 100, 200, 300, 400, 500, 600, 700, 800, 900, 1000, 1100, 1200, 1300, 1400, 1500, 1600, 1700, 1800, 1900, 2000, or more nucleotides that comprise one or more copies of the L/M minimal opsin enhancer, and the full L/M opsin enhancer (SEQ ID NO:4), or other portions thereof suitable to promote expression in a cone-specific manner. Any suitable method for identifying enhancer sequences capable of driving expression in primate cone cells can be used to identify such enhancers, as will be understood by those of skill in the art based on the teachings herein.

The length of the promoter and enhancer regions can be of any suitable length for their intended purpose, and the spacing between the promoter and enhancer regions can be any suitable spacing to promote cone-specific expression of the gene product. In various preferred embodiments, the enhancer is located 0-1500; 0-1250; 0-1000; 0-750; 0-600; 0-500; 0-400; 0-300; 0-200; 0-100; 0-90; 0-80; 0-70; 0-60; 0-50; 0-40; 0-30; 0-20; or 0-10 nucleotides upstream of the promoter. The promoter can be any suitable distance upstream of the encoded gene.

In a further preferred embodiment that can be combined with any other embodiment in any aspect of the present invention, the enhancer comprises or consists of a sequence selected from the group consisting of the L/M minimal opsin enhancer (SEQ ID NO: 51), L/M enhancer elements of 100, 200, 300, 400, 500, 600, 700, 800, 900, 1000, 1100, 1200, 1300, 1400, 1500, 1600, 1700, 1800, 1900, 2000, or more nucleotides that comprise one or more copies of the L/M minimal opsin enhancer, and the full L/M opsin enhancer (SEQ NO:4), or other portions thereof suitable to promote expression in a cone-specific manner, and the promoter comprises or consists of a sequence selected from the group consisting of L opsin promoter (SEQ ID NO: 1), the M opsin promoter (SEQ NO:2), and the S opsin promoter (SEQ ID NO:3).

in a further preferred embodiment, the gene delivery vector further comprises an intron comprising a splice donor/acceptor region, wherein the intron located downstream of the promoter region and is located upstream of the gene. Any intron can be used, so long as it comprises a splice donor/acceptor region recognized in primate cone cells, so that the intron can be spliced out of the resulting, mRNA product. In one embodiment, the intron comprises or consists of an SV40 intron according to SEQ ID NO:5. In various preferred embodiments, the 3' end of the intron is 0-20; 0-15; 0-10; 0-9; 0-8; 0-7; 0-6; or 0-5 nucleotides upstream of the gene, and its 5' end is 0-20; 0-15; 0-10; 0-9; 0-8; 0-7; 0-6; or 0-5 nucleotides downstream of the proximal promoter region.

The gene is operatively linked to the promoter region and the enhancer element, such that the promoter and enhancer elements are capable of driving expression of the gene or cDNA in cone cells of the subject.

The gene encoding a therapeutic to be expressed in the cone cells can be any gene or cDNA that encodes a polypeptide or RNA-based therapeutic (siRNA, antisense, ribozyme, shRNA, etc.) that can be used as a therapeutic for treating a cone cell disorder, or as a means to otherwise enhance vision, including but not limited to promoting tetrachromatic color vision. In various preferred embodiments, the gene encodes a therapeutic protein selected from the group consisting of (a) SEQ ID NO: 7 (SEQ ID NO: 6) *Homo sapiens* opsin 1 (cone pigments), short-wave-sensitive (OPN1SW), mRNA NCBI Reference Sequence: NM_001708.2;

(b) SEQ ID NO: 9 (SEQ ID NO: 8) *Homo sapiens* opsin 1 (cone pigments), medium-wave-sensitive (OPN1MW), mRNA NCBI Reference Sequence: NM_000513.2;

(c) SEQ ID NO: 11 (SEQ ID NO: 10) *Homo sapiens* opsin 1 (cone pigments), long-wave-sensitive (OPN1LW), mRNA NCBI Reference Sequence: NM_020061.4;

(d) SEQ ID NO: 13 (SEQ ID NO: 12) ATP binding cassette retina gene (ABCR) gene (NM_000350);

(e) SEQ ID NO: 15 (SEQ ID NO: 14) retinal pigmented epithelium-specific 65 kD protein gene (RPE65) (NM_000329);

(f) SEQ NO: 17 (SEQ ID NO: 16) retinal binding protein 1 gene (REBP1) (NM_000326);

(g) SEQ ID NO: 19 (SEQ ID NO: 8) peripherin/retinal degeneration slow gene, (NM_000322);

(h) SEQ ID NO: 21 (SEQ ID NO: 20) arrestin (SAG) (NM_000541);

(i) SEQ ID NO: 23 (SEQ ID NO: 22) alpha-transducin (GNAT1) (NM_000172);

(j) SEQ ID NO: 24 guanylate cyclase activator 1A (GUCA1A) (NP_000400.2);

(k) SEQ ID NO: 25 retina specific guanylate cyclase (GUCY2D), (NP_000171.1);

(l) SEQ ID NO: 26 & 27 alpha subunit of the cone cyclic nucleotide gated cation channel (CNGA3) (NP_001073347.1 or NP_001289.1);

(m) SEQ ID NO: 28 Human cone transducin alpha subunit (incomplete achromotopsia);

(n) SEQ ID NO: 29 cone cGMP-specific 3',5'-cyclic phosphodiesterase subunit alpha', protein (cone dystrophy type 4):

(o) SEQ ID NO: 30 retinal cone rhodopsin-sensitive cGMP 3',5'-cyclic phosphodiesterase subunit gamma, protein (retinal cone dystrophy type 3A);

(p) SEQ ID NO: 31 cone rod homeobox, protein (Cone-rod dystrophy);

(q) SEQ ID NO: 32 cone photoreceptor cyclic nucleotide-gated channel beta subunit, protein (achromatopsia);

(r) SEQ ID NO: 33 cone photoreceptor cGMP-gated cation channel beta-subunit, protein (total color blindness, for example, among Pingelapese Islanders);

(s) SEQ ID NO: 35 (SEQ ID NO: 34) retinitis pigmentosa 1 (autosomal dominant) (RP1);

(t) SEQ ID NO: 37 (SEQ ID NO: 36) retinitis pigmentosa GTPase regulator interacting protein 1 (RPGRIP1);

(u) SEQ ID NO: 39 (SEQ ID NO: 38) PRP8;

(v) SEQ ID NO: 41 (SEQ ID NO: 40) centrosomal protein 290 kDa (CEP290):

(w) SEQ ID NO: 43 (SEQ ID NO: 42) IMP (inosine 5'-monophosphate) dehydrogenase 1 (IMPDH1), transcript variant 1:

(x) SEQ ID NO: 45 (SEQ ID NO: 44) aryl hydrocarbon receptor interacting protein-like 1 (AIPLI1), transcript variant 1;

(y) SEQ ID NO: 47 (SEQ ID NO: 46) retinol dehydrogenase 12 (all-trans/9-cis/11-cis) (RDH12);

(z) SEQ ID NO: 49 (SEQ ID NO: 48) Leber congenital amaurosis 5 (LCA5), transcript variant 1; and (aa) exemplary OPN1LW/OPN1MW2 polymorphs (compared to OPN1LW (L opsin) polypeptide sequence; the amino acid to the left of the number is the residue present in the L opsin sequence; the number is the reside number in L opsin, and the reside to the right of the number is the variation from L opsin. Polymorphs according to these embodiments may comprise one or more of the amino acid substitutions in Table 1 below:

TABLE 1

| (i) | Thr65Ile |
|---|---|
| (ii) | Ile111Val |
| (iii) | Ser116Tyr |
| (iv) | Leu153Met |
| (v) | Ile171Val |
| (vi) | Ala174Val |
| (vii) | Ile178Val |
| (viii) | Ser180Ala |
| (ix) | Ile230Thr |
| (x) | Ala233Ser |
| (xi) | Val236Met |
| (xii) | Ile274Val |
| (xiii) | Phe275Leu |
| (xiv) | Tyr277Phe |
| (xv) | Val279Phe |
| (xvi) | Thr285Ala |
| (xvii) | Pro298Ala |
| (xviii) | Tyr309Phe. |

The proteins recited in (a)-(c) and (aa) are all involved in color vision. The exemplary polymorphs include ones at positions 65, 116, 180, 230, 233, 277, 285, and 309 that affect the spectra of the pigments in cone cells expressing them. Positions 274, 275, 277, 279, 285, 298 and 309 together distinguish L opsin from M opsin.

The proteins recited in (d)-(z) are exemplary eye disease-associated gene, such as in retinitis pigmentosa (polypeptides "e"-"l", "s"-"y"), incomplete achromatopsia (polypeptide "m"), Stargardt's (polypeptide "d"); Leber congenital amaurosis (polypeptide "z"); cone dystrophy, such as cone dystrophy type 4 (polypeptide "n"); retinal cone dystrophy; for example, retinal cone dystrophy type 3A (polypeptide "o"): Cone-rod dystrophy (polypeptide "p"); achromatopsia (polypeptide "q"); and total color blindness, for example, among Pingelapese Islanders (polypeptide "r").

Exemplary nucleic acids encoding these polypeptides are shown by SEQ ID NO in parenthesis. Thus, in a further preferred embodiment, the genes comprise or consist of a nucleic acid sequence according to one or more of the nucleic acid sequences recited above. In a further preferred embodiment, the vector comprises the sequence shown in SEQ ID NO: 50

Any suitable gene therapy vector that can be used for cone cell delivery can be used in the methods of the present invention; the vector may comprise single or double stranded nucleic acid; preferably single stranded or double stranded DNA. In a preferred embodiment that can be combined with any of the above embodiments, the gene delivery vector comprises a recombinant adeno-associated virus (AAV) gene delivery vector. Prior to the present invention, rAAV vectors had not been shown capable of transducing primate cone cells. In this embodiment, the gene delivery vector is bounded on the 5' and 3' end by functional AAV inverted terminal repeat (ITR) sequences. By "functional AAV ITR sequences" is meant that the ITR sequences function as intended for the rescue, replication and packaging of the AAV virion. Hence. AAV ITRs for use in the vectors of the invention need not have a wild-type nucleotide sequence, and may be altered by the insertion, deletion or substitution of nucleotides or the AAV ITRs may be derived from any of several AAV serotypes. The rAAV vector may be derived from an adeno-associated virus serotype, including without limitation. AAV-1, AAV-2. AAV-3, AAV-4, AAV-5, AAV-6, AAV-7, AAV-8, etc. Preferred AAV vectors have the wild type REP and CAP genes deleted in whole or part, but retain functional flanking ITR sequences. In a further preferred embodiment, the AAV vector comprises rAAV2/5, a "pseudotyped" version of AAV2 created by using rep from AAV2 and cap from AAV5 or AAV2, AAV3, AAV4, AAV6, AAV7, AAV8 together with a plasmid containing a vector based on AAV2. Preferably, the rAAV is replication defective, in that the AAV vector cannot independently further replicate and package its genome. For example, when cone cells are transduced with rAAV virions, the gene is expressed in the transduced cone cells, however, due to the fact that the transduced cone cells lack AAV rep and cap genes and accessory function genes, the rAAV is not able to replicate.

Recombinant AAV (rAAV) virions encapsidating the vectors recited above for use in transducing cone cells may be produced using standard methodology. In one embodiment, an AAV expression vector according to the invention is introduced into a producer cell, followed by introduction of an AAV helper construct, where the helper construct includes AAV coding regions capable of being expressed in the producer cell and which complement AAV helper functions absent in the AAV vector. This is followed by introduction of helper virus and/or additional vectors into the producer cell, wherein the helper virus and/or additional vectors provide accessory functions capable of supporting efficient rAAV virus production. The producer cells are then cultured to produce rAAV. These steps are carried out using standard methodology. Replication-defective AAV virions encapsulating the recombinant AAV vectors of the instant invention are made by standard techniques known in the art using AAV packaging cells and packaging technology. Examples of these methods may be found, for example, in U.S. Pat. Nos. 5,436,146; 5,753.500, 6,040.183, 6,093,570 and 6,548,286, expressly incorporated by reference herein in their entirety. Further compositions and methods for packaging are described in Wang et al. (US 2002/0168342), also incorporated by reference herein in its entirety.

Any suitable method for producing viral particles for delivery can be used, including but not limited to those described in the examples that follow. Any concentration of viral particles suitable to effectively transducer cone cells can be administered to the eye. In one preferred embodiment, viral particles are delivered in a concentration of at least $10^{10}$ vector genome containing particles per mL; in various preferred embodiments, the viral particles are delivered in a concentration of at least $7.5 \times 10^{10}$; $10^{11}$; $5 \times 10^{11}$; $10^{12}$; $5 \times 10^{12}$; $10^{13}$; $1.5 \times 10^{13}$; $3 \times 10^3$; $5 \times 10^{13}$; $7.5 \times 9 \times 10^{13}$; or $9 \times 10^{13}$ vector genome containing particles per mL. Similarly, any total number of viral particles suitable to provide appropriate transduction of retinal cone cells can be administered to the primate's eye. In various preferred embodiments, at least $10^{10}$; $5 \times 10^{10}$; $10^{11}$; $5 \times 10^{11}$; $10^{12}$; $1.5 \times 10^{12}$; $3 \times 10^{12}$; $5 \times 10^{12}$;

$7.5 \times 10^{12}$; $10^{13}$; $1.5 \times 10^{13}$; or $2.7 \times 10^{13}$ viral particles are injected per eye. Any suitable number of administrations of the vector to the primate eye can be made. In one embodiment, the methods comprise a single administration; in other embodiments, multiple administrations are made over time as deemed appropriate by an attending clinician.

The viral stock for delivery to the primate eye can be treated as appropriate for delivery. The viral stock can be combined with pharmaceutically-acceptable carriers, diluents and reagents useful in preparing a formulation that is generally safe, non-toxic, and desirable, and includes excipients that are acceptable for primate use. Such excipients can be solid, liquid, semisolid, or, in the case of an aerosol composition, gaseous. Examples of such carriers or diluents include, but are not limited to, water, saline, Ringer's solutions, dextrose solution, and 5% human serum albumin. Supplementary active compounds can also be incorporated into the formulations. Solutions or suspensions used for the formulations can include a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates; detergents such as Tween 20 to prevent aggregation; and compounds for the adjustment of tonicity such as sodium chloride or dextrose. The pH can be adjusted with acids or bases, such as hydrochloric acid or sodium hydroxide.

In a further preferred embodiment that can be combined with any other embodiment, the methods of the invention restore visual capacity in the primate. As used herein, "restoring visual capacity" means that some benefit to vision is provided, including but not limited to a reduction or slowing of vision loss; improved visual acuity; decrease in abnormal sensitivity to bright lights; and/or an increase in one or more visual attributes, such as improved color perception (ie: monochromatic to dichromatic vision; dichromatic to trichromatic vision; trichromatic to tetrachromatic vision; etc.). The primate is preferably of the Parvorder Catarrhini, and more preferably is a human.

In a further preferred embodiment that can be combined with all of the above embodiments, the primate suffers from color blindness, and the primate is able to visualize new colors as a result of the therapy. In this embodiment, it is preferred that the enhancer (if present) comprises or consists of a sequence selected from the group consisting of the L/M minimal opsin enhancer (SEQ ID NO: 51), L/M enhancer elements of 100, 200, 300, 400, 500, 600, 700, 800, 900, 1000, 1100, 1200, 1300, 1400, 1500, 1600, 1700, 1800, 1900, 2000, or more nucleotides that comprise one or more copies of the L/M minimal opsin enhancer, and the full L/M opsin enhancer (SEQ ID NO:4), or other portions thereof suitable to promote expression in a cone-specific manner, and the promoter comprises or consists of a sequence selected from the group consisting of L opsin promoter (SEQ ID NO: 1), the M opsin promoter (SEQ ID NO:2), and the S opsin promoter (SEQ ID NO:3), while the gene encodes one or more polypeptides comprising or consisting of a sequence selected from the group consisting of SEQ ID NO: 7 (OPN1SW), SEQ ID NO: 9 (OPN1MW), SEQ ID NO: 11 (OPN1LW), mRNA; and exemplary OPN1LW/OPN1MW2 polymorphs as described in Table 1 above. It is further preferred that the vector comprises a rAAV vector as described above.

The color blindness may be acquired or inherited, and can be full (monochromatic) or partial. In a preferred embodiment, the primate has partial color blindness selected from the group consisting of red-green and blue-yellow color blindness. The partial color blindness can comprise, for example, dichromacy or anomalous trichromacy. These methods result in the primate improved color perception (ie: monochromatic to dichromatic vision; dichromatic to trichromatic vision: trichromatic to tetrachromatic vision: etc.). The primate is preferably of the Parvorder Catarrhini, and more preferably is a human.

As described in detail below, the methods may be used to improve color perception in primates from dichromatic to trichromatic. Dichromats who are missing either the L- or the M-photopigment fail to distinguish from grey:colours near the so-called 'spectral neutral point' located in the bluegreen region of color space (near dominant wavelength of 490 nm) and complementary colors near the "extra-spectral neutral point" in the red-violet region (near dominant wavelength of 499 nm). Co-expressing the L-opsin transgene within a subset of endogenous M-cones shifted their spectral sensitivity to respond to long wavelength light, thus producing two distinct cone types absorbing in the middle-to-long wavelengths, as required for trichromacy. These results demonstrate that gene therapy changed the spectral sensitivity of a subset of the cones, and the results further demonstrate the unexpected result that adult monkeys gained new color vision capacities because of the gone therapy.

In a further preferred embodiment of all of the above embodiments, the primate has a vision disorder in which its photoreceptors are healthy, such as color blindness. As used herein, "healthy" means that the cells being treated are functioning but simply do not provide for the desired color perception, in contrast to gene therapy in which the target cells are degenerating or dying. The studies reported herein are the first to use gene therapy in primates to address a vision disorder in which all photoreceptors are intact and healthy, making it possible to assess the full potential of gene therapy to restore visual capacities. The methods of the present invention thus will allow many opportunities for functions to be added or restored in the eye.

In a further preferred embodiment that can be combined with any of the other embodiments herein, the primate is an adult primate, such as an adult human (ie: at least 16 years of age: preferably at least 18 years of age or 21 years of age). Classic visual deprivation experiments have led to the expectation that neural connections established during development would not appropriately process an input that was not present from birth. Therefore, it was believed that treatment of congenital vision disorders would be ineffective unless administered to the very young. The present study thus provides significantly unexpected results in curing a visual disorder in an adult primate.

Those of skill in the art will readily appreciate, based on the teachings herein, the variety of treatment modalities that can be accomplished using the methods of the invention. In one embodiment, the gene encodes ABCR and is administered to the eye of a primate with Stargardt disease. In other embodiments, the gene encodes:

one or more of polypeptides "e"-"l" and "s"-"y" in Table 1, and is administered to the eye of a primate with retinitis pigmentosa;

polypeptide "m" in Table 1, and is administered to the eye of a primate with incomplete achromatopsia;

polypeptide "z" in Table 1, and is administered to the eye of a primate with Leber congenital amaurosis;

polypeptide "n" in Table 1, and is administered to the eye of a primate with cone dystrophy, such as cone dystrophy type 4;

polypeptide "o" in Table 1, and is administered to the eye of a primate with retinal cone dystrophy, for example, retinal cone dystrophy type 3A;

polypeptide "p" in Table 1, and is administered to the eye of a primate with cone-rod dystrophy;

polypeptide "q" in Table 1, and is administered to the eye of a primate with achromatopsia and/or polypeptide "r" in Table 1, and is administered to the eye of a primate with total color blindness, for example, a native of the Pingelapese Islands.

Any suitable means for delivery of the gene therapy vector to the eye can be used, including but not limited to administering in a contact lens fluid, contact lens cleaning and rinsing solutions, eye drops, surgical irrigation solutions, ophthalmological devices, injection, iontophoresis, topical instillation on the eye, and topical instillation. The topical instillation can be administered, for example, in the form of a liquid solution, a paste, of a hydrogel. The topical instillation can be embedded, for example, in a foam matrix or supported in a reservoir. The injection into the primate eye can be, for example, an intracameral injection, an intracorneal injection, a subconjonctival injection, a subtenon injection, a subretinal injection, an intravitreal injection, and an injection into the anterior chamber.

The primate's progress in response to the treatment may be monitored by any suitable means. In embodiments where the methods are used to treat color blindness, monitoring or progress may comprise, for example, use of standard color vision tests, or the wide-field color multifocal electroretinogram (mf-ERG) system described below to detect spectral sensitivity shifts in the primate's vision. Thus, in another aspect, the present invention provides methods for use of the electroretinogram disclosed herein for monitoring changes in vision perception, such as color perception, of a primate undergoing gene therapy to treat a visual disorder. All embodiments of the methods disclosed above can be combined with all embodiments of the electroretinogram disclosed below.

In a second aspect, the present invention provides isolated nucleic acid expression vectors comprising:

(a) a promoter region, wherein the promoter region is specific for primate retinal cone cells; and (b) a gene encoding a therapeutic, wherein the gene is operatively linked to the promoter region.

All terms in this second aspect have the same meaning as disclosed above for the first aspect of the invention. Similarly, all embodiments and combinations thereof disclosed above in the first aspect of the invention can be used in this second aspect of the invention. The inventors have demonstrated effective treatment of congenital vision disorders in adult primates using the recombinant vectors of the invention, a result that is completely unexpected in the art.

Any suitable promoter region can be used in the isolated nucleic acid expression vector, so long as it specifically promotes expression of the gene in retinal cone cells. In a preferred embodiment, the promoter specifically promotes expression of the gene in Catarrhini retinal cone cells; even more preferably in human retinal cone cells. Exemplary suitable promoter regions include the promoter region for any cone-specific gene, such as the L opsin promoter (SEQ ID NO: 1), the M opsin promoter (SEQ ID NO: 2), and the S opsin promoter (SEQ ID NO: 3), or portions thereof suitable to promote expression in a cone-specific manner.

In a preferred embodiment, the isolated nucleic acid expression vector further comprises an enhancer element upstream of the promoter, wherein the gene is operatively linked to the enhancer element. Any suitable enhancer element can be used in the gene therapy vectors, so long as it enhances expression of the gene when used in combination with the promoter. In a preferred embodiment, the enhancer element is specific for retinal cone cells; more preferably, it is specific for primate retinal cone cells; more preferably in Catarrhini retinal cone cells; even more preferably in human retinal cone cells. Exemplary suitable enhancer regions comprise or consist of the enhancer region for any cone-specific gene, such as the L/M minimal opsin enhancer (SEQ ID NO: 51), L/M enhancer elements of 100, 200, 300, 400, 500, 600, 700, 800, 900, 1000, 1100, 1200, 1300, 1400, 1500, 1600, 1700, 1800, 1900, 2000, or more nucleotides that comprise one or more copies of the L/M minimal opsin enhancer, and the full L/M opsin enhancer (SEQ ID NO: 4), or other portions thereof suitable to promote expression in a cone-specific manner.

The length of the promoter and enhancer regions can be of any suitable length for their intended purpose, and the spacing between the promoter and enhancer regions can be any suitable spacing to promote cone-specific expression of the gene product. In various preferred embodiments, the enhancer is located 0-1500; 0-1250: 0-1000; 0-750: 0-600: 0-500; 0-400; 0-300; 0-200; 0-100; 0-90; 0-80; 0-70; 0-60: 0-50; 0-40; 0-30; 0-20; or 0-10 nucleotides upstream of the promoter. The promoter can be any suitable distance upstream of the encoded gene.

In a further preferred embodiment that can be combined with any other embodiment in any aspect of the present invention, the enhancer comprises or consists of a sequence selected from the group consisting of the L/M minimal opsin enhancer (SEQ ID NO: 51), L/M enhancer elements of 100, 200, 300, 400, 500, 600, 700, 800, 900, 1000, 1100, 1200, 1300, 1400, 1500, 1600, 1700, 1800, 1900, 2000, or more nucleotides that comprise one or more copies of the L/M minimal opsin enhancer, and the full L/M opsin enhancer (SEQ ID NO: 4), or other portions thereof suitable to promote expression in a cone-specific manner, and the promoter comprises or consists of a sequence selected from the group consisting of L opsin promoter (SEQ ID NO: 1), the M opsin promoter (SEQ ID NO: 2), and the S opsin promoter (SEQ ID NO: 3).

In a further preferred embodiment, the isolated nucleic acid expression vector further comprises an intron comprising a splice donor/acceptor region, wherein the intron is located downstream of the promoter region and is located upstream of the gene. Any intron can be used, so long as it comprises a splice donor/acceptor region recognized in primate cone cells, so that the intron can be spliced out of the resulting mRNA product. In one embodiment, the intron comprises or consists of an SV40 intron according to SEQ ID NO: 5. In various preferred embodiments, the 3' end of the intron is 0-20; 0-15; 0-10; 0-9; 0-8; 0-7; 0-6; or 0-5 nucleotides upstream of the gene, and its 5' end is 0-20; 0-15; 0-10; 0-9; 0-8; 0-7; 0-6; or 0-5 nucleotides downstream of the proximal promoter region.

The gene is operatively linked to the promoter region and the enhancer element, such that the promoter and enhancer elements are capable of driving expression of the gene or cDNA in cone cells of the subject.

The gene encoding a therapeutic to be expressed in the cone cells can be any gene or cDNA that encodes a polypeptide or RNA-based therapeutic (siRNA, antisense, ribozyme, shRNA, etc.) that can be used as a therapeutic for treating a cone cell disorder, or as a means to otherwise enhance vision, including but not limited to promoting tetrachromatic color vision. In various preferred embodiments, the gene encodes a therapeutic protein comprising or consisting of those disclosed above in the methods of the first aspect of the invention.

In a further preferred embodiment, the vector comprises the sequence shown in SEQ ID NO: 50, which details the vector used in at least some of the examples that follow.

In a further preferred embodiment that can be combined with any of the above embodiments, the gene delivery vector comprises a recombinant adeno-associated virus (AAV) gene delivery vector. In a further preferred embodiment, the AAV vector comprises rAAV2/5. Preferably, the rAAV is replication defective, in that the AAV vector cannot independently further replicate and package its genome. For example, when cone cells are transduced with rAAV virions, the gene is expressed in the transduced cone cells, however, due to the fact that the transduced cone cells lack AAV rep and cap genes and accessory function genes, the rAAV is not able to replicate.

In a third aspect, the present invention provides a formulation comprising packaged viral particles containing the nucleic acid expression vectors of the second aspect of the invention. In one preferred embodiment, viral particles are present in a concentration of at least $10^{10}$ vector genome containing particles per mL; in various preferred embodiments, the viral particles are delivered in a concentration of at least $7.5 \times 10^{10}$; $10^{11}$; $5 \times 10^{11}$; $10^{12}$; $5 \times 10^{12}$; $10^{13}$; $1.5 \times 10^{13}$; $3 \times 10^{13}$; $5 \times 10^{13}$; $7.5 \times 9 \times 10^{13}$; or $9 \times 10^{13}$ vector genome containing particles per mL. The formulation may further comprise pharmaceutically-acceptable carriers, diluents and reagents as described above in the first aspect of the invention. The formulation may be in the form of a liquid solution, a paste, a hydrogel, or may be embedded within a substrate, including but not limited to a foam matrix or supported in a reservoir.

In a fourth aspect, the present invention provides recombinant host cells transfected or transduced with the nucleic acid expression vector of the second aspect of the invention. The cells may be of any type that can be transfected with the expression vector. In one embodiment where the expression vector is a rAAV vector, the cells comprise producer cells transduced with a replication incompetent rAAV expression vector according to the second aspect of the invention, form which viral particles can be obtained by introduction of an AAV helper construct as described above and as is well known in the art.

In a fifth aspect, the present invention provides a color multifocal electroretinogram system, comprising:
  (a) an electroretinogram (ERG) comprising
  (i) a recording electrode that is (A) designed for placement on at least one of a cornea and a sclera of at least one eye of a subject and (B) arranged to output at least one signal generated by the at least one eye; and
  (ii) a computing system communicatively coupled to the recording electrode, the computing system comprising (A) at least one processor and (B) data storage containing instructions executable by the at least one processor to carry out a set of functions, the set of functions including processing and saving the at least one signal generated by the at least one eye;
  (b) a retinal stimulator comprising matched light sources selected from the group consisting of red, green, blue, and ultraviolet light sources, wherein the matched light sources are connected to the ERG and in operation can be independently frequency modulated at rates between about 1 Hz and about 60 Hz, inclusive, wherein the stimulator in operation is capable of stimulating a retinal field of a subject throughout an operating radius of at least about 70 degrees;
  (c) one or more constant current integrated circuit chips arranged to drive the stimulator; and
  (d) a pulse-frequency modulator connected to the retinal stimulator, wherein in operation the pulse-frequency modulator is capable of controlling individual stimulator segments while keeping relative spectral content of the light constant.

The electroretinograms of the present invention can be used, for example, in characterizing the topography of expression of the different opsin transgenes in the eyes of living subjects treated with gene therapy, and thus can be used with the gene therapy methods of the invention disclosed above.

As used here, a "matched" light source is one that includes light stimulus of different wavelengths, wherein the number of pixels is approximately the same, or is the same, at each wavelength. One non-limiting example is a matched light source stimulus containing 1024 doublet pixels each containing a red (653 nm, half-bandwidth 22 nm) and a green (527 nm, half-bandwidth 33 nm) LED, with a resulting matched light source with 2,048 paired green and red LEDs.

in various preferred embodiments, the stimulator in operation is capable of stimulating a retinal field of a subject throughout an operating radius of at least about 80, 90, 100, 110, 120, 130, 140, 150, or more degrees.

In one preferred embodiment, the matched light sources are paired red and green light sources. In another preferred embodiment, the matched light sources are triplets of red, green, and blue light sources. In a further preferred embodiment, the matched light sources are quartets of red, green, blue, and ultraviolet light sources.

Any suitable matched light source can be used. In one preferred embodiment, the matched light sources comprise matched light emitting diodes (LEDs).

In another preferred embodiment, that can be combined with any of the embodiments herein, the retinal stimulator comprises a concave surface comprising a series of trapezoidal-shaped circuit boards placed edge-to-edge, wherein the concave surface positions the matched light sources so in operation they are held equidistantly from and pointing toward a single focal point where a subject's pupil can be positioned. This embodiment helps to limit SNR fall-off in peripheral retinal regions. Any suitable concave surface can be used; in a preferred embodiment, the concave surface comprises a geodesic dome.

In a further embodiment that can be combined with any of the above embodiments, the set of functions executable by the processor further comprises coding and decoding topographical regions on the recording electrode using a cyclic summation technique.

In a further preferred embodiment that can be combined with any of the embodiments herein, the ERG further comprises an amplifier; and wherein the computing system is communicatively coupled to the amplifier.

Further embodiments and details of the color multifocal electroretinogram system are provided in the Examples that follow.

In a further aspect, the present invention provides methods for determining a location of functioning opsin expression in a subject, comprising use of the mf-ERG of any embodiment or combination of embodiments of the fifth aspect of the invention, wherein the recording electrode is placed on at least one of a cornea and a sclera of at least one eye of a subject; stimulating the subject's retinal field with the retinal stimulator; and determining responses of different areas of the subject's retina to different stimulation frequencies to generate a map of retinal responses, wherein the map provides a location of functioning opsin expression in a subject.

In one preferred embodiment, the subject has been treated according to the gene therapy methods for color blindness disclosed above according to any embodiment or combination of embodiments of the first aspect of the invention.

Unless the context clearly dictates otherwise, embodiments in one aspect of the invention may be used in other aspects of the invention, and can be combined with each other.

EXAMPLE 1

Red-green colour blindness, which results from the absence of either the long- (L) or middle- (M) wavelength-sensitive visual photopigments, is the most common single locus genetic disorder. Here, the possibility of curing colour blindness using gene therapy was explored in experiments on adult monkeys that had been colour blind since birth. A third type of cone pigment was added to dichromatic retinas, providing the receptoral basis for trichromatic colour vision. This opened a new avenue to explore the requirements for establishing the neural circuits for a new dimension of colour sensation. Classic visual deprivation experiments[1] have led to the expectation that neural connections established during development would not appropriately process an input that was not present from birth. Therefore, it was believed that treatment of congenital vision disorders would be ineffective unless administered to the very young. Here, however, addition of a third opsin in adult red-green colour-deficient primates was sufficient to produce trichromatic colour vision behaviour. Thus, trichromacy can arise from a single addition of a third cone class and it does not require an early developmental process. This provides a positive outlook for the potential of gene therapy to cure adult vision disorders.

Gene therapy was performed on adult squirrel monkeys (*Sainiri sciureus*) that were missing the L opsin gene. In this species, some females have trichromatic colour vision while males are red-green colour blind[2]. Serotype 2/5 recombinant adeno-associated virus (rAAV) containing a human L-opsin gene under control of the LM opsin enhancer and promoter (FIG. 1a) was delivered to the photoreceptor layer via subretinal injections. Transcriptional regulatory elements were chosen to direct expression preferentially in M cones, but not short- (S) wavelength-sensitive cones or rods[3]. To provide the receptoral basis for trichromacy, animals received three 100 µL injections (containing a total of $2.7\times10^{13}$ viral particles) in each eye which produced a relatively uniform, third submosaic of approximately 15-36% of M cones that coexpressed the transgene (FIG. 1e, f).

Prior to treatment, monkeys were trained to perform a computer-based colour vision test, the Cambridge Colour Test[4,5], which was modified for use with animals[6] (FIG. 2a). Dichromats who are missing either the L- or M-photopigment fail to distinguish from grey: colours near the so-called "spectral neutral point" located in the blue-green region of colour space (near dominant wavelength (DW) 490 nm) and complementary colours near the "extra-spectral neutral point," in the red-violet region (near DW=−499 nm). While trichromats have four main hue percepts—blue, yellow, red, and green—dichromats have only two percepts, nominally blue and yellow. Before treatment, two dichromatic monkeys completed three colour vision tests consisting of 16 hues (FIG. 2b, c). Four-to-six months was required to test all 16 hues: thus, baseline results represent testing conducted for more than a year. As predicted, prior to treatment monkeys had low thresholds (averaging<0.03 units in u', v' colour space) for colours that represent blues and yellows to their eyes, but always failed to discriminate the blue-green (DW=490 nm) and red-violet hues (DW=−499 nm) with thresholds extrapolated from psychometric functions being orders of magnitude higher (FIG. 2b, c). Results were highly repeatable, with no improvement between the first and third tests, making us confident that animals would not spontaneously improve in the absence of treatment.

Co-expressing the L-opsin transgene within a subset of endogenous M-cones shifted their spectral sensitivity to respond to long wavelength light, thus producing two distinct cone types absorbing in the middle-to-long wavelengths, as required for trichromacy. The spectral sensitivity shift was readily detected using a custom-built wide-field colour multifocal electroretinogram (mf-ERG) system (FIG. 1b, c, f) (see ref. 7 for details). In preliminary experiments, validity of the colour mf-ERG was tested using an animal that had received a mixture of the L-opsin-coding virus plus an identical virus, except that a green fluorescent protein (GFP) gene replaced the L-opsin gene. As reported previously, faint GFP fluorescence was first detected at 9 weeks post-injection, and it continued to increase in area and intensity through 24 weeks[8]. While faint signs of GFP were first detectable at 9 weeks, L-opsin levels sufficient to produce suprathreshold mf-ERG signals were still not present at 16 weeks post-injection (FIG. 1c, inset). After GFP fluorescence became robust, the red light mf-ERG, which indicates responses from the introduced L-opsin, showed highly elevated response amplitudes in two areas (FIG. 1c) corresponding to locations of subretinal injections (FIG. 1d).

The two dichromatic monkeys who participated in behavioural tests of colour vision were treated with only L-opsin-coding virus. While the elongated pattern produced by two injections in FIG. 1c and d allowed mf-ERG validation, the treatment goal was to produce a homogeneous region, as resulted from 3 injections shown in f, where the highest mf-ERG response covered about 80° of central retina, roughly the area for which humans have good red-green discrimination. These results demonstrate that gene therapy changed the spectral sensitivity of a subset of the cones. A priori, there were two possibilities for how a change in spectral sensitivity might change colour vision behaviour: 1) animals may have an increase in sensitivity to long-wavelength light, but if the neural circuitry for extracting colour information from the nascent "M+L cone" submosaic was absent, they would remain dichromatic, the hallmark of which is having two hues that are indistinguishable from grey (FIG. 2d). The spectral neutral point for individuals that have only S- and M-cones, (e.g. monkeys 1 and 2 pre-therapy), occurs near dominant wavelength (DW)=495 nm. At the limit, an increase in spectral sensitivity would shift the monkeys' neutral point toward that of individuals with only S and L cones, near DW=505 nm (dashed blue lines, FIG. 2d). 2) The second, more engaging possibility was that treatment would be sufficient to expand sensory capacity in monkeys, providing them with trichromatic vision. In this case, the animals' post-therapy results would appear similar to FIG. 2e, obtained from a trichromatic female control monkey.

Daily testing continued after treatment. After about 20 weeks post-injection (arrow, FIG. 3a), the trained monkeys' thresholds for blue-green and red-violet (DWs=490 and −499 nm, respectively, FIG. 3b, c) improved, reducing to an average of 0.08 units in u', v' colour space, indicating that they gained trichromatic vision. This time point corresponded to the same period in which robust levels of transgene expression were reported in the squirrel monkey[8]. A trichromatic female monkey and untreated dichromatic monkeys were tested in parallel. As expected, the female had low thresholds for all colours, averaging<0.03 units in u', v' colour space, but the untreated dichromats always failed to discriminate DWs=490 nm (triangle, FIG. 3a) and –499 nm, indicating a clear difference between treated and untreated monkeys.

Early experiments in which we obtained negative results served as "sham controls," demonstrating that acquiring a new dimension of colour vision requires a shift in spectral sensitivity that results from expression of an L pigment in a subset of M cones. Using similar subretinal injection procedures, we delivered fewer viral particles of an L-opsin-coding rAAV2/5 virus with an extra 146 base pair (bp) segment near the splice donor/acceptor site that had been carried over from the cloning vector and that was absent in the GFP-coding rAAV2/5 virus. The 146 bp segment contained an ATG and a duplicate mRNA start site that may have interfered with expression (see Full Methods online). Three monkeys received injections of this vector, containing an average of $1.7 \times 10^{12}$ virus particles per eye, and no reliable changes in spectral sensitivity were measured using the ERG. One animal was also tested behaviourally and his colour vision was unchanged from baseline 1 year after injection. In subsequent experiments reported here, we removed the extra 146 bp segment and also increased the amount of viral particles delivered per eye by approximately 16-fold, to $2.7 \times 10^{13}$. Negative results from earlier injections demonstrated that the subretinal injection procedure itself does not produce changes in the ERG or in colour vision.

Figure 2:
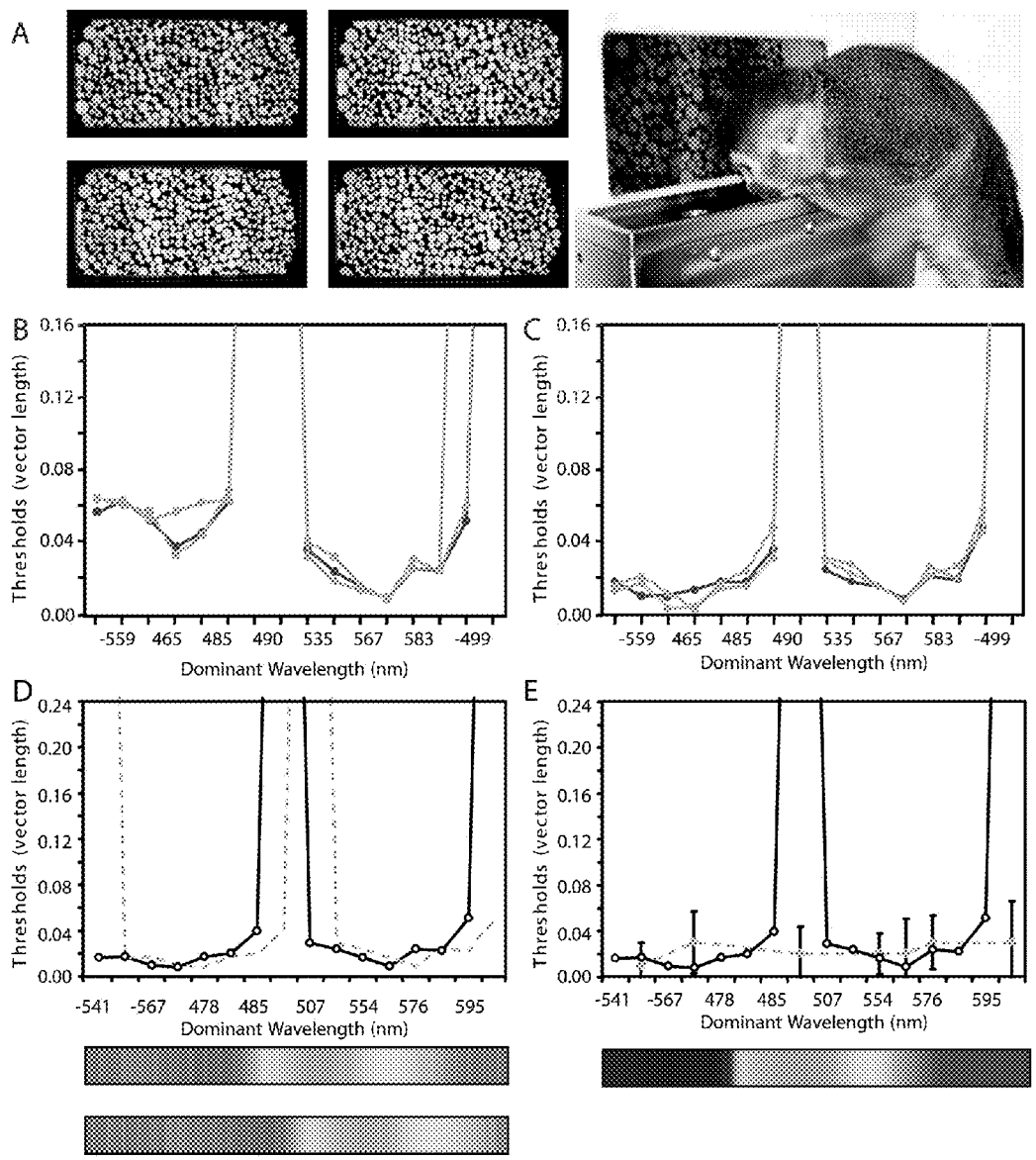
FIG. 2. Pre-therapy colour vision and possible treatment outcomes, a) Colour vision stimuli examples. b) Pre-therapy results, monkey 1. Hues tested are represented as dominant wavelengths (DWs) rather than u', v' coordinates. If a hue could not be reliably distinguished at even the highest saturation, the extrapolated threshold approached infinity. c) Pre-therapy results, monkey 2. d)-e), Possible experimental outcomes: Monkeys could have a relative increase in long-wavelength sensitivity, but remain dichromatic (dashed lines, d); theoretical colour spectrum appearances for a dichromat and a possible "spectral shift" are shown. Alternatively, dichromatic monkeys could become trichromatic. Results from a trichromatic female control monkey are plotted (dashed line, e; error bars=SEM and n varied from 7-11).
Figure 3:
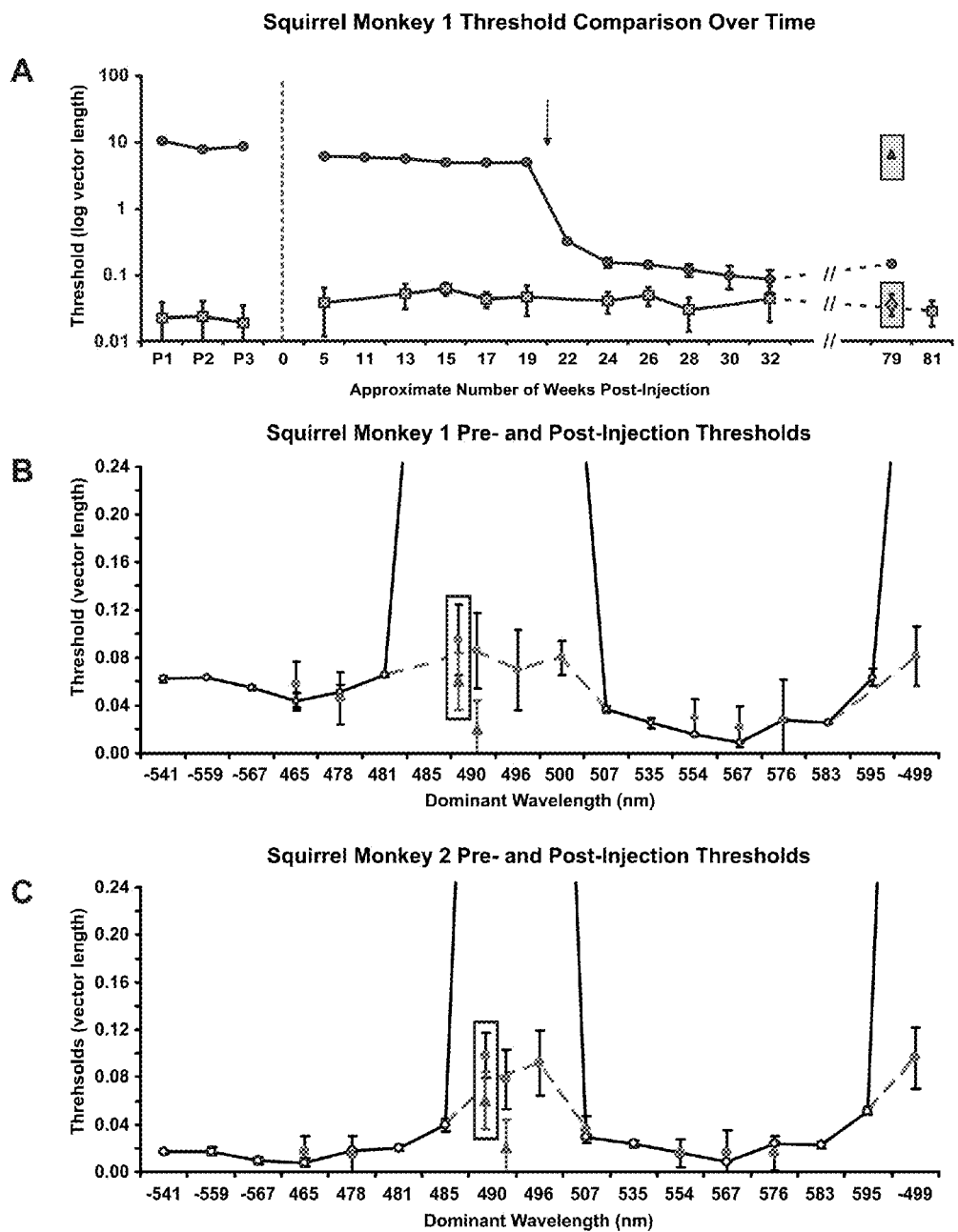
FIG. 3. Gene therapy produced trichromatic colour vision. a) Time course of thresholds for the blue-green confusion colour, DW=490 nm (circles), and a yellowish colour, DW=554 nm. (squares). A logarithmic scale was used to fit high thresholds for DW=490 nm; significant improvement occurred after 20 weeks. Enclosed data points=untreated dichromatic monkey thresholds, DW==490 nm (triangle) and DW=554 nm (diamond). b)-c) Comparison of pre-therapy (open circles, solid line) and post-therapy thresholds (solid dots, dashed line). Enclosed data points are DW=490 nm thresholds when tested against a red-violet background (DW=−499 nm); pink triangles=trichromatic female control thresholds. Error bars=SEM; n varied from 7-11.
Figure 4:
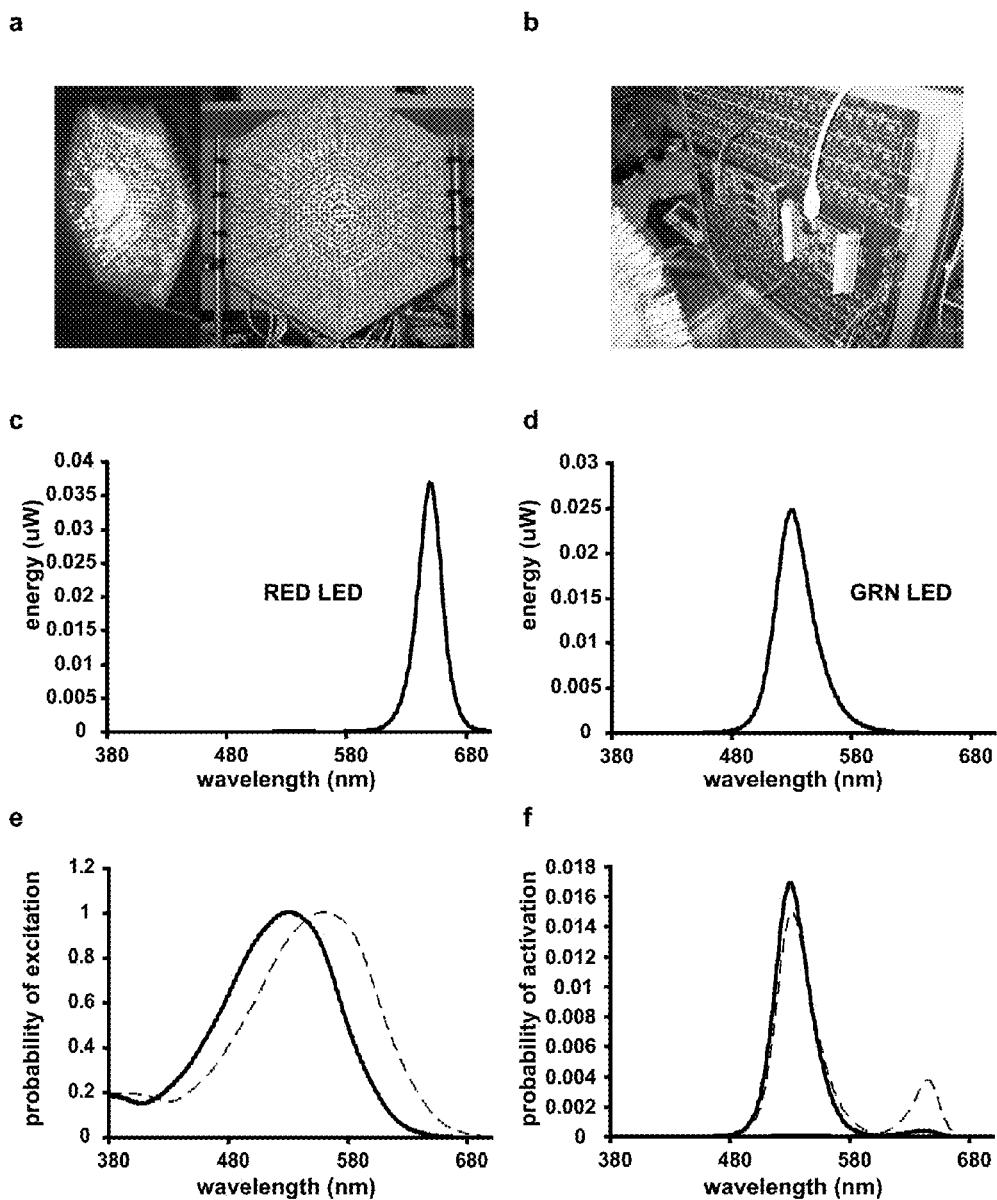
FIG. 4. a) The geodesic dome was created by placing trapezoidal-shaped circuit boards edge-to-edge. This structure holds the light emitting diodes (LEDs) so they converge on a single focal point. b) The circuit board takes the incoming control signals from the Retis-can mf-ERG and reroutes and modifies them to work with the new dome. The most frequent integrated circuit on the board are the constant current devices. c) The spectral composition of the red LED. d) The spectral composition of the green LED. e) The spectral sensitivity curves for the human M- (solid line) and L-(dashed line) cone photoreceptors. f) The activation of M-opsin (solid line) and the L-opsin (dashed line) in response to both the red and green LEDs.
Figure 5:
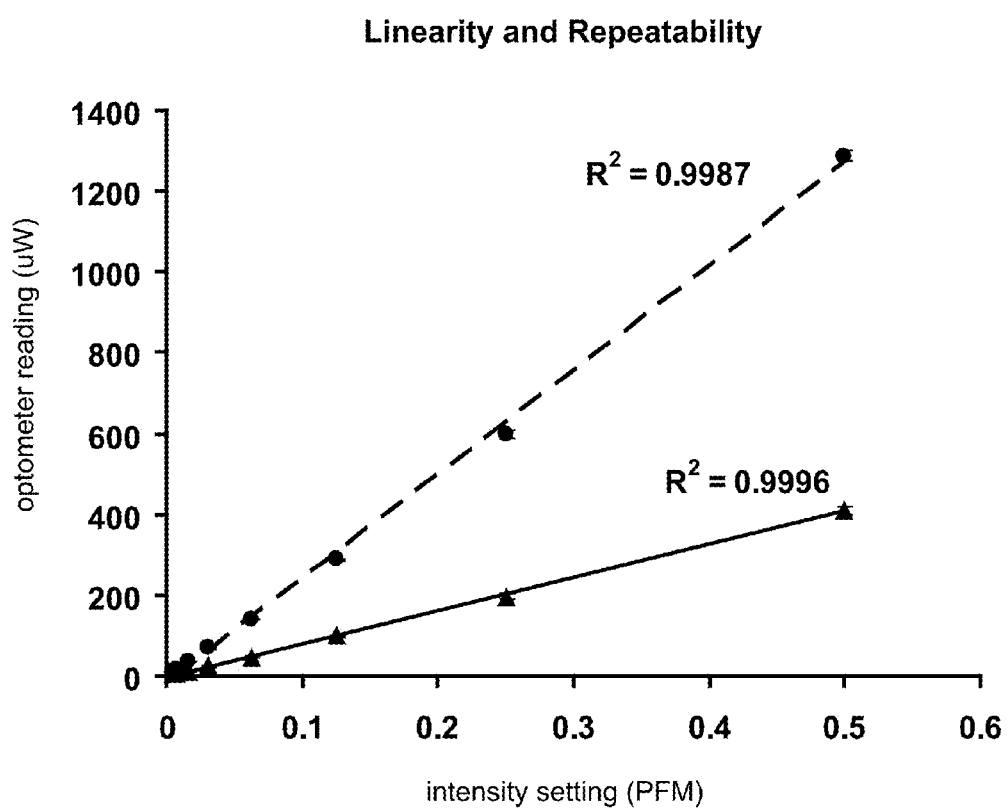
FIG. 5. Circles and dashed line represent the red LED out-puts in microwatts as a function of intensity; triangles and solid line represent the green LED outputs. Each data point represents an average of 3 measurements. Error bars are three standard deviations (99.7% confidence interval). To measure linearity, $r^2$ values were computed for both the red and green LEDs.
Figure 7:
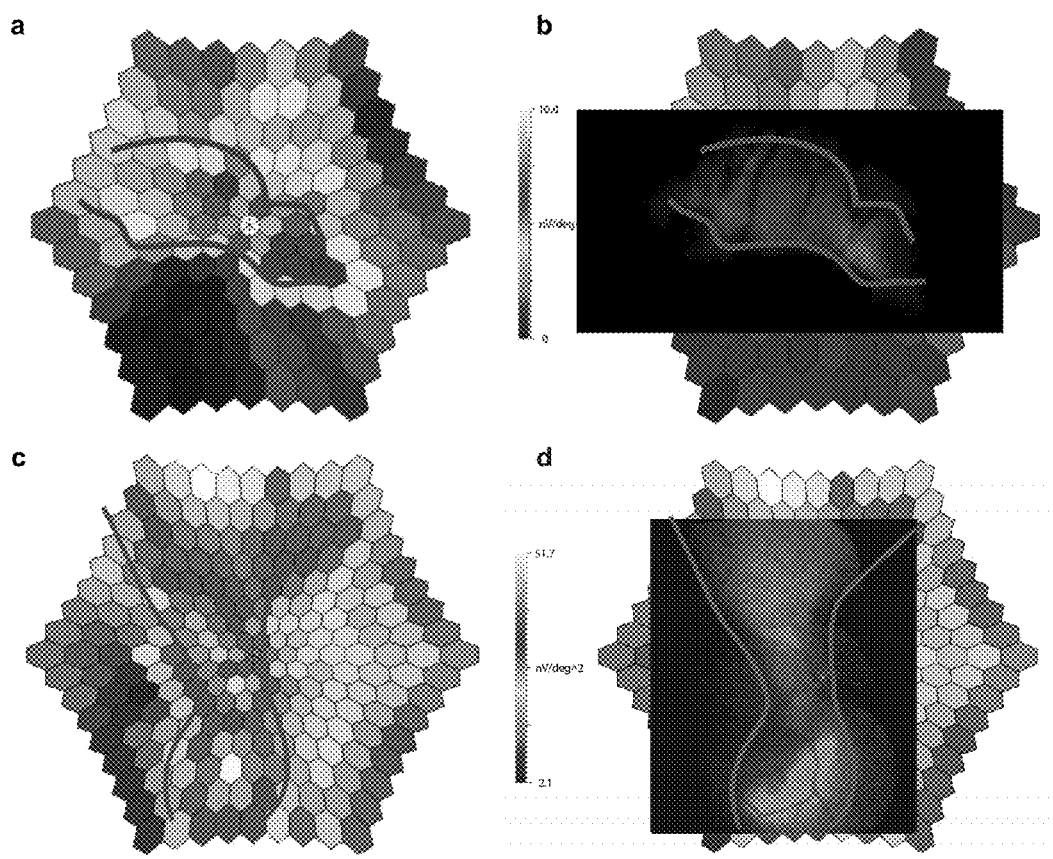
FIG. 7. a) Gerbil mf-ERG data in response to the L-cone isolating red stimulus. Locations of the retina that show a large amount of activity in response to stimulation by the red LEDs are indicated in red, while those areas that show the lowest amount of activation are indicated in blue (see scale). Gray lines show borders of the region where the mfERG response was highest. b) GFP fluorescence fundus image from the gerbil, scaled to the appropriate size, overlaid on the red-light mf-ERG data. The gray lines from (a) were copied into (b) to illustrate that areas of increased mf-ERG response corresponded to the same locations where robust GFP fluorescence was present. c) Red-light mf-ERG data from the squirrel monkey, which received two injections of the virus mixture, one superiorly and one inferiorly. d) A montage of CFP fluorescence images from the squirrel monkey, scaled to the appropriate size, overlaid on the mfERG data.
Figure 8:
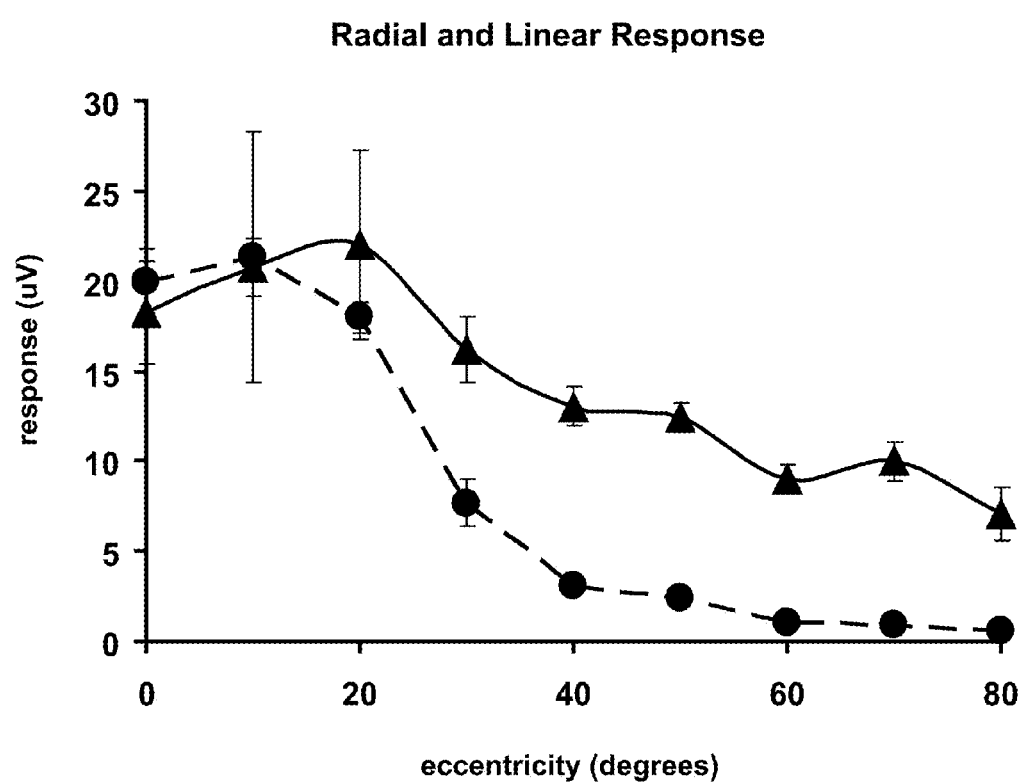
FIG. 8. The circles represent ERG response from LEDs that were moved on a linear path while the subject fixated forward. By 30 degrees, the signal is already less than half. In contrast, the triangles represent ERG response from LEDs that were fixed on a boom and rotated so that the LEDs always pointed at the pupil. Under this experimental protocol, −3 dB occurs first at 60 degrees.

The change in spectral sensitivity measured with the mf-ERG is necessary but not sufficient to produce a new colour vision capacity. For example, individuals with L but no M cones (termed deuteranopes) have a relatively enhanced sensitivity to red light but they are still as dichromatic as individuals with M but no L cones (protanopes), in that they are unable to distinguish particular "colours" from grey. To verify that the behavioural change observed in animals expressing the L pigment transgene was not purely a shift in spectral sensitivity (sc FIG. 2d), monkey 1 was also tested on DWs=496 and 500 nm, and monkey 2 was tested on DWs 496 and 507 nm. Together, these DWs span the possible confusion points for deuteranopes and protanopes and for any intermediate dichromatic forms that could arise from expressing combinations of L and M pigments. As shown in FIGS. 3b and c, both monkeys' measured thresholds for these additional hues were similar to their thresholds for DW=490 nm, demonstrating they now lacked a spectral neutral point and have become truly trichromatic. Furthermore, treated monkeys were able to discriminate blue-green (DW=490 nm) when it was tested against a red-violet background (DW=–499 nm), instead of the grey background, indicating that the monkeys' newly-acquired "green" and "red" percepts were distinct from one another. The treated monkeys' improvement in colour vision has remained stable for over 2 years and we plan to continue testing the animals to evaluate long term treatment effects.

Classic experiments in which visual deprivation of one eye during development caused permanent vision loss[1] led to the idea that inputs must be present during development for the formation of circuits to process them. From the clear change in behaviour associated with treatment, compared both between and within subjects, we conclude that adult monkeys gained new colour vision capacities because of gene therapy. These startling empirical results provide insight into the evolutionary question of what changes in the visual system are required for adding a new dimension of colour vision. Previously, it seemed possible that a transformation from dichromacy to trichromacy would require evolutionary/developmental changes, in addition to acquiring a third cone type. For example, L and M opsin-specific genetic regulatory elements might have been required to direct the opsins into distinct cone types[9] that would be recognized by L and M cone-specific retinal circuitry[10], and to account for cortical processing, multi-stage circuitry[11] might have evolved specifically for the purpose of trichromacy. However, our results demonstrate that trichromatic colour vision behaviour requires nothing more than a third cone type. As an alternative to the idea that the new dimension of colour vision arose by acquisition of a new L vs. M pathway, it is possible that it exploited the pre-existing blue-yellow circuitry. For example, if addition of the third cone class split the formerly S vs. M receptive fields into two types with differing spectral sensitivities, this would obviate the need for neural rewiring as part of the process of adopting new colour vision.

Some form of inherent plasticity in the mammalian visual system can be inferred from the acquisition of novel colour vision, as was also demonstrated in genetically engineered mice[12]; however, the point has been made that such plasticity need not imply that any rewiring of the neural circuitry has occurred[13]. Similarly, given the fact that new colour vision behaviour in adult squirrel monkeys corresponded to the same time interval as the appearance of robust levels of transgene expression, we conclude that rewiring of the visual system was not associated with the change from dichromatic to trichromatic vision.

Treated adult monkeys unquestionably respond to colours previously invisible to them. The internal experiences associated with the dramatic change in discrimination thresholds measured here cannot be determined; therefore, we cannot know whether the animals experience new internal sensations of "red" and "green." Nonetheless, we do know that evolution acts on behaviour, not on internalized experiences, and we suggest that gene therapy recapitulated what occurred during evolution of trichromacy in primates. These experiments demonstrate that a new colour vision capacity, as defined by new discrimination abilities, can be added by taking advantage of pre-existing neural circuitry and, internal experience aside, full colour vision could have evolved in the absence of any other change in the visual system except the addition of a third cone type.

Gene therapy trials are underway for Leber's congenital amaurosis[14-16]. Thus far, treatment has been administered to individuals who have suffered retinal degeneration from the disease. The experiments reported here are the first to use gene therapy in primates to address a vision disorder in which all photoreceptors are intact and healthy, making it possible to assess the full potential of gene therapy to restore visual capacities. Treatment allowing monkeys to see new colours in adulthood provides a striking counter-example to what occurs under conditions of monocular deprivation. For instance, it is impossible to restore vision in an adult who had grown up with a unilateral cataract. Future technologies will allow many opportunities for functions to be added or restored in the eye. While some changes may produce outcomes analogous to monocular deprivation, we predict that others, like gene therapy for red-green colour blindness, will provide vision where there was previously blindness.

Methods Summary for Example 1

Viral Cector. CHOPS2053 was a 2.1 kb fragment containing the locus control region (LCR) and proximal promoter (PP) upstream of the human X-chromosome opsin gene array[9,17]. These elements (also known as pR2.1) have been shown to target transgene expression to mammalian L/M cones[3,18]. RHLOPS was a 1.2 kb fragment containing recombinant human L opsin cDNA. A clone of the human L opsin cDNA[19], known as hs7, was generously provided by J. Nathans. The QuickChange kit (Stratagene) was used to convert codon 180 so that it would encode a human L pigment maximally sensitive to 562 nm[20]. The virus was made using the genome from rAAV serotype 2 and the capsid from serotype 5, and the preparation had $9\times10^{13}$ DNase-resistant vector genome containing particles per mL. To prevent vector aggregation, 0.014% Tween 20 was added to the final vector preparation. A total of $2.7\times10^{13}$ viral particles was injected per eye.

An earlier version of the L-opsin coding rAAV2/5 used in previous unsuccessful experiments contained an extra 146 base pair segment between the splice donor/acceptor site and the translational start codon of the L-opsin gene that had been carried over from the cloning vector. Because we were concerned that this fragment may have interfered with transgene expression, a second version of L-opsin rAAV2/5 in which the extra 146 bp had been removed was used in later experiments described here. In addition to modifying the vector, we also increased the amount of viral particles delivered per eye by approximately 16-fold, from $1.7\times10^{12}$ to $2.7\times10^{13}$. Thus, we cannot conclude from this set of experiments what exact titer of viral particles was required to produce the effects on color vision behaviour, or exactly what effects, if any, the extra 146 bp had on transgene expression in earlier unsuccessful attempts.

The single-stranded DNA genome of conventional rAAV vectors, including rAAV2/5 used here, is devoid of Rep coding sequences. Thus, the vector genome is stabilized predominantly in an episomal form; however, the potential for integration exists[21]. According to NIH guidelines, the viral vector used here is rated biosafety level I (BSL1), and animal biosafety level I (ABSI1) meaning no special precautions were required in handling the virus or animals treated with the virus. Following treatment, squirrel monkeys had an increase in AAV antibody titers, ranging from 4-12 fold. Antibody titers remained unchanged in untreated control animals who were housed with treated animals.

Subretinal Injections. Subretinal injections were performed by a vitreo-retinal surgeon (T. B. C.) using a KDS model 210 syringe pump under a stereomicroscope. A 500 μL Hamilton Gastight (#1750TTL) Luer Lock syringe was connected to 88.9 cm of 30 gauge teflon tubing with male Luer Lock adapters at both ends (Hamilton 30TF double hub), which was then connected to a 30 gauge Becton Dickinson Yale regular bevel cannula (ref#511258) that was manually bent to produce a 135' angle 1.5 mm from the tip. All components were sterilized prior to use. The syringe and tubing were filled with sterile lactated Ringers solution to produce a dead volume of approximately 210 μL. Just prior to injection. 300 μL of rAAV was withdrawn using a rate of 100 μL/min.

Squirrel monkeys were anesthetized using intramuscular injections of ketamine (15 mg/kg) and xylazine (2 mg/kg); atropine (0.05 mg/kg) was also given to reduce airway secretions. The eye was dilated with 2-3 drops of tropicamide (1%) and treated with 1 drop each of betadine (5%), vigamox (0.5%), and proparacaine (1%). Subconjunctival injection of 0.1 mL of lidocaine (2%) was given and the anterior portion of the eye was exposed by performing a temporal canthotomy followed by limited conjuntival peritomy. Eyelids were held open with a speculum designed for premature infants. A temporal sclerotomy was made 1 mm posterior to the limbus with a 27 gauge needle, through which the injection cannula was inserted. Three subsequent 100 μL injections were made at different subretinal locations using an infusion rate of 1060 μL/min. Post-procedure, 0.05 mL each of decadron (10 mg/mL), kenalog (40 mg/mL), and cephazolin (100 mg/mL) were injected subconjunctivaly; I drop each of betadine (5%) and vigamox (0.5%) and a 0.6 cm strip of tobradex (0.3% tobramycin. 0.1% dexamethasone) ointment were applied topically; 10-20 mL of subcutaneous fluids (sterile lactated Ringers) were also given. Subsequent administration of steroids and analgesics were administered as needed post-procedure for potential inflammation or discomfort.

Confocal Microscopy. The animal in FIG. 1 c and d succumbed to respiratory illness, unrelated to gene therapy, approximately 2 years and 3 months post-injection. The retina was fixed in 4% paraformaldehyde in phosphate buffered saline (PBS), and rinsed in PBS with 10% and 30% sucrose. It was sequentially incubated with 10% Normal Donkey Serum, rabbit monoclonal antibody to M/L opsin (Chemicon AB5405), and a Cy3 (red) conjugated donkey anti-rabbit antibody (Jackson Immunoresearch). Confocal images were analyzed using ImageJ (rsbweb.nih.gov). In the middle panel of FIG. 1e, magenta dots mark cone locations, and the red anti-M/L-opsin antibody staining was removed to show GFP-expressing (green) cells more clearly.

Behavioural Colour Vision Assessment. A three-alternative forced-choice paradigm in which position and saturation of the stimulus was randomized between trials was used. Monkeys had to discriminate the location of a coloured patch of dots that varied in size and brightness, surrounded by similarly varying grey dots. When animals touched the coloured target, a positive tone sounded and a juice reward was given; the next stimulus appeared immediately. (The squirrel monkey shown in FIG. 2c is drinking a reward from a previous trial.) If the wrong position was chosen, a negative tone sounded, and a 2-3 sec "penalty time" occurred before the next trial.

For each hue, monkeys were tested on up to 11 different saturations ranging from 0.01 to 0.11 in u', v' colour space (CIE 1976) and a threshold was calculated, which was taken as the saturation required to reach a criterion of 57% correct, the value determined to be significantly greater than chance (33% correct, P=0.05); see ref. 6 for full details.

References for Example 1

1. Wiesel, T. N. & Hubel, D. H. Single-cell responses in striate cortex of kittens deprived of vision in one eye. *J. Neurophysiol.* 26, 1003-1017 (1963).
2. Jacobs, G. H. A perspective on color vision in platyrrhine monkeys. *Vision Res.* 38, 3307-3313 (1998).
3. Li, Q., Timmers, A. M., Guy, J., Pang, J. & Hauswirth, W. W. Cone-specific expression using a human red opsin promoter in recombinant AAV. *Vision Res.* 48 (2007).
4. Reffin, J. P., Astell, S. & Mollon. J. D. Trials of a computer-controlled colour vision test that preserves the advantages of pseudo-isochromatic plates, in *Colour Vision Deficiencies X* 69-76 (Kluwer Academic Publishers, Dordrecht, 1991).
5. Regan, B. C., Reffin, J. P. & Mollon, J. D. Luminance noise and the rapid determination of discrimination ellipses in colour deficiency. *Vision Res.* 34, 1279-1299 (1994).
6. Mancuso, K., Neitz, M. & Neitz, J. An adaptation of the Cambridge Colour Test for use with animals. *Vis. Neurnsci.* (2006).
7. Kuchenbecker, J., Sahay, M., Tait, D. M., Neitz, M. & Neitz, J. Topography of the long- to middle-wavelength sensitive cone ratio in the human retina assessed with a wide-field color multifocal electroretinogram. *Vis. Neuroscl.* 25, 301-306 (2008).
8. Mancuso, K. et al. Recombinant adeno-associated virus targets passenger gene expression to cones in primate retina. *J. Opt. Soc. Am. A Opt. Image Sci. Vis.* 24, 1411-1416 (2007).
9. Nathans, J. Piantanida, T. P., Eddy. R. L., Shows, T. B. & Hogness, D. S. Molecular genetics of inherited variation in human color vision. *Science* 232, 203-210 (1986).

10. Shapley, R. Specificity of cone connections in the retina and color vision. Focus on "Specificity of cone inputs to macaque retinal ganglion cells". *J. Neurophysiol.* 95, 587-588 (2006).
11. DeValois, R. L. & DeValois, K. K. A multi-stage color model. *Vision Res.* 33, 1053-1065 (1993).
12. Jacobs, G. H., Williams, G. A., Cahill, H. & Nathans, J. Emergence of Novel Color Vision in Mice Engineered to Express a Human Cone Photopigment. *Science* 315, 1723-1725 (2007).
13. Makous, W. Comment on "Emergence of Novel Color Vision in Mice Engineered to Express a Human Cone Photopigment". *Science* 318, 196 (2007).
14. Maguire, A. M. et al. Safety and efficacy of gene transfer for Leber's congenital amaurosis. *N. Engl. J. Med.* 358, 2240-2248 (2008).
15. Bainbridge, J. W. & Ali, R. R. Success in sight: The eyes have it! Ocular gene therapy trials for LCA look promising. *Gene Ther.* 15, 1191-1192 (2008).
16. Cideciyan, A. V. et al. Human gene therapy for RPE65 isomerase deficiency activates the retinoid cycle of vision but with slow rod kinetics. *Proc. Natl. Acad. Sci. U.S.A.* 105, 15112-15117 (2008).
17. Wang, Y. et al. A locus control region adjacent to the human red and green visual pigment genes. *Neuron* 9, 429-440 (1992).
18. Mauck, M. C., Mauncuso, K., Kuchenbecker, J., Connor, T. B., Hauswirth, W. W., Neitz, J., Neitz, M. Longitudinal evaluation of expression of virally delivered transgenes in gerbil cone photoreceptors. *Vis. Neurosci.* 25, 273-282 (2008).
19. Nathans, J., Thomas, D. & Hogness, D. S. Molecular genetics of human color vision: the genes encoding blue, green, and red pigments. *Science* 232, 193-202 (1986).
20. Neitz, M., Neitz, J. & Jacobs, G. H. Spectral tuning of pigments underlying red-green color vision. *Science* 252, 971-974 (1991).
21. Büning, H., Perabo, L., Coutelle, O., Quadt-Humme, S. & Hallek, M. Recent developments in adeno-associated virus vector technology. *J. Gene Med.* 10, 717-733 (2008).

EXAMPLE 2

Description and Validation of New LED-Based, Wide-Field, Color mf-ERG

The electroretinogram (ERG) is an electrophysiologic recording technique used to measure electrical activity of the entire retina. The electrochemical potential of retinal cells change in response to light, which in turn induces voltage on an electrode placed on the cornea and/or sclera. The first ERGs were recorded by a Swedish physiologist working in the mid-1800's in amphibian retina. Since this time the technique has been widely incorporated in clinical practice as a diagnostic tool. Marriage of physiology to engineering has led to a variety of stimuli and analysis paradigms which can tease out specific cellular responses or region specific information. The latter has been motivated by the fact that the topographical organization of the retina plays an important role in disease with different diseases being characterized by different affected retinal areas. Early attempts to evaluate the function of specific retinal regions using the ERG illuminated only a small patch of retina, however, such "focal ERGs" have the drawback that light reflected from the focal area onto other retinal regions produces an ERG response that cannot be uncoupled from that produced by the region of interest. The other problem is that obtaining any type of a topographical map of retinal function using the mono-focal approach is prohibited by the time required to obtain ERGs serially from many different retinal regions. Both problems have been solved with the development of the multifocal- (mf-) ERG, pioneered by Erich Sutter in the early 1990s (Sutter, 1991). Mf-ERGs perform a series of individual focal ERG experiments simultaneously by taking advantage of either (1) correlation techniques or (2) frequency encoding. In this way, a complete topographical map of electrical responses over a large retinal region is obtained in a relatively short period of time.

The typical ERG apparatus for mf-ERGs stimulates a hexagonal patch of retina with a 20 degree radius and uses video display. More recently a display that employs white light emitting diodes (LEDs) was designed for use with a frequency encoding method for obtaining mf-ERGs. Having a stimulus that could reach further into the periphery would be useful in the early detection of retinal diseases that progress from peripheral to central retina. Additionally, individuals with normal trichromatic color vision express three distinct photopigments, or opsins, in separate classes of cone photoreceptor: short- (S-), middle- (M-), and long- (L-) wavelength sensitive. The S-cones are maximally sensitive to short wavelengths of light near 420 nm; M-cones have their maximal response near 530 nm; and the L-cones are most sensitive near 560 nm. Thus, an mf-ERG stimulus containing LEDs of different wavelengths would have applications in characterizing the topography of expression of the different opsin transgenes in the eyes of living subjects treated with gene therapy.

In particular, in gene therapy treatments administering recombinant adeno-associated virus (rAAV) carrying a human L-opsin gene M-opsin gene or S-opsin gene to primates that have two cone types to produce trichromatic color vision. As such, a non-invasive objective method is needed to determine the locations of functioning opsin expression in vivo.

Here we describe a wide-field color mf-ERG capable of stimulating a radius greater than 70 degrees. The wide field mf-ERG has a colored LED-based stimulus that incorporates a new design capable of maintaining viable signal-to-noise ratio (SNR) out into the far peripheral retina.

mf-ERG and Stimulus Panel

An LEDs as a light source was chosen because new advancements in LED technology allow for a large number of focused photons to be emitted from a point source. Additionally, LEDs are available in a variety of single peak narrow-bandwidth packages. The stimulus contained 1024 doublet pixels each containing a red (653 nm, half-bandwidth 22 nm, FIG. 2.1c) and a green (527 nm, half-bandwidth 33 nm, FIG. 2.1d) LED. Thus, the new display had 2,048 paired green and red LEDs. LEDs have inherent manufacturing variations in their breakdown resistance. Since the amount of current is proportional to the number of photons per unit time, applying a constant voltage across the LEDs would result in varying photon output. To circumvent these issues and ensure repeatability and linearity, constant current integrated circuit chips (Allegro A6276) were used to drive the LEDs (FIG. 2.1b). These devices are designed to maintain constant current despite fluctuations in anode voltage. To prevent variation in peak wavelength over varied intensities, a pulse frequency modulation (PFM) signal was used (Swanson, Ueno, Smith. & Pokorny, 1987).

Using red and green LEDs, it is possible to isolate responses of L- or M-cones using silent substitution. Integrating the spectral composition of the green LED with the spectral sensitivity curves of the human M- and L-photopigments (FIG. 2.1c) yields that approximately equal quanta are caught by both photopigments (FIG. 2.1f). In contrast, the red LED is six times more effective at stimulating the L photopigment than it is the M (FIG. 2.1f). Isolation of responses that are due to transduction from an introduced L-opsin transgene, M-opsin transgene or S-opsin transgene are straightforward in primates because red, blue or green LEDs can be chosen that are much more effective for the L-opsin M-opsin or S-opsin transgene respectively than for the endogenous pigments of the untreated dichromatic primates. In the case of Squirrel monkeys, they have S-cones maximally sensitive near 430 nm, and they can express any of several variants of middle-to-long wavelength opsin including L or M. The monkey used in validation experiments had M-cones sensitive near 532 nm, in addition to his S-cones. Thus, following the administration of the L-opsin transgene via subretinal injection, the mf-ERGs of squirrel monkey were predicted to show elevations in mf-ERG amplitude to red light in regions corresponding areas of the retina transduced, and distal areas would show progressively lower amplitudes to the L-cone isolating stimulus.

Resolution of the stimulator was 1024 LED over a larger stimulating area of about 150 degrees of visual field. Sensitivity of the measurement can be increased by summing more retinal responses per unit area and by using ultra-bright LEDs. Other new techniques that were used to prevent peripheral SNR fall-off included the use of trapezoidal shaped printed circuit boards that when placed edge-to-edge created a geodesic dome (FIG. 2.1a). The advantage of this design was that LEDs were held equidistantly from and pointing toward a single focal point where the subject's pupil was positioned. Any variation in directionality caused by imperfect sphericity was corrected by aiming each LED individually. In the typical usage, LEDs from areas of the dome shaped stimulator were summed so that there were 37 individual segments, which together subtended the 150° of visual angle, thus allowing a wide-field functional map of an area covering almost the entire retina to be produced.

There are two mathematical methodologies available to code and decode the topographical regions on the recording electrode: One is a cross-correlation technique called m-sequence and the other is a frequency encoding technique called cyclic summation. Cyclic summation is preferred in our application because it has been empirically shown to provide higher signal-to-noise ratio than m-sequence (Lindenberg, Horn, & Korth, 2003). Also, cyclic summation cannot be done using any kind of conventional CRT or LCD video display. Cyclic summation requires independent control of every segment of the display. Conventional video displays update the entire screen with every video frame typically at 60 Hz. In cyclic summation, each segment being analyzed is updating at a slightly different frequency. Typically, the "center frequency" is 30 Hz but each segment fractionally different from 30 Hz, i.e., 30.00 Hz, 30.10 Hz, 30.20 . . . etc. In the analysis, responses to different areas of the retina to different segment frequencies are used to generate a map of retinal responses which are read out as electrophysiological "activity." For example, after gene therapy using an L opsin gene in a primate retina containing only M and S cones, areas of retina that express the newly introduced L opsin will have higher electrical activity in response to the red LED light relative to the green light than areas of the retina not expressing the transgene. This allows the effectiveness of the gene therapy in terms of areas responding their time course to be monitored with an objective measure.

In practice, we define the following parameters; $f_c$=center frequency, T=total time, Q=number of segments, and n=0 . . . (Q−1). The number of cycles per segment is given by $$\text{cycles}_n = f_c \cdot T - \left[\frac{Q-1}{2} + n\right]. \quad (2.1)$$

Then, $f_n$ represents the frequencies at which each segment is encoded into the stimulus is $$f_n = \frac{\text{cycles}_n}{T}. \quad (2.2)$$

Finally, by windowing and summing the recorded retinal waveform, defined as w(t), region specific signal, $\text{Activity}_n$, can be extracted in equation 2.3, $$\text{Activity}_n = \sum_{n=0}^{(Q-1)} \sum_{m=0}^{(\text{cycles}_n-1)} w\left(\frac{m}{f_n} \ldots \frac{(m+1)}{f_n}\right). \quad (2.3)$$

For our purposes, $J_c$=30 Hz, T=40 seconds, and Q=37. In the retina, an additional advantage of the cyclic summation method are that the intensity and temporal frequency of the LEDs can be specified to isolate cone photoreceptor responses and silence rod photoreceptor responses.

Repeatability, Linearity, and SNR

Measurements for repeatability and linearity were made using a UDT S370 Optometer (UDT Instruments, San Diego, Calif.). LED outputs were measured in microwatts (uW) at seven different intensity settings, in random order. Three complete sets of data were taken on three separate days. All measurements were taken after the instrument became equilibrated with the ambient room temperature, which reflects normal operation of the instrument.

Signal-to-noise ratio was measured using a human subject by first placing an opaque material in front of the stimulus and running successive mf-ERGs. Voltages received during the blocked trials were taken as the noise of the instrument. Signal was then measured by performing mf-ERGs on four human subjects with normal trichromatic color vision. To compare SNR as a function of eccentricity, signal and noise were broken into different eccentric rings. Best subject and the average of all subjects were calculated for each ring. Tests involving human subjects were done in accordance with the principles embodied in the Declaration of Helsinki.

Viral Vector and Subretinal Injections

To validate whether the instrument operated as expected, a mixture of two recombinant adeno-associated viruses was injected sub-retinally in a gerbil (*Meriones unguiculatus*) and a squirrel monkey (*Saimiri sciureus*). One virus rAAV.CHOPS2053.GFP, carried a gene for green fluorescent protein (GFP) and the other virus, rAAV.CHOPS2053.RHLOPS, coded for human L-opsin. The L-opsin virus was identical to the GFP virus except that a Not I restriction fragment containing the coding sequence for green fluorescent protein was replaced with a 1.2 kb Not I restriction fragment containing recombinant human L opsin cDNA. The opsin gene encoded a human L pigment that is predicted from the deduced amino acid sequence to be maximally sensitive to 562 nm light. In order to provide a method for visualizing transduced cone photoreceptors using immunohistochemistry in future experiments, the sequence of the human L opsin transgene was changed so that the last 12 amino acids matched the known epitope for the monoclonal antibody OS-2. This antibody was previously shown to specifically label S or UV cones in mammalian and primate retina. The C-terminal 12 amino acids of human S opsin were demonstrated to be the epitope. The substitution of the C-terminal 12 amino acids of S-opsin into L-opsin is not predicted to change the spectral sensitivity of the L-opsin trans-gene product.

Subretinal injections were performed. Briefly, gerbils were anesthetized using a combination of Ketamine (50 mg/kg) and Xylazine (2 mg/kg), and it received two 5 uL subretinal injections of a 1:1 (volume:volume) mixture of rAAV.CHOPS2053.GFP and rAAV.CHOPS2053.RHLOPS that were placed in the superior retinal area. A color mf-ERG was then performed on this animal at 6 months post-injection. Squirrel monkeys was anesthetized using 15 mg/kg ketamine and 2 mg/kg xylazine and they received two 100 uL subretinal injections of a virus mixture containing 110 uL of rAAV.CHOPS2053.GFP and 220 uL of rAAV.CHOPS2053.RHLOPS. Both injections were positioned near the fovea, with the first injection placed superiorly, and the second injection placed in the inferotemporal region of the retina. A color mf-ERG was performed on this animal about 42 weeks, or 10.5 months post-injection. All of these procedures were conducted in accordance with the experimental animal care and usage guidelines of the United States National Institutes of Health.

Fundus Exams

Both the gerbil and squirrel monkey had fundus images taken at multiple time points post-injection to observe expression of the GFP transgene over time. Fundus images were obtained using the fluorescein angiography mode of the RetCam II digital imaging system (Massie Laboratories, Pleasanton, Calif. For the gerbil, images were taken with a lens designed for detecting retinopathy in premature infants, which provides a 130° field of view, and for the monkey, a high magnification 30° lens was used. Thus, multiple fundus images from the squirrel monkey were pieced together into a montage, in order to show a comparable retinal area.

Results

Measures of repeatability, linearity, and signal-to-noise ratio (SNR) were performed to evaluate the wide-field color ERG system. More properly, given n=2 ... 8, m=½$^n$, and t=[0, ~3.5, 7] days, then intensity, $I_m(t)$, is said to be repeatable if $$s = 3 \cdot \sqrt{\frac{1}{2}\sum_{t=1}^{3}(I_m(t) - \overline{I_m(t)})^2} \leq \epsilon \qquad (2.4)$$

where $\epsilon$ is defined as $$\epsilon = 0.05 \cdot \max(photon_m). \qquad (2.5)$$

The instrument was said to be linear if Pearson's $R^2$ was greater than 0.95. And finally, signal (in SNR) was is calculated by averaging response from four subjects, and noise was taken as the residual signal while an opaque material blocked stimulus.

Repeatability and linearity are demonstrated in FIG. 2.2. Each data point is an average of optometer measurements for the particular intensity setting taken on three separate days; error bars are the standard deviations with a 99.7% confidence interval. Pearson's R correlation was calculated and the coefficient of determination ($R^2$) values is shown. The red LEDs shared 0.9987 total variance and the green LEDs shared 0.9996 total variance demonstrating system is linear and repeatable over time. SNR values are shown in Table 2.1. The SNR was high for the inner segments of the stimulus panel; it decreased in more peripheral regions but remained high enough to allow measurements into the far periphery.

Because the GFP-coding virus and the L-opsin-coding virus were injected together at the same locations, fluorescence fundus images could be registered with mf-ERG data from the same animal in order to validate the redesigned wide-field color mf-ERG system. Areas of high GFP expression corresponded well to areas of high mf-ERG voltage in response to the L-cone isolating red stimulus (FIG. 2.3). Animals were insensitive to the red 653 nm wave-length light prior to injection, verifying that the signal measured in animals post-injection is true signal coming from the introduced L-opsin transgene product. In the squirrel monkey, the red-light mf-ERG data showed high voltage in the regions that corresponded to the fluorescence fundus images.

To evaluate whether the concave surface of the newly developed stimulator produces ERG amplitudes that are relatively constant with retinal eccentricity an experiment was performed in which flicker ERG responses were measured under two different conditions. In FIG. 2.4, the circles represent ERG responses from an LED traveling down a linear path while the subject fixated forward. On the same graph, triangles represent ERG responses from an LED traveling on a rotating boom while the subject fixated forward. The boom held the LEDs perpendicular to the cornea. Results from this experiment demonstrate the increase in signal given by the convex stimulator, compared to a traditional flat-panel LCD screen or CRT monitor. The curved stimulus design, in addition to the use of ultra-bright LEDs as the light source, increased the SNR sufficiently high in the far periphery to ensure viable signals were recorded from cone photoreceptors.

In the conventional mf-ERG, the signal amplitudes are greatly reduced in the periphery because the illumination from a flat screen falls off roughly as the cosine with increasing eccentricity. In our design, the redesigned stimulus had concave structure holding the LEDs such that the inner surface pointed perpendicular to the stimulated retinal area. In addition, similar to traditional mf-ERG stimulators, the number of LEDs in each segment was increased with eccentricity to compensate for the decrease in cone density.

If 40% of cones express the transgene the increase in red sensitivity should be that expected from a spectral ERG in which 20% of the total ERG contribution is from L opsin while 80% is from M opsin. This is consistent with the observed red sensitivity in both monkeys and gerbils.

This is the first time that measurements from cones in the far peripheral retina have been achieved. Results from these experiments indicate that the wide-field color mf-ERG system is a valid technique for measuring the topography of opsin expression in living subjects, and it will serve as an important tool for evaluating success of gene therapy in humans.

References For Example 2

Sutter, E. E. (1991). The Fast m-Transform: A Fast Computation of Cross-Correlations with Binary m-Sequences. *SIAM Journal on Computing*, 20(4), 686-694.

Swanson, W. H., Ueno, T., Smith, V. C., & Pokorny, J. (1987). Temporal modulation sensitivity and pulse-detection thresholds for chromatic and luminance perturbations. *Journal of the Optical Society of America A—Optics, Image Science and Vision*, 4(10), 13.

We claim:

1. A method for cone cell gene therapy in a primate, comprising
    (I) administering to the eye of a primate having color blindness a recombinant gene delivery vector comprising
        (a) a promoter region, wherein the promoter region is specific for retinal cone cells; and
        (b) a gene encoding a therapeutic selected from the group consisting of S-Opsin, M-Opsin and L-Opsin, wherein the gene is operatively linked to the promoter region; and
    (II) testing the eye of the primate for discrimination of blue-green colors against a red-violet background;
    wherein in vivo expression of the therapeutic in cone cells of the primate results in the primate being able to visualize and to discriminate between red and green colors.

2. The method of claim 1 wherein the primate is of the Parvorder Catarrhini.

3. The method of claim 1 wherein the promoter comprises a sequence selected from the group consisting of the L opsin promoter (SEQ ID NO: 1), the M opsin promoter (SEQ ID NO: 2), and the S opsin promoter (SEQ ID NO: 3).

4. The method of claim 1, wherein the gene delivery vector further comprises an enhancer element upstream of the promoter, wherein the gene is operatively linked to the enhancer element.

5. The method of claim 4, the enhancer element is specific for primate retinal cone cells.

6. The method of claim 5, wherein the enhancer element comprises the nucleic acid sequence of SEQ ID NO: 51.

7. The method of claim 1, wherein the gene delivery vector further comprises an intron comprising a splice donor/acceptor region, wherein the intron is located downstream of the promoter region and is located upstream of the gene.

8. The method of claim 1, wherein the gene delivery vector comprises a recombinant adeno-associated virus (AAV) gene delivery vector.

9. The method of claim 8, wherein the AAV gene vector is pseudotyped for AAV2.

10. The method of claim 1, wherein
    the gene encodes one or more therapeutic polypeptides comprising a sequence selected from the group consisting of SEQ ID NO: 7, SEQ ID NO: 9, SEQ ID NO: 11; and a polymorph of SEQ ID NO: 11 selected from the group consisting of
    (i) Thr65Ile
    (ii) Ile111Val
    (iii) Ser116Tyr
    (iv) Leu153Met
    (v) Ile171Val
    (vi) Ala174Val
    (vii) Ile178Val
    (viii) Ser180Ala
    (ix) Ile230Thr
    (x) Ala233Ser
    (xi) Val236Met
    (xii) Ile274Val (xiii) Phe275Leu
(xiv) Tyr277Phe
(xv) Val279Phe
(xvi) Thr285Ala
(xvii) Pro298Ala; and
(xviii) Tyr309Phe.

11. The method of claim 1, wherein the photoreceptors of the primate are healthy.

12. The method of claim 1, wherein the primate is an adult primate.

* * * * *

SEQUENCE LISTING

<160> NUMBER OF SEQ ID NOS: 51

<210> SEQ ID NO 1
<211> LENGTH: 494
<212> TYPE: DNA
<213> ORGANISM: Artificial Sequence
<220> FEATURE:
<223> OTHER INFORMATION: Synthetic

<400> SEQUENCE: 1

```
ggatccggtt ccaggcctcg gccctaaata gtctccctgg gctttcaaga gaaccacatg      60
agaaaggagg attcgggctc tgagcagttt caccacccac cccccagtct gcaaatcctg     120
acccgtgggt ccacctgccc caaaggcgga cgcaggacag tagaagggaa cagagaacac     180
ataaacacag agagggccac agcggctccc acagtcaccg ccaccttcct ggcggggatg     240
ggtggggcgt ctgagtttgg ttcccagcaa atccctctga gccgcccttg cgggctcgcc     300
tcaggagcag gggagcaaga ggtgggagga ggaggtctaa gtcccaggcc caattaagag     360
atcaggtagt gtagggtttg ggagcttta aggtgaagag gcccgggctg atcccacagg     420
ccagtataaa gcgccgtgac cctcaggtga tgcgccaggg ccggctgccg tcggggacag     480 ggcttttccat agcc                                                      494
```

<210> SEQ ID NO 2
<211> LENGTH: 494
<212> TYPE: DNA
<213> ORGANISM: Artificial Sequence
<220> FEATURE:
<223> OTHER INFORMATION: Synthetic

<400> SEQUENCE: 2

```
ttatttagta gaaacggggt ttcaccatgt tagtcaggct ggtcgggaac tcctgacctc      60
aggagatcta cccgccttgg cctcccaaag tgctgggatt acaggcgtgt gccactgtgc     120
ccagccactt tttttagac agagtcttgg tctgttgccc aggctagagt tcagtggcgc     180
catctcagct cactgcaacc tccgcctccc agattcaagc gattctcctg cctcgacctc     240
ccagtagctg ggattacagg tttccagcaa atccctctga gccgccccg ggggctcgcc     300 tcaggagcaa ggaagcaagg ggtgggagga ggaggtctaa gtcccaggcc caattaagag     360
atcagatggt gtaggatttg ggagcttta aggtgaagag gcccgggctg atcccactgg     420
ccggtataaa gcaccgtgac cctcaggtga cgcaccaggg ccggctgccg tcggggacag     480 ggcttttccat agcc                                                      494
```

<210> SEQ ID NO 3
<211> LENGTH: 568
<212> TYPE: DNA
<213> ORGANISM: Artificial Sequence
<220> FEATURE:
<223> OTHER INFORMATION: Synthetic

<400> SEQUENCE: 3

```
ctaggcattg tcaagttgcc taagtcctgt tccatcaagg ctgtttactg atgtgcttcc      60
agggcactcc ccactcccag ccctttcctg cagcccaggg ctggttccta gcctctcagc     120
agacttaaga tgggcacctt ccacaaaggg gcagatgagt tgaggaaaac ttaactgata     180
cagttgtgcc agaagccaaa ataagaggcg tgcccttct atagccccat taaagaaca     240
```

| | | | | |
|---|---|---|---|---|
| aaaaagtgga | agcatcttca | gtgaatatgg | gtcagcacct | cccagacctc | agggagtcca | 300 |
| cttctgttca | tcccagcacc | cagcattgca | tatccagatt | atttgagccc | aatctcttat | 360 |
| cctctgaaga | acacaatcgg | ctttggggcc | acaaaaggtt | taggtagtgg | tttagggatt | 420 |
| tctaatccca | aactttgtcc | ttgggaggtt | taggattagt | attgatcatt | cacagagccc | 480 |
| aagtgttttt | agaggagggg | ttttgtgggg | tgggaggatc | acctataaga | ggactcagag | 540 |
| gggggtgtgg | ggcatccatg | agaaaaat | | | 568 |

```
<210> SEQ ID NO 4
<211> LENGTH: 1555
<212> TYPE: DNA
<213> ORGANISM: Artificial Sequence
<220> FEATURE:
<223> OTHER INFORMATION: Synthetic

<400> SEQUENCE: 4
```

| | | | | | |
|---|---|---|---|---|---|
| ccagggtgag | attatgaggc | tgagctgaga | atatcaagac | tgtaccgagt | agggggcctt | 60 |
| ggcaagtgtg | gagagcccgg | cagctggggc | agagggcgga | gtacggtgtg | cgtttacgga | 120 |
| cctcttcaaa | cgaggtagga | aggtcagaag | tcaaaaaggg | aacaaatgat | gtttaaccac | 180 |
| acaaaatga | aaatccaatg | gttggatatc | cattccaaat | acacaaaggc | aacggataag | 240 |
| tgatccgggc | caggcacaga | aggccatgca | cccgtaggat | tgcactcaga | gctcccaaat | 300 |
| gcataggaat | agaagggtgg | gtgcaggagg | ctgaggggtg | gggaaaggc | atgggtgttt | 360 |
| catgaggaca | gagcttccgt | ttcatgcaat | gaaagagtt | tggagacgga | tggtggtgac | 420 |
| tggactatac | acttacacac | ggtagcgatg | gtacactttg | tattatgtat | attttaccac | 480 |
| gatcttttta | aagtgtcaaa | ggcaaatggc | caaatggttc | cttgtcctat | agctgtagca | 540 |
| gccatcggct | gttagtgaca | aagcccctga | gtcaagatga | cagcagcccc | cataactcct | 600 |
| aatcggctct | cccgcgtgga | gtcatttagg | agtagtcgca | ttagagacaa | gtccaacatc | 660 |
| taatcttcca | ccctggccag | ggccccagct | ggcagcgagg | gtgggagact | ccgggcagag | 720 |
| cagagggcgc | tgacattggg | gcccggcctg | gcttgggtcc | ctctggcctt | tccccagggg | 780 |
| ccctctttcc | ttggggcttt | cttggccgc | cactgctccc | gctcctctcc | ccccatccca | 840 |
| ccccctcacc | ccctcgttct | tcatatcctt | ctctagtgct | ccctccactt | tcatccaccc | 900 |
| ttctgcaaga | gtgtgggacc | acaaatgagt | tttcacctgg | cctggggaca | cacgtgcccc | 960 |
| cacaggtgct | gagtgacttt | ctaggacagt | aatctgcttt | aggctaaaat | gggacttgat | 1020 |
| cttctgttag | ccctaatcat | caattagcag | agccggtgaa | ggtgcagaac | ctaccgcctt | 1080 |
| tccaggcctc | ctcccacctc | tgccacctcc | actctccttc | ctgggatgtg | ggggctggca | 1140 |
| cacgtgtggc | ccagggcatt | ggtgggattg | cactgagctg | ggtcattagc | gtaatcctgg | 1200 |
| acaagggcag | acagggcgag | cggagggcca | gctccggggc | tcaggcaagg | ctgggggctt | 1260 |
| cccccagaca | ccccactcct | cctctgctgg | accccactt | cataggcac | ttcgtgttct | 1320 |
| caaagggctt | ccaaatagca | tggtggcctt | ggatgcccag | ggaagcctca | gagttgctta | 1380 |
| tctccctcta | gacagaaggg | gaatctcggt | caagagggag | aggtcgccct | gttcaaggcc | 1440 |
| acccagccag | ctcatggcgg | taatgggaca | aggctggcca | gccatcccac | cctcagaagg | 1500 |
| gacccggtgg | ggcaggtgat | ctcagaggag | gctcacttct | gggtctcaca | ttctt | 1555 |

```
<210> SEQ ID NO 5
<211> LENGTH: 189
<212> TYPE: DNA
<213> ORGANISM: Artificial Sequence
```

<220> FEATURE:
<223> OTHER INFORMATION: Synthetic

<400> SEQUENCE: 5

```
gatccggtac tcgaggaact gaaaaaccag aaagttaact ggtaagttta gtcttttgt      60
cttttatttc aggtcccgga tccggtggtg gtgcaaatca agaactgct cctcagtgga     120
tgttgccttt acttctaggc ctgtacggaa gtgttacttc tgctctaaaa gctgcggaat    180
tgtacccgc                                                             189
```

<210> SEQ ID NO 6
<211> LENGTH: 1114
<212> TYPE: DNA
<213> ORGANISM: Homo sapiens

<400> SEQUENCE: 6

```
atgagaaaaa tgtcggagga gagtttat ctgttcaaaa atatctcttc agtggggccg       60
tgggatgggc tcagtacca cattgcccct gtctgggcct tctacctcca ggcagctttc    120
atgggcactg tcttccttat agggttccca ctcaatgcca tggtgctggt ggccacactg    180
cgctacaaaa agttgcggca gcccctcaac tacattctgg tcaacgtgtc cttcggaggc    240
ttcctcctct gcatcttctc tgtcttccct gtcttcgtcg ccagctgtaa cggatacttc    300
gtcttcggtc gccatgtttg tgctttggag ggcttcctgg gcactgtagc aggtctggtt    360
acaggatggt cactggcctt cctggccttt gagcgctaca ttgtcatctg taagcccttc    420
ggcaacttcc gcttcagctc caagcatgca ctgacggtgg tcctggctac ctggaccatt    480
ggtattggcg tctccatccc acccttcttt ggctggagcc ggttcatccc tgagggcctg    540
cagtgttcct gtggccctga ctggtacacc gtgggcacca ataccgcag cgagtcctat    600
acgtggttcc tcttcatctt ctgcttcatt gtgcctctct ccctcatctg cttctcctac    660
actcagctgc tgagggccct gaaagctgtt gcagctcagc agcaggagtc agctacgacc    720
cagaaggctg aacgggaggt gagccgcatg gtggttgtga tggtaggatc cttctgtgtc    780
tgctacgtgc cctacgcggc cttcgccatg tacatggtca acaaccgtaa ccatgggctg    840
gacttacggc ttgtcaccat tccttcattc ttctccaaga gtgcttgcat ctacaatccc    900
atcatctact gcttcatgaa taagcagttc caagcttgca tcatgaagat ggtgtgtggg    960
aaggccatga cagatgaatc cgacacatgc agctcccaga aaacagaagt ttctactgtc   1020
tcgtctaccc aagttggccc caactgagga cccaatattg gcctgtttgc aacagctaga   1080
attaaatttt acttttaaaa aaaaaaaaaa aaaa                               1114
```

<210> SEQ ID NO 7
<211> LENGTH: 348
<212> TYPE: PRT
<213> ORGANISM: Homo sapiens

<400> SEQUENCE: 7

```
Met Arg Lys Met Ser Glu Glu Phe Tyr Leu Phe Lys Asn Ile Ser
1               5                   10                  15

Ser Val Gly Pro Trp Asp Gly Pro Gln Tyr His Ile Ala Pro Val Trp
            20                  25                  30

Ala Phe Tyr Leu Gln Ala Ala Phe Met Gly Thr Val Phe Leu Ile Gly
        35                  40                  45

Phe Pro Leu Asn Ala Met Val Leu Val Ala Thr Leu Arg Tyr Lys Lys
    50                  55                  60
```

```
Leu Arg Gln Pro Leu Asn Tyr Ile Leu Val Asn Val Ser Phe Gly Gly
 65                  70                  75                  80

Phe Leu Leu Cys Ile Phe Ser Val Phe Pro Val Phe Ala Ser Cys
                 85                  90                  95

Asn Gly Tyr Phe Val Phe Gly Arg His Val Cys Ala Leu Glu Gly Phe
                100                 105                 110

Leu Gly Thr Val Ala Gly Leu Val Thr Gly Trp Ser Leu Ala Phe Leu
            115                 120                 125

Ala Phe Glu Arg Tyr Ile Val Ile Cys Lys Pro Phe Gly Asn Phe Arg
        130                 135                 140

Phe Ser Ser Lys His Ala Leu Thr Val Val Leu Ala Thr Trp Thr Ile
145                 150                 155                 160

Gly Ile Gly Val Ser Ile Pro Pro Phe Phe Gly Trp Ser Arg Phe Ile
                165                 170                 175

Pro Glu Gly Leu Gln Cys Ser Cys Gly Pro Asp Trp Tyr Thr Val Gly
            180                 185                 190

Thr Lys Tyr Arg Ser Glu Ser Tyr Thr Trp Phe Leu Phe Ile Phe Cys
        195                 200                 205

Phe Ile Val Pro Leu Ser Leu Ile Cys Phe Ser Tyr Thr Gln Leu Leu
    210                 215                 220

Arg Ala Leu Lys Ala Val Ala Ala Gln Gln Gln Glu Ser Ala Thr Thr
225                 230                 235                 240

Gln Lys Ala Glu Arg Glu Val Ser Arg Met Val Val Met Val Met Gly
                245                 250                 255

Ser Phe Cys Val Cys Tyr Val Pro Tyr Ala Ala Phe Ala Met Tyr Met
            260                 265                 270

Val Asn Asn Arg Asn His Gly Leu Asp Leu Arg Leu Val Thr Ile Pro
        275                 280                 285

Ser Phe Phe Ser Lys Ser Ala Cys Ile Tyr Asn Pro Ile Ile Tyr Cys
    290                 295                 300

Phe Met Asn Lys Gln Phe Gln Ala Cys Ile Met Lys Met Val Cys Gly
305                 310                 315                 320

Lys Ala Met Thr Asp Glu Ser Asp Thr Cys Ser Ser Gln Lys Thr Glu
                325                 330                 335

Val Ser Thr Val Ser Ser Thr Gln Val Gly Pro Asn
            340                 345

<210> SEQ ID NO 8
<211> LENGTH: 1998
<212> TYPE: DNA
<213> ORGANISM: Homo sapiens

<400> SEQUENCE: 8
cccactggcc ggtataaagc accgtgaccc tcaggtgacg caccagggcc ggctgccgtc    60
ggggacaggg ctttccatag ccatggccca gcagtggagc ctccaaaggc tcgcaggccg   120
ccatccgcag gacagctatg aggacagcac ccagtccagc atcttcacct acaccaacag   180
caactccacc agaggcccct cgaaggcccg aattaccac atcgctccca gatgggtgta    240
ccacctcacc agtgtctgga tgatctttgt ggtcattgca tccgtcttca caaatgggct   300
tgtgctggcg gccaccatga agttcaagaa gctgcgccac ccgctgaact ggatcctggt   360
gaacctggcg gtcgctgacc tggcagagac cgtcatcgcc agcactatca gcgttgtgaa   420
ccaggtctat ggctacttcg tgctgggcca ccctatgtgt gtcctggagg ctacaccgt    480 ctccctgtgt gggatcacag gtctctggtc tctggccatc atttcctggg agagatggat   540
```

```
ggtggtctgc aagcccttg gcaatgtgag atttgatgcc aagctggcca tcgtgggcat    600
tgccttctcc tggatctggg ctgctgtgtg acagccccg cccatctttg gttggagcag    660
gtactggccc cacggcctga agacttcatg cggcccagac gtgttcagcg gcagctcgta    720
cccgggggtg cagtcttaca tgattgtcct catggtcacc tgctgcatca ccccactcag    780
catcatcgtg ctctgctacc tccaagtgtg gctggccatc cgagcggtgg caaagcagca    840
gaaagagtct gaatccaccc agaaggcaga aaggaagtg acgcgcatgg tggtggtgat    900
ggtcctggca ttctgcttct gctggggacc atacgccttc ttcgcatgct ttgctgctgc    960
caaccctggc tacccccttcc acccttgat ggctgccctg ccggccttct ttgccaaaag   1020
tgccactatc tacaaccccg ttatctatgt cttatgaac cggcagtttc gaaactgcat   1080
cttgcagctt tcgggaaga aggttgacga tggctctgaa ctctccagcg cctccaaaac   1140
ggaggtctca tctgtgtcct cggtatcgcc tgcatgaggt ctgcctccta cccatcccgc   1200
ccaccggggc tttggccacc tctccttttcc ccctccttct ccatccctgt aaaataaatg   1260
taattatct ttgccaaaac caacaaagtc acagaggctt tcactgcagt gtgggaccac   1320
ctgagcctct gcgtgtgcag gcactgggtc tcgagagggt gcaaggggga taaagaggag   1380
agagcgcttc atagacttta agttttcccg agcctcatgt ctaccgatgg cgtgaaagga   1440
tcctggcaaa acagaagtgt gaggcaggtg ggcgtctata tccatttcac caggctggtg   1500
gttacataat cggcaagcaa gagctgtgga ggggcttgct ggatgccctc agcacccagg   1560
aggagggagg gagctagcaa gctaaggcag gtggccctcc tggcccctta aggtccatct   1620
gctggaggcc cagagtcctt ggagtacagt ctacacctgg aggggaccca ttcctgccag   1680
tctgtggcag ggatggcgcg ccacctctgc caggccagga ccccaagccc gatcagcatc   1740
agcatggtgc aggtgcacag gcgtgagctg atcagtgacg aggggcaggc acacaaggtg   1800
gagacaaaga ccaagaggac ggttgccagt gagaggcgcg gactcaggaa cttgaacaac   1860
atctgcgggg gacggctttg gaggtgctcc gctgcctcca gttgggtgac ttgctgtagc   1920
atctccagct tggatattcg gctcttgaag gtctccgtga tctcctgcag gagacgaaaa   1980
tgcacgcacc agaagtca                                                 1998

<210> SEQ ID NO 9
<211> LENGTH: 364
<212> TYPE: PRT
<213> ORGANISM: Homo sapiens

<400> SEQUENCE: 9

Met Ala Gln Gln Trp Ser Leu Gln Arg Leu Ala Gly Arg His Pro Gln
1               5                   10                  15

Asp Ser Tyr Glu Asp Ser Thr Gln Ser Ser Ile Phe Thr Tyr Thr Asn
            20                  25                  30

Ser Asn Ser Thr Arg Gly Pro Phe Glu Gly Pro Asn Tyr His Ile Ala
        35                  40                  45

Pro Arg Trp Val Tyr His Leu Thr Ser Val Trp Met Ile Phe Val Val
    50                  55                  60

Ile Ala Ser Val Phe Thr Asn Gly Leu Val Leu Ala Ala Thr Met Lys
65                  70                  75                  80

Phe Lys Lys Leu Arg His Pro Leu Asn Trp Ile Leu Val Asn Leu Ala
                85                  90                  95

Val Ala Asp Leu Ala Glu Thr Val Ile Ala Ser Thr Ile Ser Val Val
            100                 105                 110
```

```
Asn Gln Val Tyr Gly Tyr Phe Val Leu Gly His Pro Met Cys Val Leu
        115                 120                 125
Glu Gly Tyr Thr Val Ser Leu Cys Gly Ile Thr Gly Leu Trp Ser Leu
130                 135                 140
Ala Ile Ile Ser Trp Glu Arg Trp Met Val Val Cys Lys Pro Phe Gly
145                 150                 155                 160
Asn Val Arg Phe Asp Ala Lys Leu Ala Ile Val Gly Ile Ala Phe Ser
                165                 170                 175
Trp Ile Trp Ala Ala Val Trp Thr Ala Pro Pro Ile Phe Gly Trp Ser
            180                 185                 190
Arg Tyr Trp Pro His Gly Leu Lys Thr Ser Cys Gly Pro Asp Val Phe
        195                 200                 205
Ser Gly Ser Ser Tyr Pro Gly Val Gln Ser Tyr Met Ile Val Leu Met
    210                 215                 220
Val Thr Cys Cys Ile Thr Pro Leu Ser Ile Ile Val Leu Cys Tyr Leu
225                 230                 235                 240
Gln Val Trp Leu Ala Ile Arg Ala Val Ala Lys Gln Gln Lys Glu Ser
                245                 250                 255
Glu Ser Thr Gln Lys Ala Glu Lys Glu Val Thr Arg Met Val Val Val
            260                 265                 270
Met Val Leu Ala Phe Cys Phe Cys Trp Gly Pro Tyr Ala Phe Phe Ala
        275                 280                 285
Cys Phe Ala Ala Ala Asn Pro Gly Tyr Pro Phe His Pro Leu Met Ala
    290                 295                 300
Ala Leu Pro Ala Phe Phe Ala Lys Ser Ala Thr Ile Tyr Asn Pro Val
305                 310                 315                 320
Ile Tyr Val Phe Met Asn Arg Gln Phe Arg Asn Cys Ile Leu Gln Leu
                325                 330                 335
Phe Gly Lys Lys Val Asp Asp Gly Ser Glu Leu Ser Ser Ala Ser Lys
            340                 345                 350
Thr Glu Val Ser Ser Val Ser Ser Val Ser Pro Ala
        355                 360

<210> SEQ ID NO 10
<211> LENGTH: 1234
<212> TYPE: DNA
<213> ORGANISM: Homo sapiens

<400> SEQUENCE: 10
cggctgccgt cggggacagg gctttccata gccatggccc agcagtggag cctccaaagg    60
ctcgcaggcc gccatccgca ggacagctat gaggacagca cccagtccag catcttcacc   120
tacaccaaca gcaactccac cagaggcccc ttcgaaggcc cgaattacca catcgctccc   180
agatgggtgt accacctcac cagtgtctgg atgatctttg tggtcactgc atccgtcttc   240
acaaatgggc ttgtgctggc ggccaccatg aagttcaaga gctgcgcca  cccgctgaac   300
tggatcctgg tgaacctggc ggtcgctgac ctagcagaga ccgtcatcgc cagcactatc   360
agcattgtga accaggtctc tggctacttc gtgctgggcc acctatgtg tgtcctggag   420
ggctacaccg tctccctgtg tgggatcaca ggtctctggt ctctggccat catttcctgg   480
gagaggtggc tggtggtgtg caagcccttt ggcaatgtga gatttgatgc caagctggcc   540
atcgtgggca ttgccttctc ctggatctgg tctgctgtgt ggacagcccc gcccatcttt   600
ggttggagca ggtactggcc ccacggcctg aagacttcat gcggcccaga cgtgttcagc   660
```

-continued

```
ggcagctcgt acccgggggt gcagtcttac atgattgtcc tcatggtcac ctgctgcatc    720
atcccactcg ctatcatcat gctctgctac ctccaagtgt ggctggccat ccgagcggtg    780
gcaaagcagc agaaagagtc tgaatccacc cagaaggcag agaaggaagt gacgcgcatg    840
gtggtggtga tgatctttgc gtactgcgtc tgctggggac cctacacctt cttcgcatgc    900
tttgctgctg ccaaccctgg ttacgccttc cacccttga tggctgccct gccggcctac     960
tttgccaaaa gtgccactat ctacaacccc gttatctatg tctttatgaa ccggcagttt   1020
cgaaactgca tcttgcagct tttcgggaag aaggttgacg atggctctga actctccagc   1080
gcctccaaaa cggaggtctc atctgtgtcc tcggtatcgc ctgcatgagg tctgcctcct   1140
acccatcccg cccaccgggg ctttggccac ctctcctttc ccctccttc tccatccctg    1200
taaaataaat gtaatttatc tttgccaaaa ccaa                                1234
```

<210> SEQ ID NO 11
<211> LENGTH: 364
<212> TYPE: PRT
<213> ORGANISM: Homo sapiens

<400> SEQUENCE: 11

```
Met Ala Gln Gln Trp Ser Leu Gln Arg Leu Ala Gly Arg His Pro Gln
1               5                   10                  15

Asp Ser Tyr Glu Asp Ser Thr Gln Ser Ser Ile Phe Thr Tyr Thr Asn
            20                  25                  30

Ser Asn Ser Thr Arg Gly Pro Phe Glu Gly Pro Asn Tyr His Ile Ala
        35                  40                  45

Pro Arg Trp Val Tyr His Leu Thr Ser Val Trp Met Ile Phe Val Val
    50                  55                  60

Thr Ala Ser Val Phe Thr Asn Gly Leu Val Leu Ala Ala Thr Met Lys
65                  70                  75                  80

Phe Lys Lys Leu Arg His Pro Leu Asn Trp Ile Leu Val Asn Leu Ala
                85                  90                  95

Val Ala Asp Leu Ala Glu Thr Val Ile Ala Ser Thr Ile Ser Ile Val
            100                 105                 110

Asn Gln Val Ser Gly Tyr Phe Val Leu Gly His Pro Met Cys Val Leu
        115                 120                 125

Glu Gly Tyr Thr Val Ser Leu Cys Gly Ile Thr Gly Leu Trp Ser Leu
    130                 135                 140

Ala Ile Ile Ser Trp Glu Arg Trp Leu Val Val Cys Lys Pro Phe Gly
145                 150                 155                 160

Asn Val Arg Phe Asp Ala Lys Leu Ala Ile Val Gly Ile Ala Phe Ser
                165                 170                 175

Trp Ile Trp Ser Ala Val Trp Thr Ala Pro Pro Ile Phe Gly Trp Ser
            180                 185                 190

Arg Tyr Trp Pro His Gly Leu Lys Thr Ser Cys Gly Pro Asp Val Phe
        195                 200                 205

Ser Gly Ser Ser Tyr Pro Gly Val Gln Ser Tyr Met Ile Val Leu Met
    210                 215                 220

Val Thr Cys Cys Ile Ile Pro Leu Ala Ile Ile Met Leu Cys Tyr Leu
225                 230                 235                 240

Gln Val Trp Leu Ala Ile Arg Ala Val Ala Lys Gln Gln Lys Glu Ser
                245                 250                 255

Glu Ser Thr Gln Lys Ala Glu Lys Glu Val Thr Arg Met Val Val Val
            260                 265                 270
```

```
Met Ile Phe Ala Tyr Cys Val Cys Trp Gly Pro Tyr Thr Phe Ala
            275                 280                 285

Cys Phe Ala Ala Ala Asn Pro Gly Tyr Ala Phe His Pro Leu Met Ala
290                 295                 300

Ala Leu Pro Ala Tyr Phe Ala Lys Ser Ala Thr Ile Tyr Asn Pro Val
305                 310                 315                 320

Ile Tyr Val Phe Met Asn Arg Gln Phe Arg Asn Cys Ile Leu Gln Leu
                325                 330                 335

Phe Gly Lys Lys Val Asp Asp Gly Ser Glu Leu Ser Ser Ala Ser Lys
            340                 345                 350

Thr Glu Val Ser Ser Val Ser Ser Val Ser Pro Ala
            355                 360

<210> SEQ ID NO 12
<211> LENGTH: 7326
<212> TYPE: DNA
<213> ORGANISM: Homo sapiens

<400> SEQUENCE: 12
aggacacagc gtccggagcc agaggcgctc ttaacggcgt ttatgtcctt tgctgtctga      60
ggggcctcag ctctgaccaa tctggtcttc gtgtggtcat tagcatgggc ttcgtgagac     120
agatacagct tttgctctgg aagaactgga ccctgcggaa aaggcaaaag attcgctttg     180
tggtggaact cgtgtggcct ttatctttat ttctggtctt gatctggtta aggaatgcca     240
acccgctcta cagccatcat gaatgccatt tccccaacaa ggcgatgccc tcagcaggaa     300
tgctgccgtg gctccagggg atcttctgca atgtgaacaa tccctgtttt caaagcccca     360
ccccaggaga atcctctgga attgtgtcaa actataacaa ctccatcttg caagggtat     420 atcgagattt tcaagaactc tcatgaatg caccagagag ccagcacctt ggccgtattt     480
ggacagagct acacatcttg tcccaattca tggacaccct ccggactcac ccggagagaa     540
ttgcaggaag aggaatacga ataagggata tcttgaaaga tgaagaaaca ctgacactat     600
ttctcattaa aaacatcggc ctgtctgact cagtggtcta ccttctgatc aactctcaag     660
tccgtccaga gcagttcgct catggagtcc cggacctggc gctgaaggac atcgcctgca     720
gcgaggccct cctggagcgc ttcatcatct tcagccagag acgcgggca aagacggtgc     780 gctatgccct gtgctccctc tcccagggca cctacagtg gatagaagac actctgtatg     840
ccaacgtgga cttcttcaag ctcttccgtg tgcttccac actcctagac agccgttctc     900
aaggtatcaa tctgagatct tggggaggaa tattatctga tatgtcacca gaattcaag     960 agtttatcca tcggccgagt atgcaggact tgctgtgggt gaccaggccc ctcatgcaga    1020
atggtggtcc agagaccttt acaaagctga tgggcatcct gtctgacctc ctgtgtggct    1080
accccgaggg aggtggctct cgggtgctct ccttcaactg gtatgaagac aataactata    1140
aggcctttct ggggattgac tccacaagga aggatcctat ctattcttat gacagaagaa    1200
caacatcctt ttgtaatgca ttgatccaga gcctggagtc aaatccttta ccaaaatcg    1260 cttggagggc ggcaaagcct ttgctgatgg gaaaaatcct gtacactcct gattcacctg    1320
cagcacgaag gatactgaag aatgccaact caacttttga agaactggaa cacgttagga    1380
agttggtcaa agcctgggaa gaagtagggc cccagatctg gtacttcttt gacaacagca    1440
cacagatgaa catgatcaga gataccctgg ggaaccaaac agtaaaagac ttttgaata    1500 ggcagcttgg tgaagaaggt attactgctg aagccatcct aaacttcctc tacaagggcc    1560
ctcgggaaag ccaggctgac gacatggcca acttcgactg gagggacata tttaacatca    1620
```

```
ctgatcgcac cctccgcctg gtcaatcaat acctggagtg cttggtcctg gataagtttg    1680
aaagctacaa tgatgaaact cagctcaccc aacgtgccct ctctctactg gaggaaaaca    1740
tgttctgggc cggagtggta ttccctgaca tgtatccctg gaccagctct ctaccacccc    1800
acgtgaagta taagatccga atggacatag acgtggtgga gaaaaccaat aagattaaag    1860
acaggtattg ggattctggt cccagagctg atcccgtgga gatttccgg tacatctggg     1920 gcgggtttgc ctatctgcag gacatggttg aacaggggat cacaaggagc caggtgcagg    1980
cggaggctcc agttggaatc tacctccagc agatgcccta cccctgcttc gtggacgatt    2040 cttttcatgat catcctgaac cgctgttttcc ctatcttcat ggtgctggca tggatctact   2100
ctgtctccat gactgtgaag agcatcgtct ggagaagga gttgcgactg aaggagacct     2160
tgaaaaatca gggtgtctcc aatgcagtga tttggtgtac ctggttcctg gacagcttct    2220
ccatcatgtc gatgagcatc ttcctcctga cgatattcat catgcatgga agaatcctac    2280
attacagcga cccattcatc ctcttcctgt tcttgttggc tttctccact gccaccatca    2340
tgctgtgctt tctgctcagc accttcttct ccaaggccag tctggcagca gcctgtagtg    2400
gtgtcatcta tttcacccctc tacctgccac acatcctgtg cttcgcctgg caggaccgca   2460
tgaccgctga gctgaagaag gctgtgagct actgtctcc ggtggcattt ggatttggca     2520
ctgagtacct ggttcgcttt gaagagcaag gcctggggct gcagtggagc aacatcggga    2580
acagtcccac ggaaggggac gaattcagct tcctgctgtc catgcagatg atgctccttg    2640
atgctgctgt ctatggctta ctcgcttggt accttgatca ggtgtttcca ggagactatg    2700 gaacccccact tccttggtac tttcttctac aagagtcgta ttggcttggc ggtgaagggt    2760
gttcaaccag agaagaaaga gccctggaaa agaccgagcc cctaacagag gaaacggagg    2820
atccagagca cccagaagga atacacgact ccttctttga acgtgagcat ccagggtggg    2880
ttcctggggt atgcgtgaag aatctggtaa agattttga gccctgtggc cggccagctg     2940
tggaccgtct gaacatcacc ttctacgaga accagatcac cgcattcctg ggccacaatg    3000
gagctgggaa aaccaccacc ttgtccatcc tgacgggtct gttgccacca acctctggga    3060
ctgtgctcgt tgggggaagg gacattgaaa ccagcctgga tgcagtccgg cagagccttg    3120
gcatgtgtcc acagcacaac atcctgttcc accactcac ggtggctgag cacatgctgt     3180
tctatgccca gctgaaagga aagtcccagg aggaggccca gctggagatg gaagccatgt    3240
tggaggacac aggcctccac cacaagcgga tgaagaggc tcaggaccta tcaggtggca     3300
tgcagagaaa gctgtcggtt gccattgcct tgtgggaga tgccaaggtg gtgattctgg     3360
acgaacccac ctctggggtg gaccttact cgagacgctc aatctgggat ctgctcctga     3420
agtatcgctc aggcagaacc atcatcatgt ccactcacca catggacgag gccgacctcc    3480
ttggggaccg cattgccatc attgcccagg aaggctcta ctgctcaggc accccactct     3540
tcctgaagaa ctgctttggc acaggcttgt acttaacctt ggtgcgcaag atgaaaaaca    3600
tccagagcca aggaaaggc agtgagggga cctgcagctg ctcgtctaag gtttctcca     3660 ccacgtgtcc agcccacgtc gatgacctaa ctccagaaca agtcctggat ggggatgtaa    3720
atgagctgat ggatgtagtt ctccaccatg ttccagaggc aaagctggtg gagtgcattg    3780
gtcaagaact tatcttcctt cttccaaata gaacttcaa gcacagagca tatgccagcc     3840
ttttcagaga gctggaggag acgctggctg accttggtct cagcagtttt ggaatttctg    3900 acactccccct ggaagagatt tttctgaagg tcacggagga ttctgattca ggacctctgt   3960
```

```
ttgcgggtgg cgctcagcag aaaagagaaa acgtcaaccc ccgacacccc tgcttgggtc    4020
ccagagagaa ggctggacag acaccccagg actccaatgt ctgctcccca ggggcgccgg    4080
ctgctcaccc agagggccag cctcccccag agccagagtg cccaggcccg cagctcaaca    4140
cggggacaca gctggtcctc cagcatgtgc aggcgctgct ggtcaagaga ttccaacaca    4200
ccatccgcag ccacaaggac ttcctggcgc agatcgtgct cccggctacc tttgtgtttt    4260
tggctctgat gctttctatt gttatccctc cttttggcga ataccccgct ttgacccttc    4320 accctggat atatgggcag cagtacacct tcttcagcat ggatgaacca ggcagtgagc    4380
agttcacggt acttgcagac gtcctcctga ataagccagg cttggcaac cgctgcctga    4440 aggaagggtg gcttccggag taccctgtg caactcaac ccctggaag actccttctg    4500 tgtccccaaa catcacccag ctgttccaga agcagaaatg acacaggtc aacccttcac    4560 catcctgcag gtgcagcacc agggagaagc tcaccatgct gccagagtgc cccgagggtg    4620 ccggggcct cccgccccc cagagaacac agcgcagcac ggaaattcta caagacctga    4680
cggacaggaa catctccgac ttcttggtaa aaacgtatcc tgctcttata agaagcagct    4740
taaagagcaa attctgggtc aatgaacaga ggtatggagg aatttccatt ggaggaaagc    4800
tcccagtcgt ccccatcacg ggggaagcac ttgttgggtt tttaagcgac cttggccgga    4860
tcatgaatgt gagcgggggc cctatcacta gagaggcctc taaagaaata cctgatttcc    4920
ttaaacatct agaaactgaa gacaacatta aggtgtggtt taataacaaa ggctggcatg    4980
ccctggtcag ctttctcaat gtggcccaca cgccatctt acgggccagc ctgcctaagg    5040
acaggagccc cgaggagtat ggaatcaccg tcattagcca accctgaac ctgaccaagg    5100 agcagctctc agagattaca gtgctgacca cttcagtgga tgctgtggtt gccatctgcg    5160
tgattttctc catgtccttc gtcccagcca gctttgtcct ttatttgatc caggagcggg    5220
tgaacaaatc caagcacctc cagtttatca gtggagtgag ccccaccacc tactgggtga    5280
ccaacttcct ctgggacatc atgaattatt ccgtgagtgc tgggctggtg gtgggcatct    5340
tcatcgggtt tcagaagaaa gcctacactt ctccagaaaa ccttcctgcc cttgtggcac    5400
tgctcctgct gtatgatgg gcggtcattc ccatgatgta cccagcatcc ttcctgtttg    5460
atgtccccag cacagcctat gtggctttat cttgtgctaa tctgttcatc ggcatcaaca    5520
gcagtgctat taccttcatc ttggaattat ttgagaataa ccggacgctg ctcaggttca    5580
acgccgtgct gaggaagctg ctcattgtct tcccccactt ctgcctgggc cggggcctca    5640
ttgaccttgc actgagccag gctgtgacag atgtctatgc ccggtttggt gaggagcact    5700
ctgcaaatcc gttccactgg gacctgattg gaagaacct gtttgccatg gtggtggaag    5760
gggtggtgta cttcctcctg accctgctgg tccagcgcca cttcttcctc tcccaatgga    5820
ttgccgagcc cactaaggag cccattgttg atgaagatga tgatgtggct gaagaaagac    5880
aaagaattat tactggtgga aataaaactg acatcttaag gctacatgaa ctaaccaaga    5940
tttatccagg cacctccagc ccagcagtgg acaggctgtg tgtcggagtt cgccctggag    6000
agtgctttgg cctcctggga gtgaatggtg ccggcaaaac aaccacattc aagatgctca    6060
ctggggacac cacagtgacc tcaggggatg ccaccgtagc aggcaagagt attttaacca    6120
atatttctga agtccatcaa aatatgggct actgtcctca gtttgatgca attgatgagc    6180
tgctcacagg acgagaacat ctttaccttt atgcccggct tcgaggtgta ccagcagaag    6240
aaatcgaaaa ggttgcaaac tggagtatta agagcctggg cctgactgtc tacgccgact    6300
gcctggctgg cacgtacagt gggggcaaca agcggaaact ctccacagcc atcgcactca    6360
```

```
ttggctgccc accgctggtg ctgctggatg agcccaccac agggatggac ccccaggcac    6420
gccgcatgct gtggaacgtc atcgtgagca tcatcagaga agggagggct gtggtcctca    6480
catcccacag catggaagaa tgtgaggcac tgtgtacccg gctggccatc atggtaaagg    6540
gcgcctttcg atgtatgggc accattcagc atctcaagtc caaatttgga gatggctata    6600
tcgtcacaat gaagatcaaa tccccgaagg acgacctgct cctgacctg aaccctgtgg     6660
agcagttctt ccaggggaac ttcccaggca gtgtgcagag ggagaggcac tacaacatgc    6720
tccagttcca ggtctcctcc tcctccctgg cgaggatctt ccagctcctc ctctcccaca    6780
aggacagcct gctcatcgag gagtactcag tcacacagac cacactggac caggtgtttg    6840
taaattttgc taaacagcag actgaaagtc atgacctccc tctgcaccct cgagctgctg    6900
gagccagtcg acaagcccag gactgatctt tcacaccgct cgttcctgca gccagaaagg    6960
aactctgggc agctggaggc gcaggagcct gtgcccatat ggtcatccaa atggactggc    7020
cagcgtaaat gaccccactg cagcagaaaa caaacacacg aggagcatgc agcgaattca    7080
gaaagaggtc tttcagaagg aaaccgaaac tgacttgctc acctggaaca cctgatggtg    7140
aaaccaaaca aatacaaaat ccttctccag accccagaac tagaaacccc gggccatccc    7200
actagcagct ttggcctcca tattgctctc atttcaagca gatctgcttt tctgcatgtt    7260
tgtctgtgtg tctgcgttgt gtgtgatttt catggaaaaa taaatgcaa atgcactcat    7320
cacaaa                                                              7326
```

<210> SEQ ID NO 13
<211> LENGTH: 2273
<212> TYPE: PRT
<213> ORGANISM: Homo sapiens

<400> SEQUENCE: 13

```
Met Gly Phe Val Arg Gln Ile Gln Leu Leu Leu Trp Lys Asn Trp Thr
1               5                   10                  15

Leu Arg Lys Arg Gln Lys Ile Arg Phe Val Val Glu Leu Val Trp Pro
            20                  25                  30

Leu Ser Leu Phe Leu Val Leu Ile Trp Leu Arg Asn Ala Asn Pro Leu
        35                  40                  45

Tyr Ser His His Glu Cys His Phe Pro Asn Lys Ala Met Pro Ser Ala
    50                  55                  60

Gly Met Leu Pro Trp Leu Gln Gly Ile Phe Cys Asn Val Asn Asn Pro
65                  70                  75                  80

Cys Phe Gln Ser Pro Thr Pro Gly Glu Ser Pro Gly Ile Val Ser Asn
                85                  90                  95

Tyr Asn Asn Ser Ile Leu Ala Arg Val Tyr Arg Asp Phe Gln Glu Leu
            100                 105                 110

Leu Met Asn Ala Pro Glu Ser Gln His Leu Gly Arg Ile Trp Thr Glu
        115                 120                 125

Leu His Ile Leu Ser Gln Phe Met Asp Thr Leu Arg Thr His Pro Glu
    130                 135                 140

Arg Ile Ala Gly Arg Gly Ile Arg Ile Arg Asp Ile Leu Lys Asp Glu
145                 150                 155                 160

Glu Thr Leu Thr Leu Phe Leu Ile Lys Asn Ile Gly Leu Ser Asp Ser
                165                 170                 175

Val Val Tyr Leu Leu Ile Asn Ser Gln Val Arg Pro Glu Gln Phe Ala
            180                 185                 190
```

```
His Gly Val Pro Asp Leu Ala Leu Lys Asp Ile Ala Cys Ser Glu Ala
            195                 200                 205

Leu Leu Glu Arg Phe Ile Ile Phe Ser Gln Arg Gly Ala Lys Thr
210                 215                 220

Val Arg Tyr Ala Leu Cys Ser Leu Ser Gln Gly Thr Leu Gln Trp Ile
225                 230                 235                 240

Glu Asp Thr Leu Tyr Ala Asn Val Asp Phe Phe Lys Leu Phe Arg Val
                245                 250                 255

Leu Pro Thr Leu Leu Asp Ser Arg Ser Gln Gly Ile Asn Leu Arg Ser
                260                 265                 270

Trp Gly Gly Ile Leu Ser Asp Met Ser Pro Arg Ile Gln Glu Phe Ile
            275                 280                 285

His Arg Pro Ser Met Gln Asp Leu Leu Trp Val Thr Arg Pro Leu Met
290                 295                 300

Gln Asn Gly Gly Pro Glu Thr Phe Thr Lys Leu Met Gly Ile Leu Ser
305                 310                 315                 320

Asp Leu Leu Cys Gly Tyr Pro Glu Gly Gly Ser Arg Val Leu Ser
                325                 330                 335

Phe Asn Trp Tyr Glu Asp Asn Asn Tyr Lys Ala Phe Leu Gly Ile Asp
                340                 345                 350

Ser Thr Arg Lys Asp Pro Ile Tyr Ser Tyr Asp Arg Arg Thr Thr Ser
            355                 360                 365

Phe Cys Asn Ala Leu Ile Gln Ser Leu Glu Ser Asn Pro Leu Thr Lys
            370                 375                 380

Ile Ala Trp Arg Ala Ala Lys Pro Leu Leu Met Gly Lys Ile Leu Tyr
385                 390                 395                 400

Thr Pro Asp Ser Pro Ala Ala Arg Arg Ile Leu Lys Asn Ala Asn Ser
                405                 410                 415

Thr Phe Glu Glu Leu Glu His Val Arg Lys Leu Val Lys Ala Trp Glu
            420                 425                 430

Glu Val Gly Pro Gln Ile Trp Tyr Phe Asp Asn Ser Thr Gln Met
            435                 440                 445

Asn Met Ile Arg Asp Thr Leu Gly Asn Pro Thr Val Lys Asp Phe Leu
450                 455                 460

Asn Arg Gln Leu Gly Glu Gly Ile Thr Ala Glu Ala Ile Leu Asn
465                 470                 475                 480

Phe Leu Tyr Lys Gly Pro Arg Glu Ser Gln Ala Asp Asp Met Ala Asn
                485                 490                 495

Phe Asp Trp Arg Asp Ile Phe Asn Ile Thr Asp Arg Thr Leu Arg Leu
                500                 505                 510

Val Asn Gln Tyr Leu Glu Cys Leu Val Leu Asp Lys Phe Glu Ser Tyr
            515                 520                 525

Asn Asp Glu Thr Gln Leu Thr Gln Arg Ala Leu Ser Leu Leu Glu Glu
            530                 535                 540

Asn Met Phe Trp Ala Gly Val Val Phe Pro Asp Met Tyr Pro Trp Thr
545                 550                 555                 560

Ser Ser Leu Pro Pro His Val Lys Tyr Lys Ile Arg Met Asp Ile Asp
                565                 570                 575

Val Val Glu Lys Thr Asn Lys Ile Lys Asp Arg Tyr Trp Asp Ser Gly
            580                 585                 590

Pro Arg Ala Asp Pro Val Glu Asp Phe Arg Tyr Ile Trp Gly Gly Phe
            595                 600                 605

Ala Tyr Leu Gln Asp Met Val Glu Gln Gly Ile Thr Arg Ser Gln Val
```

```
            610                 615                 620
Gln Ala Glu Ala Pro Val Gly Ile Tyr Leu Gln Gln Met Pro Tyr Pro
625                 630                 635                 640

Cys Phe Val Asp Asp Ser Phe Met Ile Ile Leu Asn Arg Cys Phe Pro
                    645                 650                 655

Ile Phe Met Val Leu Ala Trp Ile Tyr Ser Val Ser Met Thr Val Lys
                660                 665                 670

Ser Ile Val Leu Glu Lys Glu Leu Arg Leu Lys Glu Thr Leu Lys Asn
                675                 680                 685

Gln Gly Val Ser Asn Ala Val Ile Trp Cys Thr Trp Phe Leu Asp Ser
690                 695                 700

Phe Ser Ile Met Ser Met Ser Ile Phe Leu Leu Thr Ile Phe Ile Met
705                 710                 715                 720

His Gly Arg Ile Leu His Tyr Ser Asp Pro Phe Ile Leu Phe Leu Phe
                    725                 730                 735

Leu Leu Ala Phe Ser Thr Ala Thr Ile Met Leu Cys Phe Leu Leu Ser
                740                 745                 750

Thr Phe Phe Ser Lys Ala Ser Leu Ala Ala Ala Cys Ser Gly Val Ile
                755                 760                 765

Tyr Phe Thr Leu Tyr Leu Pro His Ile Leu Cys Phe Ala Trp Gln Asp
770                 775                 780

Arg Met Thr Ala Glu Leu Lys Lys Ala Val Ser Leu Leu Ser Pro Val
785                 790                 795                 800

Ala Phe Gly Phe Gly Thr Glu Tyr Leu Val Arg Phe Glu Glu Gln Gly
                    805                 810                 815

Leu Gly Leu Gln Trp Ser Asn Ile Gly Asn Ser Pro Thr Glu Gly Asp
                820                 825                 830

Glu Phe Ser Phe Leu Leu Ser Met Gln Met Met Leu Leu Asp Ala Ala
                835                 840                 845

Val Tyr Gly Leu Leu Ala Trp Tyr Leu Asp Gln Val Phe Pro Gly Asp
850                 855                 860

Tyr Gly Thr Pro Leu Pro Trp Tyr Phe Leu Leu Gln Glu Ser Tyr Trp
865                 870                 875                 880

Leu Gly Gly Glu Gly Cys Ser Thr Arg Glu Glu Arg Ala Leu Glu Lys
                    885                 890                 895

Thr Glu Pro Leu Thr Glu Glu Thr Glu Asp Pro Glu His Pro Glu Gly
                900                 905                 910

Ile His Asp Ser Phe Phe Glu Arg Glu His Pro Gly Trp Val Pro Gly
                915                 920                 925

Val Cys Val Lys Asn Leu Val Lys Ile Phe Glu Pro Cys Gly Arg Pro
930                 935                 940

Ala Val Asp Arg Leu Asn Ile Thr Phe Tyr Glu Asn Gln Ile Thr Ala
945                 950                 955                 960

Phe Leu Gly His Asn Gly Ala Gly Lys Thr Thr Thr Leu Ser Ile Leu
                    965                 970                 975

Thr Gly Leu Leu Pro Pro Thr Ser Gly Thr Val Leu Val Gly Gly Arg
                980                 985                 990

Asp Ile Glu Thr Ser Leu Asp Ala Val Arg Gln Ser Leu Gly Met Cys
                995                 1000                1005

Pro Gln His Asn Ile Leu Phe His His Leu Thr Val Ala Glu His
    1010                1015                1020

Met Leu Phe Tyr Ala Gln Leu Lys Gly Lys Ser Gln Glu Glu Ala
    1025                1030                1035
```

-continued

Gln Leu Glu Met Glu Ala Met Leu Glu Asp Thr Gly Leu His His
    1040            1045                1050

Lys Arg Asn Glu Glu Ala Gln Asp Leu Ser Gly Gly Met Gln Arg
    1055            1060                1065

Lys Leu Ser Val Ala Ile Ala Phe Val Gly Asp Ala Lys Val Val
    1070            1075                1080

Ile Leu Asp Glu Pro Thr Ser Gly Val Asp Pro Tyr Ser Arg Arg
    1085            1090                1095

Ser Ile Trp Asp Leu Leu Leu Lys Tyr Arg Ser Gly Arg Thr Ile
    1100            1105                1110

Ile Met Ser Thr His His Met Asp Glu Ala Asp Leu Leu Gly Asp
    1115            1120                1125

Arg Ile Ala Ile Ile Ala Gln Gly Arg Leu Tyr Cys Ser Gly Thr
    1130            1135                1140

Pro Leu Phe Leu Lys Asn Cys Phe Gly Thr Gly Leu Tyr Leu Thr
    1145            1150                1155

Leu Val Arg Lys Met Lys Asn Ile Gln Ser Gln Arg Lys Gly Ser
    1160            1165                1170

Glu Gly Thr Cys Ser Cys Ser Lys Gly Phe Ser Thr Thr Cys
    1175            1180                1185

Pro Ala His Val Asp Asp Leu Thr Pro Glu Gln Val Leu Asp Gly
    1190            1195                1200

Asp Val Asn Glu Leu Met Asp Val Val Leu His His Val Pro Glu
    1205            1210                1215

Ala Lys Leu Val Glu Cys Ile Gly Gln Glu Leu Ile Phe Leu Leu
    1220            1225                1230

Pro Asn Lys Asn Phe Lys His Arg Ala Tyr Ala Ser Leu Phe Arg
    1235            1240                1245

Glu Leu Glu Glu Thr Leu Ala Asp Leu Gly Leu Ser Ser Phe Gly
    1250            1255                1260

Ile Ser Asp Thr Pro Leu Glu Glu Ile Phe Leu Lys Val Thr Glu
    1265            1270                1275

Asp Ser Asp Ser Gly Pro Leu Phe Ala Gly Gly Ala Gln Gln Lys
    1280            1285                1290

Arg Glu Asn Val Asn Pro Arg His Pro Cys Leu Gly Pro Arg Glu
    1295            1300                1305

Lys Ala Gly Gln Thr Pro Gln Asp Ser Asn Val Cys Ser Pro Gly
    1310            1315                1320

Ala Pro Ala Ala His Pro Glu Gly Gln Pro Pro Glu Pro Glu
    1325            1330                1335

Cys Pro Gly Pro Gln Leu Asn Thr Gly Thr Gln Leu Val Leu Gln
    1340            1345                1350

His Val Gln Ala Leu Leu Val Lys Arg Phe Gln His Thr Ile Arg
    1355            1360                1365

Ser His Lys Asp Phe Leu Ala Gln Ile Val Leu Pro Ala Thr Phe
    1370            1375                1380

Val Phe Leu Ala Leu Met Leu Ser Ile Val Ile Pro Pro Phe Gly
    1385            1390                1395

Glu Tyr Pro Ala Leu Thr Leu His Pro Trp Ile Tyr Gly Gln Gln
    1400            1405                1410

Tyr Thr Phe Phe Ser Met Asp Glu Pro Gly Ser Glu Gln Phe Thr
    1415            1420                1425

```
Val Leu Ala Asp Val Leu Leu Asn Lys Pro Gly Phe Gly Asn Arg
1430                1435                1440

Cys Leu Lys Glu Gly Trp Leu Pro Glu Tyr Pro Cys Gly Asn Ser
1445                1450                1455

Thr Pro Trp Lys Thr Pro Ser Val Ser Pro Asn Ile Thr Gln Leu
1460                1465                1470

Phe Gln Lys Gln Lys Trp Thr Gln Val Asn Pro Ser Pro Ser Cys
1475                1480                1485

Arg Cys Ser Thr Arg Glu Lys Leu Thr Met Leu Pro Glu Cys Pro
1490                1495                1500

Glu Gly Ala Gly Gly Leu Pro Pro Pro Gln Arg Thr Gln Arg Ser
1505                1510                1515

Thr Glu Ile Leu Gln Asp Leu Thr Asp Arg Asn Ile Ser Asp Phe
1520                1525                1530

Leu Val Lys Thr Tyr Pro Ala Leu Ile Arg Ser Ser Leu Lys Ser
1535                1540                1545

Lys Phe Trp Val Asn Glu Gln Arg Tyr Gly Gly Ile Ser Ile Gly
1550                1555                1560

Gly Lys Leu Pro Val Val Pro Ile Thr Gly Glu Ala Leu Val Gly
1565                1570                1575

Phe Leu Ser Asp Leu Gly Arg Ile Met Asn Val Ser Gly Gly Pro
1580                1585                1590

Ile Thr Arg Glu Ala Ser Lys Glu Ile Pro Asp Phe Leu Lys His
1595                1600                1605

Leu Glu Thr Glu Asp Asn Ile Lys Val Trp Phe Asn Asn Lys Gly
1610                1615                1620

Trp His Ala Leu Val Ser Phe Leu Asn Val Ala His Asn Ala Ile
1625                1630                1635

Leu Arg Ala Ser Leu Pro Lys Asp Arg Ser Pro Glu Glu Tyr Gly
1640                1645                1650

Ile Thr Val Ile Ser Gln Pro Leu Asn Leu Thr Lys Glu Gln Leu
1655                1660                1665

Ser Glu Ile Thr Val Leu Thr Thr Ser Val Asp Ala Val Val Ala
1670                1675                1680

Ile Cys Val Ile Phe Ser Met Ser Phe Val Pro Ala Ser Phe Val
1685                1690                1695

Leu Tyr Leu Ile Gln Glu Arg Val Asn Lys Ser Lys His Leu Gln
1700                1705                1710

Phe Ile Ser Gly Val Ser Pro Thr Thr Tyr Trp Val Thr Asn Phe
1715                1720                1725

Leu Trp Asp Ile Met Asn Tyr Ser Val Ser Ala Gly Leu Val Val
1730                1735                1740

Gly Ile Phe Ile Gly Phe Gln Lys Lys Ala Tyr Thr Ser Pro Glu
1745                1750                1755

Asn Leu Pro Ala Leu Val Ala Leu Leu Leu Leu Tyr Gly Trp Ala
1760                1765                1770

Val Ile Pro Met Met Tyr Pro Ala Ser Phe Leu Phe Asp Val Pro
1775                1780                1785

Ser Thr Ala Tyr Val Ala Leu Ser Cys Ala Asn Leu Phe Ile Gly
1790                1795                1800

Ile Asn Ser Ser Ala Ile Thr Phe Ile Leu Glu Leu Phe Glu Asn
1805                1810                1815

Asn Arg Thr Leu Leu Arg Phe Asn Ala Val Leu Arg Lys Leu Leu
```

-continued

```
                1820                1825                1830
Ile Val Phe Pro His Phe Cys Leu Gly Arg Gly Leu Ile Asp Leu
    1835                1840                1845
Ala Leu Ser Gln Ala Val Thr Asp Val Tyr Ala Arg Phe Gly Glu
    1850                1855                1860
Glu His Ser Ala Asn Pro Phe His Trp Asp Leu Ile Gly Lys Asn
    1865                1870                1875
Leu Phe Ala Met Val Val Glu Gly Val Val Tyr Phe Leu Leu Thr
    1880                1885                1890
Leu Leu Val Gln Arg His Phe Phe Leu Ser Gln Trp Ile Ala Glu
    1895                1900                1905
Pro Thr Lys Glu Pro Ile Val Asp Glu Asp Asp Val Ala Glu
    1910                1915                1920
Glu Arg Gln Arg Ile Ile Thr Gly Gly Asn Lys Thr Asp Ile Leu
    1925                1930                1935
Arg Leu His Glu Leu Thr Lys Ile Tyr Pro Gly Thr Ser Ser Pro
    1940                1945                1950
Ala Val Asp Arg Leu Cys Val Gly Val Arg Pro Gly Glu Cys Phe
    1955                1960                1965
Gly Leu Leu Gly Val Asn Gly Ala Gly Lys Thr Thr Thr Phe Lys
    1970                1975                1980
Met Leu Thr Gly Asp Thr Thr Val Thr Ser Gly Asp Ala Thr Val
    1985                1990                1995
Ala Gly Lys Ser Ile Leu Thr Asn Ile Ser Glu Val His Gln Asn
    2000                2005                2010
Met Gly Tyr Cys Pro Gln Phe Asp Ala Ile Asp Glu Leu Leu Thr
    2015                2020                2025
Gly Arg Glu His Leu Tyr Leu Tyr Ala Arg Leu Arg Gly Val Pro
    2030                2035                2040
Ala Glu Glu Ile Glu Lys Val Ala Asn Trp Ser Ile Lys Ser Leu
    2045                2050                2055
Gly Leu Thr Val Tyr Ala Asp Cys Leu Ala Gly Thr Tyr Ser Gly
    2060                2065                2070
Gly Asn Lys Arg Lys Leu Ser Thr Ala Ile Ala Leu Ile Gly Cys
    2075                2080                2085
Pro Pro Leu Val Leu Leu Asp Glu Pro Thr Thr Gly Met Asp Pro
    2090                2095                2100
Gln Ala Arg Arg Met Leu Trp Asn Val Ile Val Ser Ile Ile Arg
    2105                2110                2115
Glu Gly Arg Ala Val Val Leu Thr Ser His Ser Met Glu Glu Cys
    2120                2125                2130
Glu Ala Leu Cys Thr Arg Leu Ala Ile Met Val Lys Gly Ala Phe
    2135                2140                2145
Arg Cys Met Gly Thr Ile Gln His Leu Lys Ser Lys Phe Gly Asp
    2150                2155                2160
Gly Tyr Ile Val Thr Met Lys Ile Lys Ser Pro Lys Asp Asp Leu
    2165                2170                2175
Leu Pro Asp Leu Asn Pro Val Glu Gln Phe Phe Gln Gly Asn Phe
    2180                2185                2190
Pro Gly Ser Val Gln Arg Glu Arg His Tyr Asn Met Leu Gln Phe
    2195                2200                2205
Gln Val Ser Ser Ser Ser Leu Ala Arg Ile Phe Gln Leu Leu Leu
    2210                2215                2220
```

Ser His Lys Asp Ser Leu Leu Ile Glu Glu Tyr Ser Val Thr Gln
    2225                2230                2235

Thr Thr Leu Asp Gln Val Phe Val Asn Phe Ala Lys Gln Gln Thr
    2240                2245                2250

Glu Ser His Asp Leu Pro Leu His Pro Arg Ala Ala Gly Ala Ser
    2255                2260                2265

Arg Gln Ala Gln Asp
    2270

<210> SEQ ID NO 14
<211> LENGTH: 2608
<212> TYPE: DNA
<213> ORGANISM: Homo sapiens

<400> SEQUENCE: 14

| | | |
|---|---|---|
| tccttcttca ttctgcagtt ggtgccagaa ctctggatcc tgaactggaa gaaaatgtct | 60 |
| atccaggttg agcatcctgc tggtggttac aagaaactgt ttgaaactgt ggaggaactg | 120 |
| tcctcgccgc tcacagctca tgtaacaggc aggatccccc tctggctcac cggcagtctc | 180 |
| cttcgatgtg ggccaggact cttttgaagtt ggatctgagc catttttacca cctgtttgat | 240 |
| gggcaagccc tcctgcacaa gtttgacttt aaagaaggac atgtcacata ccacagaagg | 300 |
| ttcatccgca ctgatgctta cgtacgggca atgactgaga aaaggatcgt cataacagaa | 360 |
| tttggcacct gtgctttccc agatccctgc aagaatatat tttccaggtt ttttttcttac | 420 |
| tttcgaggag tagaggttac tgacaatgcc cttgttaatg tctacccagt gggggaagat | 480 |
| tactacgctt gcacagagac caactttatt acaaagatta tccagagac cttggagaca | 540 |
| attaagcagg ttgatctttg caactatgtc tctgtcaatg gggccactgc tcaccccccac | 600 |
| attgaaaatg atggaaccgt ttacaatatt ggtaattgct ttggaaaaaa ttttttcaatt | 660 |
| gcctacaaca ttgtaaagat cccaccactg caagcagaca aggaagatcc aataagcaag | 720 |
| tcagagatcg ttgtacaatt cccctgcagt gaccgattca agccatctta cgttcatagt | 780 |
| tttggtctga ctcccaacta tatcgtttttt gtggagacac cagtcaaaat taacctgttc | 840 |
| aagttccttt cttcatggag tctttgggga gccaactaca tggattgttt tgagtccaat | 900 |
| gaaaccatgg gggtttggct tcatattgct gacaaaaaaa ggaaaaagta cctcaataat | 960 |
| aaatacagaa cttctccttt caacctcttc catcacatca acacctatga agacaatggg | 1020 |
| tttctgattg tggatctctg ctgctggaaa ggatttgagt ttgtttataa ttacttatat | 1080 |
| ttagccaatt tacgtgagaa ctgggaagag gtgaaaaaaa atgccagaaa ggctccccaa | 1140 |
| cctgaagtta ggagatatgt acttcctttg aatattgaca aggctgacac aggcaagaat | 1200 |
| ttagtcacgc tccccaatac aactgccact gcaattctgt gcagtgacga gactatctgg | 1260 |
| ctggagcctg aagttctctt ttcagggcct cgtcaagcat ttgagttttcc tcaaatcaat | 1320 |
| taccagaagt attgtgggaa accttacaca tatgcgtatg acttggcttt gaatcacttt | 1380 |
| gttccagata ggctctgtaa gctgaatgtc aaaactaaag aaacttgggt ttggcaagag | 1440 |
| cctgattcat acccatcaga acccatcttt gtttctcacc cagatgcctt ggaagaagat | 1500 |
| gatggtgtag ttctgagtgt ggtggtgagc ccaggagcag acaaaagcc tgcttatctc | 1560 |
| ctgattctga atgccaagga cttaagtgaa gttgcccggg ctgaagtgga gattaacatc | 1620 |
| cctgtcacct ttcatggact gttcaaaaaa tcttgagcat actccagcaa gatatgtttt | 1680 |
| tggtagcaaa actgagaaaa tcagcttcag gtctgcaatc aaattctgtt caattttagc | 1740 |

```
ctgctatatg tcatggtttt aacttgcaga tgcgcacaat tttgcaatgt tttacagaaa    1800
gcactgagtt gagcaagcaa ttcctttatt taaaaaaaaa agtacgtatt tagataatca    1860
tacttcctct gtgagacagg ccataactga aaaactctta aatatttagc aatcaaatag    1920
gaaatgaatg tggacttact aaatggcttt taattcctat tataagagca tattttaggt    1980
acctatctgc tccaattata tttttaacat ttaaaaacca aagtcctcta cacttgattt    2040
atattatatg tggctttgct gagtcaagga agtatcatgc ataaggctt aattactaaa     2100 tgtcaaacca aacttttcct caaaccaggg actatcatct aagattaatt acagtaatta    2160
ttttgcgtat acgtaactgc tcaaagatta tgaatcttat gaatgttaac ctttccgttt    2220
attacaagca agtactatta tttctgattt tataataaga aaatctgtgt ttaatcaact    2280
gaggcctctc aaccaaataa catctcagag attaagttat atattaaaag cttatgtaac    2340
ataaaagcaa gtacatatag tagtgactat atttaaaaaa acagcataaa atgcttaaaa    2400
atgtaatatt tactaaaatc agattatggg ataatgttgc aggattatac tttattgcat    2460
cttttttgtt taattgtatt taagcattgt gcaatcactt gggaaaaata ttaaattatt    2520
aacattgagg tattaataca ttttaagcct tttgttttta aatttctttt cttccagaga    2580
ttgtttaaaa ataaatattg acaaaaat                                      2608

<210> SEQ ID NO 15
<211> LENGTH: 533
<212> TYPE: PRT
<213> ORGANISM: Homo sapiens

<400> SEQUENCE: 15

Met Ser Ile Gln Val Glu His Pro Ala Gly Gly Tyr Lys Lys Leu Phe
1               5                   10                  15

Glu Thr Val Glu Glu Leu Ser Ser Pro Leu Thr Ala His Val Thr Gly
            20                  25                  30

Arg Ile Pro Leu Trp Leu Thr Gly Ser Leu Leu Arg Cys Gly Pro Gly
        35                  40                  45

Leu Phe Glu Val Gly Ser Glu Pro Phe Tyr His Leu Phe Asp Gly Gln
    50                  55                  60

Ala Leu Leu His Lys Phe Asp Phe Lys Glu Gly His Val Thr Tyr His
65                  70                  75                  80

Arg Arg Phe Ile Arg Thr Asp Ala Tyr Val Arg Ala Met Thr Glu Lys
                85                  90                  95

Arg Ile Val Ile Thr Glu Phe Gly Thr Cys Ala Phe Pro Asp Pro Cys
            100                 105                 110

Lys Asn Ile Phe Ser Arg Phe Ser Tyr Phe Arg Gly Val Glu Val
        115                 120                 125

Thr Asp Asn Ala Leu Val Asn Val Tyr Pro Val Gly Glu Asp Tyr Tyr
    130                 135                 140

Ala Cys Thr Glu Thr Asn Phe Ile Thr Lys Ile Asn Pro Glu Thr Leu
145                 150                 155                 160

Glu Thr Ile Lys Gln Val Asp Leu Cys Asn Tyr Val Ser Val Asn Gly
                165                 170                 175

Ala Thr Ala His Pro His Ile Glu Asn Asp Gly Thr Val Tyr Asn Ile
            180                 185                 190

Gly Asn Cys Phe Gly Lys Asn Phe Ser Ile Ala Tyr Asn Ile Val Lys
        195                 200                 205

Ile Pro Pro Leu Gln Ala Asp Lys Glu Asp Pro Ile Ser Lys Ser Glu
    210                 215                 220
```

Ile Val Val Gln Phe Pro Cys Ser Asp Arg Phe Lys Pro Ser Tyr Val
225                 230                 235                 240

His Ser Phe Gly Leu Thr Pro Asn Tyr Ile Val Phe Val Glu Thr Pro
            245                 250                 255

Val Lys Ile Asn Leu Phe Lys Phe Leu Ser Ser Trp Ser Leu Trp Gly
                260                 265                 270

Ala Asn Tyr Met Asp Cys Phe Glu Ser Asn Glu Thr Met Gly Val Trp
            275                 280                 285

Leu His Ile Ala Asp Lys Lys Arg Lys Lys Tyr Leu Asn Asn Lys Tyr
        290                 295                 300

Arg Thr Ser Pro Phe Asn Leu Phe His His Ile Asn Thr Tyr Glu Asp
305                 310                 315                 320

Asn Gly Phe Leu Ile Val Asp Leu Cys Cys Trp Lys Gly Phe Glu Phe
                325                 330                 335

Val Tyr Asn Tyr Leu Tyr Leu Ala Asn Leu Arg Glu Asn Trp Glu Glu
            340                 345                 350

Val Lys Lys Asn Ala Arg Lys Ala Pro Gln Pro Glu Val Arg Arg Tyr
        355                 360                 365

Val Leu Pro Leu Asn Ile Asp Lys Ala Asp Thr Gly Lys Asn Leu Val
    370                 375                 380

Thr Leu Pro Asn Thr Thr Ala Thr Ala Ile Leu Cys Ser Asp Glu Thr
385                 390                 395                 400

Ile Trp Leu Glu Pro Glu Val Leu Phe Ser Gly Pro Arg Gln Ala Phe
                405                 410                 415

Glu Phe Pro Gln Ile Asn Tyr Gln Lys Tyr Cys Gly Lys Pro Tyr Thr
            420                 425                 430

Tyr Ala Tyr Gly Leu Gly Leu Asn His Phe Val Pro Asp Arg Leu Cys
        435                 440                 445

Lys Leu Asn Val Lys Thr Lys Glu Thr Trp Val Trp Gln Glu Pro Asp
    450                 455                 460

Ser Tyr Pro Ser Glu Pro Ile Phe Val Ser His Pro Asp Ala Leu Glu
465                 470                 475                 480

Glu Asp Asp Gly Val Val Leu Ser Val Val Ser Pro Gly Ala Gly
                485                 490                 495

Gln Lys Pro Ala Tyr Leu Leu Ile Leu Asn Ala Lys Asp Leu Ser Glu
            500                 505                 510

Val Ala Arg Ala Glu Val Glu Ile Asn Ile Pro Val Thr Phe His Gly
        515                 520                 525

Leu Phe Lys Lys Ser
    530

<210> SEQ ID NO 16
<211> LENGTH: 1752
<212> TYPE: DNA
<213> ORGANISM: Homo sapiens

<400> SEQUENCE: 16
gagcccgatt taacggaaac tgtgggcggt gagaagttcc ttatgacaca ctaatcccaa      60
cctgctgacc ggaccacgcc tccagcggag ggaacctcta gagctccagg acattcaggt     120
accaggtagc cccaaggagg agctgccgac ctggcaggga caaccaaga ctggggttaa      180 atctcacagc ctgcaagtgg aagagaagaa cttgaaccca ggtccaactt ttgcgccaca    240
gcaggctgcc tcttggtcct gacaggaagt cacaacttgg ccctgacttc ctatcctagg    300

```
gaaggggccg gctggagagg ccaggacaga gaaagcagat cccttctttt tccaaggact    360
ctgtgtcttc cataggcaac atgtcagaag gggtgggcac gttccgcatg gtacctgaag    420
aggaacagga gctccgtgcc caactggagc agctcacaac caaggaccat ggacctgtct    480
ttggcccgtg cagccagctg ccccgccaca ccttgcagaa ggccaaggat gagctgaacg    540
agagagagga gacccgggag gaggcagtgc gagagctgca ggagatggtg caggcgcagg    600
cggcctcggg ggaggagctg gcggtggccg tggcggagag ggtgcaagag aaggacagcg    660
gcttcttcct gcgcttcatc cgcgcacgga agttcaacgt gggccgtgcc tatgagctgc    720
tcagaggcta tgtgaatttc cggctgcagt accctgagct cttt gacagc ctgtccccag    780
aggctgtccg ctgcaccatt gaagctggct accctggtgt cctctctagt cgggacaagt    840
atggccgagt ggtcatgctc ttcaacattg agaactggca agtcaagaa atcacctttg    900
atgagatctt gcaggcatat tgcttcatcc tggagaagct gctggagaat gaggaaactc    960
aaatcaatgg cttctgcatc attgagaact caagggcttt accatgcag caggctgcta   1020
gtctccggac ttcagatctc aggaagatgg tggacatgct ccaggattcc ttcccagccc   1080
ggttcaaagc catccacttc atccaccagc catggtactt caccacgacc tacaatgtgg   1140
tcaagccctt cttgaagagc aagctgcttg agagggtctt tgtccacggg gatgaccttt   1200
ctggttttcta ccaggagatc gatgagaaca tcctgccctc tgacttcggg gcacgctgc   1260
ccaagtatga tggcaaggcc gttgctgagc agctctttgg cccccaggcc caagctgaga   1320
acacagcctt ctgaaaacat ctcctgccag ctgaactgta gttagaatct ctgggcctct   1380
cctcaactgt cctggaccca aggctaggaa agggctgctt gagatgactg tggtcccccc   1440
ttagactccc taagcccgag tgagctcagg tgtcaccctg ttctcaagtt gggggatggg   1500
taataaagga gggggaattc ccttgaacaa gaagaactgg ggatagttat atttccacct   1560
gcccttgaag cttta agaca gtgattttttg tgtaaggttg tatttcaaag actcgaattc   1620
attttctcag tcatttcctt tgtaacagag ttttacgact tagagtctgt gaaaacaggc   1680
aaggagcccg ggttaaaata tccccctatt cgcccccaaa atgcaataaa agaagataaa   1740
agagagagga ta                                                       1752
```

<210> SEQ ID NO 17
<211> LENGTH: 317
<212> TYPE: PRT
<213> ORGANISM: Homo sapiens

<400> SEQUENCE: 17

```
Met Ser Glu Gly Val Gly Thr Phe Arg Met Val Pro Glu Glu Glu Gln
1               5                   10                  15

Glu Leu Arg Ala Gln Leu Glu Gln Leu Thr Thr Lys Asp His Gly Pro
            20                  25                  30

Val Phe Gly Pro Cys Ser Gln Leu Pro Arg His Thr Leu Gln Lys Ala
        35                  40                  45

Lys Asp Glu Leu Asn Glu Arg Glu Glu Thr Arg Glu Glu Ala Val Arg
    50                  55                  60

Glu Leu Gln Glu Met Val Gln Ala Gln Ala Ser Gly Glu Glu Leu
65                  70                  75                  80

Ala Val Ala Val Ala Glu Arg Val Gln Glu Lys Asp Ser Gly Phe Phe
                85                  90                  95

Leu Arg Phe Ile Arg Ala Arg Lys Phe Asn Val Gly Arg Ala Tyr Glu
            100                 105                 110
```

```
Leu Leu Arg Gly Tyr Val Asn Phe Arg Leu Gln Tyr Pro Glu Leu Phe
            115                 120                 125
Asp Ser Leu Ser Pro Glu Ala Val Arg Cys Thr Ile Glu Ala Gly Tyr
        130                 135                 140
Pro Gly Val Leu Ser Ser Arg Asp Lys Tyr Gly Arg Val Val Met Leu
145                 150                 155                 160
Phe Asn Ile Glu Asn Trp Gln Ser Gln Glu Ile Thr Phe Asp Glu Ile
                165                 170                 175
Leu Gln Ala Tyr Cys Phe Ile Leu Glu Lys Leu Leu Glu Asn Glu Glu
            180                 185                 190
Thr Gln Ile Asn Gly Phe Cys Ile Ile Glu Asn Phe Lys Gly Phe Thr
        195                 200                 205
Met Gln Gln Ala Ala Ser Leu Arg Thr Ser Asp Leu Arg Lys Met Val
210                 215                 220
Asp Met Leu Gln Asp Ser Phe Pro Ala Arg Phe Lys Ala Ile His Phe
225                 230                 235                 240
Ile His Gln Pro Trp Tyr Phe Thr Thr Thr Tyr Asn Val Val Lys Pro
                245                 250                 255
Phe Leu Lys Ser Lys Leu Leu Glu Arg Val Phe Val His Gly Asp Asp
            260                 265                 270
Leu Ser Gly Phe Tyr Gln Glu Ile Asp Glu Asn Ile Leu Pro Ser Asp
        275                 280                 285
Phe Gly Gly Thr Leu Pro Lys Tyr Asp Gly Lys Ala Val Ala Glu Gln
290                 295                 300
Leu Phe Gly Pro Gln Ala Gln Ala Glu Asn Thr Ala Phe
305                 310                 315

<210> SEQ ID NO 18
<211> LENGTH: 3027
<212> TYPE: DNA
<213> ORGANISM: Homo sapiens

<400> SEQUENCE: 18
cagcgttcag gctgcccctt cttggctggg aagggcgctg aagaaacaac gcccaggacc      60
aggactatcc cctgctcaag ctgtgattcc gagacccctg ccaccactac tgcattcacg     120
gggatcccag ctagtgggga ctcgacatgg gtagccccca gggcagctcc ctacagcttg     180
ggccatctgc acttttccca aggccctaag tctccgcctc tgggctcgtt aaggtttggg     240
gtgggagctg tgctgtggga agcaacccgg actacacttg gcaagcatgg cgctactgaa     300
agtcaagttt gaccagaaga gcgggtcaa gttggcccaa gggctctggc tcatgaactg     360
gttctccgtg ttggctggca tcatcatctt cagcctagga ctgttcctga agattgaact     420
ccgaaagagg agcgatgtga tgaataattc tgagagccat tttgtgccca actcattgat     480
agggatgggg gtgctatcct gtgtcttcaa ctcgctggct gggaagatct gctacgacgc     540
cctggaccca gccaagtatg ccagatgaa gccctggctg aagccgtacc tggctatctg     600
tgttctcttc aacatcatcc tcttccttgt ggctctctgc tgctttctgc ttcggggctc     660
gctggagaac accctgggcc aagggctcaa gaacggcatg aagtactacc gggacacaga     720
caccctggc aggtgtttca tgaagaagac catcgacatg ctgcagatcg agttcaaatg     780
ctgcggcaac aacggttttc gggactggtt tgagattcag tggatcagca atcgctacct     840
ggacttttcc tccaaagaag tcaaagatca atcaagagc aacgtggatg gccgtacct      900
ggtggacggc gtccctttca gctgctgcaa tcctagctcg ccacggccct gcatccagta     960
```

```
tcagatcacc aacaactcag cacactacag ttacgaccac cagacggagg agctcaacct      1020
gtgggtgcgt ggctgcaggg ctgccctgct gagctactac agcagcctca tgaactccat      1080
gggtgtcgtc acgctcctca tttggctctt cgaggtgacc attacaattg gctgcgcta       1140
cctacagacg tcgctggatg gtgtgtccaa ccccgaggaa tctgagagcg agagccaggg      1200
ctggctgctg gagaggagcg tgccggagac ctggaaggcc tttctggaga gtgtgaagaa      1260
gctgggcaag gcaaccagg tggaagccga gggcgcagac gcaggccagg ccccagaggc       1320
tggctgaggg ccctggggcc cctcccctcc cgaacactga gaaatagtgc actccaagaa      1380
acgtggatct ccccctcatc caactccgaa agtctgaatc tcccaaggag ggcaccatct      1440
tacagagact ctccctgacg gtggaattta agtttagggt ccctaaaagc atttgacaca      1500
cagttgttga atgactgacc caaaatgtga atgaagctaa tgtgaatgtg agtgaagctc      1560
ccttcaggcc cgctgcccta ggatatgccc tcctggtgac tcggggggctg tctcagacga    1620
ctagcccagg acccatcttt ctcacacgga tttagtccca ccctatgcc actggccgta       1680
tctgagggct gctccccttt tagaatttac ctcttatgag ctccatgttg cttcactcta      1740
tccaaagtgt cacttggtgc ataagcacag aaatctgaaa aatggccatg ttgtcttttt      1800
ttttttttt taatgccaag attgacaggt tggccgtttg cttaatgcca gaagttgggg      1860
gaaagttacg cttttctaag aataatggac tcttaaggca ttgagggctc taaacaggat      1920
tctttaatca tggagcaaga gaatttcaag gcagggggatt ttatccccca ccaaaaacac    1980
agtgaaaggc ctgcttttgt gtcccattca catgccctcg gtcactgagt ctggagtgaa      2040
ccacggggttg aggaagtcag gctgttggcg tgtcccagca ccacaccacc cctaaagtgc     2100
caggtgatct cctgtggctc atcggtggaa gcagtggggt aggctgctgc cctgctgtgg      2160
aagaggagca caatcagac atgagtccac ccttttggaga ccaggcctca gctcttggtg      2220
ggcccaggga cacccacaca ggtggccatc acagccccat ggacaacact aattgtccac      2280
agcaaagggc aaggaatcct ctgggagctt cttccgtttc ttcccccag atacccatct       2340
tgaaaaacac tatttctgga atgcttctgc atcaaggag attctttgag atagcccatc       2400
ttcctgagct agcaaataca ggagttttca ctttctttag gaaagagaag ctttcagggg      2460
aaggagagaa tgattttgct gacttcccaa gccctggtga ccagaccaag gcagggccca      2520
gcataattcc tccagttgga tgaacattca agagagctcg ttcctacctg gctggagacc      2580
gaggccagaa ggcaaaaacc agaaagggaa cagtccataa cttacctctg cttctgaccg      2640
atggtgtttg ggataggtt actttggact gagtttgggt tctctgctgt cctaagaact       2700
tcagtgtaga gaaaataaga cttctggtgc tgctggggta tgttctgggc ttaattcccc      2760
caagcagaag accagatcca agatgtttgg acaccctgtc agacgttggt cccaagttta     2820
attagatttc tgaatctcgt tgaggccaag gaatgatcca tactgaaaaa atgctgagcc      2880
agccatcttt ggcaaaggtc cctgagctct tgctatctct caagagtgct gagaaccacg      2940
gtgaaagtgc tgctctaggc ccacaagtgt aactatgctg ttaacagctg tcaatagata      3000
attaaaattc atactgtatg aaaatca                                          3027
```

<210> SEQ ID NO 19
<211> LENGTH: 346
<212> TYPE: PRT
<213> ORGANISM: Homo sapiens

<400> SEQUENCE: 19

Met Ala Leu Leu Lys Val Lys Phe Asp Gln Lys Lys Arg Val Lys Leu

```
1               5                   10                  15
Ala Gln Gly Leu Trp Leu Met Asn Trp Phe Ser Val Leu Ala Gly Ile
            20                  25                  30

Ile Ile Phe Ser Leu Gly Leu Phe Leu Lys Ile Glu Leu Arg Lys Arg
            35                  40                  45

Ser Asp Val Met Asn Asn Ser Glu Ser His Phe Val Pro Asn Ser Leu
 50                  55                  60

Ile Gly Met Gly Val Leu Ser Cys Val Phe Asn Ser Leu Ala Gly Lys
 65                  70                  75                  80

Ile Cys Tyr Asp Ala Leu Asp Pro Ala Lys Tyr Ala Arg Trp Lys Pro
                85                  90                  95

Trp Leu Lys Pro Tyr Leu Ala Ile Cys Val Leu Phe Asn Ile Ile Leu
            100                 105                 110

Phe Leu Val Ala Leu Cys Cys Phe Leu Leu Arg Gly Ser Leu Glu Asn
            115                 120                 125

Thr Leu Gly Gln Gly Leu Lys Asn Gly Met Lys Tyr Tyr Arg Asp Thr
130                 135                 140

Asp Thr Pro Gly Arg Cys Phe Met Lys Lys Thr Ile Asp Met Leu Gln
145                 150                 155                 160

Ile Glu Phe Lys Cys Cys Gly Asn Asn Gly Phe Arg Asp Trp Phe Glu
                165                 170                 175

Ile Gln Trp Ile Ser Asn Arg Tyr Leu Asp Phe Ser Ser Lys Glu Val
            180                 185                 190

Lys Asp Arg Ile Lys Ser Asn Val Asp Gly Arg Tyr Leu Val Asp Gly
            195                 200                 205

Val Pro Phe Ser Cys Cys Asn Pro Ser Ser Pro Arg Pro Cys Ile Gln
210                 215                 220

Tyr Gln Ile Thr Asn Asn Ser Ala His Tyr Ser Tyr Asp His Gln Thr
225                 230                 235                 240

Glu Glu Leu Asn Leu Trp Val Arg Gly Cys Arg Ala Ala Leu Leu Ser
                245                 250                 255

Tyr Tyr Ser Ser Leu Met Asn Ser Met Gly Val Val Thr Leu Leu Ile
            260                 265                 270

Trp Leu Phe Glu Val Thr Ile Thr Ile Gly Leu Arg Tyr Leu Gln Thr
            275                 280                 285

Ser Leu Asp Gly Val Ser Asn Pro Glu Glu Ser Glu Ser Glu Ser Gln
            290                 295                 300

Gly Trp Leu Leu Glu Arg Ser Val Pro Glu Thr Trp Lys Ala Phe Leu
305                 310                 315                 320

Glu Ser Val Lys Lys Leu Gly Lys Gly Asn Gln Val Glu Ala Glu Gly
                325                 330                 335

Ala Asp Ala Gly Gln Ala Pro Glu Ala Gly
            340                 345

<210> SEQ ID NO 20
<211> LENGTH: 1767
<212> TYPE: DNA
<213> ORGANISM: Homo sapiens

<400> SEQUENCE: 20
gtcagctggg tgactcatac atctgtgaga ccctccgtat ggagaccggg gcggggggtg    60
ttgcttaatg cttagaactg ctgaaactac cagttcactg tctcagcact aatccaactc   120
tgctccttaa gtgggatttg cttttagac attgagacct ggatgctggg catcctcgct   180
```

-continued

| | |
|---|---|
| agatccccta caaattcccc acatacgtag gccaggagcc tcagcggtgc cccttcaggc | 240 |
| tcatctggca agacggtacc agcttgctca gaacaggggc tggctattca tcatctcaga | 300 |
| gcatagagac cctctccttg ccacccggcc cttccacct ggttggtgac aaatcacaag | 360 |
| gtggtagaag ttgccaggga cagataacat ggcagccagc gggaagacca gcaagtccga | 420 |
| accgaaccat gttatcttca agaagatctc ccgggacaaa tcggtgacca tctacctggg | 480 |
| gaacagagac tacatagacc atgtcagcca agtccagcct gtggatggtg tcgtgttggt | 540 |
| tgatcctgat cttgtgaagg gaaagaaagt gtatgtcact ctgacctgcg ccttccgcta | 600 |
| tggccaagag gacattgacg tgatcggctt gaccttccgc agggacctgt acttctcccg | 660 |
| ggtccaggtg tatcctcctg tgggggccgc gagcacccc acaaaactgc aagagagcct | 720 |
| gcttaaaaag ctggggagca cacgtaccc ctttctcctg acgtttcctg actacttgcc | 780 |
| ctgttcagtg atgttgcagc cagctccaca agattcaggg aagtcctgtg gggttgactt | 840 |
| tgaggtcaaa gcattcgcca cagacagcac cgatgccgaa gaggacaaaa tccccaagaa | 900 |
| gagctccgtg cgattactga tccgcaaagt acagcatgcc ccacttgaga tgggtcccca | 960 |
| gccccgagct gaggcggcct ggcagttctt catgtctgac aagcccctgc accttgcggt | 1020 |
| ctctctcaac aaagagatct atttccatgg ggagcccatc cctgtgaccg tgactgtcac | 1080 |
| caataacaca gagaagaccg tgaagaagat taaagcattc gtggaacagg tggccaatgt | 1140 |
| ggttctctac tcgagtgatt attacgtcaa gcccgtggct atggaggaag cgcaagaaaa | 1200 |
| agtgccacca aacagcactt tgaccaagac gctgacgctg ctgcccttgc tggctaacaa | 1260 |
| tcgagaaagg agaggcattg ccctggatgg gaaaatcaag cacgaggaca caaaccttgc | 1320 |
| ctccagcacc atcattaagg agggcataga ccggaccgtc ctgggaatcc tggtgtctta | 1380 |
| ccagatcaag gtgaagctca cagtgtcagg ctttctggga gagctcacct ccagtgaagt | 1440 |
| cgccactgag gtcccattcc gcctcatgca ccctcagcct gaggacccag ctaaggaaag | 1500 |
| ttatcaggat gcaaatttag tttttgagga gtttgctcgc cataatctga agatgcagg | 1560 |
| agaagctgag gaggggaaga gagacaagaa tgacgttgat gagtgaagat gtcggctcag | 1620 |
| gatgccggaa aatgacctgt agttaccagt gcaacgagca aagccccaca gtttagtcct | 1680 |
| ttggagttat gctgcgtatg aaaggatgag tcttcttccg agaaataaag cttgtttgtt | 1740 |
| ctcccctgga aaaaaaaaaa aaaaaaa | 1767 |

<210> SEQ ID NO 21
<211> LENGTH: 405
<212> TYPE: PRT
<213> ORGANISM: Homo sapiens

<400> SEQUENCE: 21

Met Ala Ala Ser Gly Lys Thr Ser Lys Ser Glu Pro Asn His Val Ile
1               5                   10                  15

Phe Lys Lys Ile Ser Arg Asp Lys Ser Val Thr Ile Tyr Leu Gly Asn
            20                  25                  30

Arg Asp Tyr Ile Asp His Val Ser Gln Val Gln Pro Val Asp Gly Val
        35                  40                  45

Val Leu Val Asp Pro Asp Leu Val Lys Gly Lys Lys Val Tyr Val Thr
    50                  55                  60

Leu Thr Cys Ala Phe Arg Tyr Gly Gln Glu Asp Ile Asp Val Ile Gly
65                  70                  75                  80

Leu Thr Phe Arg Arg Asp Leu Tyr Phe Ser Arg Val Gln Val Tyr Pro
                85                  90                  95

Pro Val Gly Ala Ala Ser Thr Pro Thr Lys Leu Gln Glu Ser Leu Leu
            100                 105                 110

Lys Lys Leu Gly Ser Asn Thr Tyr Pro Phe Leu Leu Thr Phe Pro Asp
        115                 120                 125

Tyr Leu Pro Cys Ser Val Met Leu Gln Pro Ala Pro Gln Asp Ser Gly
    130                 135                 140

Lys Ser Cys Gly Val Asp Phe Glu Val Lys Ala Phe Ala Thr Asp Ser
145                 150                 155                 160

Thr Asp Ala Glu Glu Asp Lys Ile Pro Lys Lys Ser Ser Val Arg Leu
                165                 170                 175

Leu Ile Arg Lys Val Gln His Ala Pro Leu Glu Met Gly Pro Gln Pro
            180                 185                 190

Arg Ala Glu Ala Ala Trp Gln Phe Phe Met Ser Asp Lys Pro Leu His
        195                 200                 205

Leu Ala Val Ser Leu Asn Lys Glu Ile Tyr Phe His Gly Glu Pro Ile
    210                 215                 220

Pro Val Thr Val Thr Val Thr Asn Asn Thr Glu Lys Thr Val Lys Lys
225                 230                 235                 240

Ile Lys Ala Phe Val Glu Gln Val Ala Asn Val Val Leu Tyr Ser Ser
                245                 250                 255

Asp Tyr Tyr Val Lys Pro Val Ala Met Glu Glu Ala Gln Glu Lys Val
            260                 265                 270

Pro Pro Asn Ser Thr Leu Thr Lys Thr Leu Thr Leu Leu Pro Leu Leu
        275                 280                 285

Ala Asn Asn Arg Glu Arg Arg Gly Ile Ala Leu Asp Gly Lys Ile Lys
    290                 295                 300

His Glu Asp Thr Asn Leu Ala Ser Ser Thr Ile Ile Lys Glu Gly Ile
305                 310                 315                 320

Asp Arg Thr Val Leu Gly Ile Leu Val Ser Tyr Gln Ile Lys Val Lys
                325                 330                 335

Leu Thr Val Ser Gly Phe Leu Gly Glu Leu Thr Ser Ser Glu Val Ala
            340                 345                 350

Thr Glu Val Pro Phe Arg Leu Met His Pro Gln Pro Glu Asp Pro Ala
        355                 360                 365

Lys Glu Ser Tyr Gln Asp Ala Asn Leu Val Phe Glu Glu Phe Ala Arg
    370                 375                 380

His Asn Leu Lys Asp Ala Gly Glu Ala Glu Glu Gly Lys Arg Asp Lys
385                 390                 395                 400

Asn Asp Val Asp Glu
                405

<210> SEQ ID NO 22
<211> LENGTH: 2483
<212> TYPE: DNA
<213> ORGANISM: Homo sapiens

<400> SEQUENCE: 22
agttgattgc aggtcctcct ggggccagaa gggtgcctgg gaggccaggt tctggggatc      60
ccctccatcc agaagaacca cctgctcact ctgtcccttc gcctgctgct ggaccatgg     120 gggctggggc cagtgctgag gagaagcact ccagggagct ggaaaagaag ctgaagagg     180 acgctgagaa ggatgctcga accgtgaagc tgctgcttct gggtgccggt gagtccggga    240
agagcaccat cgtcaagcag atgaagatta tccaccagga cgggtactcg ctggaagagt    300

```
gcctcgagtt tatcgccatc atctacggca acacgttgca gtccatcctg gccatcgtac    360
gcgccatgac cacactcaac atccagtacg gagactctgc acgccaggac gacgcccgga    420
agctgatgca catggcagac actatcgagg agggcacgat gcccaaggag atgtcggaca    480
tcatccagcg gctgtggaag gactccggta tccaggcctg ttttgagcgc gcctcggagt    540
accagctcaa cgactcggcg ggctactacc tctccgacct ggagcgcctg gtaaccccgg    600
gctacgtgcc caccgagcag gacgtgctgc gctcgcgagt caagaccact ggcatcatcg    660
agacgcagtt ctccttcaag gatctcaact tccggatgtt cgatgtgggc gggcagcgct    720
cggagcgcaa gaagtggatc cactgcttcg agggcgtgac ctgcatcatc ttcatcgcgg    780
cgctgagcgc ctacgacatg gtgctagtgg aggacgacga agtgaaccgc atgcacgaga    840
gcctgcacct gttcaacagc atctgcaacc accgctactt cgccacgacg tccatcgtgc    900
tcttccttaa caagaaggac gtcttcttcg agaagatcaa gaaggcgcac ctcagcatct    960
gtttcccgga ctacgatgga cccaacacct acgaggacgc cggcaactac atcaaggtgc   1020
agttcctcga gctcaacatg cggcgcgacg tgaaggagat ctattcccac atgacgtgcg   1080
ccaccgacac gcagaacgtc aaatttgtct tcgacgctgt caccgacatc atcatcaagg   1140
agaacctcaa agactgtggc ctcttctgag gccagggcct gtgctgcagt cggggacaag   1200
gagcttccgt ctggcaaggc cggggcacaa tttgcactcc cctcagctag acgcacagac   1260
tcagcaataa acctttgcat caggctccag ctgtcctttc ttggtggagg acttaattat   1320
cacaagtcat gggcatttat taagtgccca gtgctgggtt gggcatgaag tgggaagatg   1380
gccctccca ggaagaagta cctggcctga caaggtgggg cactcttggg ggtatgggac   1440
caactcatgg cttttcacgg gagttgagga gagaggagct gtggaaaata ttcactggga   1500
cagtcttgga tcaagaggga gttttgaggt ggaggctcat tctggcaggg accgtagtgt   1560
ctaccagccc cagaaacatg ggcttatggc cacaggagtt cagtggagca agagcagggg   1620
aggagagacg tggacaggtg cccaaagcca gtcggagggc ctgggctttc tcagaaggtg   1680
atggagagtc ttggaagccc tcgaggcagg aacataattg cagggctggg attagggtga   1740
gggaagtgag gcacactcac cttgggtgca acatttaagg cgatgccaaa aaatttagta   1800
accaaggtaa ataatattag gataatattt ttaaaaatca aatgaatgca aaaccccaca   1860
atgaatgaaa tatcaaaatc caacagagga tcaaacagag gcatgctaag atatattggg   1920
gcttgaagca aagggaaaac tatttgttgc tatatgtttg tagggatttt ttgccagttt   1980
taaaaataca tgtatcataa agtttactat ctcagccact tgccggtgta tagtttggtg   2040
gtgttaagta cattcataat gttgtacaac caccgcaact gttcatctcc agaactcctt   2100
tcctcttgta aaactgtaac tctgtaccca tgaaaaaata accccccatt cctgccttcc   2160
cccggctcct ggcatccacc attctacttt ccatctctat gaatgtgact gctctaagtg   2220
cctcagatgt gtgggtccat gaagtctttg tcttttttgca actggcttat ttcacttagc   2280
atcatgtctt caaggtttat tcatgtgtag catatgcag aatctccttc cttttaagg    2340
ttgaataata ttccattgta tatattccac actttgttta tttattcatc tattgatgaa   2400
tggttacatc tgccttttgg ctattgtgaa taatgctgct atgaacatgg gtgtacaaat   2460
ctctcaaaaa aaaaaaaaaa aaa                                            2483
```

<210> SEQ ID NO 23
<211> LENGTH: 350
<212> TYPE: PRT
<213> ORGANISM: Homo sapiens

<400> SEQUENCE: 23

Met Gly Ala Gly Ala Ser Ala Glu Glu Lys His Ser Arg Glu Leu Glu
1               5                   10                  15

Lys Lys Leu Lys Glu Asp Ala Glu Lys Asp Ala Arg Thr Val Lys Leu
            20                  25                  30

Leu Leu Leu Gly Ala Gly Glu Ser Gly Lys Ser Thr Ile Val Lys Gln
        35                  40                  45

Met Lys Ile Ile His Gln Asp Gly Tyr Ser Leu Glu Glu Cys Leu Glu
50                  55                  60

Phe Ile Ala Ile Ile Tyr Gly Asn Thr Leu Gln Ser Ile Leu Ala Ile
65                  70                  75                  80

Val Arg Ala Met Thr Thr Leu Asn Ile Gln Tyr Gly Asp Ser Ala Arg
                85                  90                  95

Gln Asp Asp Ala Arg Lys Leu Met His Met Ala Asp Thr Ile Glu Glu
            100                 105                 110

Gly Thr Met Pro Lys Glu Met Ser Asp Ile Ile Gln Arg Leu Trp Lys
        115                 120                 125

Asp Ser Gly Ile Gln Ala Cys Phe Glu Arg Ala Ser Glu Tyr Gln Leu
130                 135                 140

Asn Asp Ser Ala Gly Tyr Tyr Leu Ser Asp Leu Glu Arg Leu Val Thr
145                 150                 155                 160

Pro Gly Tyr Val Pro Thr Glu Gln Asp Val Leu Arg Ser Arg Val Lys
                165                 170                 175

Thr Thr Gly Ile Ile Glu Thr Gln Phe Ser Phe Lys Asp Leu Asn Phe
            180                 185                 190

Arg Met Phe Asp Val Gly Gly Gln Arg Ser Glu Arg Lys Lys Trp Ile
        195                 200                 205

His Cys Phe Glu Gly Val Thr Cys Ile Ile Phe Ile Ala Ala Leu Ser
210                 215                 220

Ala Tyr Asp Met Val Leu Val Glu Asp Asp Glu Val Asn Arg Met His
225                 230                 235                 240

Glu Ser Leu His Leu Phe Asn Ser Ile Cys Asn His Arg Tyr Phe Ala
                245                 250                 255

Thr Thr Ser Ile Val Leu Phe Leu Asn Lys Lys Asp Val Phe Phe Glu
            260                 265                 270

Lys Ile Lys Lys Ala His Leu Ser Ile Cys Phe Pro Asp Tyr Asp Gly
        275                 280                 285

Pro Asn Thr Tyr Glu Asp Ala Gly Asn Tyr Ile Lys Val Gln Phe Leu
290                 295                 300

Glu Leu Asn Met Arg Arg Asp Val Lys Glu Ile Tyr Ser His Met Thr
305                 310                 315                 320

Cys Ala Thr Asp Thr Gln Asn Val Lys Phe Val Phe Asp Ala Val Thr
                325                 330                 335

Asp Ile Ile Ile Lys Glu Asn Leu Lys Asp Cys Gly Leu Phe
            340                 345                 350

<210> SEQ ID NO 24
<211> LENGTH: 201
<212> TYPE: PRT
<213> ORGANISM: Homo sapiens

<400> SEQUENCE: 24

Met Gly Asn Val Met Glu Gly Lys Ser Val Glu Glu Leu Ser Ser Thr
1               5                   10                  15

```
Glu Cys His Gln Trp Tyr Lys Lys Phe Met Thr Glu Cys Pro Ser Gly
             20                  25                  30

Gln Leu Thr Leu Tyr Glu Phe Arg Gln Phe Gly Leu Lys Asn Leu
         35                  40                  45

Ser Pro Ser Ala Ser Gln Tyr Val Glu Gln Met Phe Glu Thr Phe Asp
 50                  55                  60

Phe Asn Lys Asp Gly Tyr Ile Asp Phe Met Glu Tyr Val Ala Ala Leu
65                  70                  75                  80

Ser Leu Val Leu Lys Gly Lys Val Glu Gln Lys Leu Arg Trp Tyr Phe
                 85                  90                  95

Lys Leu Tyr Asp Val Asp Gly Asn Gly Cys Ile Asp Arg Asp Glu Leu
            100                 105                 110

Leu Thr Ile Ile Gln Ala Ile Arg Ala Ile Asn Pro Cys Ser Asp Thr
            115                 120                 125

Thr Met Thr Ala Glu Glu Phe Thr Asp Thr Val Phe Ser Lys Ile Asp
130                 135                 140

Val Asn Gly Asp Gly Glu Leu Ser Leu Glu Glu Phe Ile Glu Gly Val
145                 150                 155                 160

Gln Lys Asp Gln Met Leu Leu Asp Thr Leu Thr Arg Ser Leu Asp Leu
                165                 170                 175

Thr Arg Ile Val Arg Arg Leu Gln Asn Gly Glu Gln Asp Glu Glu Gly
            180                 185                 190

Ala Asp Glu Ala Ala Glu Ala Ala Gly
            195                 200

<210> SEQ ID NO 25
<211> LENGTH: 1103
<212> TYPE: PRT
<213> ORGANISM: Homo sapiens

<400> SEQUENCE: 25

Met Thr Ala Cys Ala Arg Arg Ala Gly Gly Leu Pro Asp Pro Gly Leu
 1               5                  10                  15

Cys Gly Pro Ala Trp Trp Ala Pro Ser Leu Pro Arg Leu Pro Arg Ala
             20                  25                  30

Leu Pro Arg Leu Pro Leu Leu Leu Leu Leu Leu Leu Gln Pro Pro
         35                  40                  45

Ala Leu Ser Ala Val Phe Thr Val Gly Val Leu Gly Pro Trp Ala Cys
 50                  55                  60

Asp Pro Ile Phe Ser Arg Ala Arg Pro Asp Leu Ala Ala Arg Leu Ala
65                  70                  75                  80

Ala Ala Arg Leu Asn Arg Asp Pro Gly Leu Ala Gly Pro Arg Phe
                 85                  90                  95

Glu Val Ala Leu Leu Pro Glu Pro Cys Arg Thr Pro Gly Ser Leu Gly
            100                 105                 110

Ala Val Ser Ser Ala Leu Ala Arg Val Ser Gly Leu Val Gly Pro Val
            115                 120                 125

Asn Pro Ala Ala Cys Arg Pro Ala Glu Leu Leu Ala Glu Glu Ala Gly
130                 135                 140

Ile Ala Leu Val Pro Trp Gly Cys Pro Trp Thr Gln Ala Glu Gly Thr
145                 150                 155                 160

Thr Ala Pro Ala Val Thr Pro Ala Ala Asp Ala Leu Tyr Ala Leu Leu
                165                 170                 175

Arg Ala Phe Gly Trp Ala Arg Val Ala Leu Val Thr Ala Pro Gln Asp
```

```
              180                 185                 190
Leu Trp Val Glu Ala Gly Arg Ser Leu Ser Thr Ala Leu Arg Ala Arg
            195                 200                 205
Gly Leu Pro Val Ala Ser Val Thr Ser Met Glu Pro Leu Asp Leu Ser
            210                 215                 220
Gly Ala Arg Glu Ala Leu Arg Lys Val Arg Asp Gly Pro Arg Val Thr
225                 230                 235                 240
Ala Val Ile Met Val Met His Ser Val Leu Leu Gly Gly Glu Gln
                245                 250                 255
Arg Tyr Leu Leu Glu Ala Ala Glu Leu Gly Leu Thr Asp Gly Ser
            260                 265                 270
Leu Val Phe Leu Pro Phe Asp Thr Ile His Tyr Ala Leu Ser Pro Gly
            275                 280                 285
Pro Glu Ala Leu Ala Ala Leu Ala Asn Ser Ser Gln Leu Arg Arg Ala
            290                 295                 300
His Asp Ala Val Leu Thr Leu Thr Arg His Cys Pro Ser Glu Gly Ser
305                 310                 315                 320
Val Leu Asp Ser Leu Arg Arg Ala Gln Glu Arg Arg Glu Leu Pro Ser
                325                 330                 335
Asp Leu Asn Leu Gln Gln Val Ser Pro Leu Phe Gly Thr Ile Tyr Asp
                340                 345                 350
Ala Val Phe Leu Leu Ala Arg Gly Val Ala Glu Ala Arg Ala Ala Ala
                355                 360                 365
Gly Gly Arg Trp Val Ser Gly Ala Ala Val Ala Arg His Ile Arg Asp
            370                 375                 380
Ala Gln Val Pro Gly Phe Cys Gly Asp Leu Gly Gly Asp Glu Glu Pro
385                 390                 395                 400
Pro Phe Val Leu Leu Asp Thr Asp Ala Ala Gly Asp Arg Leu Phe Ala
                405                 410                 415
Thr Tyr Met Leu Asp Pro Ala Arg Gly Ser Phe Leu Ser Ala Gly Thr
                420                 425                 430
Arg Met His Phe Pro Arg Gly Gly Ser Ala Pro Gly Pro Asp Pro Ser
            435                 440                 445
Cys Trp Phe Asp Pro Asn Asn Ile Cys Gly Gly Leu Glu Pro Gly
            450                 455                 460
Leu Val Phe Leu Gly Phe Leu Leu Val Val Gly Met Gly Leu Ala Gly
465                 470                 475                 480
Ala Phe Leu Ala His Tyr Val Arg His Arg Leu Leu His Met Gln Met
                485                 490                 495
Val Ser Gly Pro Asn Lys Ile Ile Leu Thr Val Asp Asp Ile Thr Phe
            500                 505                 510
Leu His Pro His Gly Gly Thr Ser Arg Lys Val Ala Gln Gly Ser Arg
            515                 520                 525
Ser Ser Leu Gly Ala Arg Ser Met Ser Asp Ile Arg Ser Gly Pro Ser
            530                 535                 540
Gln His Leu Asp Ser Pro Asn Ile Gly Val Tyr Glu Gly Asp Arg Val
545                 550                 555                 560
Trp Leu Lys Lys Phe Pro Gly Asp Gln His Ile Ala Ile Arg Pro Ala
                565                 570                 575
Thr Lys Thr Ala Phe Ser Lys Leu Gln Glu Leu Arg His Glu Asn Val
                580                 585                 590
Ala Leu Tyr Leu Gly Leu Phe Leu Ala Arg Gly Ala Glu Gly Pro Ala
            595                 600                 605
```

```
Ala Leu Trp Glu Gly Asn Leu Ala Val Val Ser Glu His Cys Thr Arg
610                 615                 620

Gly Ser Leu Gln Asp Leu Leu Ala Gln Arg Glu Ile Lys Leu Asp Trp
625                 630                 635                 640

Met Phe Lys Ser Ser Leu Leu Leu Asp Leu Ile Lys Gly Ile Arg Tyr
                645                 650                 655

Leu His His Arg Gly Val Ala His Gly Arg Leu Lys Ser Arg Asn Cys
                660                 665                 670

Ile Val Asp Gly Arg Phe Val Leu Lys Ile Thr Asp His Gly His Gly
            675                 680                 685

Arg Leu Leu Glu Ala Gln Lys Val Leu Pro Glu Pro Pro Arg Ala Glu
            690                 695                 700

Asp Gln Leu Trp Thr Ala Pro Glu Leu Leu Arg Asp Pro Ala Leu Glu
705                 710                 715                 720

Arg Arg Gly Thr Leu Ala Gly Asp Val Phe Ser Leu Ala Ile Ile Met
                725                 730                 735

Gln Glu Val Val Cys Arg Ser Ala Pro Tyr Ala Met Leu Glu Leu Thr
                740                 745                 750

Pro Glu Glu Val Val Gln Arg Val Arg Ser Pro Pro Leu Cys Arg
            755                 760                 765

Pro Leu Val Ser Met Asp Gln Ala Pro Val Glu Cys Ile Leu Leu Met
770                 775                 780

Lys Gln Cys Trp Ala Glu Gln Pro Glu Leu Arg Pro Ser Met Asp His
785                 790                 795                 800

Thr Phe Asp Leu Phe Lys Asn Ile Asn Lys Gly Arg Lys Thr Asn Ile
                805                 810                 815

Ile Asp Ser Met Leu Arg Met Leu Glu Gln Tyr Ser Ser Asn Leu Glu
                820                 825                 830

Asp Leu Ile Arg Glu Arg Thr Glu Glu Leu Glu Leu Glu Lys Gln Lys
            835                 840                 845

Thr Asp Arg Leu Leu Thr Gln Met Leu Pro Pro Ser Val Ala Glu Ala
850                 855                 860

Leu Lys Thr Gly Thr Pro Val Glu Pro Glu Tyr Phe Glu Gln Val Thr
865                 870                 875                 880

Leu Tyr Phe Ser Asp Ile Val Gly Phe Thr Thr Ile Ser Ala Met Ser
                885                 890                 895

Glu Pro Ile Glu Val Val Asp Leu Leu Asn Asp Leu Tyr Thr Leu Phe
            900                 905                 910

Asp Ala Ile Ile Gly Ser His Asp Val Tyr Lys Val Glu Thr Ile Gly
            915                 920                 925

Asp Ala Tyr Met Val Ala Ser Gly Leu Pro Gln Arg Asn Gly Gln Arg
930                 935                 940

His Ala Ala Glu Ile Ala Asn Met Ser Leu Asp Ile Leu Ser Ala Val
945                 950                 955                 960

Gly Thr Phe Arg Met Arg His Met Pro Glu Val Pro Val Arg Ile Arg
                965                 970                 975

Ile Gly Leu His Ser Gly Pro Cys Val Ala Gly Val Val Gly Leu Thr
                980                 985                 990

Met Pro Arg Tyr Cys Leu Phe Gly Asp Thr Val Asn Thr Ala Ser Arg
            995                 1000                1005

Met Glu Ser Thr Gly Leu Pro Tyr Arg Ile His Val Asn Leu Ser
    1010                1015                1020
```

```
Thr Val Gly Ile Leu Arg Ala Leu Asp Ser Gly Tyr Gln Val Glu
    1025                1030                1035

Leu Arg Gly Arg Thr Glu Leu Lys Gly Lys Gly Ala Glu Asp Thr
    1040                1045                1050

Phe Trp Leu Val Gly Arg Arg Gly Phe Asn Lys Pro Ile Pro Lys
    1055                1060                1065

Pro Pro Asp Leu Gln Pro Gly Ser Ser Asn His Gly Ile Ser Leu
    1070                1075                1080

Gln Glu Ile Pro Pro Glu Arg Arg Arg Lys Leu Glu Lys Ala Arg
    1085                1090                1095

Pro Gly Gln Phe Ser
    1100

<210> SEQ ID NO 26
<211> LENGTH: 676
<212> TYPE: PRT
<213> ORGANISM: Homo sapiens

<400> SEQUENCE: 26

Met Ala Lys Ile Asn Thr Gln Tyr Ser His Pro Ser Arg Thr His Leu
1               5                   10                  15

Lys Val Lys Thr Ser Asp Arg Asp Leu Asn Arg Ala Glu Asn Gly Leu
                20                  25                  30

Ser Arg Ala His Ser Ser Ser Glu Glu Thr Ser Ser Val Leu Gln Pro
            35                  40                  45

Gly Ile Ala Met Glu Thr Arg Gly Leu Ala Asp Ser Gly Gln Gly Ser
        50                  55                  60

Phe Thr Gly Gln Gly Ile Ala Arg Leu Ser Arg Leu Ile Phe Leu Leu
65                  70                  75                  80

Arg Arg Trp Ala Ala Arg His Val His His Gln Asp Gln Gly Pro Asp
                85                  90                  95

Ser Phe Pro Asp Arg Phe Arg Gly Ala Glu Leu Lys Glu Val Ser Ser
                100                 105                 110

Gln Glu Ser Asn Ala Gln Ala Asn Val Gly Ser Gln Glu Pro Ala Asp
            115                 120                 125

Arg Gly Arg Arg Lys Lys Thr Lys Lys Asp Ala Ile Val Val Asp
        130                 135                 140

Pro Ser Ser Asn Leu Tyr Tyr Arg Trp Leu Thr Ala Ile Ala Leu Pro
145                 150                 155                 160

Val Phe Tyr Asn Trp Tyr Leu Leu Ile Cys Arg Ala Cys Phe Asp Glu
                165                 170                 175

Leu Gln Ser Glu Tyr Leu Met Leu Trp Leu Val Leu Asp Tyr Ser Ala
            180                 185                 190

Asp Val Leu Tyr Val Leu Asp Val Leu Val Arg Ala Arg Thr Gly Phe
        195                 200                 205

Leu Glu Gln Gly Leu Met Val Ser Asp Thr Asn Arg Leu Trp Gln His
    210                 215                 220

Tyr Lys Thr Thr Thr Gln Phe Lys Leu Asp Val Leu Ser Leu Val Pro
225                 230                 235                 240

Thr Asp Leu Ala Tyr Leu Lys Val Gly Thr Asn Tyr Pro Glu Val Arg
                245                 250                 255

Phe Asn Arg Leu Leu Lys Phe Ser Arg Leu Phe Glu Phe Phe Asp Arg
            260                 265                 270

Thr Glu Thr Arg Thr Asn Tyr Pro Asn Met Phe Arg Ile Gly Asn Leu
        275                 280                 285
```

Val Leu Tyr Ile Leu Ile Ile His Trp Asn Ala Cys Ile Tyr Phe
290                 295                 300

Ala Ile Ser Lys Phe Ile Gly Phe Gly Thr Asp Ser Trp Val Tyr Pro
305                 310                 315                 320

Asn Ile Ser Ile Pro Glu His Gly Arg Leu Ser Arg Lys Tyr Ile Tyr
            325                 330                 335

Ser Leu Tyr Trp Ser Thr Leu Thr Leu Thr Thr Ile Gly Glu Thr Pro
            340                 345                 350

Pro Pro Val Lys Asp Glu Glu Tyr Leu Phe Val Val Asp Phe Leu
        355                 360                 365

Val Gly Val Leu Ile Phe Ala Thr Ile Val Gly Asn Val Gly Ser Met
370                 375                 380

Ile Ser Asn Met Asn Ala Ser Arg Ala Glu Phe Gln Ala Lys Ile Asp
385                 390                 395                 400

Ser Ile Lys Gln Tyr Met Gln Phe Arg Lys Val Thr Lys Asp Leu Glu
                405                 410                 415

Thr Arg Val Ile Arg Trp Phe Asp Tyr Leu Trp Ala Asn Lys Lys Thr
                420                 425                 430

Val Asp Glu Lys Glu Val Leu Lys Ser Leu Pro Asp Lys Leu Lys Ala
        435                 440                 445

Glu Ile Ala Ile Asn Val His Leu Asp Thr Leu Lys Lys Val Arg Ile
450                 455                 460

Phe Gln Asp Cys Glu Ala Gly Leu Leu Val Glu Leu Val Leu Lys Leu
465                 470                 475                 480

Arg Pro Thr Val Phe Ser Pro Gly Asp Tyr Ile Cys Lys Lys Gly Asp
                485                 490                 495

Ile Gly Lys Glu Met Tyr Ile Ile Asn Glu Gly Lys Leu Ala Val Val
                500                 505                 510

Ala Asp Asp Gly Val Thr Gln Phe Val Val Leu Ser Asp Gly Ser Tyr
        515                 520                 525

Phe Gly Glu Ile Ser Ile Leu Asn Ile Lys Gly Ser Lys Ser Gly Asn
530                 535                 540

Arg Arg Thr Ala Asn Ile Arg Ser Ile Gly Tyr Ser Asp Leu Phe Cys
545                 550                 555                 560

Leu Ser Lys Asp Asp Leu Met Glu Ala Leu Thr Glu Tyr Pro Glu Ala
                565                 570                 575

Lys Lys Ala Leu Glu Glu Lys Gly Arg Gln Ile Leu Met Lys Asp Asn
            580                 585                 590

Leu Ile Asp Glu Glu Leu Ala Arg Ala Gly Ala Asp Pro Lys Asp Leu
                595                 600                 605

Glu Glu Lys Val Glu Gln Leu Gly Ser Ser Leu Asp Thr Leu Gln Thr
610                 615                 620

Arg Phe Ala Arg Leu Leu Ala Glu Tyr Asn Ala Thr Gln Met Lys Met
625                 630                 635                 640

Lys Gln Arg Leu Ser Gln Leu Glu Ser Gln Val Lys Gly Gly Gly Asp
                645                 650                 655

Lys Pro Leu Ala Asp Gly Glu Val Pro Gly Asp Ala Thr Lys Thr Glu
            660                 665                 670

Asp Lys Gln Gln
            675

<210> SEQ ID NO 27
<211> LENGTH: 694

<212> TYPE: PRT
<213> ORGANISM: Homo sapiens

<400> SEQUENCE: 27

```
Met Ala Lys Ile Asn Thr Gln Tyr Ser His Pro Ser Arg Thr His Leu
1               5                   10                  15

Lys Val Lys Thr Ser Asp Arg Asp Leu Asn Arg Ala Glu Asn Gly Leu
            20                  25                  30

Ser Arg Ala His Ser Ser Glu Gly Thr Ser Ser Val Leu Gln Pro
                35                  40                  45

Gly Ile Ala Met Glu Thr Arg Gly Leu Ala Asp Ser Gly Gln Gly Ser
        50                  55                  60

Phe Thr Gly Gln Gly Ile Ala Arg Leu Ser Arg Leu Ile Phe Leu Leu
65                  70                  75                  80

Arg Arg Trp Ala Ala Arg His Val His His Gln Asp Gln Gly Pro Asp
                85                  90                  95

Ser Phe Pro Asp Arg Phe Arg Gly Ala Glu Leu Lys Glu Val Ser Ser
                100                 105                 110

Gln Glu Ser Asn Ala Gln Ala Asn Val Gly Ser Gln Glu Pro Ala Asp
                115                 120                 125

Arg Gly Arg Ser Ala Trp Pro Leu Ala Lys Cys Asn Thr Asn Thr Ser
130                 135                 140

Asn Asn Thr Glu Glu Glu Lys Lys Thr Lys Lys Lys Asp Ala Ile Val
145                 150                 155                 160

Val Asp Pro Ser Ser Asn Leu Tyr Tyr Arg Trp Leu Thr Ala Ile Ala
                165                 170                 175

Leu Pro Val Phe Tyr Asn Trp Tyr Leu Leu Ile Cys Arg Ala Cys Phe
                180                 185                 190

Asp Glu Leu Gln Ser Glu Tyr Leu Met Leu Trp Leu Val Leu Asp Tyr
                195                 200                 205

Ser Ala Asp Val Leu Tyr Val Leu Asp Val Leu Val Arg Ala Arg Thr
                210                 215                 220

Gly Phe Leu Glu Gln Gly Leu Met Val Ser Asp Thr Asn Arg Leu Trp
225                 230                 235                 240

Gln His Tyr Lys Thr Thr Thr Gln Phe Lys Leu Asp Val Leu Ser Leu
                245                 250                 255

Val Pro Thr Asp Leu Ala Tyr Leu Lys Val Gly Thr Asn Tyr Pro Glu
                260                 265                 270

Val Arg Phe Asn Arg Leu Leu Lys Phe Ser Arg Leu Phe Glu Phe Phe
                275                 280                 285

Asp Arg Thr Glu Thr Arg Thr Asn Tyr Pro Asn Met Phe Arg Ile Gly
                290                 295                 300

Asn Leu Val Leu Tyr Ile Leu Ile Ile His Trp Asn Ala Cys Ile
305                 310                 315                 320

Tyr Phe Ala Ile Ser Lys Phe Ile Gly Phe Gly Thr Asp Ser Trp Val
                325                 330                 335

Tyr Pro Asn Ile Ser Ile Pro Glu His Gly Arg Leu Ser Arg Lys Tyr
                340                 345                 350

Ile Tyr Ser Leu Tyr Trp Ser Thr Leu Thr Leu Thr Thr Ile Gly Glu
                355                 360                 365

Thr Pro Pro Pro Val Lys Asp Glu Glu Tyr Leu Phe Val Val Val Asp
                370                 375                 380

Phe Leu Val Gly Val Leu Ile Phe Ala Thr Ile Val Gly Asn Val Gly
385                 390                 395                 400
```

```
Ser Met Ile Ser Asn Met Asn Ala Ser Arg Ala Glu Phe Gln Ala Lys
                405                 410                 415

Ile Asp Ser Ile Lys Gln Tyr Met Gln Phe Arg Lys Val Thr Lys Asp
            420                 425                 430

Leu Glu Thr Arg Val Ile Arg Trp Phe Asp Tyr Leu Trp Ala Asn Lys
        435                 440                 445

Lys Thr Val Asp Glu Lys Glu Val Leu Lys Ser Leu Pro Asp Lys Leu
    450                 455                 460

Lys Ala Glu Ile Ala Ile Asn Val His Leu Asp Thr Leu Lys Lys Val
465                 470                 475                 480

Arg Ile Phe Gln Asp Cys Glu Ala Gly Leu Leu Val Glu Leu Val Leu
                485                 490                 495

Lys Leu Arg Pro Thr Val Phe Ser Pro Gly Asp Tyr Ile Cys Lys Lys
            500                 505                 510

Gly Asp Ile Gly Lys Glu Met Tyr Ile Ile Asn Glu Gly Lys Leu Ala
        515                 520                 525

Val Val Ala Asp Asp Gly Val Thr Gln Phe Val Val Leu Ser Asp Gly
    530                 535                 540

Ser Tyr Phe Gly Glu Ile Ser Ile Leu Asn Ile Lys Gly Ser Lys Ser
545                 550                 555                 560

Gly Asn Arg Arg Thr Ala Asn Ile Arg Ser Ile Gly Tyr Ser Asp Leu
                565                 570                 575

Phe Cys Leu Ser Lys Asp Asp Leu Met Glu Ala Leu Thr Glu Tyr Pro
            580                 585                 590

Glu Ala Lys Lys Ala Leu Glu Glu Lys Gly Arg Gln Ile Leu Met Lys
        595                 600                 605

Asp Asn Leu Ile Asp Glu Glu Leu Ala Arg Ala Gly Ala Asp Pro Lys
    610                 615                 620

Asp Leu Glu Glu Lys Val Glu Gln Leu Gly Ser Ser Leu Asp Thr Leu
625                 630                 635                 640

Gln Thr Arg Phe Ala Arg Leu Leu Ala Glu Tyr Asn Ala Thr Gln Met
                645                 650                 655

Lys Met Lys Gln Arg Leu Ser Gln Leu Glu Ser Gln Val Lys Gly Gly
            660                 665                 670

Gly Asp Lys Pro Leu Ala Asp Gly Glu Val Pro Gly Asp Ala Thr Lys
        675                 680                 685

Thr Glu Asp Lys Gln Gln
    690

<210> SEQ ID NO 28
<211> LENGTH: 354
<212> TYPE: PRT
<213> ORGANISM: Homo sapiens

<400> SEQUENCE: 28

Met Gly Ser Gly Ala Ser Ala Glu Asp Lys Glu Leu Ala Lys Arg Ser
1               5                   10                  15

Lys Glu Leu Glu Lys Lys Leu Gln Glu Asp Ala Asp Lys Glu Ala Lys
            20                  25                  30

Thr Val Lys Leu Leu Leu Leu Gly Ala Gly Glu Ser Gly Lys Ser Thr
        35                  40                  45

Ile Val Lys Gln Met Lys Ile Ile His Gln Asp Gly Tyr Ser Pro Glu
    50                  55                  60

Glu Cys Leu Glu Phe Lys Ala Ile Ile Tyr Gly Asn Val Leu Gln Ser
```

```
            65                  70                  75                  80
Ile Leu Ala Ile Ile Arg Ala Met Thr Thr Leu Gly Ile Asp Tyr Ala
                85                  90                  95
Glu Pro Ser Cys Ala Asp Asp Gly Arg Gln Leu Asn Asn Leu Ala Asp
               100                 105                 110
Ser Ile Glu Glu Gly Thr Met Pro Pro Glu Leu Val Glu Val Ile Arg
           115                 120                 125
Arg Leu Trp Lys Asp Gly Gly Val Gln Ala Cys Phe Glu Arg Ala Ala
       130                 135                 140
Glu Tyr Gln Leu Asn Asp Ser Ala Ser Tyr Leu Asn Gln Leu Glu
145                 150                 155                 160
Arg Ile Thr Asp Pro Glu Tyr Leu Pro Ser Glu Gln Asp Val Leu Arg
               165                 170                 175
Ser Arg Val Lys Thr Thr Gly Ile Ile Glu Thr Lys Phe Ser Val Lys
           180                 185                 190
Asp Leu Asn Phe Arg Met Phe Asp Val Gly Gly Gln Arg Ser Glu Arg
       195                 200                 205
Lys Lys Trp Ile His Cys Phe Glu Gly Val Thr Cys Ile Ile Phe Cys
   210                 215                 220
Ala Ala Leu Ser Ala Tyr Asp Met Val Leu Val Glu Asp Asp Glu Val
225                 230                 235                 240
Asn Arg Met His Glu Ser Leu His Leu Phe Asn Ser Ile Cys Asn His
               245                 250                 255
Lys Phe Phe Ala Ala Thr Ser Ile Val Leu Phe Leu Asn Lys Lys Asp
           260                 265                 270
Leu Phe Glu Glu Lys Ile Lys Lys Val His Leu Ser Ile Cys Phe Pro
       275                 280                 285
Glu Tyr Asp Gly Asn Asn Ser Tyr Asp Ala Gly Asn Tyr Ile Lys
   290                 295                 300
Ser Gln Phe Leu Asp Leu Asn Met Arg Lys Asp Val Lys Glu Ile Tyr
305                 310                 315                 320
Ser His Met Thr Cys Ala Thr Asp Thr Gln Asn Val Lys Phe Val Phe
               325                 330                 335
Asp Ala Val Thr Asp Ile Ile Ile Lys Glu Asn Leu Lys Asp Cys Gly
           340                 345                 350
Leu Phe

<210> SEQ ID NO 29
<211> LENGTH: 858
<212> TYPE: PRT
<213> ORGANISM: Homo sapiens

<400> SEQUENCE: 29

Met Gly Glu Ile Asn Gln Val Ala Val Glu Lys Tyr Leu Glu Glu Asn
1               5                   10                  15
Pro Gln Phe Ala Lys Glu Tyr Phe Asp Arg Lys Leu Arg Val Glu Val
               20                  25                  30
Leu Gly Glu Ile Phe Lys Asn Ser Gln Val Pro Val Gln Ser Ser Met
           35                  40                  45
Ser Phe Ser Glu Leu Thr Gln Val Glu Ser Ala Leu Cys Leu Glu
       50                  55                  60
Leu Leu Trp Thr Val Gln Glu Glu Gly Gly Thr Pro Glu Gln Gly Val
65                  70                  75                  80
His Arg Ala Leu Gln Arg Leu Ala His Leu Leu Gln Ala Asp Arg Cys
```

-continued

```
                85                  90                  95
Ser Met Phe Leu Cys Arg Ser Arg Asn Gly Ile Pro Glu Val Ala Ser
            100                 105                 110

Arg Leu Leu Asp Val Thr Pro Thr Ser Lys Phe Glu Asp Asn Leu Val
            115                 120                 125

Gly Pro Asp Lys Glu Val Val Phe Pro Leu Asp Ile Gly Ile Val Gly
    130                 135                 140

Trp Ala Ala His Thr Lys Lys Thr His Asn Val Pro Asp Val Lys Lys
145                 150                 155                 160

Asn Ser His Phe Ser Asp Phe Met Asp Lys Gln Thr Gly Tyr Val Thr
                165                 170                 175

Lys Asn Leu Leu Ala Thr Pro Ile Val Val Gly Lys Glu Val Leu Ala
            180                 185                 190

Val Ile Met Ala Val Asn Lys Val Asn Ala Ser Glu Phe Ser Lys Gln
        195                 200                 205

Asp Glu Glu Val Phe Ser Lys Tyr Leu Asn Phe Val Ser Ile Ile Leu
    210                 215                 220

Arg Leu His His Thr Ser Tyr Met Tyr Asn Ile Glu Ser Arg Arg Ser
225                 230                 235                 240

Gln Ile Leu Met Trp Ser Ala Asn Lys Val Phe Glu Leu Thr Asp
                245                 250                 255

Val Glu Arg Gln Phe His Lys Ala Leu Tyr Thr Val Arg Ser Tyr Leu
            260                 265                 270

Asn Cys Glu Arg Tyr Ser Ile Gly Leu Leu Asp Met Thr Lys Glu Lys
        275                 280                 285

Glu Phe Tyr Asp Glu Trp Pro Ile Lys Leu Gly Glu Val Glu Pro Tyr
    290                 295                 300

Lys Gly Pro Lys Thr Pro Asp Gly Arg Glu Val Asn Phe Tyr Lys Ile
305                 310                 315                 320

Ile Asp Tyr Ile Leu His Gly Lys Glu Ile Lys Val Ile Pro Thr
                325                 330                 335

Pro Pro Ala Asp His Trp Thr Leu Ile Ser Gly Leu Pro Thr Tyr Val
            340                 345                 350

Ala Glu Asn Gly Phe Ile Cys Asn Met Met Asn Ala Pro Ala Asp Glu
        355                 360                 365

Tyr Phe Thr Phe Gln Lys Gly Pro Val Asp Glu Thr Gly Trp Val Ile
    370                 375                 380

Lys Asn Val Leu Ser Leu Pro Ile Val Asn Lys Lys Glu Asp Ile Val
385                 390                 395                 400

Gly Val Ala Thr Phe Tyr Asn Arg Lys Asp Gly Lys Pro Phe Asp Glu
                405                 410                 415

His Asp Glu Tyr Ile Thr Glu Thr Leu Thr Gln Phe Leu Gly Trp Ser
            420                 425                 430

Leu Leu Asn Thr Asp Thr Tyr Asp Lys Met Asn Lys Leu Glu Asn Arg
        435                 440                 445

Lys Asp Ile Ala Gln Glu Met Leu Met Asn Gln Thr Lys Ala Thr Pro
    450                 455                 460

Glu Glu Ile Lys Ser Ile Leu Lys Phe Gln Glu Lys Leu Asn Val Asp
465                 470                 475                 480

Val Ile Asp Asp Cys Glu Glu Lys Gln Leu Val Ala Ile Leu Lys Glu
                485                 490                 495

Asp Leu Pro Asp Pro Arg Ser Ala Glu Leu Tyr Glu Phe Arg Phe Ser
            500                 505                 510
```

Asp Phe Pro Leu Thr Glu His Gly Leu Ile Lys Cys Gly Ile Arg Leu
            515                 520                 525

Phe Phe Glu Ile Asn Val Val Glu Lys Phe Lys Val Pro Val Glu Val
    530                 535                 540

Leu Thr Arg Trp Met Tyr Thr Val Arg Lys Gly Tyr Arg Ala Val Thr
545                 550                 555                 560

Tyr His Asn Trp Arg His Gly Phe Asn Val Gly Gln Thr Met Phe Thr
                565                 570                 575

Leu Leu Met Thr Gly Arg Leu Lys Lys Tyr Tyr Thr Asp Leu Glu Ala
            580                 585                 590

Phe Ala Met Leu Ala Ala Ala Phe Cys His Asp Ile Asp His Arg Gly
        595                 600                 605

Thr Asn Asn Leu Tyr Gln Met Lys Ser Thr Ser Pro Leu Ala Arg Leu
    610                 615                 620

His Gly Ser Ser Ile Leu Glu Arg His His Leu Glu Tyr Ser Lys Thr
625                 630                 635                 640

Leu Leu Gln Asp Glu Ser Leu Asn Ile Phe Gln Asn Leu Asn Lys Arg
                645                 650                 655

Gln Phe Glu Thr Val Ile His Leu Phe Glu Val Ala Ile Ile Ala Thr
            660                 665                 670

Asp Leu Ala Leu Tyr Phe Lys Lys Arg Thr Met Phe Gln Lys Ile Val
        675                 680                 685

Asp Ala Cys Glu Gln Met Gln Thr Glu Glu Ala Ile Lys Tyr Val
    690                 695                 700

Thr Val Asp Pro Thr Lys Lys Glu Ile Ile Met Ala Met Met Met Thr
705                 710                 715                 720

Ala Cys Asp Leu Ser Ala Ile Thr Lys Pro Trp Glu Val Gln Ser Gln
                725                 730                 735

Val Ala Leu Met Val Ala Asn Glu Phe Trp Glu Gln Gly Asp Leu Glu
            740                 745                 750

Arg Thr Val Leu Gln Gln Pro Ile Pro Met Met Asp Arg Asn Lys
        755                 760                 765

Arg Asp Glu Leu Pro Lys Leu Gln Val Gly Phe Ile Asp Phe Val Cys
    770                 775                 780

Thr Phe Val Tyr Lys Glu Phe Ser Arg Phe His Lys Glu Ile Thr Pro
785                 790                 795                 800

Met Leu Ser Gly Leu Gln Asn Asn Arg Val Glu Trp Lys Ser Leu Ala
                805                 810                 815

Asp Glu Tyr Asp Ala Lys Met Lys Val Ile Glu Glu Ala Lys Lys
            820                 825                 830

Gln Glu Gly Gly Ala Glu Lys Ala Ala Glu Asp Ser Gly Gly Asp
        835                 840                 845

Asp Lys Lys Ser Lys Thr Cys Leu Met Leu
    850                 855

<210> SEQ ID NO 30
<211> LENGTH: 83
<212> TYPE: PRT
<213> ORGANISM: Homo sapiens

<400> SEQUENCE: 30

Met Ser Asp Asn Thr Thr Leu Pro Ala Pro Ala Ser Asn Gln Gly Pro
1               5                   10                  15

Thr Thr Pro Arg Lys Gly Pro Pro Lys Phe Lys Gln Arg Gln Thr Arg

```
                20                  25                  30
Gln Phe Lys Ser Lys Pro Pro Lys Gly Val Lys Gly Phe Gly Asp
             35                  40                  45

Asp Ile Pro Gly Met Glu Gly Leu Gly Thr Asp Ile Thr Val Ile Cys
 50                  55                  60

Pro Trp Glu Ala Phe Ser His Leu Glu Leu His Glu Leu Ala Gln Phe
 65                  70                  75                  80

Gly Ile Ile

<210> SEQ ID NO 31
<211> LENGTH: 299
<212> TYPE: PRT
<213> ORGANISM: Homo sapiens

<400> SEQUENCE: 31

Met Met Ala Tyr Met Asn Pro Gly Pro His Tyr Ser Val Asn Ala Leu
 1               5                  10                  15

Ala Leu Ser Gly Pro Ser Val Asp Leu Met His Gln Ala Val Pro Tyr
             20                  25                  30

Pro Ser Ala Pro Arg Lys Gln Arg Arg Glu Arg Thr Thr Phe Thr Arg
         35                  40                  45

Ser Gln Leu Glu Glu Leu Glu Ala Leu Phe Ala Lys Thr Gln Tyr Pro
 50                  55                  60

Asp Val Tyr Ala Arg Glu Val Ala Leu Lys Ile Asn Leu Pro Glu
 65                  70                  75                  80

Ser Arg Val Gln Val Trp Phe Lys Asn Arg Arg Ala Lys Cys Arg Gln
                 85                  90                  95

Gln Arg Gln Gln Gln Lys Gln Gln Gln Pro Pro Gly Gly Gln Ala
             100                 105                 110

Lys Ala Arg Pro Ala Lys Arg Lys Ala Gly Thr Ser Pro Arg Pro Ser
         115                 120                 125

Thr Asp Val Cys Pro Asp Pro Leu Gly Ile Ser Asp Ser Tyr Ser Pro
 130                 135                 140

Pro Leu Pro Gly Pro Ser Gly Ser Pro Thr Thr Ala Val Ala Thr Val
145                 150                 155                 160

Ser Ile Trp Ser Pro Ala Ser Glu Ser Pro Leu Pro Glu Ala Gln Arg
                 165                 170                 175

Ala Gly Leu Val Ala Ser Gly Pro Ser Leu Thr Ser Ala Pro Tyr Ala
             180                 185                 190

Met Thr Tyr Ala Pro Ala Ser Ala Phe Cys Ser Ser Pro Ser Ala Tyr
         195                 200                 205

Gly Ser Pro Ser Ser Tyr Phe Ser Gly Leu Asp Pro Tyr Leu Ser Pro
 210                 215                 220

Met Val Pro Gln Leu Gly Gly Pro Ala Leu Ser Pro Leu Ser Gly Pro
225                 230                 235                 240

Ser Val Gly Pro Ser Leu Ala Gln Ser Pro Thr Ser Leu Ser Gly Gln
                 245                 250                 255

Ser Tyr Gly Ala Tyr Ser Pro Val Asp Ser Leu Glu Phe Lys Asp Pro
             260                 265                 270

Thr Gly Thr Trp Lys Phe Thr Tyr Asn Pro Met Asp Pro Leu Asp Tyr
         275                 280                 285

Lys Asp Gln Ser Ala Trp Lys Phe Gln Ile Leu
 290                 295
```

<210> SEQ ID NO 32
<211> LENGTH: 809
<212> TYPE: PRT
<213> ORGANISM: Homo sapiens

<400> SEQUENCE: 32

```
Met Phe Lys Ser Leu Thr Lys Val Asn Lys Val Lys Pro Ile Gly Glu
1               5                   10                  15

Asn Asn Glu Asn Glu Gln Ser Ser Arg Arg Asn Glu Glu Gly Ser His
            20                  25                  30

Pro Ser Asn Gln Ser Gln Gln Thr Ala Gln Glu Glu Asn Lys Gly
        35                  40                  45

Glu Glu Lys Ser Leu Lys Thr Lys Ser Thr Pro Val Thr Ser Glu Glu
    50                  55                  60

Pro His Thr Asn Ile Gln Asp Lys Leu Ser Lys Lys Asn Ser Ser Gly
65                  70                  75                  80

Asp Leu Thr Thr Asn Pro Asp Pro Gln Asn Ala Ala Glu Pro Thr Gly
                85                  90                  95

Thr Val Pro Glu Gln Lys Glu Met Asp Pro Gly Lys Glu Gly Pro Asn
            100                 105                 110

Ser Pro Gln Asn Lys Pro Ala Ala Pro Val Ile Asn Glu Tyr Ala
        115                 120                 125

Asp Ala Gln Leu His Asn Leu Val Lys Arg Met Arg Gln Arg Thr Ala
130                 135                 140

Leu Tyr Lys Lys Lys Leu Val Glu Gly Asp Leu Ser Ser Pro Glu Ala
145                 150                 155                 160

Ser Pro Gln Thr Ala Lys Pro Thr Ala Val Pro Pro Val Lys Glu Ser
                165                 170                 175

Asp Asp Lys Pro Thr Glu His Tyr Tyr Arg Leu Leu Trp Phe Lys Val
            180                 185                 190

Lys Lys Met Pro Leu Thr Glu Tyr Leu Lys Arg Ile Lys Leu Pro Asn
        195                 200                 205

Ser Ile Asp Ser Tyr Thr Asp Arg Leu Tyr Leu Leu Trp Leu Leu Leu
210                 215                 220

Val Thr Leu Ala Tyr Asn Trp Asn Cys Trp Phe Ile Pro Leu Arg Leu
225                 230                 235                 240

Val Phe Pro Tyr Gln Thr Ala Asp Asn Ile His Tyr Trp Leu Ile Ala
                245                 250                 255

Asp Ile Ile Cys Asp Ile Ile Tyr Leu Tyr Asp Met Leu Phe Ile Gln
            260                 265                 270

Pro Arg Leu Gln Phe Val Arg Gly Gly Asp Ile Ile Val Asp Ser Asn
        275                 280                 285

Glu Leu Arg Lys His Tyr Arg Thr Ser Thr Lys Phe Gln Leu Asp Val
290                 295                 300

Ala Ser Ile Ile Pro Phe Asp Ile Cys Tyr Leu Phe Gly Phe Asn
305                 310                 315                 320

Pro Met Phe Arg Ala Asn Arg Met Leu Lys Tyr Thr Ser Phe Phe Glu
                325                 330                 335

Phe Asn His His Leu Glu Ser Ile Met Asp Lys Ala Tyr Ile Tyr Arg
            340                 345                 350

Val Ile Arg Thr Thr Gly Tyr Leu Leu Phe Ile Leu His Ile Asn Ala
        355                 360                 365

Cys Val Tyr Tyr Trp Ala Ser Asn Tyr Glu Gly Ile Gly Thr Thr Arg
370                 375                 380
```

```
Trp Val Tyr Asp Gly Glu Gly Asn Glu Tyr Leu Arg Cys Tyr Tyr Trp
385                 390                 395                 400

Ala Val Arg Thr Leu Ile Thr Ile Gly Leu Pro Glu Pro Gln Thr
            405                 410                 415

Leu Phe Glu Ile Val Phe Gln Leu Leu Asn Phe Phe Ser Gly Val Phe
                420                 425                 430

Val Phe Ser Ser Leu Ile Gly Gln Met Arg Asp Val Ile Gly Ala Ala
            435                 440                 445

Thr Ala Asn Gln Asn Tyr Phe Arg Ala Cys Met Asp Asp Thr Ile Ala
        450                 455                 460

Tyr Met Asn Asn Tyr Ser Ile Pro Lys Leu Val Gln Lys Arg Val Arg
465                 470                 475                 480

Thr Trp Tyr Glu Tyr Thr Trp Asp Ser Gln Arg Met Leu Asp Glu Ser
                485                 490                 495

Asp Leu Leu Lys Thr Leu Pro Thr Thr Val Gln Leu Ala Leu Ala Ile
                500                 505                 510

Asp Val Asn Phe Ser Ile Ile Ser Lys Val Asp Leu Phe Lys Gly Cys
            515                 520                 525

Asp Thr Gln Met Ile Tyr Asp Met Leu Leu Arg Leu Lys Ser Val Leu
        530                 535                 540

Tyr Leu Pro Gly Asp Phe Val Cys Lys Lys Gly Glu Ile Gly Lys Glu
545                 550                 555                 560

Met Tyr Ile Ile Lys His Gly Glu Val Gln Val Leu Gly Gly Pro Asp
                565                 570                 575

Gly Thr Lys Val Leu Val Thr Leu Lys Ala Gly Ser Val Phe Gly Glu
            580                 585                 590

Ile Ser Leu Leu Ala Ala Gly Gly Gly Asn Arg Arg Thr Ala Asn Val
        595                 600                 605

Val Ala His Gly Phe Ala Asn Leu Leu Thr Leu Asp Lys Lys Thr Leu
610                 615                 620

Gln Glu Ile Leu Val His Tyr Pro Asp Ser Glu Arg Ile Leu Met Lys
625                 630                 635                 640

Lys Ala Arg Val Leu Leu Lys Gln Lys Ala Lys Thr Ala Glu Ala Thr
            645                 650                 655

Pro Pro Arg Lys Asp Leu Ala Leu Leu Phe Pro Pro Lys Glu Glu Thr
        660                 665                 670

Pro Lys Leu Phe Lys Thr Leu Leu Gly Gly Thr Gly Lys Ala Ser Leu
        675                 680                 685

Ala Arg Leu Leu Lys Leu Lys Arg Glu Gln Ala Ala Gln Lys Lys Glu
690                 695                 700

Asn Ser Glu Gly Gly Glu Glu Gly Lys Glu Asn Glu Asp Lys Gln
705                 710                 715                 720

Lys Glu Asn Glu Asp Lys Gln Lys Glu Asn Glu Asp Lys Gly Lys Glu
            725                 730                 735

Asn Glu Asp Lys Asp Lys Gly Arg Glu Pro Glu Lys Pro Leu Asp
            740                 745                 750

Arg Pro Glu Cys Thr Ala Ser Pro Ile Ala Val Glu Glu Pro His
                755                 760                 765

Ser Val Arg Arg Thr Val Leu Pro Arg Gly Thr Ser Arg Gln Ser Leu
            770                 775                 780

Ile Ile Ser Met Ala Pro Ser Ala Glu Gly Gly Glu Glu Val Leu Thr
785                 790                 795                 800

Ile Glu Val Lys Glu Lys Ala Lys Gln
```

<210> SEQ ID NO 33
<211> LENGTH: 610
<212> TYPE: PRT
<213> ORGANISM: Homo sapiens

<400> SEQUENCE: 33

Met Pro Leu Thr Glu Tyr Leu Lys Arg Ile Lys Leu Pro Asn Ser Ile
1               5                   10                  15

Asp Ser Tyr Thr Asp Arg Leu Tyr Leu Leu Trp Leu Leu Val Thr
            20                  25                  30

Leu Ala Tyr Asn Trp Asn Cys Cys Phe Ile Pro Leu Arg Leu Val Phe
        35                  40                  45

Pro Tyr Gln Thr Ala Asp Asn Ile His Tyr Trp Leu Ile Ala Asp Ile
    50                  55                  60

Ile Cys Asp Ile Ile Tyr Leu Tyr Asp Met Leu Phe Ile Gln Pro Arg
65                  70                  75                  80

Leu Gln Phe Val Arg Gly Gly Asp Ile Ile Val Asp Ser Asn Glu Leu
                85                  90                  95

Arg Lys His Tyr Arg Thr Ser Thr Lys Phe Gln Leu Asp Val Ala Ser
            100                 105                 110

Ile Ile Pro Phe Asp Ile Cys Tyr Leu Phe Phe Gly Phe Asn Pro Met
        115                 120                 125

Phe Arg Ala Asn Arg Met Leu Lys Tyr Thr Ser Phe Phe Glu Phe Asn
130                 135                 140

His His Leu Glu Ser Ile Met Asp Lys Ala Tyr Ile Tyr Arg Val Ile
145                 150                 155                 160

Arg Thr Thr Gly Tyr Leu Leu Phe Ile Leu His Ile Asn Ala Cys Val
                165                 170                 175

Tyr Tyr Trp Ala Ser Asn Tyr Glu Gly Ile Gly Thr Thr Arg Trp Val
            180                 185                 190

Tyr Asp Gly Glu Gly Asn Glu Tyr Leu Arg Cys Tyr Tyr Trp Ala Val
        195                 200                 205

Arg Thr Leu Ile Thr Ile Gly Gly Leu Pro Glu Pro Gln Thr Leu Phe
    210                 215                 220

Glu Ile Val Phe Gln Leu Leu Asn Phe Phe Ser Gly Val Phe Val Phe
225                 230                 235                 240

Ser Ser Leu Ile Gly Gln Met Arg Asp Val Ile Gly Ala Ala Thr Ala
                245                 250                 255

Asn Gln Asn Tyr Phe Arg Ala Cys Met Asp Asp Thr Ile Ala Tyr Met
            260                 265                 270

Asn Asn Tyr Ser Ile Pro Lys Leu Val Gln Lys Arg Val Arg Thr Trp
        275                 280                 285

Tyr Glu Tyr Thr Trp Asp Ser Gln Arg Met Leu Asp Glu Ser Asp Leu
    290                 295                 300

Leu Lys Thr Leu Pro Thr Thr Val Gln Leu Ala Leu Ala Ile Asp Val
305                 310                 315                 320

Asn Phe Ser Ile Ile Ser Lys Val Asp Leu Phe Lys Gly Cys Asp Thr
                325                 330                 335

Gln Met Ile Tyr Asp Met Leu Leu Arg Leu Lys Ser Val Leu Tyr Leu
            340                 345                 350

Pro Gly Asp Phe Val Cys Lys Lys Gly Glu Ile Gly Lys Glu Met Tyr
        355                 360                 365

```
Ile Ile Lys His Gly Glu Val Gln Val Leu Gly Gly Pro Asp Gly Thr
        370                 375                 380
Lys Val Leu Val Thr Leu Lys Ala Gly Ser Val Leu Ala Ala Gly
385                 390                 395                 400
Gly Gly Asn Arg Arg Thr Ala Asn Val Val Ala His Gly Phe Ala Asn
                405                 410                 415
Leu Leu Thr Leu Asp Lys Lys Thr Leu Gln Glu Ile Leu Val His Tyr
            420                 425                 430
Pro Asp Ser Glu Arg Ile Leu Met Lys Lys Ala Arg Val Leu Leu Lys
        435                 440                 445
Gln Lys Ala Lys Thr Ala Glu Ala Thr Pro Pro Arg Lys Asp Leu Ala
    450                 455                 460
Leu Leu Phe Pro Pro Lys Glu Thr Pro Lys Leu Phe Lys Thr Leu
465                 470                 475                 480
Leu Gly Gly Thr Gly Lys Ala Ser Leu Ala Arg Leu Leu Lys Leu Lys
                485                 490                 495
Arg Glu Gln Ala Ala Gln Lys Lys Glu Asn Ser Glu Gly Gly Glu Glu
                500                 505                 510
Glu Gly Lys Glu Asn Glu Asp Lys Gln Lys Glu Asn Glu Asp Lys Gln
            515                 520                 525
Lys Glu Asn Glu Asp Lys Gly Lys Glu Asn Glu Asp Lys Asp Lys Gly
        530                 535                 540
Arg Glu Pro Glu Glu Lys Pro Leu Asp Arg Pro Glu Cys Thr Ala Ser
545                 550                 555                 560
Pro Ile Ala Val Glu Glu Glu Pro His Ser Val Arg Arg Thr Val Leu
                565                 570                 575
Pro Arg Gly Thr Ser Arg Gln Ser Leu Ile Ile Ser Met Ala Pro Ser
                580                 585                 590
Ala Glu Gly Gly Glu Glu Val Leu Thr Ile Glu Val Lys Glu Lys Ala
            595                 600                 605
Lys Gln
    610

<210> SEQ ID NO 34
<211> LENGTH: 7100
<212> TYPE: DNA
<213> ORGANISM: Homo sapiens

<400> SEQUENCE: 34
gacatactga gaataaatcc aaagacatta gtttctttgc acgaaatgag gttacatatc      60
cagtgacatt tatttgagct atttaaacaa cttaaacatc ttttttcttt cttaataagg     120
gacgtttcaa gttgtggtct cagccaaaat gagtgatacc ccttctactg gtttttccat     180
cattcatcct acgtcttctg aaggtcaagt tccaccccct cgccatttga gcctcactca     240
tcctgttgtg gccaagcgaa tcagtttcta caagagcgga gaccccccaat tcggcggggt     300
cagggtggtg gtcaaccctc gctcctttaa gtcctttgat gctctgctgg ataacttgtc     360
caggaaggtg cccctcccct ttggagtgag gaacatcagc acccctcggg gcaggcacag     420
catcacgcgc ctggaggagc tggaggacgg cgagtcctac ctatgttccc acggcaggaa     480
ggtgcagcct gtagacctgg acaaagcccg tcggcgcccg cggccctggc tcagcagccg     540
ggccattagc gcgcactcac cgccccaccc cgtagccgtc gctgctcccg gcatgccccg     600
ccccccacgg agcctagtgg tcttcaggaa tggcgacccg aagacgaggc gtgcggttct     660
tctgagcagg agggtcaccc agagcttcga ggcatttcta cagcacctga cagaggtcat     720
```

```
gcagcgccct gtggtcaagc tgtacgctac ggacggaagg agggttccca gcctccaggc      780
agtgatcctg agctctggag ctgtggtggc ggcaggaagg gagccattta aaccaggaaa      840
ttatgacatc caaaaatact tgcttcctgc tagattacca gggatctctc agcgtgtgta      900
ccccaaggga aatgcaaagt cagaaagcag aaagataagc acacatatgt cttcaagctc      960
aaggtcccag atttattctg tttcttctga gaaacacat aataatgatt gctacttaga     1020
ctattctttt gttcctgaaa agtacttggc cttagaaaag aatgattctc agaatttacc     1080
aatatatcct tctgaagatg atattgagaa atcaattatt tttaatcaag acggcactat     1140
gacagttgag atgaaagttc gattcagaat aaaagaggaa gaaaccataa aatgacaac      1200 tactgtcagt aaaactggtc cttctaataa tgatgaaaag agtgagatga gttttccagg     1260
aagaacagaa agtcgatcat ctggtttaaa gcttgcagca tgttcattct ctgcagatgt     1320
gtcacctatg gagcgaagca gtaatcaaga gggcagtttg gcagaggaga taaacattca     1380
aatgacagat caagtggctg aaacttgcag ttctgctagt tgggagaatg ctactgtgga     1440
cacagatatc atccagggaa ctcaagacca agcaaagcat cgttttttata ggcccctac      1500 acctggacta agaagagtga gacaaaagaa atctgtgatt ggcagtgtga ccttagtatc     1560
tgaaactgag gttcaagaga aaatgattgg acagttttca tatagtgaag aaagggaaag     1620
tggggaaaac aagtctgagt atcacatgtt tacacattct gcagtaaaa tgtcatcagt      1680 atctaacaaa ccagtacttg ttcagatcaa taacaatgat caaatggagg agtcatcatt     1740
agaaagaaaa aaggaaaaca gtctgcttaa gtcaagtgca ataagtgctg gtgtttataga    1800 aattacaagt cagaagatgt tagagatgtc acataataat ggtttgccat caactatatc     1860
aaataactca attgtggagg aagatgtagt tgattgtgtg gtattggaca acaaaactgg     1920
tatcaagaac ttcaaaactt atggtaacac caatgatagg ttcagtccta tttcagcaga    1980
tgcaacccat ttttcaagta ataactctgg aactgacaaa atatttctg aggctccagc      2040 ttcagaagca tcctctactg tcactgcaag aattgacaga ctaattaatg aatttgctca     2100
gtgtggttta acaaaacttc caaaaaatga aagaagatt ttgtcatctg ttgccagcaa      2160
aaagaagaaa aaatctcgac agcaagcaat aaattccagg tatcaagatg gacagcttgc     2220
aaccaaagga attcttaata agaatgagag aataaacaca aaggtagaa ttacaaagga      2280 aatgatagtg caagattcag atagtcccct taaaggaggg atactttgtg aggaagacct     2340
ccagaaaagt gatactgtaa ttgaatcaaa tactttttgt tccaaaagta atctcaattc     2400
cacgatttcc aagaatttcc atagaaataa attaaatact actcaaaatt ccaaggttca     2460 aggacttta accaaaagaa aatctagatc actaaataaa ataagcttag gagcacctaa      2520
aaaaagagaa atcggtcaaa gagataaagt gtttcctcac aatgaatcta atattgcaa      2580 aagtactttt gaaaacaaaa gtttatttca tgtatttaac atccttgagc aaaaacccaa     2640
agatttttat gcaccgcaat ctcaagcaga agtggcatct gggtatttga gaggaatggc     2700
aaagaagagt ttagtttcaa agttactga ttcacacata actttaaaaa gccagaaaaa       2760
acgtaaaggg gataaagtga agcaagtgc tatttttaagt aaacaacatg ctacaaccag     2820
ggcaaattct ttagcttctt tgaaaaaacc tgattttcct gaggctattg ctcatcattc     2880
aattcaaaat tatatacaga gttggttgca gaacataaat ccatatccaa cttttaaagcc    2940 tataaaatca gctccagtat gtagaaatga aacgagtgtg gtaaattgta gcaataatag    3000
tttttcaggg aatgatcccc atacaaattc tggaaaaata agtaatttg ttatggaaag      3060
```

```
taataagcac ataactaaaa ttgccggttt gacaggagat aatctatgta aagagggaga    3120
taagtctttt attgccaatg acactggtga agaagatctc catgagacac aggttggatc    3180
tctgaatgat gcttatttgg ttcccctgca tgaacactgt actttgtcac agtcagctat    3240
taatgatcat aatactaaaa gtcatatagc tgctgaaaaa tcaggaccag agaaaaaact    3300
tgtttaccag gaaataaacc tagctagaaa aaggcaaagt gtagaggctg ccattcaagt    3360
agatcctata gaagaggaaa ctccaaaaga cctcttacca gtcctgatgc ttcaccaatt    3420
gcaagcttca gttcctggta ttcacaagac tcagaatgga gttgttcaaa tgccaggttc    3480
acttgcaggt gttcccttc attctgcaat atgtaattca tccactaatc tccttctagc    3540
ttggctcttg gtgctaaacc taagggaag tatgaatagc ttctgtcaag ttgatgctca    3600
caaggctacc aacaaatctt cagaaacact tgcattgttg gagattctaa agcacatagc    3660
tatcacagag gaagctgatg acttgaaagc tgctgttgcc aatttagtgg agtcaactac    3720
aagccacttt ggactcagtg agaaagaaca agacatggtt ccaatagatc tttctgcaaa    3780
ttgttccacg gtcaacattc agagtgttcc taagtgcagt gaaaatgaaa gaacacaagg    3840
aatctcctct ttggatggag gttgctctgc cagtgaggca tgtgcccctg aagtctgtgt    3900
tttggaagtg acttgctctc catgtgagat gtgcactgta aataaggctt attctccaaa    3960
agagacatgt aaccccagtg acactttttt tcctagtgat ggttatggtg tggatcagac    4020
ttctatgaat aaggcttgtt tcctaggaga ggtctgttca cttactgata ctgtgtttc    4080 tgataaggct tgtgctcaaa aggagaacca tacctatgag ggagcttgcc caattgatga    4140
gacctacgtt cctgtcaatg tctgcaatac cattgacttt ttaaactcca agaaaacac     4200 atatactgat aacttggatt caactgaaga gttagaaaga ggtgatgaca ttcagaaaga    4260
tctaaatatt ttgacagacc ctgaatataa aatggatttt aatacattgg tgtcacatca    4320
aaatgtcagt aatttaagct cctgtggcct ttgcctaagt gaaaaagaag cagaacttga    4380
taagaaacat agttctctag atgattttga aaattgttca ctaaggaagt ttcaggatga    4440
aaatgcatat acttcctttg atatggaaga accacggact tctgaagaac caggctcaat    4500
aaccaacagc atgacatcaa gtgaaagaaa catttcagaa ttggaatctt ttgaagaatt    4560
agaaaaccat gacactgata tctttaatac agtggtaaat ggaggagagc aagccactga    4620
agaattaatc caagaagagg tagaggctag taaaacttta gaattgatag acatctctag    4680
taagaatatt atggaagaaa aaagaatgaa cggtataatt tatgaaataa tcagtaagag    4740
gctggcaaca ccaccatctt tagatttttg ctatgattct aagcaaaata gtgaaaagga    4800
gaccaatgaa ggagaaacta agatggtaaa aatgatggtg aaaactatgg aaactggaag    4860
ttattcagag tcctctcctg atttaaaaaa atgcatcaaa agtccagtga cttctgattg    4920
gtcagactat cggcctgaca gtgacagtga gcagccatat aaaacatcca gtgatgatcc    4980
caatgacagt ggcgaactta cccaagagaa agaatataac ataggatttg ttaaaagggc    5040
aatagaaaaa ctgtacggta aagcagatat tatcaaacca tctttttttc ctgggtctac    5100
ccgcaaatct caggtttgtc cttataattc tgtggaattt cagtgttcca ggaaagcaag    5160
tctttatgat tctgaagggc agtcatttgg ctcttctgaa caggtatcta gtagttcatc    5220
tatgttgcag gaattccagg aggaaagaca agataagtgt gatgttagtg ctgtgaggga    5280
caattattgt aggggtgaca ttgtagaacc tggtacaaaa caaatgatg atagcagaat    5340 cctcacagac atagaggaag gagtactgat tgacaaaggc aaatggcttc tgaaagaaaa    5400
tcatttgcta aggatgtcat ctgaaaatcc tggcatgtgt ggcaatgcag acaccacatc    5460
```

```
agtggacacc ctacttgata ataacagcag tgaggtacca tattcacatt ttggtaattt    5520
ggccccaggc ccaacgatgg atgaactctc ctcttcagaa ctcgaggaac tgactcaacc    5580
ccttgaacta aaatgcaatt actttaacat gcctcatggt agtgactcag aaccttttca    5640
tgaggacttg ctggatgttc gcaatgaaac ctgtgccaag gaaagaatag caaatcatca    5700
tacagaggag aagggtagtc atcagtcaga aagagtatgc acatctgtca ctcattcctt    5760
tatttctgct ggtaacaaag tctaccctgt ctctgatgat gctattaaaa accaaccatt    5820
gcctggcagt aatatgattc atggtacact tcaggaagct gactctttgg ataaactgta    5880
tgctctttgt ggtcaacatt gcccaatact aactgttatt atccaaccca tgaatgagga    5940
agaccgagga tttgcatatc gcaaagaatc tgatattgaa aatttcttgg gttttatttt    6000
atggatgaaa atacacccat atttacttca gacagacaaa aatgtgttca gggaagagaa    6060
caataaagca gtatgagac aaaatcttat tgataatgcc attggtgata tatttgatca    6120
gttttatttc agtaacacat ttgacttgat gggtaaaaga agaaaacaaa aaagaattaa    6180
cttcttgggg ttagaggaag aaggtaattt aaagaaattt caaccagatt tgaaggaaag    6240
gttttgtatg aatttcttgc acacatcatt gttagttgtg ggtaatgtgg attcaaatac    6300
acaagacctc agcggtcaga caaatgaaat ctttaaagca gtcgatgaga ataacaactt    6360
attaaataac agattccagg gctcaagaac aaatctcaac caagtagtaa gagaaaatat    6420
caactgtcat tacttctttg aaatgcttgg tcaagcttgc ctcttagata tttgccaagt    6480
tgagacctcc ttaaatatta gcaacagaaa tattttagaa ctttgtatgt ttgagggtga    6540
aaatcttttc atttgggaag aggaagacat attaaattta actgatcttg aaagcagtag    6600
agaacaagaa gatttataat ttcaatatca gcacactcat tctttgtcaa ttcatttttt    6660
cccatgagat gaagcacatg tgacgaatac ggactagata acctctaaga attttccact    6720
tcttcaaaat gaacttactc tagaaagctt acccttggat aaccagtttg actttcataa    6780
tgtctctgtt ttttgttttt ccaacaatta cagactcagg ttctcttatt ttggaagttt    6840
ctatctggtt ttgttctgaa cttacatttt ttttttttt ggtatctatg atttttttg    6900
ctcagggcat caaaatgtgc taaggacaag aattatatcc tttttaaaaa atgttgttag    6960
cttggtgtaa aatgtatatt gactgtattg gtgaataaat tgaatagaca taacctcaaa    7020
gtacttcact tattctttt aactactgat ttgataaaaa gtatgattat aagatatcca    7080
cgacaatctc atagtttctt                                                7100
```

<210> SEQ ID NO 35
<211> LENGTH: 2156
<212> TYPE: PRT
<213> ORGANISM: Homo sapiens

<400> SEQUENCE: 35

Met Ser Asp Thr Pro Ser Thr Gly Phe Ser Ile Ile His Pro Thr Ser
1               5                   10                  15

Ser Glu Gly Gln Val Pro Pro Arg His Leu Ser Leu Thr His Pro
            20                  25                  30

Val Val Ala Lys Arg Ile Ser Phe Tyr Lys Ser Gly Asp Pro Gln Phe
        35                  40                  45

Gly Gly Val Arg Val Val Val Asn Pro Arg Ser Phe Lys Ser Phe Asp
    50                  55                  60

Ala Leu Leu Asp Asn Leu Ser Arg Lys Val Pro Leu Pro Phe Gly Val
65                  70                  75                  80

-continued

Arg Asn Ile Ser Thr Pro Arg Gly Arg His Ser Ile Thr Arg Leu Glu
            85                  90                  95

Glu Leu Glu Asp Gly Glu Ser Tyr Leu Cys Ser His Gly Arg Lys Val
            100                 105                 110

Gln Pro Val Asp Leu Asp Lys Ala Arg Arg Pro Arg Pro Trp Leu
            115                 120                 125

Ser Ser Arg Ala Ile Ser Ala His Ser Pro Pro His Pro Val Ala Val
            130                 135                 140

Ala Ala Pro Gly Met Pro Arg Pro Arg Ser Leu Val Val Phe Arg
145                 150                 155                 160

Asn Gly Asp Pro Lys Thr Arg Arg Ala Val Leu Leu Ser Arg Arg Val
            165                 170                 175

Thr Gln Ser Phe Glu Ala Phe Leu Gln His Leu Thr Glu Val Met Gln
            180                 185                 190

Arg Pro Val Val Lys Leu Tyr Ala Thr Asp Gly Arg Arg Val Pro Ser
            195                 200                 205

Leu Gln Ala Val Ile Leu Ser Ser Gly Ala Val Val Ala Ala Gly Arg
            210                 215                 220

Glu Pro Phe Lys Pro Gly Asn Tyr Asp Ile Gln Lys Tyr Leu Leu Pro
225                 230                 235                 240

Ala Arg Leu Pro Gly Ile Ser Gln Arg Val Tyr Pro Lys Gly Asn Ala
            245                 250                 255

Lys Ser Glu Ser Arg Lys Ile Ser Thr His Met Ser Ser Ser Ser Arg
            260                 265                 270

Ser Gln Ile Tyr Ser Val Ser Ser Glu Lys Thr His Asn Asn Asp Cys
            275                 280                 285

Tyr Leu Asp Tyr Ser Phe Val Pro Glu Lys Tyr Leu Ala Leu Glu Lys
            290                 295                 300

Asn Asp Ser Gln Asn Leu Pro Ile Tyr Pro Ser Glu Asp Asp Ile Glu
305                 310                 315                 320

Lys Ser Ile Ile Phe Asn Gln Asp Gly Thr Met Thr Val Glu Met Lys
            325                 330                 335

Val Arg Phe Arg Ile Lys Glu Glu Glu Thr Ile Lys Trp Thr Thr Thr
            340                 345                 350

Val Ser Lys Thr Gly Pro Ser Asn Asn Asp Glu Lys Ser Glu Met Ser
            355                 360                 365

Phe Pro Gly Arg Thr Glu Ser Arg Ser Ser Gly Leu Lys Leu Ala Ala
370                 375                 380

Cys Ser Phe Ser Ala Asp Val Ser Pro Met Glu Arg Ser Ser Asn Gln
385                 390                 395                 400

Glu Gly Ser Leu Ala Glu Glu Ile Asn Ile Gln Met Thr Asp Gln Val
            405                 410                 415

Ala Glu Thr Cys Ser Ser Ala Ser Trp Glu Asn Ala Thr Val Asp Thr
            420                 425                 430

Asp Ile Ile Gln Gly Thr Gln Asp Gln Ala Lys His Arg Phe Tyr Arg
            435                 440                 445

Pro Pro Thr Pro Gly Leu Arg Arg Val Arg Gln Lys Lys Ser Val Ile
            450                 455                 460

Gly Ser Val Thr Leu Val Ser Glu Thr Glu Val Gln Glu Lys Met Ile
465                 470                 475                 480

Gly Gln Phe Ser Tyr Ser Glu Glu Arg Glu Ser Gly Glu Asn Lys Ser
            485                 490                 495

-continued

```
Glu Tyr His Met Phe Thr His Ser Cys Ser Lys Met Ser Ser Val Ser
            500                 505                 510

Asn Lys Pro Val Leu Val Gln Ile Asn Asn Asp Gln Met Glu Glu
        515                 520                 525

Ser Ser Leu Glu Arg Lys Lys Glu Asn Ser Leu Leu Lys Ser Ser Ala
    530                 535                 540

Ile Ser Ala Gly Val Ile Glu Ile Thr Ser Gln Lys Met Leu Glu Met
545                 550                 555                 560

Ser His Asn Asn Gly Leu Pro Ser Thr Ile Ser Asn Asn Ser Ile Val
                565                 570                 575

Glu Glu Asp Val Val Asp Cys Val Val Leu Asp Asn Lys Thr Gly Ile
            580                 585                 590

Lys Asn Phe Lys Thr Tyr Gly Asn Thr Asn Asp Arg Phe Ser Pro Ile
        595                 600                 605

Ser Ala Asp Ala Thr His Phe Ser Ser Asn Asn Ser Gly Thr Asp Lys
    610                 615                 620

Asn Ile Ser Glu Ala Pro Ala Ser Glu Ala Ser Ser Thr Val Thr Ala
625                 630                 635                 640

Arg Ile Asp Arg Leu Ile Asn Glu Phe Ala Gln Cys Gly Leu Thr Lys
                645                 650                 655

Leu Pro Lys Asn Glu Lys Lys Ile Leu Ser Ser Val Ala Ser Lys Lys
            660                 665                 670

Lys Lys Lys Ser Arg Gln Ala Ile Asn Ser Arg Tyr Gln Asp Gly
        675                 680                 685

Gln Leu Ala Thr Lys Gly Ile Leu Asn Lys Asn Glu Arg Ile Asn Thr
    690                 695                 700

Lys Gly Arg Ile Thr Lys Glu Met Ile Val Gln Asp Ser Asp Ser Pro
705                 710                 715                 720

Leu Lys Gly Gly Ile Leu Cys Glu Glu Asp Leu Gln Lys Ser Asp Thr
                725                 730                 735

Val Ile Glu Ser Asn Thr Phe Cys Ser Lys Ser Asn Leu Asn Ser Thr
            740                 745                 750

Ile Ser Lys Asn Phe His Arg Asn Lys Leu Asn Thr Thr Gln Asn Ser
        755                 760                 765

Lys Val Gln Gly Leu Leu Thr Lys Arg Lys Ser Arg Ser Leu Asn Lys
    770                 775                 780

Ile Ser Leu Gly Ala Pro Lys Lys Arg Glu Ile Gly Gln Arg Asp Lys
785                 790                 795                 800

Val Phe Pro His Asn Glu Ser Lys Tyr Cys Lys Ser Thr Phe Glu Asn
                805                 810                 815

Lys Ser Leu Phe His Val Phe Asn Ile Leu Glu Gln Lys Pro Lys Asp
            820                 825                 830

Phe Tyr Ala Pro Gln Ser Gln Ala Glu Val Ala Ser Gly Tyr Leu Arg
        835                 840                 845

Gly Met Ala Lys Lys Ser Leu Val Ser Lys Val Thr Asp Ser His Ile
    850                 855                 860

Thr Leu Lys Ser Gln Lys Lys Arg Lys Gly Asp Lys Val Lys Ala Ser
865                 870                 875                 880

Ala Ile Leu Ser Lys Gln His Ala Thr Thr Arg Ala Asn Ser Leu Ala
                885                 890                 895

Ser Leu Lys Lys Pro Asp Phe Pro Glu Ala Ile Ala His Ser Ile
            900                 905                 910

Gln Asn Tyr Ile Gln Ser Trp Leu Gln Asn Ile Asn Pro Tyr Pro Thr
```

-continued

```
              915                 920                 925
Leu Lys Pro Ile Lys Ser Ala Pro Val Cys Arg Asn Glu Thr Ser Val
              930                 935                 940
Val Asn Cys Ser Asn Asn Ser Phe Ser Gly Asn Asp Pro His Thr Asn
945                 950                 955                 960
Ser Gly Lys Ile Ser Asn Phe Val Met Glu Ser Asn Lys His Ile Thr
              965                 970                 975
Lys Ile Ala Gly Leu Thr Gly Asp Asn Leu Cys Lys Glu Gly Asp Lys
              980                 985                 990
Ser Phe Ile Ala Asn Asp Thr Gly Glu Glu Asp Leu His Glu Thr Gln
              995                 1000                1005
Val Gly Ser Leu Asn Asp Ala Tyr Leu Val Pro Leu His Glu His
    1010                1015                1020
Cys Thr Leu Ser Gln Ser Ala Ile Asn Asp His Asn Thr Lys Ser
    1025                1030                1035
His Ile Ala Ala Glu Lys Ser Gly Pro Glu Lys Lys Leu Val Tyr
    1040                1045                1050
Gln Glu Ile Asn Leu Ala Arg Lys Arg Gln Ser Val Glu Ala Ala
    1055                1060                1065
Ile Gln Val Asp Pro Ile Glu Glu Thr Pro Lys Asp Leu Leu
    1070                1075                1080
Pro Val Leu Met Leu His Gln Leu Gln Ala Ser Val Pro Gly Ile
    1085                1090                1095
His Lys Thr Gln Asn Gly Val Val Gln Met Pro Gly Ser Leu Ala
    1100                1105                1110
Gly Val Pro Phe His Ser Ala Ile Cys Asn Ser Ser Thr Asn Leu
    1115                1120                1125
Leu Leu Ala Trp Leu Leu Val Leu Asn Leu Lys Gly Ser Met Asn
    1130                1135                1140
Ser Phe Cys Gln Val Asp Ala His Lys Ala Thr Asn Lys Ser Ser
    1145                1150                1155
Glu Thr Leu Ala Leu Leu Glu Ile Leu Lys His Ile Ala Ile Thr
    1160                1165                1170
Glu Glu Ala Asp Asp Leu Lys Ala Ala Val Ala Asn Leu Val Glu
    1175                1180                1185
Ser Thr Thr Ser His Phe Gly Leu Ser Glu Lys Glu Gln Asp Met
    1190                1195                1200
Val Pro Ile Asp Leu Ser Ala Asn Cys Ser Thr Val Asn Ile Gln
    1205                1210                1215
Ser Val Pro Lys Cys Ser Glu Asn Glu Arg Thr Gln Gly Ile Ser
    1220                1225                1230
Ser Leu Asp Gly Gly Cys Ser Ala Ser Glu Ala Cys Ala Pro Glu
    1235                1240                1245
Val Cys Val Leu Glu Val Thr Cys Ser Pro Cys Glu Met Cys Thr
    1250                1255                1260
Val Asn Lys Ala Tyr Ser Pro Lys Glu Thr Cys Asn Pro Ser Asp
    1265                1270                1275
Thr Phe Phe Pro Ser Asp Gly Tyr Gly Val Asp Gln Thr Ser Met
    1280                1285                1290
Asn Lys Ala Cys Phe Leu Gly Glu Val Cys Ser Leu Thr Asp Thr
    1295                1300                1305
Val Phe Ser Asp Lys Ala Cys Ala Gln Lys Glu Asn His Thr Tyr
    1310                1315                1320
```

```
Glu Gly Ala Cys Pro Ile Asp Glu Thr Tyr Val Pro Val Asn Val
            1325                1330                1335

Cys Asn Thr Ile Asp Phe Leu Asn Ser Lys Glu Asn Thr Tyr Thr
    1340                1345                1350

Asp Asn Leu Asp Ser Thr Glu Glu Leu Glu Arg Gly Asp Asp Ile
    1355                1360                1365

Gln Lys Asp Leu Asn Ile Leu Thr Asp Pro Glu Tyr Lys Asn Gly
    1370                1375                1380

Phe Asn Thr Leu Val Ser His Gln Asn Val Ser Asn Leu Ser Ser
    1385                1390                1395

Cys Gly Leu Cys Leu Ser Glu Lys Glu Ala Glu Leu Asp Lys Lys
    1400                1405                1410

His Ser Ser Leu Asp Asp Phe Glu Asn Cys Ser Leu Arg Lys Phe
    1415                1420                1425

Gln Asp Glu Asn Ala Tyr Thr Ser Phe Asp Met Glu Glu Pro Arg
    1430                1435                1440

Thr Ser Glu Glu Pro Gly Ser Ile Thr Asn Ser Met Thr Ser Ser
    1445                1450                1455

Glu Arg Asn Ile Ser Glu Leu Glu Ser Phe Glu Glu Leu Glu Asn
    1460                1465                1470

His Asp Thr Asp Ile Phe Asn Thr Val Val Asn Gly Gly Glu Gln
    1475                1480                1485

Ala Thr Glu Glu Leu Ile Gln Glu Val Glu Ala Ser Lys Thr
    1490                1495                1500

Leu Glu Leu Ile Asp Ile Ser Ser Lys Asn Ile Met Glu Glu Lys
    1505                1510                1515

Arg Met Asn Gly Ile Ile Tyr Glu Ile Ile Ser Lys Arg Leu Ala
    1520                1525                1530

Thr Pro Pro Ser Leu Asp Phe Cys Tyr Asp Ser Lys Gln Asn Ser
    1535                1540                1545

Glu Lys Glu Thr Asn Glu Gly Glu Thr Lys Met Val Lys Met Met
    1550                1555                1560

Val Lys Thr Met Glu Thr Gly Ser Tyr Ser Glu Ser Ser Pro Asp
    1565                1570                1575

Leu Lys Lys Cys Ile Lys Ser Pro Val Thr Ser Asp Trp Ser Asp
    1580                1585                1590

Tyr Arg Pro Asp Ser Asp Ser Glu Gln Pro Tyr Lys Thr Ser Ser
    1595                1600                1605

Asp Asp Pro Asn Asp Ser Gly Glu Leu Thr Gln Glu Lys Glu Tyr
    1610                1615                1620

Asn Ile Gly Phe Val Lys Arg Ala Ile Glu Lys Leu Tyr Gly Lys
    1625                1630                1635

Ala Asp Ile Ile Lys Pro Ser Phe Phe Pro Gly Ser Thr Arg Lys
    1640                1645                1650

Ser Gln Val Cys Pro Tyr Asn Ser Val Glu Phe Gln Cys Ser Arg
    1655                1660                1665

Lys Ala Ser Leu Tyr Asp Ser Glu Gly Gln Ser Phe Gly Ser Ser
    1670                1675                1680

Glu Gln Val Ser Ser Ser Ser Met Leu Gln Glu Phe Gln Glu
    1685                1690                1695

Glu Arg Gln Asp Lys Cys Asp Val Ser Ala Val Arg Asp Asn Tyr
    1700                1705                1710
```

```
Cys Arg Gly Asp Ile Val Glu Pro Gly Thr Lys Gln Asn Asp Asp
    1715                1720                1725

Ser Arg Ile Leu Thr Asp Ile Glu Glu Gly Val Leu Ile Asp Lys
    1730                1735                1740

Gly Lys Trp Leu Leu Lys Glu Asn His Leu Leu Arg Met Ser Ser
    1745                1750                1755

Glu Asn Pro Gly Met Cys Gly Asn Ala Asp Thr Thr Ser Val Asp
    1760                1765                1770

Thr Leu Leu Asp Asn Asn Ser Ser Glu Val Pro Tyr Ser His Phe
    1775                1780                1785

Gly Asn Leu Ala Pro Gly Pro Thr Met Asp Glu Leu Ser Ser Ser
    1790                1795                1800

Glu Leu Glu Glu Leu Thr Gln Pro Leu Glu Leu Lys Cys Asn Tyr
    1805                1810                1815

Phe Asn Met Pro His Gly Ser Asp Ser Glu Pro Phe His Glu Asp
    1820                1825                1830

Leu Leu Asp Val Arg Asn Glu Thr Cys Ala Lys Glu Arg Ile Ala
    1835                1840                1845

Asn His His Thr Glu Glu Lys Gly Ser His Gln Ser Glu Arg Val
    1850                1855                1860

Cys Thr Ser Val Thr His Ser Phe Ile Ser Ala Gly Asn Lys Val
    1865                1870                1875

Tyr Pro Val Ser Asp Asp Ala Ile Lys Asn Gln Pro Leu Pro Gly
    1880                1885                1890

Ser Asn Met Ile His Gly Thr Leu Gln Glu Ala Asp Ser Leu Asp
    1895                1900                1905

Lys Leu Tyr Ala Leu Cys Gly Gln His Cys Pro Ile Leu Thr Val
    1910                1915                1920

Ile Ile Gln Pro Met Asn Glu Glu Asp Arg Gly Phe Ala Tyr Arg
    1925                1930                1935

Lys Glu Ser Asp Ile Glu Asn Phe Leu Gly Phe Tyr Leu Trp Met
    1940                1945                1950

Lys Ile His Pro Tyr Leu Leu Gln Thr Asp Lys Asn Val Phe Arg
    1955                1960                1965

Glu Glu Asn Asn Lys Ala Ser Met Arg Gln Asn Leu Ile Asp Asn
    1970                1975                1980

Ala Ile Gly Asp Ile Phe Asp Gln Phe Tyr Phe Ser Asn Thr Phe
    1985                1990                1995

Asp Leu Met Gly Lys Arg Lys Gln Lys Arg Ile Asn Phe Leu
    2000                2005                2010

Gly Leu Glu Glu Glu Gly Asn Leu Lys Lys Phe Gln Pro Asp Leu
    2015                2020                2025

Lys Glu Arg Phe Cys Met Asn Phe Leu His Thr Ser Leu Leu Val
    2030                2035                2040

Val Gly Asn Val Asp Ser Asn Thr Gln Asp Leu Ser Gly Gln Thr
    2045                2050                2055

Asn Glu Ile Phe Lys Ala Val Asp Glu Asn Asn Asn Leu Leu Asn
    2060                2065                2070

Asn Arg Phe Gln Gly Ser Arg Thr Asn Leu Asn Gln Val Val Arg
    2075                2080                2085

Glu Asn Ile Asn Cys His Tyr Phe Phe Glu Met Leu Gly Gln Ala
    2090                2095                2100

Cys Leu Leu Asp Ile Cys Gln Val Glu Thr Ser Leu Asn Ile Ser
```

```
                 2105                2110                 2115

Asn Arg Asn Ile Leu Glu Leu Cys Met Phe Glu Gly Glu Asn Leu
        2120                2125                2130

Phe Ile Trp Glu Glu Glu Asp Ile Leu Asn Leu Thr Asp Leu Glu
    2135                2140                2145

Ser Ser Arg Glu Gln Glu Asp Leu
        2150                2155

<210> SEQ ID NO 36
<211> LENGTH: 3950
<212> TYPE: DNA
<213> ORGANISM: Homo sapiens

<400> SEQUENCE: 36
atgtcacatc tggtggaccc tacatcagga gacttgccag ttagagacat agatgctata      60
cctctggtgc taccagcctc aaaaggtaag aatatgaaaa ctcaaccacc cttgagcagg     120
atgaaccggg aggaattgga ggacagtttc tttcgacttc gcaagatca catgttggtg      180 aaggagcttt cttggaagca acaggatgag atcaaaaggc tgaggaccac cttgctgcgg    240
ttgaccgctg ctggccggga cctgcgggtc gcggaggagg cggcgccgct ctcggagacc    300
gcaaggcgcg ggcagaaggc gggatggcgg cagcgcctct ccatgcacca gcgccccag    360 atgcaccgac tgcaagggca tttccactgc gtcggccctg ccagcccccg ccgcgcccag    420
cctcgcgtcc aagtgggaca cagacagctc cacacagccg gtgcaccggt gccggagaaa    480
cccaagaggg ggccaaggga caggctgagc tacacagccc ctccatcgtt taaggagcat    540
gcgacaaatg aaaacagagg tgaagtagcc agtaaaccca gtgaacttgt ttctggttct    600
aacagcataa tttctttcag cagtgtcata agtatggcta aacccattgg tctatgcatg    660
cctaacagtg cccacatcat ggccagcaat accatgcaag tggaagagcc acccaagtct    720
cctgagaaaa tgtggcctaa agatgaaaat tttgaacaga gaagctcatt ggagtgtgct    780
cagaaggctg cagagcttcg agcttccatt aaagagaagg tagagctgat tcgacttaag    840
aagctcttac atgaaagaaa tgcttcattg gttatgacaa agcacaatt aacagaagtt    900 caagaggcat acgaaacctt gctccagaag aatcagggaa tcctgagtgc agcccatgag    960 gcccctcctca gcaagtgaa tgagctcagg gcagagctga ggaagaaag caagaaggct   1020 gtgagcttga agagccaact ggaagatgtg tctatcttgc agatgactct gaaggagttt  1080
caggagagag ttgaagattt ggaaaaagaa cgaaaattgc tgaatgacaa ttatgacaaa    1140
ctcttagaaa gcatgctgga cagcagtgac agctccagtc agccccactg gagcaacgag    1200
ctcatagcgg aacagctaca gcagcaagtc tctcagctgc aggatcagct ggatgctgag    1260
ctggaggaca gagaaaagt tttacttgag ctgtccaggg agaaagccca aaatgaggat   1320
ctgaagcttg aagtcaccaa catacttcag aagcataaac aggaagtaga gctcctccaa   1380
aatgcagcca caatttccca acctcctgac aggcaatctg aaccagccac tcacccagct   1440
gtattgcaag agaacactca gatcgagcca gtgaaccca aaaccaaga agaaaagaaa      1500 ctgtcccagg tgctaaatga gttgcaagta tcacacgcag agaccacatt ggaactagaa    1560
aagaccaggg acatgcttat tctgcagcgc aaaatcaacg tgtgttatca ggaggaactg    1620
gaggcaatga tgacaaaagc tgacaatgat aatagagatc acaagaaaa gctggagagg    1680 ttgactcgac tactagacct caagaataac cgtatcaagc agctggaagg tatttttaaga    1740 agccatgacc ttccaacatc tgaacagctc aaagatgttg cttatggcac ccgaccgttg    1800
```

```
tcgttatgtt tggaaacact gccagcccat ggagatgagg ataaagtgga tatttctctg    1860
ctgcatcagg gtgagaatct ttttgaactg cacatccacc aggccttcct gacatctgcc    1920
gccctagctc aggctggaga tacccaacct accactttct gcacctattc cttctatgac    1980
tttgaaaccc actgtacccc attatctgtg gggccacagc ccctctatga cttcacctcc    2040
cagtatgtga tggagacaga ttcgcttttc ttacactacc ttcaagaggc ttcagcccgg    2100
cttgacatac accaggccat ggccagtgaa cacagcactc ttgctgcagg atggatttgc    2160
tttgacaggg tgctagagac tgtggagaaa gtccatggct tggccacact gattggagct    2220
ggtggagaag agttcggggt tctagagtac tggatgaggc tgcgtttccc cataaaaccc    2280
agcctacagg cgtgcaataa acgaaagaaa gcccaggtct acctgtcaac cgatgtgctt    2340
ggaggccgga aggcccagga agaggagttc agatcggagt cttgggaacc tcagaacgag    2400
ctgtggattg aaatcaccaa gtgctgtggc ctccggagtc gatggctggg aactcaaccc    2460
agtccatatg ctgtgtaccg cttcttcacc ttttctgacc atgacactgc catcattcca    2520
gccagtaaca cccctactt tagagaccag gctcgattcc cagtgcttgt gacctctgac    2580
ctggaccatt atctgagacg ggaggccttg tctatacatg tttttgatga tgaagactta    2640
gagcctggct cgtatcttgg ccgagcccga gtgcctttac tgcctcttgc aaaaaatgaa    2700
tctatcaaag gtgattttaa cctcactgac cctgcagaga aacccaacgg atctattcaa    2760
gtgcaactgg attggaagtt tccctacata cccccctgaga gcttcctgaa accagaagct    2820
cagactaagg ggaaggatac caaggacagt tcaaagatct catctgaaga ggaaaaggct    2880
tcatttcctt cccaggatca gatggcatct cctgaggttc ccattgaagc tggccagtat    2940
cgatctaaga gaaaacctcc tcatgggga gaaagaaagg agaaggagca ccaggttgtg    3000
agctactcaa gaagaaaaca tggcaaaaga ataggtgttc aaggaaagaa tagaatggag    3060
tatcttagcc ttaacatctt aaatggaaat acaccagagc aggtgaatta cactgagtgg    3120
aagttctcag agactaacag cttcataggt gatggctttta aaaatcagca cgaggaagag    3180
gaaatgacat tatcccattc agcactgaaa cagaaggaac ctctacatcc tgtaaatgac    3240
aaagaatcct ctgaacaagg ttctgaagtc agtgaagcac aaactaccga cagtgatgat    3300
gtcatagtgc cacccatgtc tcagaaatat cctaaggcag attcagagaa gatgtgcatt    3360
gaaattgtct ccctggcctt ctacccagag cagaagtga tgtctgatga gaacataaaa    3420
caggtgtatg tggagtacaa attctacgac ctaccccttgt cggagacaga gactccagtg    3480
tccctaagga agcctagggc aggagaagaa atccactttc actttagcaa ggtaatagac    3540
ctggacccac aggagcagca aggccgaagg cggtttctgt tcgacatgct gaatggacaa    3600
gatcctgatc aaggacattt aaagtttaca gtggtaagtg atcctctgga tgaagaaaag    3660
aaagaatgtg aagaagtggg atatgcatat cttcaactgt ggcagatcct ggagtcagga    3720
agagatattc tagagcaaga gctagacatt gttagccctg aagatctggc tacccccata    3780
ggaaggctga aggtttccct tcaagcagct gctgtcctcc atgctatttta caaggagatg    3840
actgaagatt tgttttcatg aaggaacaag tgctattcca atctaaaagt ctctgaggga    3900
accatagtaa aaagtctctt ataaagttag cttgctataa catgaaaaaa               3950
```

<210> SEQ ID NO 37
<211> LENGTH: 1286
<212> TYPE: PRT
<213> ORGANISM: Homo sapiens

<400> SEQUENCE: 37

-continued

```
Met Ser His Leu Val Asp Pro Thr Ser Gly Asp Leu Pro Val Arg Asp
1               5                   10                  15

Ile Asp Ala Ile Pro Leu Val Leu Pro Ala Ser Lys Gly Lys Asn Met
            20                  25                  30

Lys Thr Gln Pro Pro Leu Ser Arg Met Asn Arg Glu Glu Leu Glu Asp
            35                  40                  45

Ser Phe Phe Arg Leu Arg Glu Asp His Met Leu Val Lys Glu Leu Ser
    50                  55                  60

Trp Lys Gln Gln Asp Glu Ile Lys Arg Leu Thr Thr Leu Leu Arg
65                  70                  75                  80

Leu Thr Ala Ala Gly Arg Asp Leu Arg Val Ala Glu Glu Ala Ala Pro
                85                  90                  95

Leu Ser Glu Thr Ala Arg Arg Gly Gln Lys Ala Gly Trp Arg Gln Arg
                100                 105                 110

Leu Ser Met His Gln Arg Pro Gln Met His Arg Leu Gln Gly His Phe
            115                 120                 125

His Cys Val Gly Pro Ala Ser Pro Arg Arg Ala Gln Pro Arg Val Gln
            130                 135                 140

Val Gly His Arg Gln Leu His Thr Ala Gly Ala Pro Val Pro Glu Lys
145                 150                 155                 160

Pro Lys Arg Gly Pro Arg Asp Arg Leu Ser Tyr Thr Ala Pro Pro Ser
                165                 170                 175

Phe Lys Glu His Ala Thr Asn Glu Asn Arg Gly Glu Val Ala Ser Lys
            180                 185                 190

Pro Ser Glu Leu Val Ser Gly Ser Asn Ser Ile Ile Ser Phe Ser Ser
            195                 200                 205

Val Ile Ser Met Ala Lys Pro Ile Gly Leu Cys Met Pro Asn Ser Ala
210                 215                 220

His Ile Met Ala Ser Asn Thr Met Gln Val Glu Glu Pro Pro Lys Ser
225                 230                 235                 240

Pro Glu Lys Met Trp Pro Lys Asp Glu Asn Phe Glu Gln Arg Ser Ser
                245                 250                 255

Leu Glu Cys Ala Gln Lys Ala Ala Glu Leu Arg Ala Ser Ile Lys Glu
            260                 265                 270

Lys Val Glu Leu Ile Arg Leu Lys Lys Leu His Glu Arg Asn Ala
            275                 280                 285

Ser Leu Val Met Thr Lys Ala Gln Leu Thr Glu Val Gln Glu Ala Tyr
    290                 295                 300

Glu Thr Leu Leu Gln Lys Asn Gln Gly Ile Leu Ser Ala Ala His Glu
305                 310                 315                 320

Ala Leu Leu Lys Gln Val Asn Glu Leu Arg Ala Glu Leu Lys Glu Glu
            325                 330                 335

Ser Lys Lys Ala Val Ser Leu Lys Ser Gln Leu Glu Asp Val Ser Ile
            340                 345                 350

Leu Gln Met Thr Leu Lys Glu Phe Gln Glu Arg Val Glu Asp Leu Glu
            355                 360                 365

Lys Glu Arg Lys Leu Leu Asn Asp Asn Tyr Asp Lys Leu Leu Glu Ser
            370                 375                 380

Met Leu Asp Ser Ser Asp Ser Ser Gln Pro His Trp Ser Asn Glu
385                 390                 395                 400

Leu Ile Ala Glu Gln Leu Gln Gln Gln Val Ser Gln Leu Gln Asp Gln
                405                 410                 415
```

```
Leu Asp Ala Glu Leu Glu Asp Lys Arg Lys Val Leu Glu Leu Ser
            420                 425                 430

Arg Glu Lys Ala Gln Asn Glu Asp Leu Lys Leu Glu Val Thr Asn Ile
                435                 440                 445

Leu Gln Lys His Lys Gln Glu Val Glu Leu Leu Gln Asn Ala Ala Thr
            450                 455                 460

Ile Ser Gln Pro Pro Asp Arg Gln Ser Glu Pro Ala Thr His Pro Ala
465                 470                 475                 480

Val Leu Gln Glu Asn Thr Gln Ile Glu Pro Ser Glu Pro Lys Asn Gln
                485                 490                 495

Glu Glu Lys Lys Leu Ser Gln Val Leu Asn Glu Leu Gln Val Ser His
            500                 505                 510

Ala Glu Thr Thr Leu Glu Leu Glu Lys Thr Arg Asp Met Leu Ile Leu
            515                 520                 525

Gln Arg Lys Ile Asn Val Cys Tyr Gln Glu Glu Leu Glu Ala Met Met
            530                 535                 540

Thr Lys Ala Asp Asn Asp Asn Arg Asp His Lys Glu Lys Leu Glu Arg
545                 550                 555                 560

Leu Thr Arg Leu Leu Asp Leu Lys Asn Asn Arg Ile Lys Gln Leu Glu
                565                 570                 575

Gly Ile Leu Arg Ser His Asp Leu Pro Thr Ser Glu Gln Leu Lys Asp
            580                 585                 590

Val Ala Tyr Gly Thr Arg Pro Leu Ser Leu Cys Leu Glu Thr Leu Pro
            595                 600                 605

Ala His Gly Asp Glu Asp Lys Val Asp Ile Ser Leu Leu His Gln Gly
610                 615                 620

Glu Asn Leu Phe Glu Leu His Ile His Gln Ala Phe Leu Thr Ser Ala
625                 630                 635                 640

Ala Leu Ala Gln Ala Gly Asp Thr Gln Pro Thr Thr Phe Cys Thr Tyr
                645                 650                 655

Ser Phe Tyr Asp Phe Glu Thr His Cys Thr Pro Leu Ser Val Gly Pro
            660                 665                 670

Gln Pro Leu Tyr Asp Phe Thr Ser Gln Tyr Val Met Glu Thr Asp Ser
            675                 680                 685

Leu Phe Leu His Tyr Leu Gln Glu Ala Ser Ala Arg Leu Asp Ile His
            690                 695                 700

Gln Ala Met Ala Ser Glu His Ser Thr Leu Ala Ala Gly Trp Ile Cys
705                 710                 715                 720

Phe Asp Arg Val Leu Glu Thr Val Glu Lys Val His Gly Leu Ala Thr
                725                 730                 735

Leu Ile Gly Ala Gly Glu Glu Phe Gly Val Leu Glu Tyr Trp Met
            740                 745                 750

Arg Leu Arg Phe Pro Ile Lys Pro Ser Leu Gln Ala Cys Asn Lys Arg
            755                 760                 765

Lys Lys Ala Gln Val Tyr Leu Ser Thr Asp Val Leu Gly Gly Arg Lys
770                 775                 780

Ala Gln Glu Glu Glu Phe Arg Ser Glu Ser Trp Glu Pro Gln Asn Glu
785                 790                 795                 800

Leu Trp Ile Glu Ile Thr Lys Cys Cys Gly Leu Arg Ser Arg Trp Leu
                805                 810                 815

Gly Thr Gln Pro Ser Pro Tyr Ala Val Tyr Arg Phe Phe Thr Phe Ser
            820                 825                 830

Asp His Asp Thr Ala Ile Ile Pro Ala Ser Asn Asn Pro Tyr Phe Arg
```

-continued

```
            835                 840                 845
Asp Gln Ala Arg Phe Pro Val Leu Val Thr Ser Asp Leu Asp His Tyr
        850                 855                 860
Leu Arg Arg Glu Ala Leu Ser Ile His Val Phe Asp Asp Glu Asp Leu
865                 870                 875                 880
Glu Pro Gly Ser Tyr Leu Gly Arg Ala Arg Val Pro Leu Leu Pro Leu
                885                 890                 895
Ala Lys Asn Glu Ser Ile Lys Gly Asp Phe Asn Leu Thr Asp Pro Ala
            900                 905                 910
Glu Lys Pro Asn Gly Ser Ile Gln Val Gln Leu Asp Trp Lys Phe Pro
            915                 920                 925
Tyr Ile Pro Pro Glu Ser Phe Leu Lys Pro Glu Ala Gln Thr Lys Gly
            930                 935                 940
Lys Asp Thr Lys Asp Ser Ser Lys Ile Ser Ser Glu Glu Lys Ala
945                 950                 955                 960
Ser Phe Pro Ser Gln Asp Gln Met Ala Ser Pro Glu Val Pro Ile Glu
                965                 970                 975
Ala Gly Gln Tyr Arg Ser Lys Arg Lys Pro His Gly Gly Glu Arg
            980                 985                 990
Lys Glu Lys Glu His Gln Val Val Ser Tyr Ser Arg Arg Lys His Gly
            995                 1000                1005
Lys Arg Ile Gly Val Gln Gly Lys Asn Arg Met Glu Tyr Leu Ser
    1010                1015                1020
Leu Asn Ile Leu Asn Gly Asn Thr Pro Glu Gln Val Asn Tyr Thr
    1025                1030                1035
Glu Trp Lys Phe Ser Glu Thr Asn Ser Phe Ile Gly Asp Gly Phe
    1040                1045                1050
Lys Asn Gln His Glu Glu Glu Met Thr Leu Ser His Ser Ala
    1055                1060                1065
Leu Lys Gln Lys Glu Pro Leu His Pro Val Asn Asp Lys Glu Ser
    1070                1075                1080
Ser Glu Gln Gly Ser Glu Val Ser Glu Ala Gln Thr Thr Asp Ser
    1085                1090                1095
Asp Asp Val Ile Val Pro Pro Met Ser Gln Lys Tyr Pro Lys Ala
    1100                1105                1110
Asp Ser Glu Lys Met Cys Ile Glu Ile Val Ser Leu Ala Phe Tyr
    1115                1120                1125
Pro Glu Ala Glu Val Met Ser Asp Glu Asn Ile Lys Gln Val Tyr
    1130                1135                1140
Val Glu Tyr Lys Phe Tyr Asp Leu Pro Leu Ser Glu Thr Glu Thr
    1145                1150                1155
Pro Val Ser Leu Arg Lys Pro Arg Ala Gly Glu Glu Ile His Phe
    1160                1165                1170
His Phe Ser Lys Val Ile Asp Leu Asp Pro Gln Glu Gln Gln Gly
    1175                1180                1185
Arg Arg Arg Phe Leu Phe Asp Met Leu Asn Gly Gln Asp Pro Asp
    1190                1195                1200
Gln Gly His Leu Lys Phe Thr Val Val Ser Asp Pro Leu Asp Glu
    1205                1210                1215
Glu Lys Lys Glu Cys Glu Glu Val Gly Tyr Ala Tyr Leu Gln Leu
    1220                1225                1230
Trp Gln Ile Leu Glu Ser Gly Arg Asp Ile Leu Glu Gln Glu Leu
    1235                1240                1245
```

| Asp | Ile | Val | Ser | Pro | Glu | Asp | Leu | Ala | Thr | Pro | Ile | Gly | Arg | Leu |
|---|---|---|---|---|---|---|---|---|---|---|---|---|---|---|
| 1250 | | | | | 1255 | | | | | 1260 | | | | |

| Lys | Val | Ser | Leu | Gln | Ala | Ala | Ala | Val | Leu | His | Ala | Ile | Tyr | Lys |
|---|---|---|---|---|---|---|---|---|---|---|---|---|---|---|
| 1265 | | | | | 1270 | | | | | 1275 | | | | |

| Glu | Met | Thr | Glu | Asp | Leu | Phe | Ser |
|---|---|---|---|---|---|---|---|
| 1280 | | | | | 1285 | | |

<210> SEQ ID NO 38
<211> LENGTH: 7221
<212> TYPE: DNA
<213> ORGANISM: Homo sapiens

<400> SEQUENCE: 38

```
cgggcggcct cttgtgtgag ggcctgtggg attctccgga tatggccgga gtgtttcctt    60
atcgagggcc gggtaacccg gtgcctggcc ctctagcccc gctaccggac tacatgtcgg   120
aggagaagct gcaggagaaa gctcgaaaat ggcagcaatt gcaggccaag cgctatgcag   180
aaaagcggaa gtttgggttt gtggatgccc agaaggaaga catgccccca gaacatgtca   240
gggagatcat tcgagaccat ggagacatga ccaacaggaa gttccgccat gacaaaaggg   300
tttacttggg tgccctaaag tacatgcccc acgcagtcct caaactcctg gagaacatgc   360
ctatgccttg ggagcagatt cgggatgtgc ccgtgctgta ccacatcact ggagccattt   420
ccttcgtcaa tgagattccc tgggtcattg aacctgtcta catctcccag tgggggtcaa   480
tgtggattat gatgcgccga gaaaaagag ataggaggca tttcaagaga atgcgttttc   540
cccctttga tgatgaggag ccgcccttgg actatgctga acatcctaa atgttgagc    600
cactggaggc cattcagcta gagctggacc ctgaggagga cgcccctgtg ttggactggt   660
tctatgacca ccagccgttg agggacagca ggaagtatgt aaatggctcc acttaccagc   720
gctggcagtt cacactacct atgatgtcaa ctctctaccg cctggctaat cagctcctga   780
cagacttggt ggatgacaac tacttctacc tgttttgattt gaaggccttc tttacgtcca   840
aggcactcaa tatggccatt cctggaggcc ccaaatttga acctcttgtt cgagacatca   900
acctacagga tgaagactgg aatgaattca atgatattaa caagattatc atccggcagc   960
ctatccggac tgagtacaag attgcttttc cttacttgta caacaatctt ccacaccatg  1020
tccacctcac ctggtaccat actcccaatg ttgtattcat caaaactgaa gatcctgact  1080
tgccagcttt ctactttgac ccctttgatca acccaatctc ccataggcac tcagtcaaga  1140
gccaggaacc attgccggat gatgatgagg aatttgagct cccggagttt gtggagccct  1200
tcctgaagga cacacccctc tatacagaca atacagccaa tggcattgcc ctgctctggg  1260
ccccgcggcc cttcaaccta cgctctggtc gcacccgtcg ggccctggac atacccttg   1320
tcaagaactg gtatcgggag cattgtcctg ccgggcagcc tgtgaaagtg agggtctcct  1380
accagaagct gcttaagtac tatgtgctga atgcccctga agcatcggcc cctaaggctc  1440
aaaagaagag gtatttgttc cgctccttca agccaccaa attcttttcag tccacaaagc  1500
tggactgggt ggagggttgg ctccaggttt gccgccaggg ctacaacatg ctcaaccttc  1560
tcattcaccg caaaaacctc aactacctgc acctggacta caacttcaac ctcaagcctg  1620
tgaaaacgct caccaccaag gaaagaaaga atctcgtttt tgggaatgct ttccacctgt  1680
gtcgggaagt tctgcgtttg actaagctgg tggtggatag tcacgtgcag tatcggctgg  1740
gcaatgtgga tgccttccag ctggcagatg gattgcagta tatatttgcc catgttgggc  1800
agttgacggg catgtatcga tacaaataca agctgatgcg acagattcgc gtgtgcaagg  1860
```

```
acctgaagca tctcatctat tatcgtttca acacaggccc tgtagggaag ggtcctggct    1920
gtggcttctg ggctgccggt tggcgagtct ggctcttttt catgcgtggc attacccctt    1980
tattagagcg atggcttggc aacctcctgg cccggcagtt tgaaggtcga cactcaaagg    2040
gggtggcaaa gacagtaaca aagcagcgag tggagtcaca ttttgacctt gagctgcggg    2100
cagctgtgat gcatgatatt ctggacatga tgcctgaggg gatcaagcag aacaaggccc    2160
ggacaatcct gcagcacctc agtgaagcct ggcgctgctg gaaagccaac attccctgga    2220
aggtccctgg gctgccgacg cccatagaga atatgatcct tcgatacgtg aaggccaagg    2280
ctgactggtg gaccaacact gcccactaca accgagaacg gatccgccga ggggccactg    2340
tggacaagac tgtttgtaaa aagaatctgg gccgcctcac ccggctctat ctgaaggcag    2400
aacaggagcg gcagcacaac tacctgaagg acgggcctta catcacagcg gaggaaacag    2460
tggcagtata taccaccaca gtgcattggt tggaaagccg caggttttca cccatcccat    2520
tccccccact ctcctataag catgacacca agttgctcat cttggcattg gagcggctca    2580
aggaagctta tagtgtgaag tctcggttga accagtctca gagggaggag ctaggtctga    2640
tcgagcaggc ctacgataac ctccacgagg cgctgtcccg cataaagcgt cacctcctca    2700
cacagagagc cttcaaagag gtgggcattg agttcatgga tctgtatagc cacctcgttc    2760
cagtatatga tgttgagccc ctggagaaga taactgatgc ttacctggac cagtacctgt    2820
ggtatgaagc cgacaagcgc cgcctgttcc caccctggat taagcctgca gacacagaac    2880
cacctccact gcttgtttac aagtggtgtc aaggcatcaa taacctgcag gacgtgtggg    2940
agacgagtga aggcgagtgc aatgtcatgc tggaatcccg ctttgagaag atgtatgaga    3000
agatcgactt gactctgctc aacaggctcg tgcgcctcat cgtggaccac aacatagccg    3060
actacatgac agccaagaac aacgtcgtca tcaactataa ggacatgaac catacgaatt    3120
catatgggat catcagaggc ctgcagtttg cctcattcat agtgcagtat tatggcctgg    3180
tgatggattt gcttgtattg ggattgcacc gggccagtga gatggctggg ccccctcaga    3240
tgccaaatga ctttctcagt ttccaggaca tagccactga ggctgcccac cccatccgtc    3300
tcttctgcag atacattgat cgcatccata tttttttcag gttcacagca gatgaggctc    3360
gggacctgat tcaacgttac ctgacagagc accctgaccc caataatgaa acatcgttg    3420 gctataataa caagaagtgc tggccccgag atgcccgcat cgcctcatg aaacatgatg    3480 ttaacttagg ccgggcggta ttctgggaca tcaagaaccg cttgccacgg tcagtgacta    3540
cagttcagtg ggagaacagc ttcgtgtctg tgtacagtaa ggcaaccccc aacctgctgt    3600
tcaacatgtg tggcttcgag tgccgcatcc tgcctaagtg ccgcaccagc tatgaggagt    3660
tcacccacaa ggacgggggtc tggaacctgc agaatgaggt tactaaggag cgcacagctc    3720 agtgttttcct gcgtgtggac gatgagtcaa tgcagcgctt ccacaaccgc gtgcgtcaga    3780
ttctcatggc ctctgggtcc accaccttca ccaagattgt gaataagtgg aatacagctc    3840
tcattggcct tatgacatac tttcgggagg ctgtggtgaa cacccaagag ctcttggact    3900
tactggtgaa gtgtgagcac aaaatccaga cacgtatcaa gattggactc aactccaaga    3960
tgccaagtcg gttcccccg gttgtgttct acacccctaa ggagttgggt ggactcggca    4020
tgctctcaat gggccatgtg ctcatccccc aatccgacct caggtggtcc aaacagacag    4080
atgtaggtat cacacacttt cgttcaggaa tgagccatga agaagaccag ctcattccca    4140
acttgtaccg ctacatacag ccatgggaga gcgagttcat tgattctcag cgggtctggg    4200
```

```
ctgagtactc actcaagaga caagaggcca ttgctcagaa cagacgcctg actttagaag    4260
acctagaaga ttcatgggat cgtggcattc ctcgaatcaa taccctcttc cagaaggacc    4320
ggcacacact ggcttatgat aagggctggc gtgtcagaac tgactttaag cagtatcagg    4380
ttttgaagca gaatccgttc tggtggacac accagcggca tgatgggaag ctctggaacc    4440
tgaacaacta ccgtacagac atgatccagg ccctgggcgg tgtggaaggc attctggaac    4500
acacactctt taagggcact tacttcccta cctgggaggg gcttttctgg gagaaggcca    4560
gtggctttga ggaatctatg aagtggaaga agctaactaa tgctcagcga tcaggactga    4620
accagattcc caatcgtaga ttcaccctct ggtggtcccc gaccattaat cgagccaatg    4680
tatatgtagg ctttcaggtg cagctagacc tgacgggtat cttcatgcac ggcaagatcc    4740
ccacgctgaa gatctctctc atccagatct tccgagctca cttgtggcag aagatccatg    4800
agagcattgt tatggactta tgtcaggtgt ttgaccagga acttgatgca ctggaaattg    4860
agacagtaca aaaggagaca atccatcccc gaaagtcata taagatgaac tcttcctgtg    4920
cagatatcct gctctttgcc tcctataagt ggaatgtctc ccggccctca ttgctggctg    4980
actccaagga tgtgatggac agcaccacca cccagaaata ctggattgac atccagttgc    5040
gctgggggga ctatgattcc cacgacattg agcgctacgc ccgggccaag ttcctggact    5100
acaccaccga caacatgagt atctaccctt cgcccacagg tgtactcatc gccattgacc    5160
tggcctataa cttgcacagt gcctatggaa actggttccc aggcagcaag cctctcatac    5220
aacaggccat ggccaagatc atgaaggcaa accctgccct gtatgtgtta cgtgaacgga    5280
tccgcaaggg gctacagctc tattcatctg aacccactga gccttatttg tcttctcaga    5340
actatggtga gctcttctcc aaccagatta tctggtttgt ggatgacacc aacgtctaca    5400
gagtgactat tcacaagacc tttgaaggga acttgacaac caagcccatc aacggagcca    5460
tcttcatctt caacccacgc acagggcagc tgttcctcaa gataatccac acgtccgtgt    5520
gggcgggaca gaagcgtttg gggcagttgg ctaagtggaa gacagctgag gaggtggccg    5580
ccctgatccg atctctgcct gtggaggagc agcccaagca gatcattgtc accaggaagg    5640
acatgctgga cccactggag gtgcacttac tggacttccc caatattgtc atcaaaggat    5700
cggagctcca actccctttc caggcgtgtc tcaaggtgga aaaattcggg gatctcatcc    5760
ttaaagccac tgagccccag atggttctct caacctcta tgacgactgg ctcaagacta    5820
tttcatctta cacggccttc tcccgtctca tcctgattct gcgtgcccta catgtgaaca    5880
acgatcgggc aaaagtgatc ctgaagccag acaagactac tattacagaa ccacaccaca    5940
tctggcccac tctgactgac gaagaatgga tcaaggtcga ggtgcagctc aaggatctga    6000
tcttggctga ctacggcaag aaaaacaatg tgaacgtggc atcactgaca caatcagaaa    6060
ttcgagacat catcctgggt atggagatct cggcaccgtc acagcagcgg cagcagatcg    6120
ctgagatcga gaagcagacc aaggaacaat cgcagctgac ggcaacacag actcgcactg    6180
tcaacaagca tggcgatgag atcatcacct ccaccaccag caactatgag acccagactt    6240
tctcatccaa gactgagtgg agggtcaggg ccatctctgc tgccaacctg cacctaagga    6300
ccaatcacat ctatgtttca tctgacgaca tcaaggagac tggctacacc tacatccttc    6360
ccaagaatgt gcttaagaag ttcatctgca tatctgacct tcgggcccaa attgcaggat    6420
acctatatgg ggtgagccca ccagataacc cccaggtgaa ggagatccgc tgcattgtga    6480
tggtgccgca gtgggcact caccagaccg tgcacctgcc tggccagctg ccccagcatg    6540
agtacctcaa ggagatggaa cccttaggtt ggatccacac tcagcccaat gagtcccgc     6600
```

-continued

```
agttatcacc ccaggatgtc accacccatg ccaagatcat ggctgacaac ccatcttggg    6660
atggcgagaa gaccattatc atcacatgca gcttcacgcc aggctcctgt acactgacgg    6720
cctacaagct gacccctagt ggctacgaat ggggccgcca gaacacagac aagggcaaca    6780
accccaaggg ctacctgcct tcacactatg agagggtgca gatgctgctg tcggaccgtt    6840
tccttggctt cttcatggtc cctgcccagt cctcgtggaa ctacaacttc atgggtgttc    6900
ggcatgaccc caacatgaaa tatgagctac agctggcgaa ccccaaagag ttctaccacg    6960
aggtgcacag gccctctcac ttcctcaact ttgctctcct gcaggagggg gaggtttact    7020
ctgcggatcg ggaggacctg tatgcctgac cgtttccctg cctcctgctt cagcctcccg    7080
aggccgaagc ctcagcccct ccagacaggc cgctgacatt cagcagtttg gcctctttcc    7140
ctctgtctgt gcttgtgttg ttgacctcct gatggcttgt catcctgaat aaaatataat    7200
aataaatttt gtataaatag g                                              7221
```

<210> SEQ ID NO 39
<211> LENGTH: 2335
<212> TYPE: PRT
<213> ORGANISM: Homo sapiens

<400> SEQUENCE: 39

```
Met Ala Gly Val Phe Pro Tyr Arg Gly Pro Gly Asn Pro Val Pro Gly
1               5                   10                  15

Pro Leu Ala Pro Leu Pro Asp Tyr Met Ser Glu Glu Lys Leu Gln Glu
            20                  25                  30

Lys Ala Arg Lys Trp Gln Gln Leu Gln Ala Lys Arg Tyr Ala Glu Lys
        35                  40                  45

Arg Lys Phe Gly Phe Val Asp Ala Gln Lys Glu Asp Met Pro Pro Glu
    50                  55                  60

His Val Arg Glu Ile Ile Arg Asp His Gly Asp Met Thr Asn Arg Lys
65                  70                  75                  80

Phe Arg His Asp Lys Arg Val Tyr Leu Gly Ala Leu Lys Tyr Met Pro
                85                  90                  95

His Ala Val Leu Lys Leu Leu Glu Asn Met Pro Met Pro Trp Glu Gln
            100                 105                 110

Ile Arg Asp Val Pro Val Leu Tyr His Ile Thr Gly Ala Ile Ser Phe
        115                 120                 125

Val Asn Glu Ile Pro Trp Val Ile Glu Pro Val Tyr Ile Ser Gln Trp
    130                 135                 140

Gly Ser Met Trp Ile Met Met Arg Arg Glu Lys Arg Asp Arg Arg His
145                 150                 155                 160

Phe Lys Arg Met Arg Phe Pro Pro Phe Asp Asp Glu Glu Pro Pro Leu
                165                 170                 175

Asp Tyr Ala Asp Asn Ile Leu Asn Val Glu Pro Leu Glu Ala Ile Gln
            180                 185                 190

Leu Glu Leu Asp Pro Glu Glu Asp Ala Pro Val Leu Asp Trp Phe Tyr
        195                 200                 205

Asp His Gln Pro Leu Arg Asp Ser Arg Lys Tyr Val Asn Gly Ser Thr
    210                 215                 220

Tyr Gln Arg Trp Gln Phe Thr Leu Pro Met Met Ser Thr Leu Tyr Arg
225                 230                 235                 240

Leu Ala Asn Gln Leu Leu Thr Asp Leu Val Asp Asp Asn Tyr Phe Tyr
                245                 250                 255
```

-continued

```
Leu Phe Asp Leu Lys Ala Phe Phe Thr Ser Lys Ala Leu Asn Met Ala
            260                 265                 270

Ile Pro Gly Gly Pro Lys Phe Glu Pro Leu Val Arg Asp Ile Asn Leu
        275                 280                 285

Gln Asp Glu Asp Trp Asn Glu Phe Asn Asp Ile Asn Lys Ile Ile Ile
290                 295                 300

Arg Gln Pro Ile Arg Thr Glu Tyr Lys Ile Ala Phe Pro Tyr Leu Tyr
305                 310                 315                 320

Asn Asn Leu Pro His Val His Leu Thr Trp Tyr His Thr Pro Asn
                325                 330                 335

Val Val Phe Ile Lys Thr Glu Asp Pro Asp Leu Pro Ala Phe Tyr Phe
            340                 345                 350

Asp Pro Leu Ile Asn Pro Ile Ser His Arg His Ser Val Lys Ser Gln
        355                 360                 365

Glu Pro Leu Pro Asp Asp Glu Glu Phe Glu Leu Pro Glu Phe Val
370                 375                 380

Glu Pro Phe Leu Lys Asp Thr Pro Leu Tyr Thr Asp Asn Thr Ala Asn
385                 390                 395                 400

Gly Ile Ala Leu Leu Trp Ala Pro Arg Pro Phe Asn Leu Arg Ser Gly
            405                 410                 415

Arg Thr Arg Arg Ala Leu Asp Ile Pro Leu Val Lys Asn Trp Tyr Arg
        420                 425                 430

Glu His Cys Pro Ala Gly Gln Pro Val Lys Val Arg Val Ser Tyr Gln
                435                 440                 445

Lys Leu Leu Lys Tyr Tyr Val Leu Asn Ala Leu Lys His Arg Pro Pro
450                 455                 460

Lys Ala Gln Lys Lys Arg Tyr Leu Phe Arg Ser Phe Lys Ala Thr Lys
465                 470                 475                 480

Phe Phe Gln Ser Thr Lys Leu Asp Trp Val Glu Gly Trp Leu Gln Val
            485                 490                 495

Cys Arg Gln Gly Tyr Asn Met Leu Asn Leu Leu Ile His Arg Lys Asn
        500                 505                 510

Leu Asn Tyr Leu His Leu Asp Tyr Asn Phe Asn Leu Lys Pro Val Lys
                515                 520                 525

Thr Leu Thr Thr Lys Glu Arg Lys Lys Ser Arg Phe Gly Asn Ala Phe
530                 535                 540

His Leu Cys Arg Glu Val Leu Arg Leu Thr Lys Leu Val Val Asp Ser
545                 550                 555                 560

His Val Gln Tyr Arg Leu Gly Asn Val Asp Ala Phe Gln Leu Ala Asp
            565                 570                 575

Gly Leu Gln Tyr Ile Phe Ala His Val Gly Gln Leu Thr Gly Met Tyr
        580                 585                 590

Arg Tyr Lys Tyr Lys Leu Met Arg Gln Ile Arg Val Cys Lys Asp Leu
                595                 600                 605

Lys His Leu Ile Tyr Tyr Arg Phe Asn Thr Gly Pro Val Gly Lys Gly
610                 615                 620

Pro Gly Cys Gly Phe Trp Ala Ala Gly Trp Arg Val Trp Leu Phe Phe
625                 630                 635                 640

Met Arg Gly Ile Thr Pro Leu Leu Glu Arg Trp Leu Gly Asn Leu Leu
            645                 650                 655

Ala Arg Gln Phe Glu Gly Arg His Ser Lys Gly Val Ala Lys Thr Val
        660                 665                 670

Thr Lys Gln Arg Val Glu Ser His Phe Asp Leu Glu Leu Arg Ala Ala
```

-continued

```
            675                 680                 685
Val Met His Asp Ile Leu Asp Met Met Pro Glu Gly Ile Lys Gln Asn
    690                 695                 700
Lys Ala Arg Thr Ile Leu Gln His Leu Ser Glu Ala Trp Arg Cys Trp
705                 710                 715                 720
Lys Ala Asn Ile Pro Trp Lys Val Pro Gly Leu Pro Thr Pro Ile Glu
                725                 730                 735
Asn Met Ile Leu Arg Tyr Val Lys Ala Lys Ala Asp Trp Trp Thr Asn
                740                 745                 750
Thr Ala His Tyr Asn Arg Glu Arg Ile Arg Arg Gly Ala Thr Val Asp
            755                 760                 765
Lys Thr Val Cys Lys Lys Asn Leu Gly Arg Leu Thr Arg Leu Tyr Leu
        770                 775                 780
Lys Ala Glu Gln Glu Arg Gln His Asn Tyr Leu Lys Asp Gly Pro Tyr
785                 790                 795                 800
Ile Thr Ala Glu Glu Thr Val Ala Val Tyr Thr Thr Thr Val His Trp
                805                 810                 815
Leu Glu Ser Arg Arg Phe Ser Pro Ile Pro Phe Pro Pro Leu Ser Tyr
                820                 825                 830
Lys His Asp Thr Lys Leu Leu Ile Leu Ala Leu Glu Arg Leu Lys Glu
            835                 840                 845
Ala Tyr Ser Val Lys Ser Arg Leu Asn Gln Ser Gln Arg Glu Glu Leu
        850                 855                 860
Gly Leu Ile Glu Gln Ala Tyr Asp Asn Leu His Glu Ala Leu Ser Arg
865                 870                 875                 880
Ile Lys Arg His Leu Leu Thr Gln Arg Ala Phe Lys Glu Val Gly Ile
                885                 890                 895
Glu Phe Met Asp Leu Tyr Ser His Leu Val Pro Val Tyr Asp Val Glu
                900                 905                 910
Pro Leu Glu Lys Ile Thr Asp Ala Tyr Leu Asp Gln Tyr Leu Trp Tyr
            915                 920                 925
Glu Ala Asp Lys Arg Arg Leu Phe Pro Pro Trp Ile Lys Pro Ala Asp
        930                 935                 940
Thr Glu Pro Pro Pro Leu Leu Val Tyr Lys Trp Cys Gln Gly Ile Asn
945                 950                 955                 960
Asn Leu Gln Asp Val Trp Glu Thr Ser Glu Gly Glu Cys Asn Val Met
                965                 970                 975
Leu Glu Ser Arg Phe Glu Lys Met Tyr Glu Lys Ile Asp Leu Thr Leu
            980                 985                 990
Leu Asn Arg Leu Val Arg Leu Ile Val Asp His Asn Ile Ala Asp Tyr
        995                 1000                1005
Met Thr Ala Lys Asn Asn Val Val Ile Asn Tyr Lys Asp Met Asn
    1010                1015                1020
His Thr Asn Ser Tyr Gly Ile Ile Arg Gly Leu Gln Phe Ala Ser
    1025                1030                1035
Phe Ile Val Gln Tyr Tyr Gly Leu Val Met Asp Leu Leu Val Leu
    1040                1045                1050
Gly Leu His Arg Ala Ser Glu Met Ala Gly Pro Gln Met Pro
    1055                1060                1065
Asn Asp Phe Leu Ser Phe Gln Asp Ile Ala Thr Glu Ala Ala His
    1070                1075                1080
Pro Ile Arg Leu Phe Cys Arg Tyr Ile Asp Arg Ile His Ile Phe
    1085                1090                1095
```

```
Phe Arg Phe Thr Ala Asp Glu Ala Arg Asp Leu Ile Gln Arg Tyr
    1100            1105                1110

Leu Thr Glu His Pro Asp Pro Asn Asn Glu Asn Ile Val Gly Tyr
    1115            1120                1125

Asn Asn Lys Lys Cys Trp Pro Arg Asp Ala Arg Met Arg Leu Met
    1130            1135                1140

Lys His Asp Val Asn Leu Gly Arg Ala Val Phe Trp Asp Ile Lys
    1145            1150                1155

Asn Arg Leu Pro Arg Ser Val Thr Thr Val Gln Trp Glu Asn Ser
    1160            1165                1170

Phe Val Ser Val Tyr Ser Lys Asp Asn Pro Asn Leu Leu Phe Asn
    1175            1180                1185

Met Cys Gly Phe Glu Cys Arg Ile Leu Pro Lys Cys Arg Thr Ser
    1190            1195                1200

Tyr Glu Glu Phe Thr His Lys Asp Gly Val Trp Asn Leu Gln Asn
    1205            1210                1215

Glu Val Thr Lys Glu Arg Thr Ala Gln Cys Phe Leu Arg Val Asp
    1220            1225                1230

Asp Glu Ser Met Gln Arg Phe His Asn Arg Val Arg Gln Ile Leu
    1235            1240                1245

Met Ala Ser Gly Ser Thr Thr Phe Thr Lys Ile Val Asn Lys Trp
    1250            1255                1260

Asn Thr Ala Leu Ile Gly Leu Met Thr Tyr Phe Arg Glu Ala Val
    1265            1270                1275

Val Asn Thr Gln Glu Leu Leu Asp Leu Leu Val Lys Cys Glu His
    1280            1285                1290

Lys Ile Gln Thr Arg Ile Lys Ile Gly Leu Asn Ser Lys Met Pro
    1295            1300                1305

Ser Arg Phe Pro Pro Val Val Phe Tyr Thr Pro Lys Glu Leu Gly
    1310            1315                1320

Gly Leu Gly Met Leu Ser Met Gly His Val Leu Ile Pro Gln Ser
    1325            1330                1335

Asp Leu Arg Trp Ser Lys Gln Thr Asp Val Gly Ile Thr His Phe
    1340            1345                1350

Arg Ser Gly Met Ser His Glu Glu Asp Gln Leu Ile Pro Asn Leu
    1355            1360                1365

Tyr Arg Tyr Ile Gln Pro Trp Glu Ser Glu Phe Ile Asp Ser Gln
    1370            1375                1380

Arg Val Trp Ala Glu Tyr Ser Leu Lys Arg Gln Glu Ala Ile Ala
    1385            1390                1395

Gln Asn Arg Arg Leu Thr Leu Glu Asp Leu Glu Asp Ser Trp Asp
    1400            1405                1410

Arg Gly Ile Pro Arg Ile Asn Thr Leu Phe Gln Lys Asp Arg His
    1415            1420                1425

Thr Leu Ala Tyr Asp Lys Gly Trp Arg Val Arg Thr Asp Phe Lys
    1430            1435                1440

Gln Tyr Gln Val Leu Lys Gln Asn Pro Phe Trp Trp Thr His Gln
    1445            1450                1455

Arg His Asp Gly Lys Leu Trp Asn Leu Asn Asn Tyr Arg Thr Asp
    1460            1465                1470

Met Ile Gln Ala Leu Gly Gly Val Glu Gly Ile Leu Glu His Thr
    1475            1480                1485
```

```
Leu Phe Lys Gly Thr Tyr Phe Pro Thr Trp Glu Gly Leu Phe Trp
    1490            1495            1500

Glu Lys Ala Ser Gly Phe Glu Glu Ser Met Lys Trp Lys Lys Leu
    1505            1510            1515

Thr Asn Ala Gln Arg Ser Gly Leu Asn Gln Ile Pro Asn Arg Arg
    1520            1525            1530

Phe Thr Leu Trp Trp Ser Pro Thr Ile Asn Arg Ala Asn Val Tyr
    1535            1540            1545

Val Gly Phe Gln Val Gln Leu Asp Leu Thr Gly Ile Phe Met His
    1550            1555            1560

Gly Lys Ile Pro Thr Leu Lys Ile Ser Leu Ile Gln Ile Phe Arg
    1565            1570            1575

Ala His Leu Trp Gln Lys Ile His Glu Ser Ile Val Met Asp Leu
    1580            1585            1590

Cys Gln Val Phe Asp Gln Glu Leu Asp Ala Leu Glu Ile Glu Thr
    1595            1600            1605

Val Gln Lys Glu Thr Ile His Pro Arg Lys Ser Tyr Lys Met Asn
    1610            1615            1620

Ser Ser Cys Ala Asp Ile Leu Leu Phe Ala Ser Tyr Lys Trp Asn
    1625            1630            1635

Val Ser Arg Pro Ser Leu Leu Ala Asp Ser Lys Asp Val Met Asp
    1640            1645            1650

Ser Thr Thr Thr Gln Lys Tyr Trp Ile Asp Ile Gln Leu Arg Trp
    1655            1660            1665

Gly Asp Tyr Asp Ser His Asp Ile Glu Arg Tyr Ala Arg Ala Lys
    1670            1675            1680

Phe Leu Asp Tyr Thr Thr Asp Asn Met Ser Ile Tyr Pro Ser Pro
    1685            1690            1695

Thr Gly Val Leu Ile Ala Ile Asp Leu Ala Tyr Asn Leu His Ser
    1700            1705            1710

Ala Tyr Gly Asn Trp Phe Pro Gly Ser Lys Pro Leu Ile Gln Gln
    1715            1720            1725

Ala Met Ala Lys Ile Met Lys Ala Asn Pro Ala Leu Tyr Val Leu
    1730            1735            1740

Arg Glu Arg Ile Arg Lys Gly Leu Gln Leu Tyr Ser Ser Glu Pro
    1745            1750            1755

Thr Glu Pro Tyr Leu Ser Ser Gln Asn Tyr Gly Glu Leu Phe Ser
    1760            1765            1770

Asn Gln Ile Ile Trp Phe Val Asp Asp Thr Asn Val Tyr Arg Val
    1775            1780            1785

Thr Ile His Lys Thr Phe Glu Gly Asn Leu Thr Thr Lys Pro Ile
    1790            1795            1800

Asn Gly Ala Ile Phe Ile Phe Asn Pro Arg Thr Gly Gln Leu Phe
    1805            1810            1815

Leu Lys Ile Ile His Thr Ser Val Trp Ala Gly Gln Lys Arg Leu
    1820            1825            1830

Gly Gln Leu Ala Lys Trp Lys Thr Ala Glu Glu Val Ala Ala Leu
    1835            1840            1845

Ile Arg Ser Leu Pro Val Glu Glu Gln Pro Lys Gln Ile Ile Val
    1850            1855            1860

Thr Arg Lys Asp Met Leu Asp Pro Leu Glu Val His Leu Leu Asp
    1865            1870            1875

Phe Pro Asn Ile Val Ile Lys Gly Ser Glu Leu Gln Leu Pro Phe
```

-continued

```
            1880                 1885                 1890
Gln Ala Cys Leu Lys Val Glu Lys Phe Gly Asp Leu Ile Leu Lys
            1895                 1900                 1905

Ala Thr Glu Pro Gln Met Val Leu Phe Asn Leu Tyr Asp Asp Trp
            1910                 1915                 1920

Leu Lys Thr Ile Ser Ser Tyr Thr Ala Phe Ser Arg Leu Ile Leu
            1925                 1930                 1935

Ile Leu Arg Ala Leu His Val Asn Asn Asp Arg Ala Lys Val Ile
            1940                 1945                 1950

Leu Lys Pro Asp Lys Thr Thr Ile Thr Glu Pro His His Ile Trp
            1955                 1960                 1965

Pro Thr Leu Thr Asp Glu Glu Trp Ile Lys Val Glu Val Gln Leu
            1970                 1975                 1980

Lys Asp Leu Ile Leu Ala Asp Tyr Gly Lys Lys Asn Asn Val Asn
            1985                 1990                 1995

Val Ala Ser Leu Thr Gln Ser Glu Ile Arg Asp Ile Ile Leu Gly
            2000                 2005                 2010

Met Glu Ile Ser Ala Pro Ser Gln Gln Arg Gln Gln Ile Ala Glu
            2015                 2020                 2025

Ile Glu Lys Gln Thr Lys Glu Gln Ser Gln Leu Thr Ala Thr Gln
            2030                 2035                 2040

Thr Arg Thr Val Asn Lys His Gly Asp Glu Ile Ile Thr Ser Thr
            2045                 2050                 2055

Thr Ser Asn Tyr Glu Thr Gln Thr Phe Ser Ser Lys Thr Glu Trp
            2060                 2065                 2070

Arg Val Arg Ala Ile Ser Ala Ala Asn Leu His Leu Arg Thr Asn
            2075                 2080                 2085

His Ile Tyr Val Ser Ser Asp Asp Ile Lys Glu Thr Gly Tyr Thr
            2090                 2095                 2100

Tyr Ile Leu Pro Lys Asn Val Leu Lys Lys Phe Ile Cys Ile Ser
            2105                 2110                 2115

Asp Leu Arg Ala Gln Ile Ala Gly Tyr Leu Tyr Gly Val Ser Pro
            2120                 2125                 2130

Pro Asp Asn Pro Gln Val Lys Glu Ile Arg Cys Ile Val Met Val
            2135                 2140                 2145

Pro Gln Trp Gly Thr His Gln Thr Val His Leu Pro Gly Gln Leu
            2150                 2155                 2160

Pro Gln His Glu Tyr Leu Lys Glu Met Glu Pro Leu Gly Trp Ile
            2165                 2170                 2175

His Thr Gln Pro Asn Glu Ser Pro Gln Leu Ser Pro Gln Asp Val
            2180                 2185                 2190

Thr Thr His Ala Lys Ile Met Ala Asp Asn Pro Ser Trp Asp Gly
            2195                 2200                 2205

Glu Lys Thr Ile Ile Ile Thr Cys Ser Phe Thr Pro Gly Ser Cys
            2210                 2215                 2220

Thr Leu Thr Ala Tyr Lys Leu Thr Pro Ser Gly Tyr Glu Trp Gly
            2225                 2230                 2235

Arg Gln Asn Thr Asp Lys Gly Asn Asn Pro Lys Gly Tyr Leu Pro
            2240                 2245                 2250

Ser His Tyr Glu Arg Val Gln Met Leu Leu Ser Asp Arg Phe Leu
            2255                 2260                 2265

Gly Phe Phe Met Val Pro Ala Gln Ser Ser Trp Asn Tyr Asn Phe
            2270                 2275                 2280
```

Met Gly Val Arg His Asp Pro Asn Met Lys Tyr Glu Leu Gln Leu
2285              2290              2295

Ala Asn Pro Lys Glu Phe Tyr His Glu Val His Arg Pro Ser His
2300              2305              2310

Phe Leu Asn Phe Ala Leu Leu Gln Glu Gly Glu Val Tyr Ser Ala
2315              2320              2325

Asp Arg Glu Asp Leu Tyr Ala
2330              2335

<210> SEQ ID NO 40
<211> LENGTH: 7972
<212> TYPE: DNA
<213> ORGANISM: Homo sapiens

<400> SEQUENCE: 40

```
atttgaagtc ctcgttccac gccttctcat catcctgaac accgagctct gggactccgg     60
cggagaatct aaacgtaaag catcacccac ggtcgtgaac tgtaggctct cctggcatcc    120
gggatcttat tctggccttg gcggagttgg ggatggtgtc gcctagcagc cgctgccgct    180
ttggcttgct cgggaccatt tggctggacc cagagtccgc gtggaaccgc gatagggatc    240
tgtcagggcc cgcggccggg tccagcttgg tggttgcggt agtgagaggc ctccgctggt    300
tgccaggctt ggtctagagg tggagcacag tgaaagaatt caagatgcca cctaatataa    360
actggaaaga aataatgaaa gttgacccag atgacctgcc ccgtcaagaa gaactggcag    420
ataatttatt gatttcctta tccaaggtgg aagtaaatga gctaaaaagt gaaaagcaag    480
aaaatgtgat acacctttc agaattactc agtcactaat gaagatgaaa gctcaagaag    540
tggagctggc tttggaagaa gtagaaaaag ctggagaaga caagcaaaaa tttgaaaatc    600
aattaaaaac taaagtaatg aaactggaaa atgaactgga gatggctcag cagtctgcag    660
gtggacgaga tactcggttt ttacgtaatg aaatttgcca acttgaaaaa caattagaac    720
aaaaagatag agaattggag gacatggaaa aggagttgga gaaagagaag aaagttaatg    780
agcaattggc tcttcgaaat gaggaggcag aaaatgaaaa cagcaaatta gaagagaga    840
acaaacgtct aaagaaaaag aatgaacaac tttgtcagga tattattgac taccagaaac    900
aaatagattc acagaagaa acactttat caagaagagg ggaagacagt gactaccgat    960
cacagttgtc taaaaaaaac tatgagctta tccaatatct tgatgaaatt cagactttaa   1020
cagaagctaa tgagaaaatt gaagttcaga atcaagaaat gagaaaaaat ttagaagagt   1080
ctgtacagga aatggaaaag atgactgatg aatataatag aatgaaagct attgtgcatc   1140
agacagataa tgtaatagat cagttaaaaa agaaaacga tcattatcaa cttcaagtgc   1200
aggagcttac agatcttctg aaatcaaaaa atgaagaaga tgatccaatt atggtagctg   1260
tcaatgcaaa agtagaagaa tggaagctaa ttttgtcttc taaagatgat gaaattattg   1320
agtatcagca atgttacat aacctaaggg agaaacttaa gaatgctcag cttgatgctg   1380
ataaaagtaa tgttatggct ctacagcagg gtatacagga acgagacagt caaattaaga   1440
tgctcaccga acaagtagaa caatatacaa aagaaatgga aaagaatact tgtattattg   1500
aagatttgaa aaatgagctc caaagaaaca aaggtgcttc aaccctttct caacagactc   1560
atatgaaaat tcagtcaacg ttagacattt taaaagagaa aactaaagag gctgagagaa   1620
cagctgaact ggctgaggct gatgctaggg aaaaggataa agaattagtt gaggctctga   1680
agaggttaaa agattatgaa tcgggagtat atggtttaga agatgctgtc gttgaaataa   1740
```

| | |
|---|---|
| agaattgtaa aaaccaaatt aaaataagag atcgagagat tgaaatatta acaaaggaaa | 1800 |
| tcaataaact tgaattgaag atcagtgatt tccttgatga aaatgaggca cttagagagc | 1860 |
| gtgtgggcct tgaaccaaag acaatgattg atttaactga atttagaaat agcaaacact | 1920 |
| taaaacagca gcagtacaga gctgaaaacc agattctttt gaaagagatt gaaagtctag | 1980 |
| aggaagaacg acttgatctg aaaaaaaaaa ttcgtcaaat ggctcaagaa agaggaaaaa | 2040 |
| gaagtgcaac ttcaggatta accactgagg acctgaacct aactgaaaac atttctcaag | 2100 |
| gagatagaat aagtgaaaga aaattggatt tattgagcct caaaaatatg agtgaagcac | 2160 |
| aatcaaagaa tgaatttctt tcaagagaac taattgaaaa agaaagagat ttagaaagga | 2220 |
| gtaggacagt gatagccaaa tttcagaata aattaaaaga attagttgaa gaaaataagc | 2280 |
| aacttgaaga aggtatgaaa gaaatattgc aagcaattaa ggaaatgcag aaagatcctg | 2340 |
| atgttaaagg aggagaaaca tctctaatta tccctagcct tgaaagacta gttaatgcta | 2400 |
| tagaatcaaa gaatgcagaa ggaatctttg atgcgagtct gcatttgaaa gcccaagttg | 2460 |
| atcagcttac cggaagaaat gaagaattaa gacaggagct cagggaatct cggaaagagg | 2520 |
| ctataaatta ttcacagcag ttggcaaaag ctaatttaaa gatagaccat cttgaaaaag | 2580 |
| aaactagtct tttacgacaa tcagaaggat cgaatgttgt ttttaaagga attgacttac | 2640 |
| ctgatgggat agcaccatct agtgccagta tcattaattc tcagaatgaa tatttaatac | 2700 |
| atttgttaca ggaactagaa aataaagaaa aaagttaaa gaatttagaa gattctcttg | 2760 |
| aagattacaa cagaaaattt gctgtaattc gtcatcaaca aagtttgttg tataaagaat | 2820 |
| acctaagtga aaaggagacc tggaaaacag aatctaaaac aataaaagag gaaaagagaa | 2880 |
| aacttgagga tcaagtccaa caagatgcta taaaagtaaa agaatataat aatttgctca | 2940 |
| atgctcttca gatggattcg gatgaaatga aaaaaatact tgcagaaaat agtaggaaaa | 3000 |
| ttactgtttt gcaagtgaat gaaaaatcac ttataaggca atatacaacc ttagtagaat | 3060 |
| tggagcgaca acttagaaaa gaaaatgaga agcaaaagaa tgaattgttg tcaatggagg | 3120 |
| ctgaagtttg tgaaaaaatt gggtgttttgc aaagatttaa ggaaatggcc attttcaaga | 3180 |
| ttgcagctct ccaaaaagtt gtagataata gtgtttcttt gtctgaacta gaactggcta | 3240 |
| ataaacagta caatgaactg actgctaagt acagggacat cttgcaaaaa gataatatgc | 3300 |
| ttgttcaaag aacaagtaac ttggaacacc tggagtgtga aaacatctcc ttaaaagaac | 3360 |
| aagtggagtc tataaataaa gaactggaga ttaccaagga aaaacttcac actattgaac | 3420 |
| aagcctggga acaggaaact aaattaggta atgaatctag catggataag gcaaagaaat | 3480 |
| caataaccaa cagtgacatt gtttccattt caaaaaaaat aactatgctg gaaatgaagg | 3540 |
| aattaaatga aaggcagcgg gctgaacatt gtcaaaaaat gtatgaacac ttacggactt | 3600 |
| cgttaaagca aatggaggaa cgtaattttg aattggaaac caaatttgct gagcttacca | 3660 |
| aaatcaattt ggatgcacag aaggtggaac agatgttaag agatgaatta gctgatagtg | 3720 |
| tgagcaaggc agtaagtgat gctgataggc aacggattct agaattagag aagaatgaaa | 3780 |
| tggaactaaa agttgaagtg tcaaaactga gagagatttc tgatattgcc agaagacaag | 3840 |
| ttgaaatttt gaatgcacaa caacaatcta gggacaagga agtagagtcc ctcagaatgc | 3900 |
| aactgctaga ctatcaggca cagtctgatg aaaagtcgct cattgccaag ttgcaccaac | 3960 |
| ataatgtctc tcttcaactg agtgaggcta ctgctcttgg taagttggag tcaattacat | 4020 |
| ctaaactgca agatggag gcctacaact tgcgcttaga gcagaaactt gatgaaaaag | 4080 |
| aacaggctct ctattatgct cgtttggagg gaagaaacag agcaaaacat ctgcgccaaa | 4140 |

```
caattcagtc tctacgacga cagtttagtg gagctttacc cttggcacaa caggaaaagt   4200
tctccaaaac aatgattcaa ctacaaaatg acaaacttaa gataatgcaa gaaatgaaaa   4260
attctcaaca agaacataga aatatggaga acaaaacatt ggagatggaa ttaaaattaa   4320
agggcctgga agagttaata agcactttaa aggataccaa aggagcccaa aagtaatca    4380 actggcatat gaaaatagaa gaacttcgtc ttcaagaact taaactaaat cgggaattag   4440
tcaaggataa agaagaaata aaatatttga ataacataat ttctgaatat gaacgtacaa   4500
tcagcagtct tgaagaagaa attgtgcaac agaacaagtt tcatgaagaa agacaaatgg   4560
cctgggatca aagagaagtt gacctggaac gccaactaga catttttgac cgtcagcaaa   4620
atgaaatact aaatgcggca caaaagtttg aagaagctac aggatcaatc cctgaccta    4680 gtttgcccct tccaaatcaa cttgagatcg ctctaaggaa aattaaggag aacattcgaa   4740
taattctaga aacacgggca acttgcaaat cactagaaga gaaactaaaa gagaaagaat   4800
ctgctttaag gttagcagaa caaaatatac tgtcaagaga caaagtaatc aatgaactga   4860
ggcttcgatt gcctgccact gcagaaagag aaaagctcat agctgagcta ggcagaaaag   4920
agatggaacc aaaatctcac cacacattga aaattgctca tcaaaccatt gcaaacatgc   4980
aagcaaggtt aaatcaaaaa gaagaagtat taagaagta tcaacgtctt ctagaaaaag   5040
ccagagagga gcaaagagaa attgtgaaga aacatgagga agaccttcat attcttcatc   5100
acagattaga actacaggct gatagttcac taaataaatt caaacaaacg gcttgggatt   5160
taatgaaaca gtctcccact ccagttccta ccaacaagca ttttattcgt ctggctgaga   5220
tggaacagac agtagcagaa caagatgact ctctttcctc actcttggtc aaactaaaga   5280
aagtatcaca agatttggag agacaaagag aaatcactga attaaaagta aagaatttg    5340 aaaatatcaa attcagcttt caagaaaacc atgaagatga agtgaaaaaa gtaaaagcgg   5400
aagtagagga tttaaagtat cttctggacc agtcacaaaa ggagtcacag tgtttaaaat   5460
ctgaacttca ggctcaaaaa gaagcaaatt caagagctcc aacaactaca atgagaaatc   5520
tagtagaacg gctaaagagc caattagcct tgaaggagaa acaacagaaa gcacttagtc   5580
gggcactttt agaactccgg gcagaaatga cagcagctgc tgaagaacgt attatttctg   5640
caacttctca aaaagaggcc catctcaatg ttcaacaaat cgttgatcga catactagag   5700
agctaaagac acaagttgaa gatttaaatg aaaatctttt aaaattgaaa gaagcactta   5760
aaacaagtaa aaacagagaa aactcactaa ctgataattt gaatgactta aataatgaac   5820
tgcaaaagaa acaaaaagcc tataataaaa tacttagaga gaaagaggaa attgatcaag   5880 agatgatga actgaaaagg caaattaaaa gactaaccag tggattacag ggcaaacccc    5940
tgacagataa taaacaaagt ctaattgaag aactccaaag gaaagttaaa aaactagaga   6000
accaattaga gggaaaggtg gaggaagtag acctaaaacc tatgaaagaa aagaatgcta   6060
aagaagaatt aattaggtgg gaagaaggta aaaagtggca agccaaaata gaaggaattc   6120
gaaacaagtt aaaagagaaa gaggggggaag tctttacttt aacaaagcag ttgaatactt   6180
tgaaggatct ttttgccaaa gccgataaag agaaacttac tttgcagagg aaactaaaaa   6240
caactggcat gactgttgat caggtttttgg gaatacgagc tttggagtca gaaaaagaat   6300
tggaagaatt aaaaaagaga atcttgact tagaaaatga tatattgtat atgagggccc    6360
accaagctct tcctcgagat tctgttgtag aagatttaca tttacaaaat agataccctcc  6420 aagaaaaact tcatgcttta gaaaacagt tttcaaagga tacatattct aagccttcaa    6480
```

| | |
|---|---:|
| tttcaggaat agagtcagat gatcattgtc agagagaaca ggagcttcag aaggaaaact | 6540 |
| tgaagttgtc atctgaaaat attgaactga aatttcagct tgaacaagca aataaagatt | 6600 |
| tgccaagatt aaagaatcaa gtcagagatt tgaaggaaat gtgtgaattt cttaagaaag | 6660 |
| aaaaagcaga agttcagcgg aaacttggcc atgttagagg gtctggtaga agtggaaaga | 6720 |
| caatcccaga actggaaaaa accattggtt taatgaaaaa agtagttgaa aaagtccaga | 6780 |
| gagaaaatga acagttgaaa aaagcatcag gaatattgac tagtgaaaaa atggctaata | 6840 |
| ttgagcagga aaatgaaaaa ttgaaggctg aattagaaaa acttaaagct catcttgggc | 6900 |
| atcagttgag catgcactat gaatccaaga ccaaaggcac agaaaaaatt attgctgaaa | 6960 |
| atgaaaggct tcgtaaagaa cttaaaaaag aaactgatgc tgcagagaaa ttacggatag | 7020 |
| caaagaataa tttagagata ttaaatgaga agatgacagt tcaactagaa gagactggta | 7080 |
| agagattgca gtttgcagaa agcagaggtc acagcttga aggtgctgac agtaagagct | 7140 |
| ggaaatccat tgtggttaca agaatgtatg aaaccaagtt aaaagaattg gaaactgata | 7200 |
| ttgccaaaaa aaatcaaagc attactgacc ttaaacagct tgtaaagaa gcaacagaga | 7260 |
| gagaacaaaa agttaacaaa tacaatgaag accttgaaca acagattaag attcttaaac | 7320 |
| atgttcctga aggtgctgag acagagcaag gccttaaacg ggagcttcaa gttcttagat | 7380 |
| tagctaatca tcagctggat aaagagaaag cagaattaat ccatcagata gaagctaaca | 7440 |
| aggaccaaag tggagctgaa agcaccatac ctgatgctga tcaactaaag gaaaaaataa | 7500 |
| aagatctaga gacacagctc aaaatgtcag atctagaaaa gcagcatttg aaggaggaaa | 7560 |
| taaagaagct gaaaaagaa ctggaaaatt ttgatccttc attttttgaa gaaattgaag | 7620 |
| atcttaagta taattacaag gaagaagtga agaagaatat tctcttagaa gagaaggtaa | 7680 |
| aaaaactttc agaacaattg ggagttgaat taactagccc tgttgctgct tctgaagagt | 7740 |
| ttgaagatga agaagaaagt cctgttaatt tccccatta ctaaaggtca cctataaact | 7800 |
| ttgtttcatt taactattta ttaactttat aagttaaata tacttggaaa taagcagttc | 7860 |
| tccgaactgt agtatttcct tctcactacc ttgtacctt atacttagat tggaattctt | 7920 |
| aataaataaa attatatgaa attttcaact tattaaaaaa aaaaaaaaaa aa | 7972 |

```
<210> SEQ ID NO 41
<211> LENGTH: 2479
<212> TYPE: PRT
<213> ORGANISM: Homo sapiens

<400> SEQUENCE: 41

Met Pro Pro Asn Ile Asn Trp Lys Glu Ile Met Lys Val Asp Pro Asp
1               5                   10                  15

Asp Leu Pro Arg Gln Glu Glu Leu Ala Asp Asn Leu Leu Ile Ser Leu
            20                  25                  30

Ser Lys Val Glu Val Asn Glu Leu Lys Ser Glu Lys Gln Glu Asn Val
        35                  40                  45

Ile His Leu Phe Arg Ile Thr Gln Ser Leu Met Lys Met Lys Ala Gln
    50                  55                  60

Glu Val Glu Leu Ala Leu Glu Glu Val Glu Lys Ala Gly Glu Glu Gln
65                  70                  75                  80

Ala Lys Phe Glu Asn Gln Leu Lys Thr Lys Val Met Lys Leu Glu Asn
                85                  90                  95

Glu Leu Glu Met Ala Gln Gln Ser Ala Gly Gly Arg Asp Thr Arg Phe
            100                 105                 110
```

```
Leu Arg Asn Glu Ile Cys Gln Leu Glu Lys Gln Leu Glu Gln Lys Asp
        115                 120                 125

Arg Glu Leu Glu Asp Met Glu Lys Glu Leu Glu Lys Glu Lys Lys Val
    130                 135                 140

Asn Glu Gln Leu Ala Leu Arg Asn Glu Glu Ala Glu Asn Glu Asn Ser
145                 150                 155                 160

Lys Leu Arg Arg Glu Asn Lys Arg Leu Lys Lys Asn Glu Gln Leu
            165                 170                 175

Cys Gln Asp Ile Ile Asp Tyr Gln Lys Gln Ile Asp Ser Gln Lys Glu
        180                 185                 190

Thr Leu Leu Ser Arg Arg Gly Glu Asp Ser Asp Tyr Arg Ser Gln Leu
        195                 200                 205

Ser Lys Lys Asn Tyr Glu Leu Ile Gln Tyr Leu Asp Glu Ile Gln Thr
    210                 215                 220

Leu Thr Glu Ala Asn Glu Lys Ile Glu Val Gln Asn Gln Glu Met Arg
225                 230                 235                 240

Lys Asn Leu Glu Glu Ser Val Gln Glu Met Lys Met Thr Asp Glu
            245                 250                 255

Tyr Asn Arg Met Lys Ala Ile Val His Gln Thr Asp Asn Val Ile Asp
        260                 265                 270

Gln Leu Lys Lys Glu Asn Asp His Tyr Gln Leu Gln Val Gln Glu Leu
        275                 280                 285

Thr Asp Leu Leu Lys Ser Lys Asn Glu Glu Asp Asp Pro Ile Met Val
    290                 295                 300

Ala Val Asn Ala Lys Val Glu Glu Trp Lys Leu Ile Leu Ser Ser Lys
305                 310                 315                 320

Asp Asp Glu Ile Ile Glu Tyr Gln Gln Met Leu His Asn Leu Arg Glu
            325                 330                 335

Lys Leu Lys Asn Ala Gln Leu Asp Ala Asp Lys Ser Asn Val Met Ala
        340                 345                 350

Leu Gln Gln Gly Ile Gln Glu Arg Asp Ser Gln Ile Lys Met Leu Thr
        355                 360                 365

Glu Gln Val Glu Gln Tyr Thr Lys Glu Met Glu Lys Asn Thr Cys Ile
    370                 375                 380

Ile Glu Asp Leu Lys Asn Glu Leu Gln Arg Asn Lys Gly Ala Ser Thr
385                 390                 395                 400

Leu Ser Gln Gln Thr His Met Lys Ile Gln Ser Thr Leu Asp Ile Leu
            405                 410                 415

Lys Glu Lys Thr Lys Glu Ala Glu Arg Thr Ala Glu Leu Ala Glu Ala
        420                 425                 430

Asp Ala Arg Glu Lys Asp Lys Glu Leu Val Glu Ala Leu Lys Arg Leu
        435                 440                 445

Lys Asp Tyr Glu Ser Gly Val Tyr Gly Leu Glu Asp Ala Val Val Glu
    450                 455                 460

Ile Lys Asn Cys Lys Asn Gln Ile Lys Ile Arg Asp Arg Glu Ile Glu
465                 470                 475                 480

Ile Leu Thr Lys Glu Ile Asn Lys Leu Glu Leu Lys Ile Ser Asp Phe
            485                 490                 495

Leu Asp Glu Asn Glu Ala Leu Arg Glu Arg Val Gly Leu Glu Pro Lys
        500                 505                 510

Thr Met Ile Asp Leu Thr Glu Phe Arg Asn Ser Lys His Leu Lys Gln
        515                 520                 525

Gln Gln Tyr Arg Ala Glu Asn Gln Ile Leu Leu Lys Glu Ile Glu Ser
```

```
                530             535             540
Leu Glu Glu Arg Leu Asp Leu Lys Lys Ile Arg Gln Met Ala
545                 550             555                 560

Gln Glu Arg Gly Lys Arg Ser Ala Thr Ser Gly Leu Thr Thr Glu Asp
                565             570             575

Leu Asn Leu Thr Glu Asn Ile Ser Gln Gly Asp Arg Ile Ser Glu Arg
            580             585             590

Lys Leu Asp Leu Leu Ser Leu Lys Asn Met Ser Glu Ala Gln Ser Lys
                595             600             605

Asn Glu Phe Leu Ser Arg Glu Leu Ile Glu Lys Glu Arg Asp Leu Glu
        610             615             620

Arg Ser Arg Thr Val Ile Ala Lys Phe Gln Asn Lys Leu Lys Glu Leu
625                 630             635                 640

Val Glu Glu Asn Lys Gln Leu Glu Glu Gly Met Lys Glu Ile Leu Gln
                645             650             655

Ala Ile Lys Glu Met Gln Lys Asp Pro Asp Val Lys Gly Gly Glu Thr
                660             665             670

Ser Leu Ile Ile Pro Ser Leu Glu Arg Leu Val Asn Ala Ile Glu Ser
                675             680             685

Lys Asn Ala Glu Gly Ile Phe Asp Ala Ser Leu His Leu Lys Ala Gln
690                 695             700

Val Asp Gln Leu Thr Gly Arg Asn Glu Glu Leu Arg Gln Glu Leu Arg
705                 710             715                 720

Glu Ser Arg Lys Glu Ala Ile Asn Tyr Ser Gln Gln Leu Ala Lys Ala
                725             730             735

Asn Leu Lys Ile Asp His Leu Glu Lys Glu Thr Ser Leu Leu Arg Gln
                740             745             750

Ser Glu Gly Ser Asn Val Val Phe Lys Gly Ile Asp Leu Pro Asp Gly
            755             760             765

Ile Ala Pro Ser Ser Ala Ser Ile Ile Asn Ser Gln Asn Glu Tyr Leu
        770             775             780

Ile His Leu Leu Gln Glu Leu Glu Asn Lys Glu Lys Lys Leu Lys Asn
785                 790             795                 800

Leu Glu Asp Ser Leu Glu Asp Tyr Asn Arg Lys Phe Ala Val Ile Arg
                805             810             815

His Gln Gln Ser Leu Leu Tyr Lys Glu Tyr Leu Ser Glu Lys Glu Thr
            820             825             830

Trp Lys Thr Glu Ser Lys Thr Ile Lys Glu Glu Lys Arg Lys Leu Glu
            835             840             845

Asp Gln Val Gln Gln Asp Ala Ile Lys Val Lys Glu Tyr Asn Asn Leu
850                 855             860

Leu Asn Ala Leu Gln Met Asp Ser Asp Glu Met Lys Lys Ile Leu Ala
865                 870             875                 880

Glu Asn Ser Arg Lys Ile Thr Val Leu Gln Val Asn Glu Lys Ser Leu
                885             890             895

Ile Arg Gln Tyr Thr Thr Leu Val Glu Leu Glu Arg Gln Leu Arg Lys
                900             905             910

Glu Asn Glu Lys Gln Lys Asn Glu Leu Leu Ser Met Glu Ala Glu Val
            915             920             925

Cys Glu Lys Ile Gly Cys Leu Gln Arg Phe Lys Glu Met Ala Ile Phe
            930             935             940

Lys Ile Ala Ala Leu Gln Lys Val Val Asp Asn Ser Val Ser Leu Ser
945                 950             955             960
```

```
Glu Leu Glu Leu Ala Asn Lys Gln Tyr Asn Glu Leu Thr Ala Lys Tyr
            965                 970                 975

Arg Asp Ile Leu Gln Lys Asp Asn Met Leu Val Gln Arg Thr Ser Asn
            980                 985                 990

Leu Glu His Leu Glu Cys Glu Asn Ile Ser Leu Lys Glu Gln Val Glu
            995                1000                1005

Ser Ile Asn Lys Glu Leu Glu Ile Thr Lys Glu Lys Leu His Thr
        1010                1015                1020

Ile Glu Gln Ala Trp Glu Gln Glu Thr Lys Leu Gly Asn Glu Ser
        1025                1030                1035

Ser Met Asp Lys Ala Lys Lys Ser Ile Thr Asn Ser Asp Ile Val
        1040                1045                1050

Ser Ile Ser Lys Lys Ile Thr Met Leu Glu Met Lys Glu Leu Asn
        1055                1060                1065

Glu Arg Gln Arg Ala Glu His Cys Gln Lys Met Tyr Glu His Leu
        1070                1075                1080

Arg Thr Ser Leu Lys Gln Met Glu Glu Arg Asn Phe Glu Leu Glu
        1085                1090                1095

Thr Lys Phe Ala Glu Leu Thr Lys Ile Asn Leu Asp Ala Gln Lys
        1100                1105                1110

Val Glu Gln Met Leu Arg Asp Glu Leu Ala Asp Ser Val Ser Lys
        1115                1120                1125

Ala Val Ser Asp Ala Asp Arg Gln Arg Ile Leu Glu Leu Glu Lys
        1130                1135                1140

Asn Glu Met Glu Leu Lys Val Glu Val Ser Lys Leu Arg Glu Ile
        1145                1150                1155

Ser Asp Ile Ala Arg Arg Gln Val Glu Ile Leu Asn Ala Gln Gln
        1160                1165                1170

Gln Ser Arg Asp Lys Glu Val Glu Ser Leu Arg Met Gln Leu Leu
        1175                1180                1185

Asp Tyr Gln Ala Gln Ser Asp Glu Lys Ser Leu Ile Ala Lys Leu
        1190                1195                1200

His Gln His Asn Val Ser Leu Gln Leu Ser Glu Ala Thr Ala Leu
        1205                1210                1215

Gly Lys Leu Glu Ser Ile Thr Ser Lys Leu Gln Lys Met Glu Ala
        1220                1225                1230

Tyr Asn Leu Arg Leu Glu Gln Lys Leu Asp Glu Lys Glu Gln Ala
        1235                1240                1245

Leu Tyr Tyr Ala Arg Leu Glu Gly Arg Asn Arg Ala Lys His Leu
        1250                1255                1260

Arg Gln Thr Ile Gln Ser Leu Arg Arg Gln Phe Ser Gly Ala Leu
        1265                1270                1275

Pro Leu Ala Gln Gln Glu Lys Phe Ser Lys Thr Met Ile Gln Leu
        1280                1285                1290

Gln Asn Asp Lys Leu Lys Ile Met Gln Glu Met Lys Asn Ser Gln
        1295                1300                1305

Gln Glu His Arg Asn Met Glu Asn Lys Thr Leu Glu Met Glu Leu
        1310                1315                1320

Lys Leu Lys Gly Leu Glu Glu Leu Ile Ser Thr Leu Lys Asp Thr
        1325                1330                1335

Lys Gly Ala Gln Lys Val Ile Asn Trp His Met Lys Ile Glu Glu
        1340                1345                1350
```

```
Leu Arg Leu Gln Glu Leu Lys Leu Asn Arg Glu Leu Val Lys Asp
    1355                1360                1365

Lys Glu Glu Ile Lys Tyr Leu Asn Asn Ile Ile Ser Glu Tyr Glu
    1370                1375                1380

Arg Thr Ile Ser Ser Leu Glu Glu Ile Val Gln Gln Asn Lys
    1385                1390                1395

Phe His Glu Glu Arg Gln Met Ala Trp Asp Gln Arg Glu Val Asp
    1400                1405                1410

Leu Glu Arg Gln Leu Asp Ile Phe Asp Arg Gln Gln Asn Glu Ile
    1415                1420                1425

Leu Asn Ala Ala Gln Lys Phe Glu Glu Ala Thr Gly Ser Ile Pro
    1430                1435                1440

Asp Pro Ser Leu Pro Leu Pro Asn Gln Leu Glu Ile Ala Leu Arg
    1445                1450                1455

Lys Ile Lys Glu Asn Ile Arg Ile Ile Leu Glu Thr Arg Ala Thr
    1460                1465                1470

Cys Lys Ser Leu Glu Glu Lys Leu Lys Glu Lys Glu Ser Ala Leu
    1475                1480                1485

Arg Leu Ala Glu Gln Asn Ile Leu Ser Arg Asp Lys Val Ile Asn
    1490                1495                1500

Glu Leu Arg Leu Arg Leu Pro Ala Thr Ala Glu Arg Glu Lys Leu
    1505                1510                1515

Ile Ala Glu Leu Gly Arg Lys Glu Met Glu Pro Lys Ser His His
    1520                1525                1530

Thr Leu Lys Ile Ala His Gln Thr Ile Ala Asn Met Gln Ala Arg
    1535                1540                1545

Leu Asn Gln Lys Glu Glu Val Leu Lys Lys Tyr Gln Arg Leu Leu
    1550                1555                1560

Glu Lys Ala Arg Glu Glu Gln Arg Glu Ile Val Lys Lys His Glu
    1565                1570                1575

Glu Asp Leu His Ile Leu His His Arg Leu Glu Leu Gln Ala Asp
    1580                1585                1590

Ser Ser Leu Asn Lys Phe Lys Gln Thr Ala Trp Asp Leu Met Lys
    1595                1600                1605

Gln Ser Pro Thr Pro Val Pro Thr Asn Lys His Phe Ile Arg Leu
    1610                1615                1620

Ala Glu Met Glu Gln Thr Val Ala Glu Gln Asp Asp Ser Leu Ser
    1625                1630                1635

Ser Leu Leu Val Lys Leu Lys Lys Val Ser Gln Asp Leu Glu Arg
    1640                1645                1650

Gln Arg Glu Ile Thr Glu Leu Lys Val Lys Glu Phe Glu Asn Ile
    1655                1660                1665

Lys Leu Gln Leu Gln Glu Asn His Glu Asp Glu Val Lys Lys Val
    1670                1675                1680

Lys Ala Glu Val Glu Asp Leu Lys Tyr Leu Leu Asp Gln Ser Gln
    1685                1690                1695

Lys Glu Ser Gln Cys Leu Lys Ser Glu Leu Gln Ala Gln Lys Glu
    1700                1705                1710

Ala Asn Ser Arg Ala Pro Thr Thr Thr Met Arg Asn Leu Val Glu
    1715                1720                1725

Arg Leu Lys Ser Gln Leu Ala Leu Lys Glu Lys Gln Gln Lys Ala
    1730                1735                1740

Leu Ser Arg Ala Leu Leu Glu Leu Arg Ala Glu Met Thr Ala Ala
```

```
            1745                1750               1755
Ala Glu Glu Arg Ile Ile Ser Ala Thr Ser Gln Lys Glu Ala His
    1760                1765               1770

Leu Asn Val Gln Gln Ile Val Asp Arg His Thr Arg Glu Leu Lys
    1775                1780               1785

Thr Gln Val Glu Asp Leu Asn Glu Asn Leu Leu Lys Leu Lys Glu
    1790                1795               1800

Ala Leu Lys Thr Ser Lys Asn Arg Glu Asn Ser Leu Thr Asp Asn
    1805                1810               1815

Leu Asn Asp Leu Asn Asn Glu Leu Gln Lys Lys Gln Lys Ala Tyr
    1820                1825               1830

Asn Lys Ile Leu Arg Glu Lys Glu Glu Ile Asp Gln Glu Asn Asp
    1835                1840               1845

Glu Leu Lys Arg Gln Ile Lys Arg Leu Thr Ser Gly Leu Gln Gly
    1850                1855               1860

Lys Pro Leu Thr Asp Asn Lys Gln Ser Leu Ile Glu Glu Leu Gln
    1865                1870               1875

Arg Lys Val Lys Lys Leu Glu Asn Gln Leu Glu Gly Lys Val Glu
    1880                1885               1890

Glu Val Asp Leu Lys Pro Met Lys Glu Lys Asn Ala Lys Glu Glu
    1895                1900               1905

Leu Ile Arg Trp Glu Glu Gly Lys Lys Trp Gln Ala Lys Ile Glu
    1910                1915               1920

Gly Ile Arg Asn Lys Leu Lys Glu Lys Glu Gly Glu Val Phe Thr
    1925                1930               1935

Leu Thr Lys Gln Leu Asn Thr Leu Lys Asp Leu Phe Ala Lys Ala
    1940                1945               1950

Asp Lys Glu Lys Leu Thr Leu Gln Arg Lys Leu Lys Thr Thr Gly
    1955                1960               1965

Met Thr Val Asp Gln Val Leu Gly Ile Arg Ala Leu Glu Ser Glu
    1970                1975               1980

Lys Glu Leu Glu Glu Leu Lys Lys Arg Asn Leu Asp Leu Glu Asn
    1985                1990               1995

Asp Ile Leu Tyr Met Arg Ala His Gln Ala Leu Pro Arg Asp Ser
    2000                2005               2010

Val Val Glu Asp Leu His Leu Gln Asn Arg Tyr Leu Gln Glu Lys
    2015                2020               2025

Leu His Ala Leu Glu Lys Gln Phe Ser Lys Asp Thr Tyr Ser Lys
    2030                2035               2040

Pro Ser Ile Ser Gly Ile Glu Ser Asp Asp His Cys Gln Arg Glu
    2045                2050               2055

Gln Glu Leu Gln Lys Glu Asn Leu Lys Leu Ser Ser Glu Asn Ile
    2060                2065               2070

Glu Leu Lys Phe Gln Leu Glu Gln Ala Asn Lys Asp Leu Pro Arg
    2075                2080               2085

Leu Lys Asn Gln Val Arg Asp Leu Lys Glu Met Cys Glu Phe Leu
    2090                2095               2100

Lys Lys Glu Lys Ala Glu Val Gln Arg Lys Leu Gly His Val Arg
    2105                2110               2115

Gly Ser Gly Arg Ser Gly Lys Thr Ile Pro Glu Leu Glu Lys Thr
    2120                2125               2130

Ile Gly Leu Met Lys Lys Val Val Glu Lys Val Gln Arg Glu Asn
    2135                2140               2145
```

| | | | | | | | | | | |
|---|---|---|---|---|---|---|---|---|---|---|
| Glu | Gln | Leu | Lys | Lys | Ala | Ser | Gly | Ile | Leu | Thr | Ser | Glu | Lys | Met |
| | 2150 | | | | 2155 | | | | 2160 | |

Glu Gln Leu Lys Lys Ala Ser Gly Ile Leu Thr Ser Glu Lys Met
    2150                2155                2160

Ala Asn Ile Glu Gln Glu Asn Glu Lys Leu Lys Ala Glu Leu Glu
    2165                2170                2175

Lys Leu Lys Ala His Leu Gly His Gln Leu Ser Met His Tyr Glu
    2180                2185                2190

Ser Lys Thr Lys Gly Thr Glu Lys Ile Ile Ala Glu Asn Glu Arg
    2195                2200                2205

Leu Arg Lys Glu Leu Lys Lys Glu Thr Asp Ala Ala Glu Lys Leu
    2210                2215                2220

Arg Ile Ala Lys Asn Asn Leu Glu Ile Leu Asn Glu Lys Met Thr
    2225                2230                2235

Val Gln Leu Glu Glu Thr Gly Lys Arg Leu Gln Phe Ala Glu Ser
    2240                2245                2250

Arg Gly Pro Gln Leu Glu Gly Ala Asp Ser Lys Ser Trp Lys Ser
    2255                2260                2265

Ile Val Val Thr Arg Met Tyr Glu Thr Lys Leu Lys Glu Leu Glu
    2270                2275                2280

Thr Asp Ile Ala Lys Lys Asn Gln Ser Ile Thr Asp Leu Lys Gln
    2285                2290                2295

Leu Val Lys Glu Ala Thr Glu Arg Glu Gln Lys Val Asn Lys Tyr
    2300                2305                2310

Asn Glu Asp Leu Glu Gln Gln Ile Lys Ile Leu Lys His Val Pro
    2315                2320                2325

Glu Gly Ala Glu Thr Glu Gln Gly Leu Lys Arg Glu Leu Gln Val
    2330                2335                2340

Leu Arg Leu Ala Asn His Gln Leu Asp Lys Glu Lys Ala Glu Leu
    2345                2350                2355

Ile His Gln Ile Glu Ala Asn Lys Asp Gln Ser Gly Ala Glu Ser
    2360                2365                2370

Thr Ile Pro Asp Ala Asp Gln Leu Lys Glu Lys Ile Lys Asp Leu
    2375                2380                2385

Glu Thr Gln Leu Lys Met Ser Asp Leu Glu Lys Gln His Leu Lys
    2390                2395                2400

Glu Glu Ile Lys Lys Leu Lys Lys Glu Leu Glu Asn Phe Asp Pro
    2405                2410                2415

Ser Phe Phe Glu Glu Ile Glu Asp Leu Lys Tyr Asn Tyr Lys Glu
    2420                2425                2430

Glu Val Lys Lys Asn Ile Leu Leu Glu Glu Lys Val Lys Lys Leu
    2435                2440                2445

Ser Glu Gln Leu Gly Val Glu Leu Thr Ser Pro Val Ala Ala Ser
    2450                2455                2460

Glu Glu Phe Glu Asp Glu Glu Ser Pro Val Asn Phe Pro Ile
    2465                2470                2475

Tyr

<210> SEQ ID NO 42
<211> LENGTH: 2625
<212> TYPE: DNA
<213> ORGANISM: Homo sapiens

<400> SEQUENCE: 42
actcgaccgg gctgcgctca ctgcccagcc ggggccccgg gagcctccag gctcccgccc    60

```
gccctgagct gcggcctccg catggagggg ccactcactc caccaccgct gcagggaggc    120
ggagccgccg ctgttccgga gcccggagcc cggcaacacc cgggacacga dacggcggcg    180
cagcggtaca gcgcccgact gctgcaggcc ggctacgagc ccgagagccc tagattggac    240
ctcgctacac acccgacgac accccgttca gaactatctt cagtggtctt actggcaggt    300
gttggtgtcc agatggatcg ccttcgcagg gctagcatgg cggactacct gatcagcggc    360
ggcaccggct acgtgcccga ggatgggctc accgcgcagc agctcttcgc cagcgccgac    420
ggcctcacct acaacgactt cctgattctc ccaggattca tagacttcat agctgatgag    480
gtggacctga cctcagccct gacccggaag atcacgctga agacgccact gatctcctcc    540
cccatggaca ctgtgacaga ggctgacatg gccattgcca tggctctgat gggaggtatt    600
ggtttcattc accacaactg cacccccagag ttccaggcca acgaggtgcg gaaggtcaag    660
aagtttgaac agggcttcat cacggaccct gtggtgctga gcccctcgca cactgtgggc    720
gatgtgctgg aggccaagat gcggcatggc ttctctggca tccccatcac tgagacgggc    780
accatgggca gcaagctggt gggcatcgtc acctcccgag acatcgactt tcttgctgag    840
aaggaccaca ccaccctcct cagtgaggtg atgacgccaa ggattgaact ggtggtggct    900
ccagcaggtg tgacgttgaa agaggcaaat gagatcctgc agcgtagcaa gaaagggaag    960
ctgcctatcg tcaatgattg cgatgagctg gtggccatca tcgcccgcac cgacctgaag   1020
aagaaccgag actaccctct ggcctccaag gattcccaga agcagctgct ctgtggggca   1080
gctgtgggca cccgtgagga tgacaaatac cgtctggacc tgctcaccca ggcgggcgtc   1140
gacgtcatag tcttggactc gtcccaaggg aattcggtgt atcagatcgc catggtgcat   1200
tacatcaaac agaagtaccc ccacctccag gtgattgggg ggaacgtggt gacagcagcc   1260
caggccaaga acctgattga tgctggtgtg gacgggctgc gcgtgggcat gggctgcggc   1320
tccatctgca tcacccagga agtgatggcc tgtggtcggc cccagggcac tgctgtgtac   1380
aaggtggctg agtatgcccg cgcctttggt gtgcccatca tagccgatgg cggcatccag   1440
accgtgggac acgtggtcaa ggccctggcc cttggagcct ccacagtgat gatgggctcc   1500
ctgctggccg ccactacgga ggcccctggc gagtacttct tctcagacgg ggtgcggctc   1560
aagaagtacc ggggcatggg ctcactggat gccatggaga agagcagcag cagccagaaa   1620
cgatacttca gcgaggggga taaagtgaag atcgcgcagg gtgtctcggg ctccatccag   1680
gacaaaggat ccattcagaa gttcgtgccc tacctcatag caggcatcca acacggctgc   1740
caggatatcg gggcccgcag cctgtctgtc cttcggtcca tgatgtactc aggagagctc   1800
aagtttgaga gcggaccat gtcggcccag attgagggtg gtgtccatgg cctgcactct   1860
tacgaaaagc ggctgtactg aggacagcgg tggaggccga ggtggtggag gggatgcacc   1920
ccagtgtcca cttttgggca cagcctccct ccataactga gtggtccaca gatttgcact   1980
acgggttctc cagctccttt ccaggcagag aggaggggag gtcctgaggg gactgctgcc   2040
cctcactcgg catcccctgc agagtcagga ctgctcccgg ggccaggctg ccctgggagc   2100 cccccctccga gccagccag ccaggctctc aggccctgcg cctgcctcag gtctttcttg   2160
ctgcagcctg ctccagcctg gccccacccc caggggcagg cggcccctcc tggcttctcc   2220
tgtagggcac ctccctgccc ctagcctccc aggaaatggt gctctcctgg ccctgcctct   2280
ggcccttccc gggccgctgc ccctcagcca tgtggcactt ctgagctcct gacctaggcc   2340
aaggggaggt ctctgccccc ttccccggcc ctgggctacc cttgggtcct gctcctcagg   2400
ccgctcccct gtccctggcc atgggtagga gactgccctg gtcatggccg cctgcctgtc   2460
```

```
attcctgact caccaccgtc cccaggtgaa ccattcctcc cttctcctca gctgcagtcg    2520
aaggctttaa ctttgcacac ttgggatcac agttgcgtca ttgtgtatta aatacttgga    2580
ataaatcaag caggtctcaa cgcctccact aaaaaaaaaa aaaaa                   2625
```

<210> SEQ ID NO 43
<211> LENGTH: 599
<212> TYPE: PRT
<213> ORGANISM: Homo sapiens

<400> SEQUENCE: 43

```
Met Glu Gly Pro Leu Thr Pro Pro Leu Gln Gly Gly Ala Ala
1               5                   10                  15

Ala Val Pro Glu Pro Gly Ala Arg Gln His Pro Gly His Glu Thr Ala
            20                  25                  30

Ala Gln Arg Tyr Ser Ala Arg Leu Leu Gln Ala Gly Tyr Glu Pro Glu
        35                  40                  45

Ser Pro Arg Leu Asp Leu Ala Thr His Pro Thr Thr Pro Arg Ser Glu
    50                  55                  60

Leu Ser Ser Val Val Leu Leu Ala Gly Val Gly Val Gln Met Asp Arg
65                  70                  75                  80

Leu Arg Arg Ala Ser Met Ala Asp Tyr Leu Ile Ser Gly Gly Thr Gly
                85                  90                  95

Tyr Val Pro Glu Asp Gly Leu Thr Ala Gln Gln Leu Phe Ala Ser Ala
            100                 105                 110

Asp Gly Leu Thr Tyr Asn Asp Phe Leu Ile Leu Pro Gly Phe Ile Asp
        115                 120                 125

Phe Ile Ala Asp Glu Val Asp Leu Thr Ser Ala Leu Thr Arg Lys Ile
    130                 135                 140

Thr Leu Lys Thr Pro Leu Ile Ser Ser Pro Met Asp Thr Val Thr Glu
145                 150                 155                 160

Ala Asp Met Ala Ile Ala Met Ala Leu Met Gly Gly Ile Gly Phe Ile
                165                 170                 175

His His Asn Cys Thr Pro Glu Phe Gln Ala Asn Glu Val Arg Lys Val
            180                 185                 190

Lys Lys Phe Glu Gln Gly Phe Ile Thr Asp Pro Val Val Leu Ser Pro
        195                 200                 205

Ser His Thr Val Gly Asp Val Leu Glu Ala Lys Met Arg His Gly Phe
    210                 215                 220

Ser Gly Ile Pro Ile Thr Glu Thr Gly Thr Met Gly Ser Lys Leu Val
225                 230                 235                 240

Gly Ile Val Thr Ser Arg Asp Ile Asp Phe Leu Ala Glu Lys Asp His
                245                 250                 255

Thr Thr Leu Leu Ser Glu Val Met Thr Pro Arg Ile Glu Leu Val Val
            260                 265                 270

Ala Pro Ala Gly Val Thr Leu Lys Glu Ala Asn Glu Ile Leu Gln Arg
        275                 280                 285

Ser Lys Lys Gly Lys Leu Pro Ile Val Asn Asp Cys Asp Glu Leu Val
    290                 295                 300

Ala Ile Ile Ala Arg Thr Asp Leu Lys Lys Asn Arg Asp Tyr Pro Leu
305                 310                 315                 320

Ala Ser Lys Asp Ser Gln Lys Gln Leu Leu Cys Gly Ala Ala Val Gly
                325                 330                 335

Thr Arg Glu Asp Asp Lys Tyr Arg Leu Asp Leu Leu Thr Gln Ala Gly
```

```
                    340                 345                 350
Val Asp Val Ile Val Leu Asp Ser Ser Gln Gly Asn Ser Val Tyr Gln
                355                 360                 365

Ile Ala Met Val His Tyr Ile Lys Gln Lys Tyr Pro His Leu Gln Val
            370                 375                 380

Ile Gly Gly Asn Val Val Thr Ala Ala Gln Ala Lys Asn Leu Ile Asp
385                 390                 395                 400

Ala Gly Val Asp Gly Leu Arg Val Gly Met Gly Cys Gly Ser Ile Cys
                405                 410                 415

Ile Thr Gln Glu Val Met Ala Cys Gly Arg Pro Gln Gly Thr Ala Val
            420                 425                 430

Tyr Lys Val Ala Glu Tyr Ala Arg Arg Phe Gly Val Pro Ile Ile Ala
        435                 440                 445

Asp Gly Gly Ile Gln Thr Val Gly His Val Val Lys Ala Leu Ala Leu
    450                 455                 460

Gly Ala Ser Thr Val Met Met Gly Ser Leu Leu Ala Ala Thr Thr Glu
465                 470                 475                 480

Ala Pro Gly Glu Tyr Phe Phe Ser Asp Gly Val Arg Leu Lys Lys Tyr
                485                 490                 495

Arg Gly Met Gly Ser Leu Asp Ala Met Glu Lys Ser Ser Ser Ser Gln
            500                 505                 510

Lys Arg Tyr Phe Ser Glu Gly Asp Lys Val Lys Ile Ala Gln Gly Val
        515                 520                 525

Ser Gly Ser Ile Gln Asp Lys Gly Ser Ile Gln Lys Phe Val Pro Tyr
    530                 535                 540

Leu Ile Ala Gly Ile Gln His Gly Cys Gln Asp Ile Gly Ala Arg Ser
545                 550                 555                 560

Leu Ser Val Leu Arg Ser Met Met Tyr Ser Gly Glu Leu Lys Phe Glu
                565                 570                 575

Lys Arg Thr Met Ser Ala Gln Ile Glu Gly Gly Val His Gly Leu His
            580                 585                 590

Ser Tyr Glu Lys Arg Leu Tyr
        595

<210> SEQ ID NO 44
<211> LENGTH: 2981
<212> TYPE: DNA
<213> ORGANISM: Homo sapiens

<400> SEQUENCE: 44
gctgggtaaa tcccagagtc tcagccgcct aagtgtcttc cccggaggtg agattatctc      60
cgcctgtgct ggacacctcc ctttctcctg cagccatgga tgccgctctg ctcctgaacg     120 tggaagggt caagaaaacc attctgcacg ggggcacggg cgagctccca aacttcatca     180
ccggatcccg agtgatcttt catttccgca ccatgaaatg tgatgaggag cggacagtca     240
ttgacgacag tcggcaggtg ggccagccca tgcacatcat catcggaaac atgttcaagc     300
tcgaggtctg ggagatcctg cttacctcca tgcgggtgca cgaggtggcc gagttctggt     360
gcgacaccat ccacacgggg gtctacccca tcctatcccg gagcctgagg cagatggccc     420
agggcaagga ccccacagag tggcacgtgc acacgtgcgg gctggccaac atgttcgcct     480
accacacgct gggctacgag gacctggacg agctgcagaa ggagcctcag cctctggtct     540
ttgtgatcga gctgctgcag gttgatgccc cgagtgatta ccagagggag acctggaacc     600
tgagcaatca tgagaagatg aaggcggtgc ccgtcctcca cggagaggga aatcggctct     660
```

```
tcaagctggg ccgctacgag gaggcctctt ccaagtacca ggaggccatc atctgcctaa      720
ggaacctgca gaccaaggag aagccatggg aggtgcagtg gctgaagctg agaagatga       780 tcaatactct gatcctcaac tactgccagt gcctgctgaa gaaggaggag tactatgagg      840
tgctggagca caccagtgat attctccggc accacccagg catcgtgaag gcctactacg      900
tgcgtgcccg ggctcacgca gaggtgtgga atgaggccga ggccaaggcg gacctccaga      960
aagtgctgga gctggagccg tccatgcaga aggcggtgcg cagggagctg aggctgctgg     1020
agaaccgcat ggcggagaag caggaggagg agcggctgcg ctgccggaac atgctgagcc     1080
agggtgccac gcagcctccc gcagagccac ccacagagcc acccgcacag tcatccacag     1140
agccacctgc agagccaccc acagcaccat ctgcagagct gtccgcaggg cccctgcag      1200 agccagccac agagccaccc ccgtccccag ggcactcgct gcagcactga gccccctgag     1260
gcccacagcc acccaggcag ggagcaagtg gcctggtcac ttctggttcg attgaccagg     1320
atcgtggtgt cacttttta aatttaaaat taatttttga aatcaaagtc agacacaccc      1380
atggtaaaaa aaaaaaaaaa aacaatccca agggtacaga agagcttatg aataaaagta     1440
gttttctcct ctacccctct cattccttcc gtgccatggt tttaattgac cctgttttta     1500
attcttctgg tagttttctc tatttccaag taatctgttt aaatcagttt ctagatttta     1560
ccccatgtca atgacaaatg aggatttgat gctctgatcc tttctcatgc ctgataccc      1620 tccctgtctc cccattttgg atagttacat ttgggggtca tctcggtgat ttttgtaact     1680
ttacgcagga cacttagagc tctctagaat cccactgact ttagtgggtc ttgatgtagg     1740
gtgggcaagc cccgacactg gagcttagcc tgagagggtt cttggcctcc cccaggaaag     1800
atttcaaagg caagcgccag tggtagggta gaagaaaaca gctgtggtcg ggcacggtgg     1860
ctcacgccta taatcccagc actttgggag gccgaggcgg gtggatcacc tgaggtcagg     1920
agttccagac cagcctggcc aacatggtga aacctcatct ctactaaaaa tacaaaaaaa     1980
ctagctgggc gtggtggcgg gcgcctataa tcccagctac ttgggaggct gaggcaggag     2040
aattgattga acctgggagg cggaggttgc agtgagccaa gatcacgtca ttgcactcca     2100
gcctggtcaa caagagtaaa acttcatctc aaaaaacaaa acaaaacaaa aacaacaaca     2160
aaaaacaaaa gaaaaacaaa caaaaccaaa accaaaacag ctgtattgaa gctgcagtgt     2220
tgcagctctg tgactgccct gcagagcagg gctaccccat aggcagcgag cagcagctca     2280
gggcagttct gcagtcagat ttatacccac ttttaattac atgtagatta aggagctgca     2340
tatacaaaga tttctaggga aggagtagta acttctgggt cctggggtct ttgccacgga     2400
acagggcagt atgccagggt gttgccacgg caatggtaaa ctgacatggc accctggggg     2460
tcatgcctta gggaaagccg cttccactcg cccctgtttt agctcatctt caagttagtc     2520
tggtgtccaa gctccaccgc ctgcctcagt ctggtgacct ccttctgtgt ctgatgagca     2580
tggcagcgtt gggaccttcc ccttccaact ctctccctcc tcttcgtcct ccctaaagga     2640
cgggtacgag gagggctat cacgccagcg acatcctcta gcaccaccca ggtgtgtggg      2700
gtggggcagg ggggcgacga agtatccagc ccagggccac gtagtcaact gccaagggct     2760
tcctgggctt ctcttctgcc ccagagcttg tctccaccca gcagggttc ccccagcgct      2820 aactgtatcc ctaaagttct gatgtacttt acttttccat cttccttgtt gttaacatct     2880
accttctgct ctgtaagcaa aactaaatct tctgtgcttt gtccataggt tgattctaca     2940
atctgaaaat caataaacag catttgcatg aaaaaaaaaa a                         2981
```

<210> SEQ ID NO 45
<211> LENGTH: 384
<212> TYPE: PRT
<213> ORGANISM: Homo sapiens

<400> SEQUENCE: 45

Met Asp Ala Ala Leu Leu Asn Val Glu Gly Val Lys Lys Thr Ile
1               5                   10                  15

Leu His Gly Gly Thr Gly Glu Leu Pro Asn Phe Ile Thr Gly Ser Arg
            20                  25                  30

Val Ile Phe His Phe Arg Thr Met Lys Cys Asp Glu Glu Arg Thr Val
                35                  40                  45

Ile Asp Asp Ser Arg Gln Val Gly Gln Pro Met His Ile Ile Gly
50                  55                      60

Asn Met Phe Lys Leu Glu Val Trp Glu Ile Leu Leu Thr Ser Met Arg
65                  70                  75                  80

Val His Glu Val Ala Glu Phe Trp Cys Asp Thr Ile His Thr Gly Val
                    85                  90                  95

Tyr Pro Ile Leu Ser Arg Ser Leu Arg Gln Met Ala Gln Gly Lys Asp
                100                 105                 110

Pro Thr Glu Trp His Val His Thr Cys Gly Leu Ala Asn Met Phe Ala
                115                 120                 125

Tyr His Thr Leu Gly Tyr Glu Asp Leu Asp Glu Leu Gln Lys Glu Pro
            130                 135                 140

Gln Pro Leu Val Phe Val Ile Glu Leu Leu Gln Val Asp Ala Pro Ser
145                 150                 155                 160

Asp Tyr Gln Arg Glu Thr Trp Asn Leu Ser Asn His Glu Lys Met Lys
                165                 170                 175

Ala Val Pro Val Leu His Gly Glu Gly Asn Arg Leu Phe Lys Leu Gly
                180                 185                 190

Arg Tyr Glu Glu Ala Ser Ser Lys Tyr Gln Glu Ala Ile Ile Cys Leu
            195                 200                 205

Arg Asn Leu Gln Thr Lys Glu Lys Pro Trp Glu Val Gln Trp Leu Lys
210                 215                 220

Leu Glu Lys Met Ile Asn Thr Leu Ile Leu Asn Tyr Cys Gln Cys Leu
225                 230                 235                 240

Leu Lys Lys Glu Glu Tyr Tyr Glu Val Leu His Thr Ser Asp Ile
                245                 250                 255

Leu Arg His His Pro Gly Ile Val Lys Ala Tyr Tyr Val Arg Ala Arg
            260                 265                 270

Ala His Ala Glu Val Trp Asn Glu Ala Glu Ala Lys Ala Asp Leu Gln
            275                 280                 285

Lys Val Leu Glu Leu Glu Pro Ser Met Gln Lys Ala Val Arg Arg Glu
290                 295                 300

Leu Arg Leu Leu Glu Asn Arg Met Ala Glu Lys Gln Glu Glu Arg
305                 310                 315                 320

Leu Arg Cys Arg Asn Met Leu Ser Gln Gly Ala Thr Gln Pro Pro Ala
                325                 330                 335

Glu Pro Pro Thr Glu Pro Pro Ala Gln Ser Ser Thr Gly Pro Pro Ala
            340                 345                 350

Glu Pro Pro Thr Ala Pro Ser Ala Glu Leu Ser Ala Gly Pro Pro Ala
            355                 360                 365

Glu Pro Ala Thr Glu Pro Pro Ser Pro Gly His Ser Leu Gln His
            370                 375                 380

<210> SEQ ID NO 46
<211> LENGTH: 1934
<212> TYPE: DNA
<213> ORGANISM: Homo sapiens

<400> SEQUENCE: 46

| | | | | | |
|---|---|---|---|---|---|
| gggcacaagc | aatcctccct | tctcagcttc | ctgagtggcc | aggactacag | aggactgtat | 60 |
| gctgttctta | aggactctct | gcttcctgga | caagctcaag | ctaaggacta | catctcccag | 120 |
| caggctgtgc | tctgacagct | cttggattta | aataggattc | tgggctctgc | tcagagtcag | 180 |
| gctgctgctc | agcacccagg | acggagagga | gcagagaagc | agcagaagca | gccaagagct | 240 |
| ggagccagac | caggaacctg | agccagagct | ggggttgaag | ctggagcagc | agcaaaagca | 300 |
| acagcagcta | cagaagttgg | aacgatgctg | gtcaccttgg | gactgctcac | ctccttcttc | 360 |
| tcgttcctgt | atatggtagc | tccatccatc | aggaagttct | ttgctggtgg | agtgtgtaga | 420 |
| acaaatgtgc | agcttcctgg | caaggtagtg | gtgatcactg | cgccaacac | gggcattggc | 480 |
| aaggagacgg | ccagagagct | cgctagccga | ggagcccgag | tctatattgc | ctgcagagat | 540 |
| gtactgaagg | gggagtctgc | tgccagtgaa | atccgagtgg | atacaaagaa | ctcccaggtg | 600 |
| ctggtgcgga | aattggacct | atccgacacc | aaatctatcc | gagcctttgc | tgagggcttt | 660 |
| ctggcagagg | aaaagcagct | ccatattctg | atcaacaatg | cgggagtaat | gatgtgtcca | 720 |
| tattccaaga | cagctgatgg | ctttgaaacc | cacctgggag | tcaaccacct | gggccacttc | 780 |
| ctcctcacct | acctgctcct | ggagcggcta | aaggtgtctg | ccctgcacg | ggtggttaat | 840 |
| gtgtcctcgg | tggctcacca | cattggcaag | attcccttcc | acgacctcca | gagcgagaag | 900 |
| cgctacagca | ggggttttgc | ctattgccac | agcaagctgg | ccaatgtgct | ttttactcgt | 960 |
| gagctggcca | agaggctcca | aggcaccggg | gtcaccacct | acgcagtgca | cccaggcgtc | 1020 |
| gtccgctctg | agctggtccg | gcactcctcc | ctgctctgcc | tgctctggcg | gctcttctcc | 1080 |
| cccttgtca | agacggcacg | ggagggggcg | cagaccagcc | tgcactgcgc | cctggctgag | 1140 |
| ggcctggagc | ccctgagtgg | caagtacttc | agtgactgca | agaggacctg | ggtgtctcca | 1200 |
| agggcccgaa | ataacaaaac | agctgagcgc | ctatggaatg | tcagctgtga | gcttctagga | 1260 |
| atccggtggg | agtagctggt | ggaagagctg | cagctttatc | aggcccaatc | catgccataa | 1320 |
| tgaacaggga | ccaaggagaa | ggccaaccct | aaaggattgt | cctcttggcc | agctggtgct | 1380 |
| gcgaatcctg | cctgctctga | tcctcttgac | ccttctggga | atgtttgcac | acctgacact | 1440 |
| cttgtgagac | tggcttatgg | catgagttgt | ggacacctat | agagtgttct | tctctaagac | 1500 |
| ctggaaagtc | agcaaccctc | tgggggcagc | aggactgggc | agatcccagg | ctgggcatgg | 1560 |
| gggtggcaga | agagcccgag | aaattgggtc | agttccctca | tcagcaccag | aggctcagct | 1620 |
| gaggcaagaa | gagcaccatc | actgcctatt | tctagggct | atacactcca | actcttggtt | 1680 |
| gatctctttc | tttttaaaaa | tatttgccac | caccctggag | tctagaccaa | cacacaaaga | 1740 |
| tcctggctaa | ccctggccta | tttagattcc | ttcctctcac | ctggaccttc | ccatttcaat | 1800 |
| catgcagatg | gtttctttt | gtaaagagtt | ccgtttgcct | ttcaattttt | agagaaaata | 1860 |
| aagactgcat | tcatctcaaa | aaaaaaaaaa | aaaaaaaaaa | aaaaaaaaaa | aaaaaaaaaa | 1920 |
| aaaaaaaaaa | aaaa | | | | | 1934 |

<210> SEQ ID NO 47
<211> LENGTH: 316
<212> TYPE: PRT

<213> ORGANISM: Homo sapiens

<400> SEQUENCE: 47

```
Met Leu Val Thr Leu Gly Leu Leu Thr Ser Phe Phe Ser Phe Leu Tyr
1               5                   10                  15
Met Val Ala Pro Ser Ile Arg Lys Phe Phe Ala Gly Gly Val Cys Arg
            20                  25                  30
Thr Asn Val Gln Leu Pro Gly Lys Val Val Ile Thr Gly Ala Asn
        35                  40                  45
Thr Gly Ile Gly Lys Glu Thr Ala Arg Glu Leu Ala Ser Arg Gly Ala
    50                  55                  60
Arg Val Tyr Ile Ala Cys Arg Asp Val Leu Lys Gly Glu Ser Ala Ala
65                  70                  75                  80
Ser Glu Ile Arg Val Asp Thr Lys Asn Ser Gln Val Leu Val Arg Lys
                85                  90                  95
Leu Asp Leu Ser Asp Thr Lys Ser Ile Arg Ala Phe Ala Glu Gly Phe
            100                 105                 110
Leu Ala Glu Glu Lys Gln Leu His Ile Leu Ile Asn Asn Ala Gly Val
        115                 120                 125
Met Met Cys Pro Tyr Ser Lys Thr Ala Asp Gly Phe Glu Thr His Leu
130                 135                 140
Gly Val Asn His Leu Gly His Phe Leu Leu Thr Tyr Leu Leu Leu Glu
145                 150                 155                 160
Arg Leu Lys Val Ser Ala Pro Ala Arg Val Val Asn Val Ser Ser Val
                165                 170                 175
Ala His His Ile Gly Lys Ile Pro His Asp Leu Gln Ser Glu Lys
            180                 185                 190
Arg Tyr Ser Arg Gly Phe Ala Tyr Cys His Ser Lys Leu Ala Asn Val
        195                 200                 205
Leu Phe Thr Arg Glu Leu Ala Lys Arg Leu Gln Gly Thr Gly Val Thr
    210                 215                 220
Thr Tyr Ala Val His Pro Gly Val Val Arg Ser Glu Leu Val Arg His
225                 230                 235                 240
Ser Ser Leu Leu Cys Leu Leu Trp Arg Leu Phe Ser Pro Phe Val Lys
                245                 250                 255
Thr Ala Arg Glu Gly Ala Gln Thr Ser Leu His Cys Ala Leu Ala Glu
            260                 265                 270
Gly Leu Glu Pro Leu Ser Gly Lys Tyr Phe Ser Asp Cys Lys Arg Thr
        275                 280                 285
Trp Val Ser Pro Arg Ala Arg Asn Asn Lys Thr Ala Glu Arg Leu Trp
    290                 295                 300
Asn Val Ser Cys Glu Leu Leu Gly Ile Arg Trp Glu
305                 310                 315
```

<210> SEQ ID NO 48
<211> LENGTH: 4729
<212> TYPE: DNA
<213> ORGANISM: Homo sapiens

<400> SEQUENCE: 48

```
agtctaggcc tccgcctccg ttaccctgga gcccaggtta ccgccgctgc cacccaggag      60
ccccgatcct cgcctctgtc ccatccttgt gttcaaacct cccgcatctc ggcaacctcg     120
gcacccgccc ggcagcctcc gcaggaacca ggcacccgct ctttggcggt cagacgccga     180
ggccccagct gggagtttgg tcctaagagg gaaggcaagg aggcgggacg ccgcatcggc     240
```

```
tctgctgaag agcctgcggg ttggaggtgg gctttgaagt gggcgtggag acggcggggg    300
aggtggaggt gcgagtataa atgatcaacc agaaattatc ttcaaaggaa taaaaccaga    360
agtatgtaaa taaaaagccc aagataaaga aacagaaaag ctgacactac atgaagcaga    420
gggcaaaaaa gtttatcttc tggatgccaa tgtgaattgt ggtctacaaa tacattgtgg    480
agaaaataga ttgcacagaa atgaatatta tcaggatctg aagactgtga aaatgttttt    540
cagtattgtc atagtctcct ctggagaaaa taatctgtga aattatgtga atagagacca    600
ttttcaaaa caatggggga aagagcagga agtccaggta ctgatcaaga aagaaaggca    660
ggcaaacacc attattctta cttatctgat tttgaaacgc cacagtcttc tggccgatca    720
tcgctggtca gttcttcacc tgcaagtgtt aggagaaaaa atcctaaaag acaaacttca    780
gatggccaag tacatcacca agccctcgg aaaccaagcc ctaagggtct accaaacaga    840
aagggagtcc gagtgggatt tcgctcccag agcctcaata gagagccact tcggaaagat    900
actgatcttg ttacaaaacg gattctgtct gcaagactgc taaaaatcaa tgagttgcag    960
aatgaagtat ctgaactcca ggtcaagtta gctgagctgc taaaagaaaa taaatctttg   1020
aaaaggcttc agtacagaca ggagaaagcc ctgaataagt ttgaagatgc cgaaaatgaa   1080
atctcacaac ttatatttcg tcataacaat gagattacag cactcaaaga acgcttaaga   1140
aaatctcaag agaaagaacg ggcaactgag aaaagggtaa aagatacaga aagtgaacta   1200
tttaggacaa aattttcctt acagaaactg aaagagatct ctgaagctag acacctacct   1260
gaacgagatg atttggcaaa gaaactagtt tcagcagagt taaagttaga tgacaccgag   1320
agaagaatta aggagctatc gaaaaacctt gaactgagta ctaacagttt ccaacgacag   1380
ttgcttgctg aaaggaaaag ggcatatgag gctcatgatg aaaataaagt tcttcaaaag   1440
gaggtacagc gactatatca caaattaaag gaaaaggaga gagaactgga tataaaaat    1500
atatattcta atcgtctgcc aaagtcctct ccaaataaag agaagaact tgcattaaga    1560
aaaaatgctg catgccagag tgattttgca gacctgtgta caaaaggagt acaaaccatg   1620
gaagacttca agccagaaga atatccttta actccagaaa caattatgtg ttacgaaaac   1680
aaatgggaag aaccaggaca tcttactttg gacttgcaat ctcaaaagca agacaggcat   1740
ggagaagcag ggattctaaa cccaattatg gaaagagaag aaaaatttgt tacagatgaa   1800
gaactccatg tcgtaaaaca ggaggttgaa aagctgagg atgaatggga agagaagaa    1860
cttgataaaa agcaaaaaga aaaggcatct ttactggaaa gagaagaaaa gccagagtgg   1920
gaaactggaa ggtaccaact aggaatgtat ccaattcaga atatggataa attgcaagga   1980
gaggaagaag aaagactgaa gagagaaatg ctacttgcta aactgaatga aattgacaga   2040
gaactccaag attctcgaaa tctaaaatac cctgttttgc cattgttacc tgattttgaa   2100
tcaaaactac actccccaga gagaagcccc aaaacataca ggttctctga atcctcagag   2160
agattattta tgggcatca tttgcaagac atcagttct caactccaaa aggagaaggt    2220
cagaattcag gaaatgttag aagtccagcc tcccctaatg agttcgcatt tggtagctac   2280
gtgccttcgt ttgcaaaaac atcagagagg tcaaatccat ttagtcaaaa aagtagtttt   2340
ttggatttcc aaagaaacag tatggaaaaa cttagtaaaa atggtgtaga tttaattaca   2400
agaaaagaga aaaagctaa tttgatggaa cagttatttg gtgccagtgg tagcagcacc   2460
atttcctcca aaagcagtga cccaaattct gtggcttcca gtaaaggaga cattgaccct   2520
ctaaattttc tccctgggaa taaaggcagc agagatcaag aacatgatga agatgaaggc   2580
```

-continued

```
ttttcctca gtgaaggaag aagttttaat ccaaataggc accgattaaa acatgcagac    2640
gataaaccag cagtaaaagc agctgattct gtagaagatg aaattgaaga agtagcactg    2700
agatgactga ctagagtata catttttct aattgtaaat attgaaatat tttaatacag     2760
tatttattat aaacatttag acttttaat gctaaaatgt ccttattaag gaatgatttt     2820
taatagctaa atacaatgca gttaaaaaga agtagatcat acatacacca catagatagt    2880
ttgccaagaa tgaaggaggc ttttttgaat gaaaccaaaa ataaaaatat gtcttgaaaa    2940
atgaaataga ttttaactct tcatccagtg ctatggcaag tttaactgca ctggaggtgg    3000 tattccttt ctactttat tcctatttat gtatttattt ttaatcatat tctcactgtg      3060
ctaaatacag tcttcccact aattgttgaa tgaaaattaa gggtgaaagt ctgtgttggg    3120
aagtgtagct ccggatggtg gagaaccagt gcttcttagg agcccttccc tttatggata    3180
gggccagggg tccctatctt acgtggcagt cctaagctac tcttgagtga tagcagtcac    3240
aacattggga tttcccattc ctctgaaagt acccacagct aaacactact catttcccaa    3300
tttcagtatt tactgaaatc acttacctac aattctgtta gaatattatg ttgagttcgg    3360
aagacatttc tctgttttgca aggacagtta gttgctctct gtcatagccc gcagaagctt   3420
ggctacagtg taattcctct ccttgttctc ctacactctt tgtatctcag tgactgggtg    3480
taagatttca tgccaaatgc aaggaatagt ggaaatacat accaactgca aagaatagaa    3540
aaactttatc ccaatatatt atagaaagat cttcagttca attatgtcca gagtaatata    3600
atttggcaat gttaatgctt ttaagatttg aacttgtcct caaaccaagg agacaacaat    3660
agtgtaatac tattggactt acaggattag ttttaaagca actttgaata gaagtgtttc    3720
agacatagga cttctgcctt gttgactaga gtggatagtt ttctgtttaa atgcattggt    3780
cttttggctg tttgtaattc acttcagctt atagagaagt tgatgacctt ggatcatgct    3840
gggtatgatt ggtctttaaa aagcagtaat ataccaccag cccaaggaga aaacattgtt    3900
aaaatgaaga gtggtggaaa tagtgtgttg ggaagaataa aaaatttaga ttggcactta    3960
ttctaaagtg agctgttttt ttcaagaatt tactagcatt tgctcgtagt atgatttctg    4020
acgccagtca tatatactga tgaggggaag gagttactgt gttattctga gttcttataa    4080
atgcatatta ttgaatttca ttgcatgact attttgtcaag acttacctgg ttaggtctcc   4140
aattaaaaga tgtaccacct gtcatcttct aaattgtgtt cctttcattt attgggaaca   4200
gaatctctca aaagtgctaa actatattaa aaagttttct taatagattt gtatgtctga    4260
tatgtataac catttactat aatatgttgc aaatcattct aatatatgta aaacaatatt    4320
atttgtaatg cagttattgg taaaatatta tgtaatgtta attttgttcc tagctgctaa    4380 ttttctgcc aaaagtattc taattttcag gttgttttaa aggcttttaa aactttttag     4440 ttaagtttt tattcacgtc atttaaatta gttttttgct tttttctac ctgataatct      4500 ctttaacaag atgcaacaag acagaattat taaaattaaa cctaaagtta agttacagat    4560
ttaaaggcat tatgatatta agcattaaaa ttggagatta aaatgtacaa aacagggttt    4620
tccttatgaa caaaccttac agggtaaatt gttttttttt ctaaatgtca ttaaatttat    4680
ttgtactcag aactgttact aataaaaatt aaaaatgcaa aaaaaaaaa                4729
```

<210> SEQ ID NO 49
<211> LENGTH: 697
<212> TYPE: PRT
<213> ORGANISM: Homo sapiens

<400> SEQUENCE: 49

```
Met Gly Glu Arg Ala Gly Ser Pro Gly Thr Asp Gln Glu Arg Lys Ala
1               5                   10                  15

Gly Lys His His Tyr Ser Tyr Leu Ser Asp Phe Glu Thr Pro Gln Ser
                20                  25                  30

Ser Gly Arg Ser Ser Leu Val Ser Ser Pro Ala Ser Val Arg Arg
            35                  40                  45

Lys Asn Pro Lys Arg Gln Thr Ser Asp Gly Gln Val His His Gln Ala
    50                  55                  60

Pro Arg Lys Pro Ser Pro Lys Gly Leu Pro Asn Arg Lys Gly Val Arg
65                  70                  75                  80

Val Gly Phe Arg Ser Gln Ser Leu Asn Arg Glu Pro Leu Arg Lys Asp
                85                  90                  95

Thr Asp Leu Val Thr Lys Arg Ile Leu Ser Ala Arg Leu Leu Lys Ile
                100                 105                 110

Asn Glu Leu Gln Asn Glu Val Ser Glu Leu Gln Val Lys Leu Ala Glu
            115                 120                 125

Leu Leu Lys Glu Asn Lys Ser Leu Lys Arg Leu Gln Tyr Arg Gln Glu
        130                 135                 140

Lys Ala Leu Asn Lys Phe Glu Asp Ala Glu Asn Glu Ile Ser Gln Leu
145                 150                 155                 160

Ile Phe Arg His Asn Asn Glu Ile Thr Ala Leu Lys Glu Arg Leu Arg
                165                 170                 175

Lys Ser Gln Glu Lys Glu Arg Ala Thr Glu Lys Arg Val Lys Asp Thr
            180                 185                 190

Glu Ser Glu Leu Phe Arg Thr Lys Phe Ser Leu Gln Lys Leu Lys Glu
        195                 200                 205

Ile Ser Glu Ala Arg His Leu Pro Glu Arg Asp Leu Ala Lys Lys
        210                 215                 220

Leu Val Ser Ala Glu Leu Lys Leu Asp Asp Thr Glu Arg Arg Ile Lys
225                 230                 235                 240

Glu Leu Ser Lys Asn Leu Glu Leu Ser Thr Asn Ser Phe Gln Arg Gln
                245                 250                 255

Leu Leu Ala Glu Arg Lys Arg Ala Tyr Glu Ala His Asp Glu Asn Lys
            260                 265                 270

Val Leu Gln Lys Glu Val Gln Arg Leu Tyr His Lys Leu Lys Glu Lys
        275                 280                 285

Glu Arg Glu Leu Asp Ile Lys Asn Ile Tyr Ser Asn Arg Leu Pro Lys
290                 295                 300

Ser Ser Pro Asn Lys Glu Lys Glu Leu Ala Leu Arg Lys Asn Ala Ala
305                 310                 315                 320

Cys Gln Ser Asp Phe Ala Asp Leu Cys Thr Lys Gly Val Gln Thr Met
                325                 330                 335

Glu Asp Phe Lys Pro Glu Glu Tyr Pro Leu Thr Pro Glu Thr Ile Met
            340                 345                 350

Cys Tyr Glu Asn Lys Trp Glu Pro Gly His Leu Thr Leu Asp Leu
        355                 360                 365

Gln Ser Gln Lys Gln Asp Arg His Gly Glu Ala Gly Ile Leu Asn Pro
370                 375                 380

Ile Met Glu Arg Glu Glu Lys Phe Val Thr Asp Glu Leu His Val
385                 390                 395                 400

Val Lys Gln Glu Val Lys Leu Glu Asp Glu Trp Glu Arg Glu Glu
                405                 410                 415
```

```
Leu Asp Lys Lys Gln Lys Glu Lys Ala Ser Leu Leu Glu Arg Glu Glu
            420                 425                 430

Lys Pro Glu Trp Glu Thr Gly Arg Tyr Gln Leu Gly Met Tyr Pro Ile
        435                 440                 445

Gln Asn Met Asp Lys Leu Gln Gly Glu Glu Glu Arg Leu Lys Arg
    450                 455                 460

Glu Met Leu Leu Ala Lys Leu Asn Glu Ile Asp Arg Glu Leu Gln Asp
465                 470                 475                 480

Ser Arg Asn Leu Lys Tyr Pro Val Leu Pro Leu Leu Pro Asp Phe Glu
                485                 490                 495

Ser Lys Leu His Ser Pro Glu Arg Ser Pro Lys Thr Tyr Arg Phe Ser
            500                 505                 510

Glu Ser Ser Glu Arg Leu Phe Asn Gly His His Leu Gln Asp Ile Ser
        515                 520                 525

Phe Ser Thr Pro Lys Gly Glu Gly Gln Asn Ser Gly Asn Val Arg Ser
    530                 535                 540

Pro Ala Ser Pro Asn Glu Phe Ala Phe Gly Ser Tyr Val Pro Ser Phe
545                 550                 555                 560

Ala Lys Thr Ser Glu Arg Ser Asn Pro Phe Ser Gln Lys Ser Ser Phe
                565                 570                 575

Leu Asp Phe Gln Arg Asn Ser Met Glu Lys Leu Ser Lys Asp Gly Val
            580                 585                 590

Asp Leu Ile Thr Arg Lys Glu Lys Ala Asn Leu Met Glu Gln Leu
        595                 600                 605

Phe Gly Ala Ser Gly Ser Ser Thr Ile Ser Ser Lys Ser Ser Asp Pro
    610                 615                 620

Asn Ser Val Ala Ser Ser Lys Gly Asp Ile Asp Pro Leu Asn Phe Leu
625                 630                 635                 640

Pro Gly Asn Lys Gly Ser Arg Asp Gln Glu His Asp Glu Asp Glu Gly
                645                 650                 655

Phe Phe Leu Ser Glu Gly Arg Ser Phe Asn Pro Asn Arg His Arg Leu
            660                 665                 670

Lys His Ala Asp Asp Lys Pro Ala Val Lys Ala Ala Asp Ser Val Glu
        675                 680                 685

Asp Glu Ile Glu Glu Val Ala Leu Arg
    690                 695

<210> SEQ ID NO 50
<211> LENGTH: 3771
<212> TYPE: DNA
<213> ORGANISM: Homo sapiens

<400> SEQUENCE: 50
ccagggtgag attatgaggc tgagctgaga atatcaagac tgtaccgagt agggggcctt      60
ggcaagtgtg gagagcccgg cagctggggc agagggcgga gtacggtgtg cgtttacgga     120
cctcttcaaa cgaggtagga aggtcagaag tcaaaaaggg aacaaatgat gtttaaccac     180
acaaaaatga aaatccaatg gttggatatc cattccaaat acacaaaggc aacggataag     240
tgatccgggc caggcacaga aggccatgca cccgtaggat tgcactcaga gctcccaaat     300
gcataggaat agaagggtgg gtgcaggagg ctgaggggtg gggaagggc atgggtgttt      360 catgaggaca gagcttccgt ttcatgcaat gaaagagtt tggagacgga tggtggtgac      420
tggactatac acttacacac ggtagcgatg gtacactttg tattatgtat attttaccac     480 gatctttta aagtgtcaaa ggcaaatggc caaatggttc cttgtcctat agctgtagca      540
```

```
gccatcggct gttagtgaca aagcccctga gtcaagatga cagcagcccc cataactcct   600
aatcggctct cccgcgtgga gtcatttagg agtagtcgca ttagagacaa gtccaacatc   660
taatcttcca ccctggccag ggccccagct ggcagcgagg gtgggagact ccgggcagag   720
cagagggcgc tgacattggg gcccggcctg gcttgggtcc ctctggcctt tccccagggg   780
ccctctttcc ttggggcttt cttgggccgc cactgctccc gctcctctcc ccccatccca   840
cccctcacc ccctcgttct tcatatcctt ctctagtgct ccctccactt tcatccaccc   900
ttctgcaaga gtgtgggacc acaaatgagt tttcacctgg cctggggaca cacgtgcccc   960
cacaggtgct gagtgacttt ctaggacagt aatctgcttt aggctaaaat gggacttgat  1020
cttctgttag ccctaatcat caattagcag agccggtgaa ggtgcagaac ctaccgcctt  1080
tccaggcctc ctcccacctc tgccacctcc actctccttc ctgggatgtg ggggctggca  1140
cacgtgtggc ccagggcatt ggtgggattg cactgagctg ggtcattagc gtaatcctgg  1200
acaagggcag acagggcgag cggagggcca gctccggggc tcaggcaagg ctgggggctt  1260
cccccagaca ccccactcct cctctgctgg acccccactt catagggcac ttcgtgttct  1320
caaagggctt ccaaatagca tggtggcctt ggatgcccag ggaagcctca gagttgctta  1380
tctccctcta gacagaaggg gaatctcggt caagagggag aggtcgccct gttcaaggcc  1440
acccagccag ctcatggcgg taatgggaca aggctggcca gccatcccac cctcagaagg  1500
gacccggtgg ggcaggtgat ctcagaggag gctcacttct gggtctcaca ttcttggatc  1560
cggttccagg cctcggccct aaatagtctc cctgggcttt caagagaacc acatgagaaa  1620
ggaggattcg ggctctgagc agtttcacca cccaccccc agtctgcaaa tcctgacccg  1680
tgggtccacc tgccccaaag gcggacgcag gacagtagaa gggaacagag aacacataaa  1740
cacagagagg gccacagcgg ctcccacagt caccgccacc ttcctggcgg ggatgggtgg  1800
ggcgtctgag tttggttccc agcaaatccc tctgagccgc ccttgcgggc tcgcctcagg  1860
agcaggggag caagaggtgg gaggaggagg tctaagtccc aggcccaatt aagagatcag  1920
gtagtgtagg gttggggagc ttttaaggtg aagaggcccg ggctgatccc acaggccagt  1980
ataaagcgcc gtgaccctca ggtgatgcgc cagggccggc tgccgtcggg gacagggctt  2040
tccatagcca tgctagagga tccggtactc gaggaactga aaaaccagaa agttaactgg  2100
taagtttagt cttttttgtct tttatttcag gtcccggatc cggtggtggt gcaaatcaaa  2160
gaactgctcc tcagtggatg ttgccttta ttctaggcct gtacggaagt gttacttctg  2220
ctctaaaagc tgcggaattg tacccgcggc cgcgggacag ggctttccat agccatggcc  2280
cagcagtgga gcctccaaag gctcgcaggc cgccatccgc aggacagcta tgaggacagc  2340
acccagtcca gcatcttcac ctacaccaac agcaactcca ccagaggccc cttcgaaggc  2400
ccgaattacc acatcgctcc cagatgggtg taccacctca ccagtgtctg gatgatcttt  2460
gtggtcactg catccgtctt cacaaatggg cttgtgctgg cggccaccat gaagttcaag  2520
aagctgcgcc acccgctgaa ctggatcctg gtgaacctgg cggtcgctga cctagcagag  2580
accgtcatcg ccagcactat cagcattgtg aaccaggtct ctggctactt cgtgctgggc  2640
caccctatgt gtgtcctgga gggctacacc gtctccctgt gtgggatcac aggtctctgg  2700
tctctggcca tcatttcctg ggagagatgg atggtggtct gcaagccctt tggcaatgtg  2760
agatttgatg ccaagctggc catcgtgggc attgccttct cctggatctg gtctgctgtg  2820
tggacagccc cgcccatctt tggttggagc aggtactggc cccacggcct gaagacttca  2880
```

```
tgcggcccag acgtgttcag cggcagctcg taccccgggg tgcagtctta catgattgtc    2940
ctcatggtca cctgctgcat catcccactc gctatcatca tgctctgcta cctccaagtg    3000
tggctggcca tccgagcggt ggcaaagcag cagaaagagt ctgaatccac ccagaaggca    3060
gagaaggaag tgacgcgcat ggtggtggtg atgatctttg cgtactgcgt ctgctgggga    3120
ccctacacct tcttcgcatg ctttgctgct gccaaccctg gttacgcctt ccaccctttg    3180
atggctgccc tgccggccta ctttgccaaa agtgccacta tctacaaccc cgttatctat    3240
gtctttatga accggcagtt tcgaaactgc atcttgcagc ttttcgggaa gaaggttgac    3300
gatggctctg aactctccag cgcctccaaa acggaggtct caactgtgtc ctcgacccag    3360
gtagggccta actgaggtct gcctcctacc catcccgccc accggggctt tggccacctc    3420
tcctttcccc ctccttctcc atccctgtaa aataaatgta atttatcttt gccaaaacca    3480
aaaaaaacgg aattcgtaat catgtcatag ctgtttcctg tgtgaaattg ttatccgctc    3540
acaattccac acaacatacg aggcggccgc gcggatccag acatgataag atacattgat    3600
gagtttggac aaaccacaac tagaatgcag tgaaaaaaat gctttatttg tgaaatttgt    3660
gatgctattg ctttatttgt aaccattata agctgcaata aacaagttaa caacaacaat    3720
tgcattcatt ttatgtttca ggttcagggg gaggtgtggg aggttttta g              3771

<210> SEQ ID NO 51
<211> LENGTH: 36
<212> TYPE: DNA
<213> ORGANISM: Artificial Sequence
<220> FEATURE:
<223> OTHER INFORMATION: Synthetic

<400> SEQUENCE: 51
gacttgatct tctgttagcc ctaatcatca attagc                                36
```